United States Patent
Tsui et al.

(10) Patent No.: US 8,623,857 B2
(45) Date of Patent: Jan. 7, 2014

(54) N-PHENYL IMIDAZOLE CARBOXAMIDE INHIBITORS OF 3-PHOSPHOINOSITIDE-DEPENDENT PROTEIN KINASE-1

(75) Inventors: Hon-Chung Tsui, Shanghai (CN); Sunil Paliwal, Monroe Township, NJ (US); Hyunjin M. Kim, Livingston, NJ (US); Angela D. Kerekes, Plainfield, NJ (US); Mary Ann Caplen, Sayreville, NJ (US); Sara J. Esposite, Neptune, NJ (US); Brian A. McKittrick, New Vernon, NJ (US); Thierry Olivier Fischmann, Scotch Plains, NJ (US); Ronald J. Doll, Convent Station, NJ (US); Matthew Paul Rainka, Schenectady, NY (US); Ang Li, Cranberry Township, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 13/699,547

(22) PCT Filed: May 24, 2011

(86) PCT No.: PCT/US2011/037651
§ 371 (c)(1), (2), (4) Date: Nov. 21, 2012

(87) PCT Pub. No.: WO2011/149874
PCT Pub. Date: Dec. 1, 2011

(65) Prior Publication Data
US 2013/0079326 A1    Mar. 28, 2013

Related U.S. Application Data
(60) Provisional application No. 61/348,538, filed on May 26, 2010.

(51) Int. Cl.
| | | |
|---|---|---|
| C07D 498/08 | (2006.01) |
| C07D 243/00 | (2006.01) |
| C07D 401/14 | (2006.01) |
| C07D 409/14 | (2006.01) |
| C07D 405/14 | (2006.01) |
| C07D 413/14 | (2006.01) |
| C07D 403/04 | (2006.01) |
| A61K 31/5386 | (2006.01) |
| A61K 31/5377 | (2006.01) |
| A61K 31/506 | (2006.01) |
| A61K 31/551 | (2006.01) |
| A61K 31/454 | (2006.01) |
| A61K 31/4545 | (2006.01) |
| A61K 31/4178 | (2006.01) |
| A61K 31/437 | (2006.01) |
| A61K 31/4995 | (2006.01) |
| A61K 45/06 | (2006.01) |

(52) U.S. Cl.
USPC ............. 514/210.18; 514/230.5; 514/235.8; 514/255.01; 514/275; 514/256; 514/249; 514/221; 514/326; 514/318; 514/341; 514/316; 544/105; 544/121; 544/122; 544/130; 544/295; 544/324; 544/328; 544/360; 544/333; 540/556; 546/211; 546/194; 546/210; 546/274.1; 546/187

(58) Field of Classification Search
CPC .................................................. C07D 403/02
USPC .......... 544/242–404; 546/184–248, 255–335; 548/311–373
See application file for complete search history.

(56) References Cited

U.S. PATENT DOCUMENTS
| | | | | |
|---|---|---|---|---|
| 7,705,042 B2 * | 4/2010 | Illig et al. | ....................... | 514/461 |
| 2006/0100201 A1* | 5/2006 | Illig et al. | ................... | 514/227.5 |
| 2007/0249649 A1* | 10/2007 | Illig et al. | ....................... | 514/278 |
| 2009/0048313 A1 | 2/2009 | Dickson | | |

FOREIGN PATENT DOCUMENTS
| | | |
|---|---|---|
| WO | 02094808 A1 | 11/2002 |
| WO | 03104481 A2 | 12/2003 |

(Continued)

OTHER PUBLICATIONS
Peifer, C. and Alessi, D. R. "Small-Molecule Inhibitors of PDK1." Chem. Med. Chem. 2008, 3, 1810-1838.*

(Continued)

Primary Examiner — Samantha Shterengarts
Assistant Examiner — Amanda L Aguirre
(74) Attorney, Agent, or Firm — Yong Zhao; Laura M. Ginkel

(57) ABSTRACT

The present invention provide Imidazole Carboxamide Compounds of Formula (I): wherein D, T, $R^1$, $R^2$, $R^3$, and $R^6$ are as defined herein, and pharmaceutically acceptable salts of such Imidazole Carboxamide Compounds. The Imidazole Carboxamide Compounds are useful in the treatment of cancer and other aberrant conditions that result from overstimulation of the PDK-1 signaling pathway.

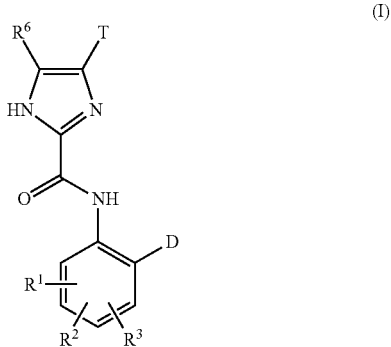

18 Claims, No Drawings

(56) References Cited

FOREIGN PATENT DOCUMENTS

WO  WO 2007124318 A1 * 11/2007
WO     2009014637 A2    1/2009

OTHER PUBLICATIONS

Nagashima, K. et al. "Genetic and Pharmacological Inhibition of PDK1 in Cancer Cells." J. Biol. Chem. 2011, 286, 6433-6488.*

Ellwood-Yen, K. et al. "PDK1 Attenuation Fails to Prevent Tumor Formation in PTEN-Deficient Transgenic Mouse Models." Cancer Res. 2011, 71, 3052-3065.*

Osborne, C. et al. "Oncogenes and Tumor Suppressor Genes in Breast Cancer: Potential Diagnostic and Therapeutic Applications." The Oncologist 2004, 9, 361-377.*

Zhu et al., From the Cyclooxygenase-2 Inhibitor Celecoxib to a Novel Class of 3-Phosphoinositide-Dependent Protein Kinase-1 Inhibitors. Cancer Res. 64:4309-4318; 2004.

* cited by examiner

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: fluorescently-labeled peptide substrate from
      glycogen synthase-1
<221> NAME/KEY: MOD_RES
<222> LOCATION: (1)...(1)
<223> OTHER INFORMATION: 5-FAM
<221> NAME/KEY: MOD_RES
<222> LOCATION: (14)...(14)
<223> OTHER INFORMATION: AMIDATION

<400> SEQUENCE: 1

Pro Leu Ser Arg Thr Leu Ser Val Ser Ser Leu Pro Gly Leu
 1               5                  10

<210> SEQ ID NO 2
<211> LENGTH: 25
<212> TYPE: PRT
<213> ORGANISM: Artificial Sequence
<220> FEATURE:
<223> OTHER INFORMATION: PIFtide
<221> NAME/KEY: MOD_RES
<222> LOCATION: (25)...(25)
<223> OTHER INFORMATION: AMIDATION

<400> SEQUENCE: 2

Arg Arg Glu Pro Arg Ile Leu Ser Glu Glu Glu Gln Glu Met Phe Arg
 1               5                  10                  15

Asp Phe Asp Tyr Ile Ala Asp Trp Cys
             20                  25
```

N-PHENYL IMIDAZOLE CARBOXAMIDE INHIBITORS OF 3-PHOSPHOINOSITIDE-DEPENDENT PROTEIN KINASE-1

FIELD OF THE INVENTION

This invention relates to certain N-phenyl imidazole carboxamide compounds of Formula (I) as inhibitors of 3-phosphoinositide-dependent protein kinase (PDK-1). The compounds are useful in inhibiting the proliferation of cancer cells, and other aberrant conditions where the PDK-1 signaling pathway is overstimulated.

REFERENCE TO SEQUENCE LISTING SUBMITTED ELECTRONICALLY

The sequence listing of the present application is being submitted electronically via EFS-Web as an ASCII formatted sequence listing with a file name "OC2010.7144USPCT-SE-QTXT-14NOV2012.txt", creation date of Nov. 14, 2012 and a size of 1409 bytes. This sequence listing submitted via EFS-Web is part of the specification and is herein incorporated by reference in its entirety.

BACKGROUND OF THE INVENTION

Certain kinases that belong to the serine/threonine kinase family are located intracellularly and are involved in the transmission of biochemical signals such as those that affect cell proliferation and survival. One such serine/threonine kinase is PDK1, which is a regulator of at least 23 protein kinases that belong to the AGC kinase family (cAMP-dependent, cGMP-dependent, and protein kinase C). Signal transduction pathways downstream of PDK1 include the serine/threonine kinases protein kinase B (PKB/Akt), p70 ribosomal S6 kinase (p70S6K1), serum- and glucocorticoid-induced protein kinase (SGK), p90 ribosomal S6 kinase (RSK), and protein kinase C (PKC). Peifer et al., *ChemMed Chem* 3, 1810-1838 (2008).

The binding of growth factors to the cell surface receptors activates phosphoinositide-3 kinase (PI3K), which phosphorylates the substrate, phosphoinositidylinositol-4,5-triphosphate (PIP2) to form the second messenger, phosphoinositidylinositol-3,4,5-triphosphate (PIP3). PIP3 binds to both PDK1 and PKB/Akt, which are believed to co-localize at the cell membrane as a consequence. In addition to its interaction with PKB/Akt, PDK1 also phosphorylates and activates p70S6K1, SGK, RSK and PKC, which influences cell growth, proliferation, and survival, and regulates metabolism. Bayascas, J. R., *Cell Cycle*, 7, 2978-2982 (2008).

Cancer cells of common human tumor types, including breast, lung, gastric, prostate, haemotological and ovarian cancers, have gene mutations that result in abnormally high levels of PIP3. High levels of PIP3 cause overstimulation of PDK1 which result in constitutive activation the members of the AGC kinase family. As a consequence, tumor cell proliferation, reduced apoptosis and angiogenesis occur. In addition, cells lacking functioning PTEN, a lipid phosphatase that reduces cellular PIP3, are associated with a variety of human tumours including breast, prostate, endometrial cancers along with melanomas and glioblastomas. Steck et al., *Nat. Genetics*, 15, 356-362 (1997).

PDK1 function is critical to downstream signaling that results from activation of cells by growth factors because PKB/Akt, p70S6K, and RSK cannot be activated in cells lacking PDK1. Indeed, disrupting the PDK1 gene in mouse embryonic cells prevents activation of PKB/Akt, p70S6K, and RSK. Williams et al., *Current Biology* 10, 439-447 (2000). Additionally, in an in vivo model, reducing the expression of PDK1 protects mice from developing tumors under conditions where PIP3 is elevated due to the deletion of PTEN. Bayascas et al., *Current Biology* 15, 1839-1846 (2005). Thus, while not being bound by any specific theory, inhibiting PDK1 function is expected to mitigate tumor cell proliferation by abrogating cell signaling.

Accordingly, there exists a need in the art for small-molecule inhibitors of PDK1 that are useful for treating cancer and other disorders associated with aberrant PDK1 activity.

SUMMARY OF THE INVENTION

In one aspect, the present invention provides compounds of Formula (I) (herein referred to as the "Imidazole Carboxamide Compounds" or "compounds of Formula (I)") or pharmaceutically acceptable salts thereof:

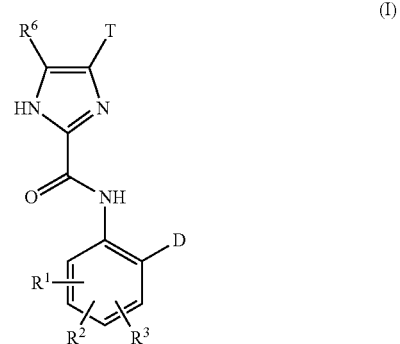

wherein:
T is $R^4$, H, halo, $C_1$-$C_6$ alkyl, ($C_2$-$C_3$ alkynylene)-($C_1$-$C_6$ alkyl), or ($C_2$-$C_3$ alkynylene)-cyclopropyl;
wherein $R^4$ is selected from the group consisting of:
(i) 5- to 10-membered mono- or bicyclic heteroaryl wherein said heteroaryl of $R^4$ contains one to three heteroatoms selected from the group consisting of nitrogen, oxygen, and sulfur;
(ii) 4- to 7-membered monocyclic heterocyclyl wherein said heterocyclyl of $R^4$ contains at least one ring nitrogen atom ring member, and optionally one additional heteroatom selected from the group consisting of nitrogen, oxygen, and sulfur;
(iii) 4- to 7-membered monocyclic heterocyclenyl wherein said heterocyclenyl of $R^4$ contains one heteroatom selected from the group consisting of nitrogen, oxygen, and sulfur;
(iv) phenyl;
(v) $C_3$-$C_7$ cycloalkyl; and
(vi) $C_3$-$C_7$ cycloalkenyl;
wherein said $R^4$ is unsubstituted or substituted by one to three moieties selected from the group consisting of $C_1$-$C_3$ alkyl, $C_1$-$C_3$ alkoxy, halo, $C_1$-$C_3$ fluoroalkyl, hydroxy, amino, $C_1$-$C_6$ alkylamino, $C_1$-$C_6$ dialkylamino, $C_1$-$C_6$ hydroxyalkyl, $C_1$-$C_6$ alkylamino, cyano, —C(O)—($C_1$-$C_6$ alkyl), —C(O)—O—($C_1$-$C_6$ alkyl), sulfonamido, —N(H)—C(O)—($C_1$-$C_6$ alkyl), benzylamino, —Y—$R^9$, and —C(O)—N($R^{11}$)$_2$;
Y is a bond, $C_1$-$C_3$ alkylene, —O—, —N(H)—, or —N(H)—($C_1$-$C_3$ alkylene), wherein said $C_1$-$C_3$ alkylene or —N(H)—($C_1$-$C_3$ alkylene) of Y is unsubstituted or substituted by $C_1$-$C_3$ hydroxyalkyl;

$R^9$ is
(i) phenyl;
(ii) 5- to 6-membered heteroaryl, wherein said heteroaryl of $R^9$ contains one to two heteroatoms selected from the group consisting of nitrogen, oxygen, and sulfur; or
(iii) $C_3$-$C_7$ cycloalkyl;
wherein said $R^9$ is unsubstituted or substituted by one to two $C_1$-$C_3$ alkyl, $C_1$-$C_3$ alkoxy, halo, or $C_1$-$C_3$ fluoroalkyl;
each $R^{11}$ is independently H, $C_1$-$C_6$ alkyl, —($C_1$-$C_3$ alkylene)-N($C_1$-$C_3$ alkyl)$_2$, —($C_1$-$C_3$ alkylene)-$R^B$, or optionally, the $R^{11}$ groups together with the nitrogen atom to which they are attached, form a 5- to 6-membered heterocyclyl containing one to two nitrogen atoms, which is heterocyclyl is optionally substituted by $C_1$-$C_3$ alkyl;
wherein $R^B$ is phenyl, pyridinyl, pyrimidinyl, pyrazinyl, or pyridazinyl, wherein said $R^B$ is unsubstituted or substituted by one to two $C_1$-$C_3$ alkyl, $C_1$-$C_3$ alkoxy, halo, or $C_1$-$C_3$ fluoroalkyl;

$R^6$ is H, $^2$H, $C_1$-$C_3$ alkyl, $C_1$-$C_3$ alkoxy, or halogen;

D is
(i) —($C_1$-$C_3$ dialkylamino)-($C_1$-$C_3$ alkoxy);
(ii) —C(O)—N(H)-heterocyclyl wherein said heterocyclyl moiety is a 5- to 6-membered ring containing one to two nitrogen atoms, and is unsubstituted or substituted by one to two $C_1$-$C_3$ alkyl, $C_1$-$C_3$ alkoxy, halo, or phenyl;
(iii) a group of the formula

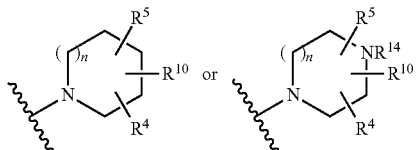

wherein
n is 0, 1, or 2;
$R^4$, $R^5$ and $R^{10}$ are independently H, $C_1$-$C_3$ alkyl, fluoro, hydroxy, amino, $C_1$-$C_3$ alkylamino, $C_1$-$C_3$ dialkylamino, ureido, azetidinyl, pyrrolidinyl, piperidino, pyrazolyl, —($C_1$-$C_3$)alkylene-OH, —M—N($R^7$)($R^8$), or —N($R^7$)—C(O)($R^8$);

M is
(i) a direct bond;
(ii) —C(O)—;
(iii) —($C_1$-$C_3$ alkylene)-C(O)—;
(iv) $C_1$-$C_3$ alkylene; or
(v) a ring of the formula E

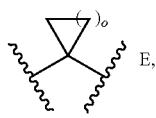

wherein o is 1, 2, 3, or 4;
wherein ring E or said alkylene of M is unsubstituted or substituted by one to two $C_1$-$C_3$ alkyl;

$R^7$ and $R^8$ are independently selected from the group consisting of H, $C_1$-$C_3$ alkyl, ($C_1$-$C_6$ alkylene)-NH$_2$, ($C_1$-$C_6$ alkylene)-N(H)($C_1$-$C_3$ alkyl), ($C_1$-$C_6$ alkylene)-N($C_1$-$C_3$ alkyl)$_2$, ($C_3$-$C_6$ cycloalkyl)-NH$_2$, ($C_1$-$C_3$ alkylene)-($C_3$-$C_6$ cycloalkyl)-NH$_2$, (3,3,3-trifluoro-2-hydroxy)propyl, and $C_1$-$C_3$ alkanoyl;
or optionally, wherein $R^4$, $R^5$, or $R^{10}$ is —M—N($R^7$)($R^8$), $R^7$ and $R^8$ together with the nitrogen atom to which it is attached form
(i) $R^C$, wherein $R^C$ is a 4- to 10-membered mono- or bicyclic heterocyclyl containing one nitrogen atom and one additional heteroatom selected from the group consisting of nitrogen, oxygen and sulfur, and wherein $R^C$ is unsubstituted or substituted by 1 to 4 $R^{15}$ moieties; or
(ii) $R^D$, wherein $R^D$ is a 4- to 10-membered mono- or bicyclic heterocyclyl containing one nitrogen atom and wherein $R^D$ is substituted by $R^{16}$, and wherein $R^D$ is optionally and additionally substituted by 1 to 3 $R^{15}$;
wherein each $R^{15}$ is independently selected from the group consisting of $C_1$-$C_3$ alkyl, fluoro, $C_1$-$C_3$ trifluoroalkyl, ($C_1$-$C_3$ alkylene)-OH, ($C_1$-$C_3$ alkylene)-NH$_2$, and ($C_1$-$C_3$ alkylene)-C(O)NH$_2$, or optionally two $R^{15}$ moieties together with the carbon atom to which they are attached form a carbonyl;
wherein $R^{16}$ is selected from the group consisting of ($C_1$-$C_3$ alkylene)-OH, ($C_1$-$C_3$ alkylene)-NH$_2$, and ($C_1$-$C_3$ alkylene)-C(O)NH$_2$;
or two of $R^4$, $R^5$ and $R^{10}$ together with the carbon atom(s) to which they are attached form a 5- or 6-membered cycloalkyl or heterocyclyl ring containing one to two heteroatoms selected from the group consisting of nitrogen, oxygen, and sulfur;

$R^{14}$ is H or $C_1$-$C_3$ alkyl;

$R^1$, $R^2$ and $R^3$ are independently selected from the group consisting of H, $^2$H, halo, $C_1$-$C_3$ alkyl, amino, $C_1$-$C_3$ alkylamino, $C_1$-$C_3$ dialkylamino, carbamyl, hydroxy, cyano, trifluoromethyl, $C_3$-$C_7$ cycloalkyl, and 5- to 6-membered heteroaryl containing one two heteroatoms selected from the group consisting of nitrogen, oxygen, and sulfur.

In another aspect, the invention provides a pharmaceutical composition comprising an Imidazole Carboxamide Compound, or a pharmaceutically acceptable salt thereof, and a pharmaceutically acceptable carrier.

In still another aspect, the invention provides an Imidazole Carboxamide Compound or a pharmaceutically acceptable salt thereof for use in therapy.

In another aspect, the invention provides an Imidazole Carboxamide Compound or a pharmaceutically acceptable salt thereof for use in treating a disease or disorder characterized by excessive or pathologically elevated cell growth. In some embodiments, the disease or disorder is cancer.

In yet another aspect, the invention provides a combination comprising an Imidazole Carboxamide Compound or a pharmaceutically acceptable salt thereof and an additional anticancer agent for simultaneous, separate or sequential use in treating cancer.

DETAILED DESCRIPTION OF THE INVENTION

The present invention provides Imidazole Carboxamide Compounds and pharmaceutical compositions comprising an Imidazole Carboxamide Compound. In addition, the present invention provides methods of using the Imidazole Carboxamide Compounds in treating a disease or disorder characterized by excessive or pathologically elevated cell growth, e.g., cancer, in a patient in need of such treatment.

DEFINITIONS

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl. The term "$C_1$-$C_6$ alkyl" refers to an alkyl group having from 1 to 6 carbon atoms.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene groups include methylene, ethylene and propylene. In one embodiment, an alkylene group has from 1 to 6 carbon atoms. In one embodiment, an alkylene is branched. In another embodiment, the alkylene is linear.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The "alkynyl" may be unsubstituted or optionally substituted by one or more substituents which may be the same or different, each substituent being independently selected from the group consisting of aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide (indicated herein as "N(O)"). "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In describing the heteroatoms contained in the heteroaryl group the expressions, "having one to x heteroatoms selected from the group of N, O, and S" or "having one to x heteroatoms selected from the group of N, N(O), O, and S" (wherein x is an a specified integer), for example, mean that each heteroatom in the specified heteroaryl is independently selected from the specified selection of heteroatoms.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which ring system contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. A non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred halogens are fluorine, chlorine and bromine.

"Fluoroalkyl" means an alkyl as defined above wherein one or more hydrogen atoms on the alkyl is replaced by a fluoro atom. Non-limiting examples of fluoroalkyl include trifluoromethyl and 2,2,2-trifluoroethyl.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$^1$Y$^2$, -alkyl-NY$^1$Y$^2$, —C(O)NY$^1$Y$^2$, —SO$_2$NY$^1$Y$^2$ and —S(O)NY$_1$Y$_2$, wherein Y$^1$ and Y$^2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such a moiety are methylenedioxy, ethylenedioxy, —C(CH$_3$)$_2$— and the like which form moieties such as, for example:

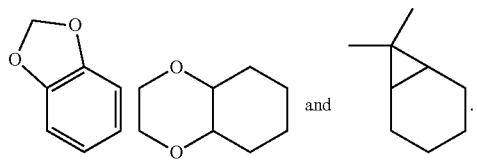

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example, nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom, respectively, is present as a ring atom. Any —NH in a heterocyclyl ring may exist in protected form such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

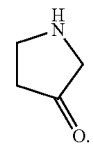

In describing the heteroatoms contained in a specified heterocyclyl group, the expression, "having one to x heteroatoms selected from the group of N, O, and S" (wherein x is an a specified integer), for example, means that each heteroatom in the specified heterocyclyl is independently selected from the specified selection of heteroatoms.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6- tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

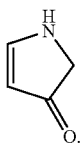

In describing the heteroatoms contained in a specified heterocyclenyl group, the expression, "having one to x heteroatoms selected from the group of N, O, and S" (wherein x is an a specified integer), for example, means that each heteroatom in the specified heterocyclenyl is independently selected from the specified selection of heteroatoms.

"Heterocyclenylalkyl" means a heterocyclenyl moiety as defined above linked via an alkyl moiety (defined above) to a parent core.

It should be noted that in heteroatom-containing ring systems of this invention, there are no hydroxyl groups on carbon atoms adjacent to a N, O or S, as well as there are no N or S groups on carbon adjacent to another heteroatom. Thus, for example, in the ring:

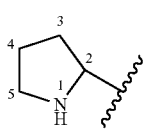

there is no —OH attached directly to carbons marked 2 and 5.

It should also be noted that tautomeric forms such as, for example, the moieties:

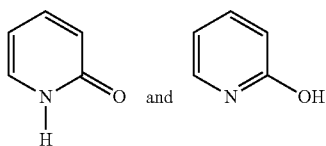 [SMILES: O=c1cccc[nH]1 ; Oc1ccccn1]

are considered equivalent in certain embodiments of this invention.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. A non-limiting example of a suitable aralkylthio group is benzylthio. The bond to the parent moiety is through the sulfur.

"Alkoxycarbonyl" means an alkyl-O—C(O)— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. A reference to a "stable compound' or "stable structure" means that the compound is sufficiently robust to survive isolation to a useful degree of purity from a reaction mixture, and to survive formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g., from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterized by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. In addition, any one or more of these hydrogen atoms can be deuterium.

It should also be noted that in case of a discrepancy between the chemical name and structural formula for a specified compound, the description provided by the structural formula will be controlling.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl,
—C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$ alkyl, carboxy $(C_1-C_6)$alkyl, amino$(C_1-C_4)$alkyl or mono-N— or di-N,N—$(C_1-C_6)$alkylaminoalkyl, —C(Y$^4$)$_{y5}$ wherein Y$^4$ is H or methyl and Y$^5$ is mono-N— or di-N, N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

"PDK1" is meant to refer to wild type PDK1.

"PDK1 variant" or "variant of PDK1" is meant to refer to PDK1 having at least one point mutation, insertion, or deletion.

The compounds of Formula (I) can form salts which are also within the scope of this invention. Reference to a compound of Formula (I) or an Imidazole Carboxamide Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

The compounds of Formula (I), and salts thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, 36Cl and $^{123}$I, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Further, substitution of compounds with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution of a compound at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula (I), and of the salts, of the compounds of Formula (I), are intended to be included in the present invention.

The present invention further includes the compounds of Formula (I) in all their isolated forms. For example, the above-identified compounds are intended to encompass all forms of the compounds such as, any solvates, hydrates, stereoisomers, and tautomers thereof.

The compounds according to the invention have pharmacological properties; in particular, the compounds of Formula (I) can be inhibitors of PDK-1.

Compounds of Formula (I)

The present invention provides Imidazole Carboxamide Compounds having the Formula (I), or pharmaceutically acceptable salts thereof, wherein D, T, R$^1$, R$^2$, R$^3$, and R$^6$ are as defined above for the compound of Formula (I). The compounds of Formulas (Ia) and (Ib), as are described in detail below, are embodiments of the compound of Formula (I).

In some embodiments of the compound of Formula (I), R$^6$ is H. In other embodiments, R$^6$ is $^2$H.

In certain embodiments of the compound of Formula (I), D is selected from the group consisting of:

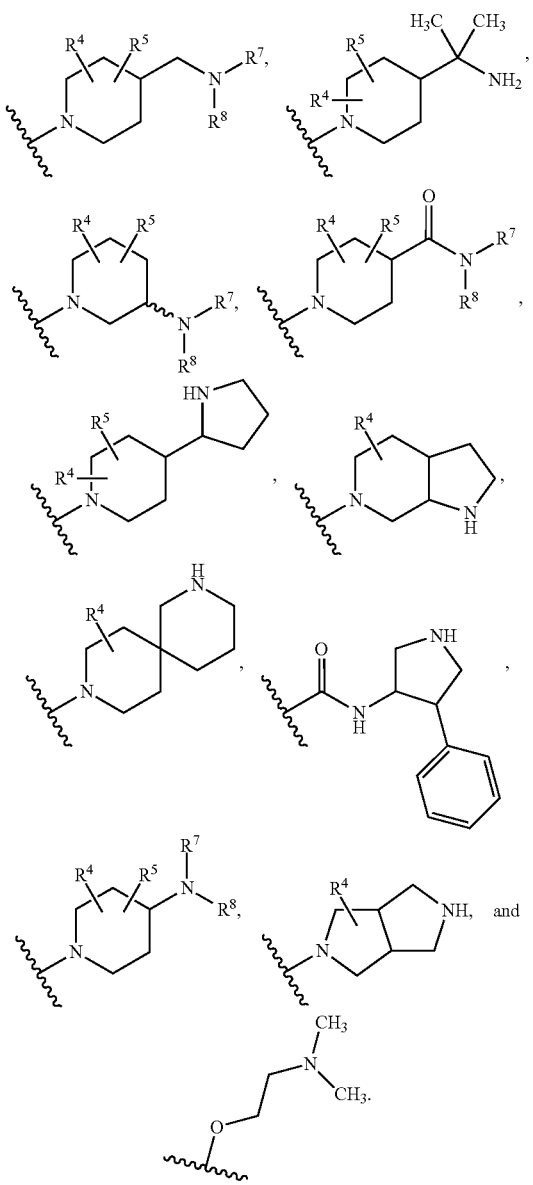

In some embodiments of the compound of Formula (I), D is

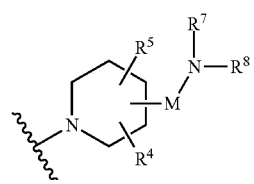

wherein
M is a direct bond, —C(O)—, or methylene;
R$^4$ and R$^5$ are independently selected from the group consisting of H, C$_1$-C$_3$ alkyl, and fluoro, and
R$^7$ and R$^8$ are independently selected from the group consisting of H, C$_1$-C$_3$ alkyl, —CH$_2$CH$_2$NH$_2$, —CH$_2$CH$_2$NHCH$_2$CH$_3$, —CH$_2$CH$_2$CH$_2$CH$_2$NHCH$_3$, cyclohexylamino, or optionally R[7] and R[8] together with the nitrogen atom to which it is attached form:
- (i) R[C], wherein R[C] is a 4- to 10-membered mono- or bicyclic heterocyclyl containing one nitrogen atom and one additional heteroatom selected from the group consisting of nitrogen, oxygen and sulfur, and wherein R[C] is unsubstituted or substituted by 1 to 4 R[15] moieties; or
- (ii) R[D], wherein R[D] is a 4- to 10-membered mono- or bicyclic heterocyclyl containing one nitrogen atom and wherein R[D] is substituted by R[16], and wherein R[D] is optionally and additionally substituted by 1 to 3 R[15];

wherein each R[15] is independently selected from the group consisting of $C_1$-$C_3$ alkyl, fluoro, $C_1$-$C_3$ trifluoroalkyl, ($C_1$-$C_3$ alkylene)-OH, ($C_1$-$C_3$ alkylene)-NH$_2$, and ($C_1$-$C_3$ alkylene)-C(O)NH$_2$, or optionally two R[15] moieties together with the carbon atom to which they are attached form a carbonyl;

wherein R[16] is selected from the group consisting of ($C_1$-$C_3$ alkylene)-OH, ($C_1$-$C_3$ alkylene)-NH$_2$, and ($C_1$-$C_3$ alkylene)-C(O)NH$_2$.

In a specific embodiment, wherein D is

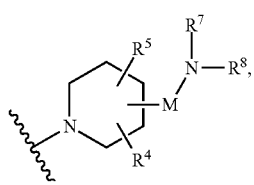

and R[4], R[5], R[7], and R[8] are as described above, M is —C(O)—.

In some embodiments of the compound of Formula (I), T is selected from the group consisting of H, and Br; and R[A], wherein R[A] is selected from the group consisting of cyclopropyl, phenyl, pyrazolyl, thienyl, pyridinyl, pyrimidinyl, pyridazinyl, indolyl, piperidinyl, piperazinyl, and dihydropyranyl, wherein R[A] is unsubstituted or substituted by one to three moieties selected from the group consisting of $C_1$-$C_3$ alkyl, $C_1$-$C_3$ alkoxy, halo, trifluoromethyl, hydroxy, amino, $C_1$-$C_6$ alkylamino, $C_1$-$C_6$ dialkylamino, $C_1$-$C_6$ hydroxyalkyl, cyano, —C(O)—($C_1$-$C_6$ alkyl), —C(O)—O—($C_1$-$C_6$ alkyl), sulfonamido, —N(H)—C(O)—($C_1$-$C_6$ alkyl), benzylamino, —Y—R[9], and —C(O)N(R[11])$_2$.

In specific embodiments of the compound of Formula (I), T is selected from the group consisting of H, Br; and R[A], wherein R[A] is selected from the group consisting of phenyl, pyrazolyl, thienyl, pyridinyl, pyrimidinyl, indolyl, and dihydropyranyl, wherein said cyclic moiety of T is unsubstituted or substituted by 1 to 2 moieties selected from the group consisting of methyl, ethyl, fluoro, chloro, methoxy, cyclopropyl, amino, methylamino, dimethylamino, cyclopropylamino, benzylamino, cyano, hydroxymethyl, 2-hydroxyethyl, sulfonamido, acetamido, acetyl, trifluoromethyl, pyrazolyl, benzyl, thienylmethyl, and pyridinylmethyl.

In specific embodiments of the compound of Formula (I), T is selected from the group consisting of:

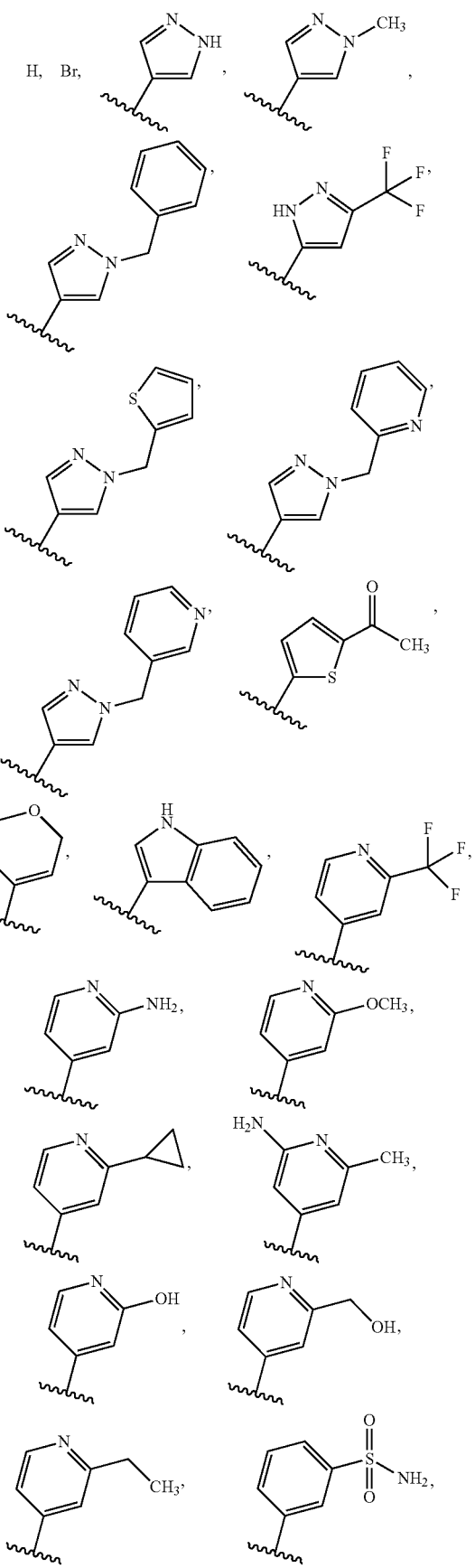

-continued
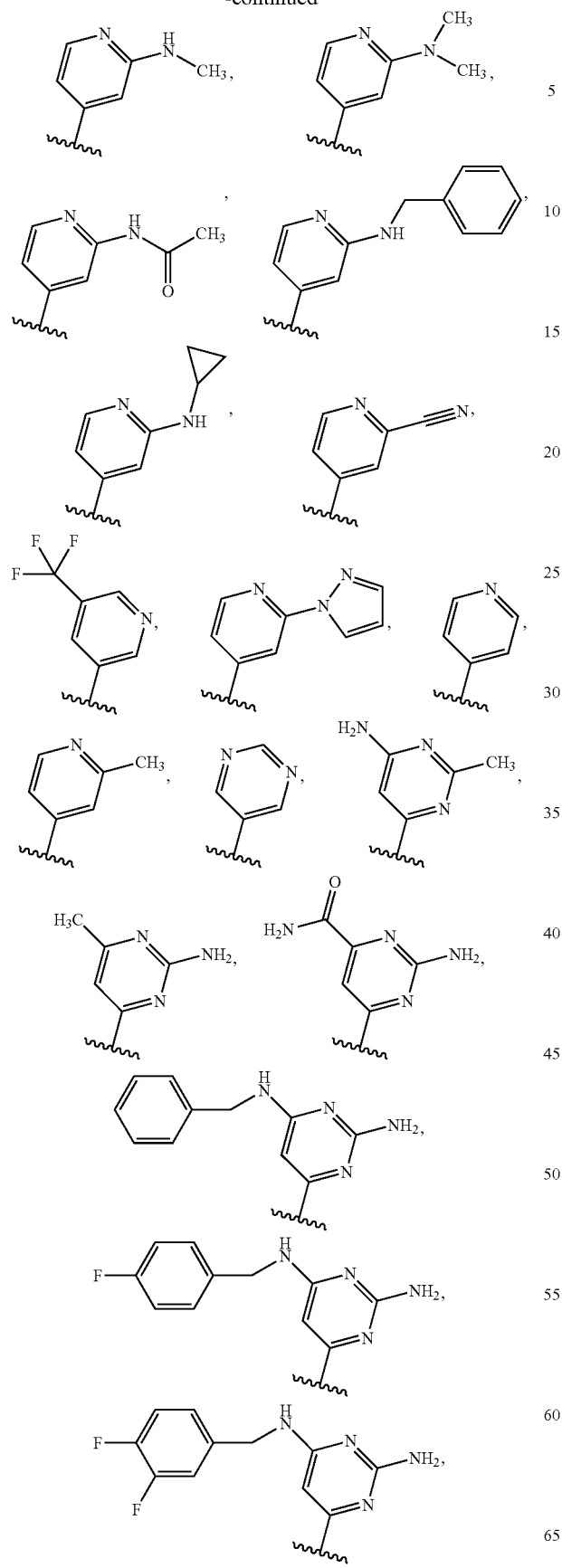
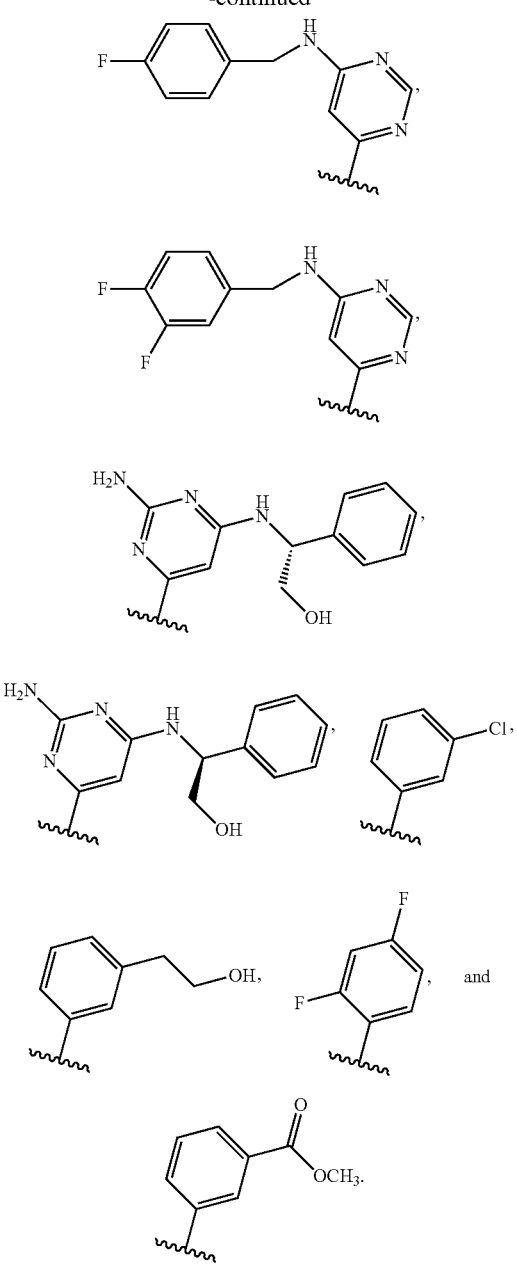
In specific embodiments of the compound of Formula (I), T is selected from the group consisting of:
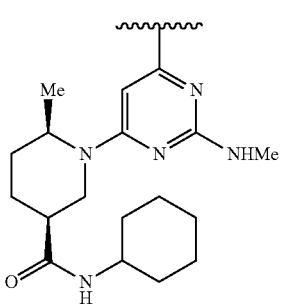

-continued

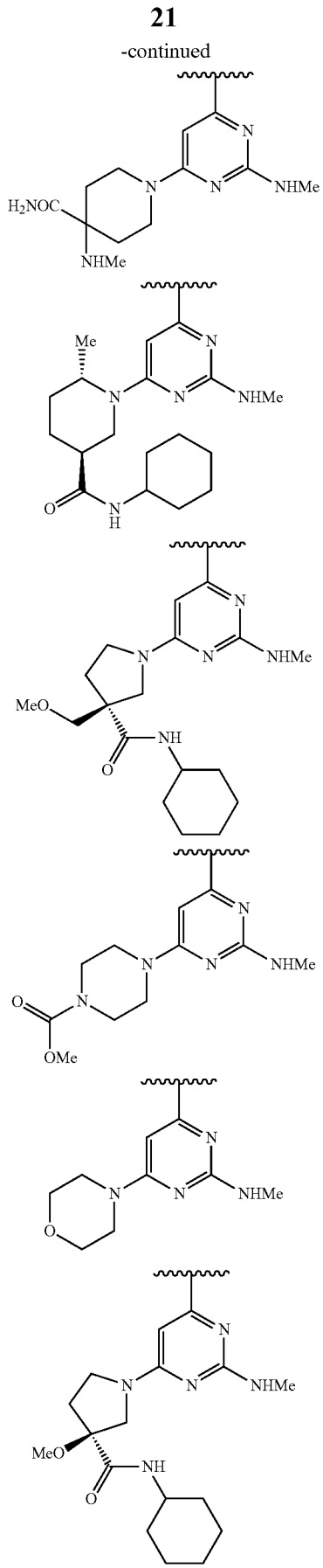

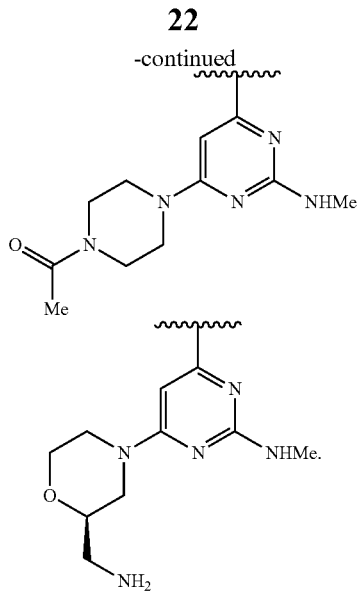

In certain embodiments of the compound of Formula (I):

T is $R^A$, wherein $R^A$ is selected from the group consisting of substituted or unsubstituted cyclopropyl, phenyl, pyrazolyl, pyridinyl, pyrimidinyl, indolyl, piperidinyl, piperazinyl, and dihydropyranyl, wherein $R^A$ is unsubstituted or substituted by one to three moieties selected from the group consisting of $C_1$-$C_3$ alkyl, $C_1$-$C_3$ alkoxy, halo, trifluoromethyl, hydroxy, amino, $C_1$-$C_6$ alkylamino, $C_1$-$C_6$ dialkylamino, $C_1$-$C_6$ hydroxyalkyl, sulfonamido, —N(H)—C(O)—($C_1$-$C_3$ alkyl), benzylamino, —Y—$R^9$, and —C(O)N($R^{11}$)$_2$;

D is

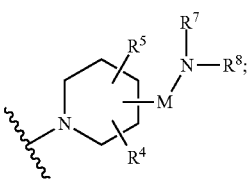

M is a direct bond, —C(O)—, or methylene;

$R^4$ and $R^5$ are independently selected from the group consisting of H, $C_1$-$C_3$ alkyl, and fluoro;

$R^7$ and $R^8$ are independently selected from the group consisting of H, $C_1$-$C_3$ alkyl, —CH$_2$CH$_2$NH$_2$, —CH$_2$CH$_2$NHCH$_2$CH$_3$, —CH$_2$CH$_2$CH$_2$CH$_2$NHCH$_3$, cyclohexylamino, or optionally $R^7$ and $R^8$ together with the nitrogen atom to which it is attached form:

(i) $R^C$, wherein $R^C$ is a 4- to 10-membered mono- or bicyclic heterocyclyl containing one nitrogen atom and one additional heteroatom selected from the group consisting of nitrogen, oxygen and sulfur, and wherein $R^C$ is unsubstituted or substituted by 1 to 4 $R^{15}$ moieties; or (ii) $R^D$, wherein $R^D$ is a 4- to 10-membered mono- or bicyclic heterocyclyl containing one nitrogen atom and wherein $R^D$ is substituted by $R^{16}$, and wherein $R^D$ is optionally and additionally substituted by 1 to 3 $R^{15}$;

wherein each $R^{15}$ is independently selected from the group consisting of $C_1$-$C_3$ alkyl, fluoro, $C_1$-$C_3$ trifluoroalkyl, (C₁-C₃ alkylene)-OH, (C₁-C₃ alkylene)-NH₂, and (C₁-C₃ alkylene)-C(O)NH₂, or optionally two R¹⁵ moieties together with the carbon atom to which they are attached form a carbonyl;

wherein R¹⁶ is selected from the group consisting of (C₁-C₃ alkylene)-OH, (C₁-C₃ alkylene)-NH₂, and (C₁-C₃ alkylene)-C(O)NH₂;

R⁶ is H; and

R¹, R², and R³ are independently selected from the group consisting of H, fluoro, and pyrazolyl.

In certain embodiments of the compound of Formula (I):

T is:

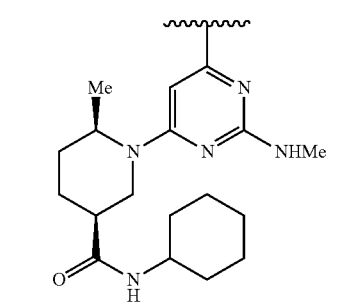

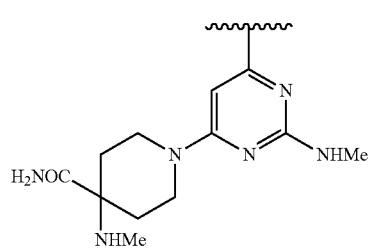

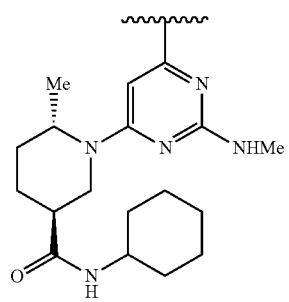

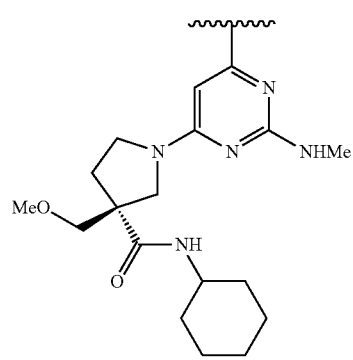

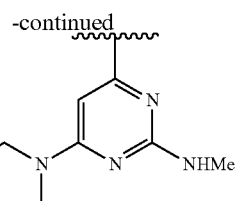

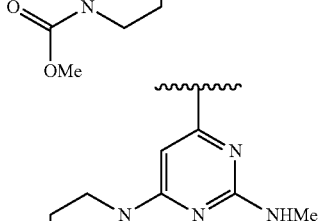

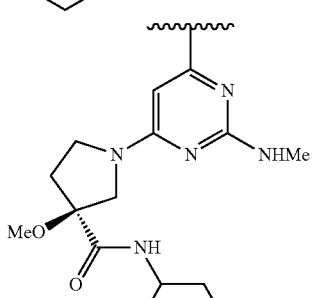

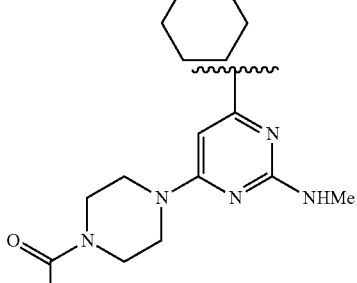

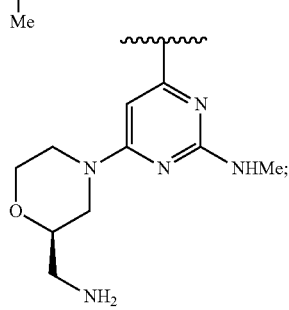

D is

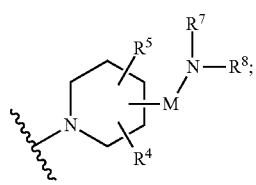

M is a direct bond, —C(O)—, or methylene;

R⁴ and R⁵ are independently selected from the group consisting of H, C₁-C₃ alkyl, and fluoro;

$R^7$ and $R^8$ are independently selected from the group consisting of H, $C_1$-$C_3$ alkyl, —$CH_2CH_2NH_2$, —$CH_2CH_2NHCH_2CH_3$, —$CH_2CH_2CH_2CH_2NHCH_3$, cyclohexylamino, or optionally $R^7$ and $R^8$ together with the nitrogen atom to which it is attached form:
(i) $R^C$, wherein $R^C$ is a 4- to 10-membered mono- or bicyclic heterocyclyl containing one nitrogen atom and one additional heteroatom selected from the group consisting of nitrogen, oxygen and sulfur, and wherein $R^C$ is unsubstituted or substituted by 1 to 4 $R^{15}$ moieties; or
(ii) $R^D$, wherein $R^D$ is a 4- to 10-membered mono- or bicyclic heterocyclyl containing one nitrogen atom and wherein $R^D$ is substituted by $R^{16}$, and wherein $R^D$ is optionally and additionally substituted by 1 to 3 $R^{15}$;
wherein each $R^{15}$ is independently selected from the group consisting of $C_1$-$C_3$ alkyl, fluoro, $C_1$-$C_3$ trifluoroalkyl, ($C_1$-$C_3$ alkylene)-OH, ($C_1$-$C_3$ alkylene)-$NH_2$, and ($C_1$-$C_3$ alkylene)-C(O)$NH_2$, or optionally two $R^{15}$ moieties together with the carbon atom to which they are attached form a carbonyl;
wherein $R^{16}$ is selected from the group consisting of ($C_1$-$C_3$ alkylene)-OH, ($C_1$-$C_3$ alkylene)-$NH_2$, and ($C_1$-$C_3$ alkylene)-C(O)$NH_2$;
$R^6$ is H; and
$R^1$, $R^2$, and $R^3$ are independently selected from the group consisting of H, fluoro, and pyrazolyl.

In specific embodiments of the compound of Formula (I), $R^1$, $R^2$, and $R^3$ are independently selected from the group consisting of H, halo, and pyrazolyl.

In another aspect, the compound of Formula (I) has the Formula (Ia):

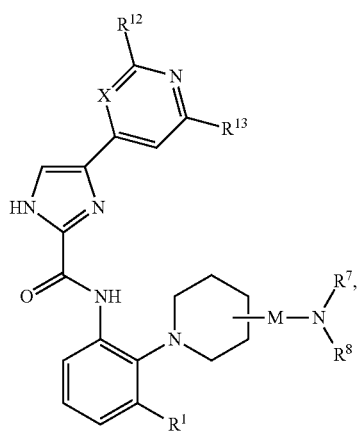

(Ia)

wherein
X is CH or N;
$R^{12}$ and $R^{13}$ are independently selected from the group consisting of H, $C_1$-$C_3$ alkyl, amino, $C_1$-$C_3$ alkylamino, and hydroxymethyl;
$R^1$ is H or halo;
M is a direct bond or methylene; and
$R^7$ and $R^8$ are independently H or $C_1$-$C_3$ alkyl.

In another aspect, the compound of Formula (I) has the Formula (Ia):

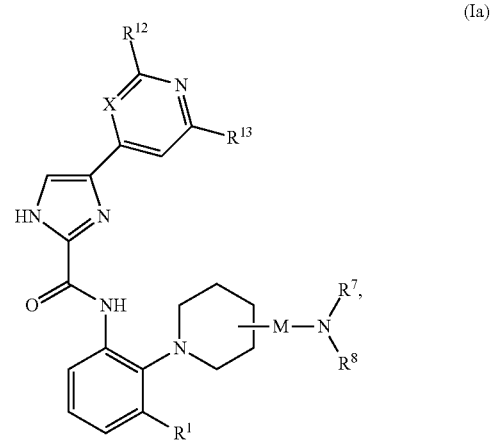

(Ia)

wherein

X is CH or N;
$R^{12}$ is $C_1$-$C_3$ alkylamino;
$R^{13}$ is a 4- to 7-membered monocyclic heterocyclyl wherein said heterocyclyl contains at least one ring nitrogen atom ring member, and optionally one additional heteroatom selected from the group consisting of nitrogen, oxygen, and sulfur; wherein said monocyclic heterocyclyl is unsubstituted or substituted by one to three moieties selected from the group consisting of $C_1$-$C_3$ alkyl, $C_1$-$C_3$ alkoxy, halo, $C_1$-$C_3$ fluoroalkyl, hydroxy, amino, $C_1$-$C_6$ alkylamino, $C_1$-$C_6$ dialkylamino, $C_1$-$C_6$ hydroxyalkyl, $C_1$-$C_6$ alkylamino, cyano, —C(O)—($C_1$-$C_6$ alkyl), —C(O)—O—($C_1$-$C_6$ alkyl), sulfonamido, —N(H)—C(O)—($C_1$-$C_6$ alkyl), benzylamino, —Y—$R^9$, and —C(O)—N($R^{11}$)$_2$;
Y is a bond, $C_1$-$C_3$ alkylene, —O—, —N(H)—, or —N(H)—($C_1$-$C_3$ alkylene), wherein said $C_1$-$C_3$ alkylene or —N(H)—($C_1$-$C_3$ alkylene) of Y is unsubstituted or substituted by $C_1$-$C_3$ hydroxyalkyl;
$R^9$ is
(i) phenyl;
(ii) 5- to 6-membered heteroaryl, wherein said heteroaryl of $R^9$ contains one to two heteroatoms selected from the group consisting of nitrogen, oxygen, and sulfur; or
(iii) $C_3$-$C_7$ cycloalkyl;
wherein said $R^9$ is unsubstituted or substituted by one to two $C_1$-$C_3$ alkyl, $C_1$-$C_3$ alkoxy, halo, or $C_1$-$C_3$ fluoroalkyl;
each $R^{11}$ is independently H, $C_1$-$C_6$ alkyl, ($C_3$-$C_7$) cycloalkyl, ($C_6$-$C_{10}$) aryl, —($C_1$-$C_3$ alkylene)-N($C_1$-$C_3$ alkyl)$_2$, —($C_1$-$C_3$ alkylene)-$R^B$, or optionally, the $R^{11}$ groups together with the nitrogen atom to which they are attached, form a 5- to 6-membered heterocyclyl containing one to two nitrogen atoms, which is heterocyclyl is optionally substituted by $C_1$-$C_3$ alkyl;
wherein $R^B$ is phenyl, pyridinyl, pyrimidinyl, pyrazinyl, or pyridazinyl, wherein said $R^B$ is unsubstituted or substituted by one to two $C_1$-$C_3$ alkyl, $C_1$-$C_3$ alkoxy, halo, or $C_1$-$C_3$ fluoroalkyl;
$R^1$ is H or halo;
M is a direct bond or methylene; and
$R^7$ and $R^8$ are independently H or $C_1$-$C_3$ alkyl.

In specific embodiments of the compound of Formula (Ia), $R^1$ is fluoro.

In certain embodiments of the compound of Formula (Ia), the moiety

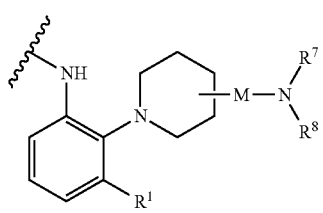
is selected from the group consisting of
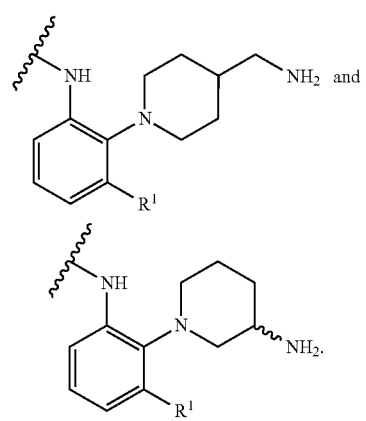
In specific embodiments of the compound of Formula (Ia), the moiety
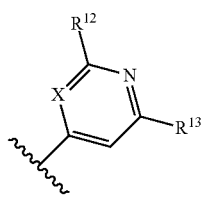
is selected from the group consisting of
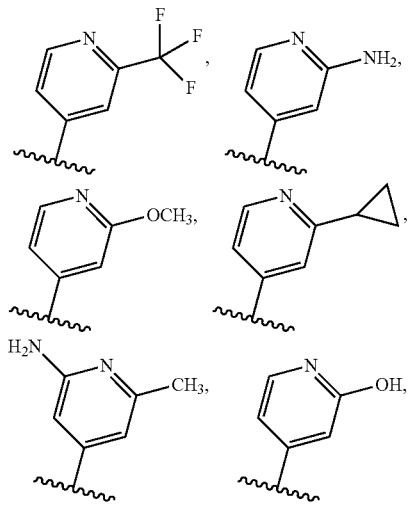
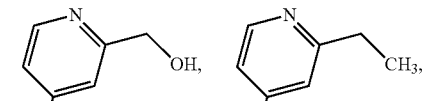
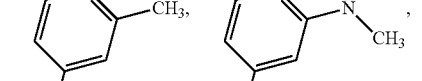
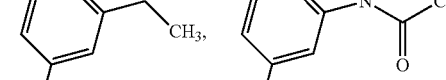
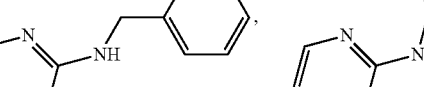
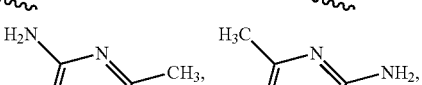
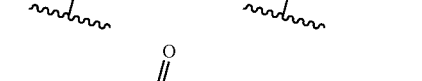
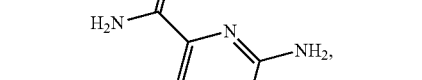
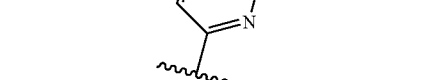
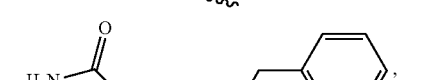
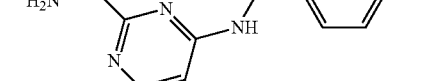
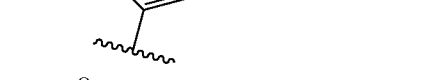
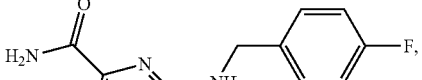
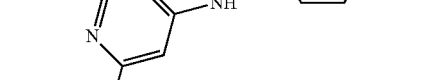
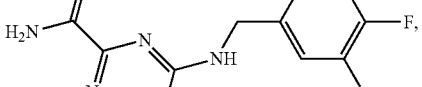

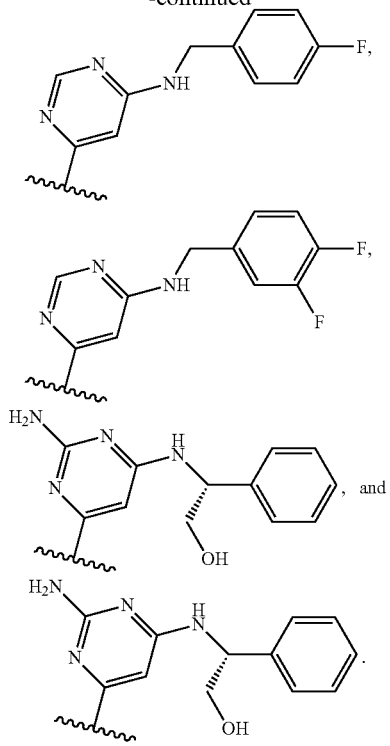
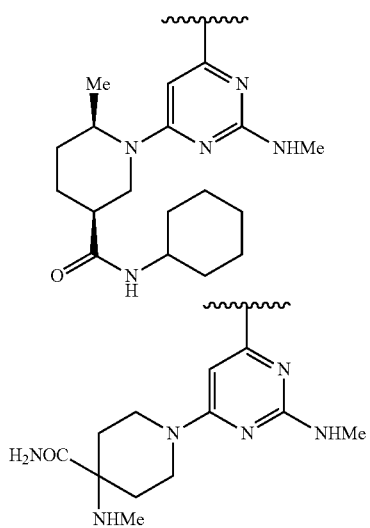
In specific embodiments of the compound of Formula (Ia), the moiety
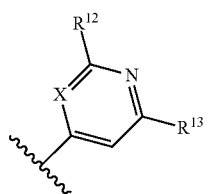
is selected from the group consisting of
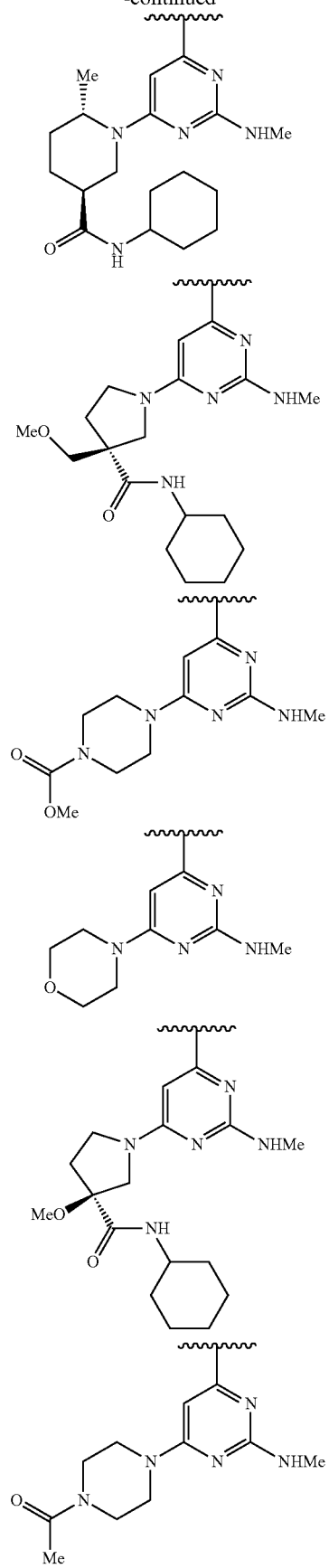

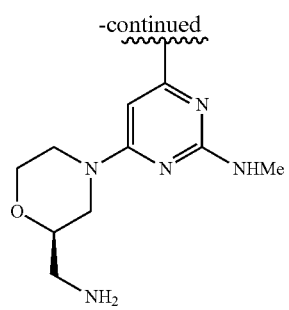

In still another aspect, the compound of Formula (I) has the Formula (Ib):

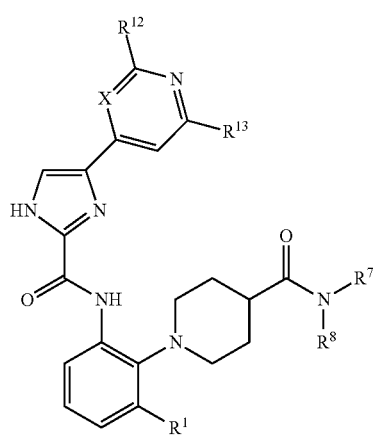

(Ib)

wherein:
X is CH or N;
$R^{12}$ and $R^{13}$ are independently selected from the group consisting of H, $C_1$-$C_3$ alkyl, amino, $C_1$-$C_3$ alkylamino, carbamyl, hydroxymethyl, benzylamino, 4-fluorobenzylamino, 3,4-difluorobenzylamino, 4-trifluorobenzylamino, 3,4-dimethoxybenzylamino, and 2-hydroxy-1-phenylethylamino;
$R^1$ is H or halo;
$R^7$ and $R^8$ are independently H, $C_1$-$C_3$ alkyl, ($C_1$-$C_6$ alkylene)-$NH_2$, ($C_1$-$C_6$ alkylene)-N(H)($C_1$-$C_3$ alkyl), ($C_1$-$C_6$ alkylene)-N($C_1$-$C_3$ alkyl)$_2$, ($C_3$-$C_6$ cycloalkyl)-$NH_2$, ($C_1$-$C_3$ alkylene)-($C_3$-$C_6$ cycloalkyl)-$NH_2$,
or, optionally, $R^7$ and $R^8$ together with the nitrogen atom to which it is attached form
(i) $R^C$, wherein $R^C$ is a 4- to 10-membered mono- or bicyclic heterocyclyl containing one nitrogen atom and one additional heteroatom selected from the group consisting of nitrogen, oxygen and sulfur, and wherein $R^C$ is unsubstituted or substituted by 1 to 2 $R^{15}$ moieties; or
(ii) $R^D$, wherein $R^D$ is a 4- to 10-membered mono- or bicyclic heterocyclyl containing one nitrogen atom and wherein $R^D$ is substituted by $R^{16}$, and wherein $R^D$ is optionally and additionally substituted by 1 to 2 $R^{15}$ moieties;
wherein each $R^{15}$ is independently selected from the group consisting of $C_1$-$C_3$ alkyl, fluoro, $C_1$-$C_3$ trifluoroalkyl, ($C_1$-$C_3$ alkylene)-OH, ($C_1$-$C_3$ alkylene)-$NH_2$, and ($C_1$-$C_3$ alkylene)-C(O)$NH_2$; and
wherein $R^{16}$ is selected from the group consisting of ($C_1$-$C_3$ alkylene)-OH, ($C_1$-$C_3$ alkylene)-$NH_2$, and ($C_1$-$C_3$ alkylene)-C(O)$NH_2$.

In some embodiments of the compound of Formula (Ib), the group

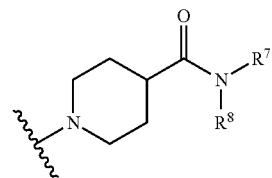

is selected from one of the following moieties:

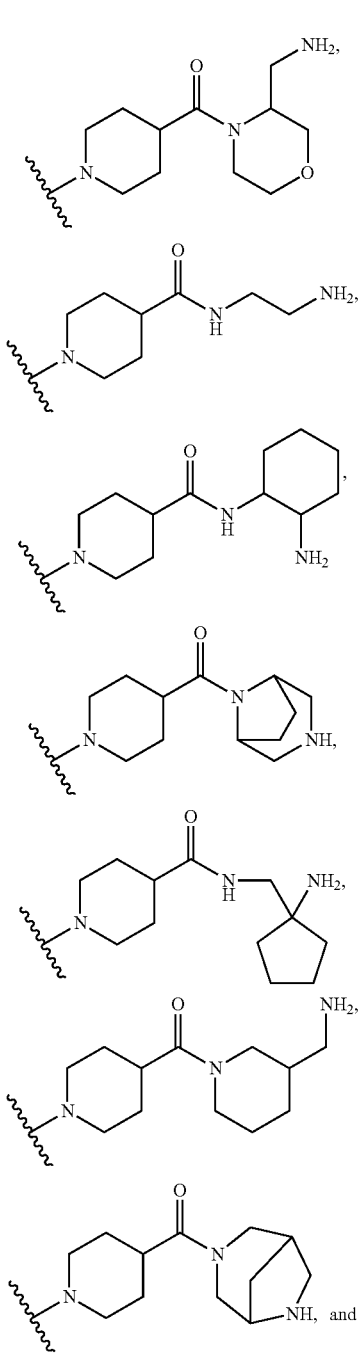

-continued
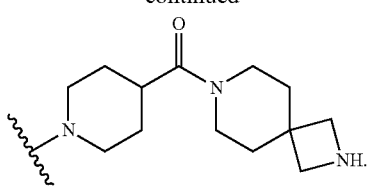
In other embodiments of the compounds of Formula (Ib):
X is CH,
$R^{12}$ is H;
$R^{13}$ is $CH_3$; and
the group
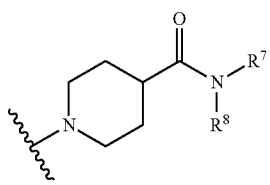
is selected from one of the following moieties:
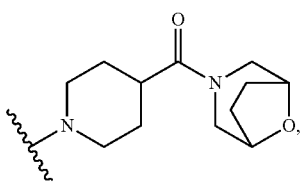
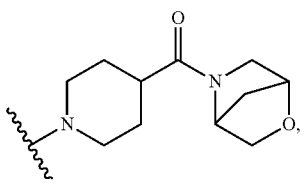
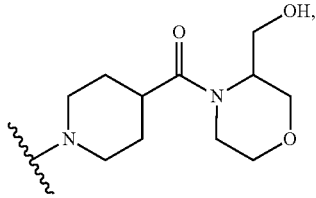
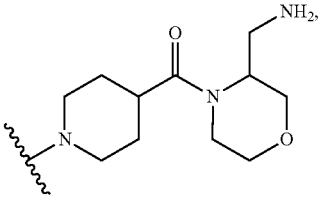
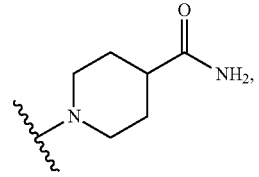
-continued
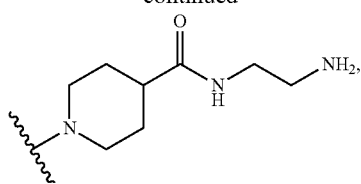
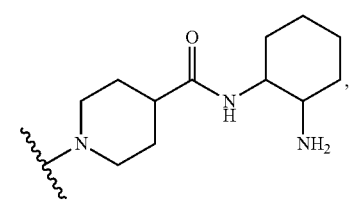
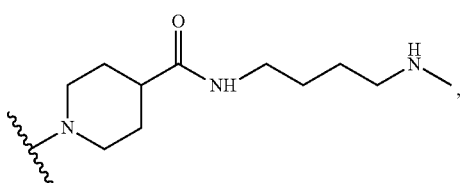
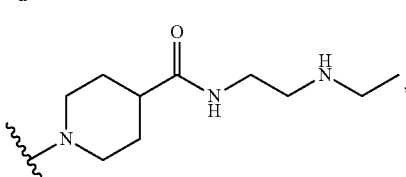
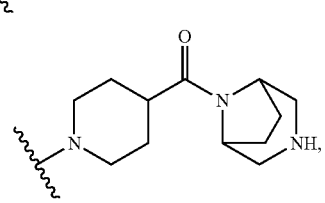
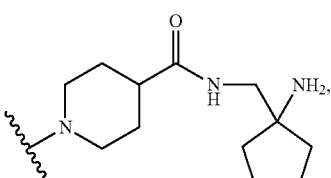
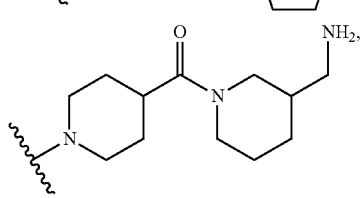
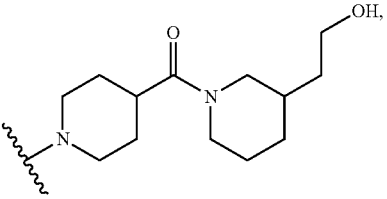
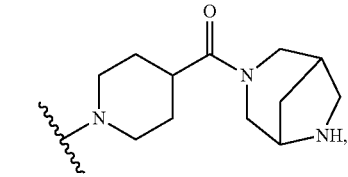

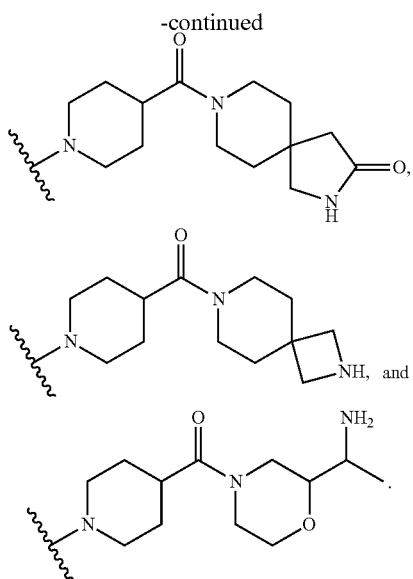

The invention provides also provides compounds I-96 as set forth below, and pharmaceutically acceptable salts thereof:

N-[5-amino-2-(3(R)-amino-1-piperidinyl)phenyl]-1H-imidazole-2-carboxamide (1);
1-[4-amino-2-[(1H-imidazol-2-ylcarbonyl)amino]phenyl]-4-(methylamino)-4-piperidinecarboxamide (2);
N-[5-amino-2-[4-(aminomethyl)-1-piperidinyl]phenyl]-1H-imidazole-2-carboxamide (3);
N-[2-(3(R)-amino-1-piperidinyl)-3-fluorophenyl]-4-[1-(phenylmethyl)-1H-pyrazol-4-yl]-1H-imidazole-2-carboxamide (4);
N-[2-(3(R)-amino-1-piperidinyl)-3-fluorophenyl]-4-[1-(2-thienylmethyl)-1H-pyrazol-4-yl]-1H-imidazole-2-carboxamide (5);
N-[2-[2-(dimethylamino)ethoxy]phenyl]-4-[1-(phenylmethyl)-1H-pyrazol-4-yl]-1H-imidazole-2-carboxamide (6);
N-[2-(3(R)-amino-1-piperidinyl)-3-fluorophenyl]-4-[1-(2-pyridinylmethyl)-1H-pyrazol-4-yl]-1H-imidazole-2-carboxamide (7);
N-[2-(3(R)-amino-1-piperidinyl)-3-fluorophenyl]-4-(2-methyl-4-pyridinyl)-1H-imidazole-2-carboxamide (8);
N-[2-(3(R)-amino-1-piperidinyl)-3-fluorophenyl]-4-[5-(trifluoromethyl)-3-pyridinyl]-1H-imidazole-2-carboxamide (9);
N-[2-(3(R)-amino-1-piperidinyl)-3-fluorophenyl]-4-(4-pyridinyl)-1H-imidazole-2-carboxamide (10);
N-[2-(3(R)-amino-1-piperidinyl)-3-fluorophenyl]-4-(1H-pyrazol-4-yl)-1H-imidazole-2-carboxamide (11);
N-[2-(3(R)-amino-1-piperidinyl)-3-fluorophenyl]-4-bromo-1H-imidazole-2-carboxamide (12);
N-[2-(3(R)-amino-1-piperidinyl)-3-fluorophenyl]-4-[1-(3-pyridinylmethyl)-1H-pyrazol-4-yl]-1H-imidazole-2-carboxamide (13);
N-[2-(3(R)-amino-1-piperidinyl)-3-fluorophenyl]-4-(1-methyl-1H-pyrazol-4-yl)-1H-imidazole-2-carboxamide (14);
N-[2-[3(R)-[(aminocarbonyl)amino]-1-piperidinyl]-3-fluorophenyl]-4-bromo-1H-imidazole-2-carboxamide (15);
N-[5-amino-2-(3(R)-amino-1-piperidinyl)phenyl]-4-bromo-1H-imidazole-2-carboxamide (16);
N-[2-[2-(dimethylamino)ethoxy]phenyl]-4-(1H-indol-3-yl)-1H-imidazole-2-carboxamide (17);
N-[2-[4-(aminomethyl)-1-piperidinyl]-3-fluorophenyl]-4-(2-methyl-4-pyridinyl)-1H-imidazole-2-carboxamide (18);
N-[2-(3(R)-amino-1-piperidinyl)-3-fluorophenyl]-4-[2-(trifluoromethyl)-4-pyridinyl]-1H-imidazole-2-carboxamide (19);
N-[2-(-3(R)-amino-1-piperidinyl)-3-fluorophenyl]-4-(2-amino-4-pyridinyl)-1H-imidazole-2-carboxamide (20);
N-[2-(3(R)-amino-1-piperidinyl)-3-fluorophenyl]-4-(2-methoxy-4-pyridinyl)-1H-imidazole-2-carboxamide (21);
N-[2-(3(R)-amino-1-piperidinyl)-3-fluorophenyl]-4-(3,6-dihydro-2h-pyran-4-yl)-1H-imidazole-2-carboxamide (22);
N-[2-(3(R)-amino-1-piperidinyl)-3-fluorophenyl]-4-(2-cyclopropyl-4-pyridinyl)-1H-imidazole-2-carboxamide (23);
4-(2-amino-6-methyl-4-pyridinyl)-N-[2-(3(R)-amino-1-piperidinyl)-3-fluorophenyl]-1H-imidazole-2-carboxamide (24);
N-[2-(3(R)-amino-1-piperidinyl)-3-fluorophenyl]-4-(2-hydroxy-4-pyridinyl)-1H-imidazole-2-carboxamide (25);
N-[2-(3(R)-amino-1-piperidinyl)-3-fluorophenyl]-4-[2-(hydroxymethyl)-4-pyridinyl]-1H-imidazole-2-carboxamide (26);
N-[2-[4-(aminomethyl)-1-piperidinyl]-3-fluorophenyl]-4-(2-amino-4-pyridinyl)-1H-imidazole-2-carboxamide (27);
N-[2-[4-(aminomethyl)-1-piperidinyl]-3,4-difluorophenyl]-4-(2-amino-4-pyridinyl)-1H-imidazole-2-carboxamide (28);
4-(2-amino-6-methyl-4-pyrimidinyl)-N-[2-(3(R)-amino-1-piperidinyl)-3-fluorophenyl]-1H-imidazole-2-carboxamide (29);
N-[2-[4-(aminomethyl)-1-piperidinyl]-3-fluorophenyl]-4-(2-ethyl-4-pyridinyl)-1H-imidazole-2-carboxamide (30);
N-[2-[4-(aminomethyl)-1-piperidinyl]-3-fluorophenyl]-4-[3-(aminosulfonyl)phenyl]-1H-imidazole-2-carboxamide (31);
N-[2-[4-(aminomethyl)-1-piperidinyl]-3-fluorophenyl]-4-[2-(methylamino)-4-pyridinyl]-1H-imidazole-2-carboxamide (32);
4-[2-(acetylamino)-4-pyridinyl]-N-[2-[4-(aminomethyl)-1-piperidinyl]-3-fluorophenyl]-1H-imidazole-2-carboxamide (33);
N-[2-[4-(aminomethyl)-1-piperidinyl]-3-fluorophenyl]-4-(3-chlorophenyl)-1H-imidazole-2-carboxamide (34);
N-[2-[4-(aminomethyl)-1-piperidinyl]-3-fluorophenyl]-4-[2-[(phenylmethyl)amino]-4-pyridinyl]-1H-imidazole-2-carboxamide (35);
N-[2-[4-(aminomethyl)-1-piperidinyl]-3-fluorophenyl]-4-[2-(dimethylamino)-4-pyridinyl]-1H-imidazole-2-carboxamide (36);
N-[2-[4-(aminomethyl)-1-piperidinyl]-3-fluorophenyl]-4-(2,5-dimethylphenyl)-1H-imidazole-2-carboxamide (37);
N-[2-(3(R)-amino-1-piperidinyl)-3-fluorophenyl]-4-(2,4-difluorophenyl)-1H-imidazole-2-carboxamide (38);
N-[2-(3(R)-amino-1-piperidinyl)-3-fluorophenyl]-4-[2-(1H-pyrazol-1-yl)-4-pyridinyl]-1H-imidazole-2-carboxamide (39);

4-(2-amino-4-pyridinyl)-N-[2-[4-[(dimethylamino)methyl]-1-piperidinyl]phenyl]-1H-imidazole-2-carboxamide (40);

N-[2-[4-(aminomethyl)-1-piperidinyl]-3-fluorophenyl]-4-[3-(2-hydroxyethyl)phenyl]-1H-imidazole-2-carboxamide (41);

N-[2-[4-(aminomethyl)-1-piperidinyl]-3-fluorophenyl]-4-[2-(cyclopropylamino)-4-pyridinyl]-1H-imidazole-2-carboxamide (42);

N-[3-fluoro-2-(octahydro-6h-pyrrolo[2,3-c]pyridin-6-yl)phenyl]-4-(2-methyl-4-pyridinyl)-1H-imidazole-2-carboxamide (43);

N-[2-[4-(aminomethyl)-1-piperidinyl]-3-fluorophenyl]-4-(6-cyano-2-pyridinyl)-1H-imidazole-2-carboxamide (44);

4-(5-acetyl-2-thienyl)-N-[2-[4-(aminomethyl)-1-piperidinyl]-3-fluorophenyl]-1H-imidazole-2-carboxamide (45);

N-[2-(2,9-diazaspiro[5,5]undec-9-yl)-3-fluorophenyl]-4-(2-methyl-4-pyridinyl)-1H-imidazole-2-carboxamide (46);

N-[2-[4-(aminomethyl)-1-piperidinyl]-3-fluorophenyl]-4-(2-amino-6-methyl-4-pyrimidinyl)-1H-imidazole-2-carboxamide (47);

N-[2-[4-(aminomethyl)-1-piperidinyl]-3-fluorophenyl]-4-[3-(trifluoromethyl)-1H-pyrazol-5-yl]-1H-imidazole-2-carboxamide (48);

N-[2-[4-(aminomethyl)-1-piperidinyl]-3-fluorophenyl]-4-(6-amino-2-methyl-4-pyrimidinyl)-1H-imidazole-2-carboxamide (49);

N-[2-[4-[(dimethylamino)methyl]-1-piperidinyl]-3-fluorophenyl]-4-(2-methyl-4-pyridinyl)-1H-imidazole-2-carboxamide (50);

N-[2-[4-(aminomethyl)-1-piperidinyl]-5-(1H-pyrazol-4-yl)phenyl]-4-(1H-pyrazol-4-yl)-1H-imidazole-2-carboxamide (51);

N-[2-[4-(aminomethyl)-4-ethyl-1-piperidinyl]-3-fluorophenyl]-4-(2-methyl-4-pyridinyl)-1H-imidazole-2-carboxamide (52);

N-[2-[4-(aminomethyl)-1-piperidinyl]-3-fluorophenyl]-4-(1H-pyrazol-4-yl)-1H-imidazole-2-carboxamide (53);

N-[2-(3,8-diazabicyclo[3.2.1]oct-3-yl)-3-fluorophenyl]-4-(2-methyl-4-pyridinyl)-1H-imidazole-2-carboxamide (54);

N-[2-[4-(aminomethyl)-4-methyl-1-piperidinyl]-3-fluorophenyl]-4-(2-methyl-4-pyridinyl)-1H-imidazole-2-carboxamide (55);

methyl 3-[2-[[[2-[4-(aminomethyl)-1-piperidinyl]-3-fluorophenyl]amino]carbonyl]-1H-imidazol-4-yl]benzoate (56);

N-[3-fluoro-2-[4-[(methylamino)methyl]-1-piperidinyl]phenyl]-4-(2-methyl-4-pyridinyl)-1H-imidazole-2-carboxamide (57);

N-[3-fluoro-2-(hexahydropyrrolo[3,4-c]pyrrol-2(1H)-yl)phenyl]-4-(2-methyl-4-pyridinyl)-1H-imidazole-2-carboxamide (58);

1-[2-fluoro-6-[[[4-(2-methyl-4-pyridinyl)-1H-imidazol-2-yl]carbonyl]amino]phenyl]-N-methyl-4-piperidinecarboxamide (59);

N-ethyl-1-[2-fluoro-6-[[[4-(2-methyl-4-pyridinyl)-1H-imidazol-2-yl]carbonyl]amino]phenyl]-4-piperidinecarboxamide (60);

1-[2-fluoro-6-[[[4-(2-methyl-4-pyridinyl)-1H-imidazol-2-yl]carbonyl]amino]phenyl]-N,N-dimethyl-4-piperidinecarboxamide (61);

1-[2-fluoro-6-[[[4-(2-methyl-4-pyridinyl)-1H-imidazol-2-yl]carbonyl]amino]phenyl]-N-(3,3,3-trifluoro-2-hydroxypropyl)-4-piperidinecarboxamide (62);

N-[2-[4-(aminomethyl)-1-piperidinyl]-3-fluorophenyl]-4-(5-pyrimidinyl)-1H-imidazole-2-carboxamide (63);

N-[3-fluoro-2-[4-[(3(S)-fluoro-1-pyrrolidinyl)carbonyl]-1-piperidinyl]phenyl]-4-(2-methyl-4-pyridinyl)-1H-imidazole-2-carboxamide (64);

1-[2-fluoro-6-[[[4-(2-methyl-4-pyridinyl)-1H-imidazol-2-yl]carbonyl]amino]phenyl]-N-(1(R)-phenylethyl)-4-piperidinecarboxamide (65);

N-[2-[4-(1-azetidinylcarbonyl)-1-piperidinyl]-3-fluorophenyl]-4-(2-methyl-4-pyridinyl)-1H-imidazole-2-carboxamide (66);

N-[2-[4-(1-amino-1-methylethyl)-1-piperidinyl]-3-fluorophenyl]-4-(2-methyl-4-pyridinyl)-1H-imidazole-2-carboxamide (67);

6-[2-[[[2-[4-(aminomethyl)-1-piperidinyl]-3-fluorophenyl]amino]carbonyl]-1H-imidazol-4-yl]-2-hydroxy-4-pyrimidinecarboxamide (68);

N-[2-[4-(aminomethyl)-1-piperidinyl]-3-fluorophenyl]-4-[2-amino-6-[(phenylmethyl)amino]-4-pyrimidinyl]-1H-imidazole-2-carboxamide (69);

N-[2-[4-(aminomethyl)-1-piperidinyl]-3-fluorophenyl]-4-[2-amino-6-[[[4-(trifluoromethyl)phenyl]methyl]amino]-4-pyrimidinyl]-1H-imidazole-2-carboxamide (70);

4-[2-amino-6-[[(4-fluorophenyl)methyl]amino]-4-pyrimidinyl]-N-[2-[4-(aminomethyl)-1-piperidinyl]-3-fluorophenyl]-1H-imidazole-2-carboxamide (71);

4-[2-amino-6-[[2-hydroxy-1(R)-phenylethyl]amino]-4-pyrimidinyl]-N-[2-[4-(aminomethyl)-1-piperidinyl]-3-fluorophenyl]-1H-imidazole-2-carboxamide (72);

N-[2-[4-(aminomethyl)-1-piperidinyl]-3-fluorophenyl]-4-[6-[[(4-fluorophenyl)methyl]amino]-4-pyrimidinyl]-1H-imidazole-2-carboxamide (73);

N-[2-[4-(aminomethyl)-1-piperidinyl]-3-fluorophenyl]-4-[6-[[(3,4-difluorophenyl)methyl]amino]-4-pyrimidinyl]-1H-imidazole-2-carboxamide (74);

4-[2-amino-6-[[(3,4-difluorophenyl)methyl]amino]-4-pyrimidinyl]-N-[2-[4-(aminomethyl)-1-piperidinyl]-3-fluorophenyl]-1H-imidazole-2-carboxamide (75);

4-[2-amino-6-[[(3,4-dimethoxyphenyl)methyl]amino]-4-pyrimidinyl]-N-[2-[4-(aminomethyl)-1-piperidinyl]-3-fluorophenyl]-1H-imidazole-2-carboxamide (76);

4-[2-amino-6-[(2-hydroxy-1(S)-phenylethyl)amino]-4-pyrimidinyl]-N-[2-[4-(aminomethyl)-1-piperidinyl]-3-fluorophenyl]-1H-imidazole-2-carboxamide (77);

N-[3-fluoro-2-[4-(8-oxa-3-azabicyclo[3.2.1]oct-3-ylcarbonyl)-1-piperidinyl]phenyl]-4-(2-methyl-4-pyridinyl)-1H-imidazole-2-carboxamide (78);

N-[3-fluoro-2-[4-(2-oxa-5-azabicyclo[2.2.1]hept-5-ylcarbonyl)-1-piperidinyl]phenyl]-4-(2-methyl-4-pyridinyl)-1H-imidazole-2-carboxamide (79);

N-[3-fluoro-2-[4-[[3-(hydroxymethyl)-4-morpholinyl]carbonyl]-1-piperidinyl]phenyl]-4-(2-methyl-4-pyridinyl)-1H-imidazole-2-carboxamide (80);

N-[2-[4-[[3-(aminomethyl)-4-morpholinyl]carbonyl]-1-piperidinyl]-3-fluorophenyl]-4-(2-methyl-4-pyridinyl)-1H-imidazole-2-carboxamide (81);

1-[2-fluoro-6-[[[4-(2-methyl-4-pyridinyl)-1H-imidazol-2-yl]carbonyl]amino]phenyl]-4-piperidinecarboxamide (82);

N-(2-aminoethyl)-1-[2-fluoro-6-[[[4-(2-methyl-4-pyridinyl)-1H-imidazol-2-yl]carbonyl]amino]phenyl]-4-piperidinecarboxamide (83);

N-(2-aminocyclohexyl)-1-[2-fluoro-6-[[[4-(2-methyl-4-pyridinyl)-1H-imidazol-2-yl]carbonyl]amino]phenyl]-4-piperidinecarboxamide (84);
1-[2-fluoro-6-[[[4-(2-methyl-4-pyridinyl)-1H-imidazol-2-yl]carbonyl]amino]phenyl]-N-[4-(methylamino)butyl]-4-piperidinecarboxamide (85);
N-[2-(ethylamino)ethyl]-1-[2-fluoro-6-[[[4-(2-methyl-4-pyridinyl)-1H-imidazol-2-yl]carbonyl]amino]phenyl]-4-piperidinecarboxamide (86);
N-[2-[4-(3,8-diazabicyclo[3.2.1]oct-8-ylcarbonyl)-1-piperidinyl]-3-fluorophenyl]-4-(2-methyl-4-pyridinyl)-1H-imidazole-2-carboxamide (87);
N-[(1-aminocyclopentyl)methyl]-1-[2-fluoro-6-[[[4-(2-methyl-4-pyridinyl)-1H-imidazol-2-yl]carbonyl]amino]phenyl]-4-piperidinecarboxamide (88);
N-[2-[4-[[2-(aminomethyl)-4-morpholinyl]carbonyl]-1-piperidinyl]-3-fluorophenyl]-4-(2-methyl-4-pyridinyl)-1H-imidazole-2-carboxamide (89);
N-[3-fluoro-2-[4-[[2-(2-hydroxyethyl)-4-morpholinyl]carbonyl]-1-piperidinyl]phenyl]-4-(2-methyl-4-pyridinyl)-1H-imidazole-2-carboxamide (90);
N-[2-[4-(3,6-diazabicyclo[3.2.1]oct-3-ylcarbonyl)-1-piperidinyl]-3-fluorophenyl]-4-(2-methyl-4-pyridinyl)-1H-imidazole-2-carboxamide (91);
N-[3-fluoro-2-[4-[(3(R)-fluoro-1-pyrrolidinyl)carbonyl]-1-piperidinyl]phenyl]-4-(2-methyl-4-pyridinyl)-1H-imidazole-2-carboxamide (92);
N-[3-fluoro-2-[4-[(3-oxo-2,8-diazaspiro[4.5]dec-8-yl)carbonyl]-1-piperidinyl]phenyl]-4-(2-methyl-4-pyridinyl)-1H-imidazole-2-carboxamide (93);
N-[2-[4-(2,7-diazaspiro[3.5]noN-7-ylcarbonyl)-1-piperidinyl]-3-fluorophenyl]-4-(2-methyl-4-pyridinyl)-1H-imidazole-2-carboxamide (94);
N-[2-[4-[[2-(1-aminoethyl)-4-morpholinyl]carbonyl]-1-piperidinyl]-3-fluorophenyl]-4-(2-methyl-4-pyridinyl)-1H-imidazole-2-carboxamide (95);
N-[3-fluoro-2-[4-[[4-hydroxy-4-(2-pyridinyl)-1-piperidinyl]carbonyl]-1-piperidinyl]phenyl]-4-(2-methyl-4-pyridinyl)-1H-imidazole-2-carboxamide (96);
N-(2-(4-(aminomethyl)piperidin-1-yl)-3-fluorophenyl)-4-(1-(difluoromethyl)-6-oxo-1,6-dihydropyridin-3-yl)-1H-imidazole-2-carboxamide (97);
(R)—N-(2-(3-aminopiperidin-1-yl)-3-fluorophenyl)-4-(2-chloro-6-methylpyridin-4-yl)-1H-imidazole-2-carboxamide (98);
4-(2-amino-6-morpholinopyrimidin-4-yl)-N-(2-(4-(aminomethyl)piperidin-1-yl)-3-fluorophenyl)-1H-imidazole-2-carboxamide (99);
methyl 4-(6-(2-(2-(4-(aminomethyl)piperidin-1-yl)-3-fluorophenylcarbamoyl)-1H-imidazol-4-yl)-2-(methylamino)pyrimidin-4-yl)piperazine-1-carboxylate (100);
4-(6-(4-acetylpiperazin-1-yl)-2-(methylamino)pyrimidin-4-yl)-N-(2-(4-(aminomethyl)piperidin-1-yl)-3-fluorophenyl)-1H-imidazole-2-carboxamide (101);
N-cyclohexyl-6-methyl-1-(2-(methylamino)-6-(2-(2-(piperazin-1-yl)phenylcarbamoyl)-1H-imidazol-4-yl)pyrimidin-4-yl)piperidine-3-carboxamide (102);
4-(6-(4-acetylpiperazin-1-yl)-2-(methylamino)pyrimidin-4-yl)-N-(2-(piperazin-1-yl)phenyl)-1H-imidazole-2-carboxamide (103);
N-cyclohexyl-6-methyl-1-(2-(methylamino)-6-(2-(2-(piperazin-1-yl)phenylcarbamoyl)-1H-imidazol-4-yl)pyrimidin-4-yl)piperidine-3-carboxamide (104);
benzyl 4-(2-(methylamino)-6-(2-(2-(piperazin-1-yl)phenylcarbamoyl)-1H-imidazol-4-yl)pyrimidin-4-yl)piperazine-1-carboxylate (105);
N-cyclohexyl-4-(2-(methylamino)-6-(2-(2-(piperazin-1-yl)phenylcarbamoyl)-1H-imidazol-4-yl)pyrimidin-4-yl)morpholine-2-carboxamide (106);
1-(6-(2-(2-(4-(aminomethyl)piperidin-1-yl)-3-fluorophenylcarbamoyl)-1H-imidazol-4-yl)-2-(methylamino)pyrimidin-4-yl)-N-cyclohexyl-6-methylpiperidine-3-carboxamide (107);
N-cyclohexyl-6-methyl-1-(2-(methylamino)-6-(2-(2-(piperidin-4-yloxy)phenylcarbamoyl)-1H-imidazol-4-yl)pyrimidin-4-yl)piperidine-3-carboxamide (108);
N-cyclohexyl-1-(6-(2-(3-fluoro-2-morpholinophenylcarbamoyl)-1H-imidazol-4-yl)-2-(methylamino)pyrimidin-4-yl)-6-methylpiperidine-3-carboxamide (109);
1-(6-(2-(2-((S)-2-(aminomethyl)morpholino)-3-fluorophenylcarbamoyl)-1H-imidazol-4-yl)-2-(methylamino)pyrimidin-4-yl)-N-cyclohexyl-6-methylpiperidine-3-carboxamide (110);
1-(6-(2-(2-((R)-2-(aminomethyl)morpholino)-3-fluorophenylcarbamoyl)-1H-imidazol-4-yl)-2-(methylamino)pyrimidin-4-yl)-N-cyclohexyl-6-methylpiperidine-3-carboxamide (11);
1-(2-amino-6-(2-(5-amino-2-(2,9-diazaspiro[5.5]undecan-9-yl)phenylcarbamoyl)-1H-imidazol-4-yl)pyrimidin-4-yl)-N-cyclohexyl-6-methylpiperidine-3-carboxamide (112);
1-(6-(2-(2-(2-(1,4-dioxa-8-azaspiro[4.5]decan-8-yl)phenylcarbamoyl)-1H-imidazol-4-yl)-2-(methylamino)pyrimidin-4-yl)-N-cyclohexyl-6-methylpiperidine-3-carboxamide (113);
1-(6-(2-(2-((R)-3-aminopiperidin-1-yl)-3-fluorophenylcarbamoyl)-1H-imidazol-4-yl)-2-(methylamino)pyrimidin-4-yl)-N-cyclohexyl-6-methylpiperidine-3-carboxamide (114);
(3S,6R)-1-(6-(2-(2-(4-(aminomethyl)piperidin-1-yl)-3-fluorophenylcarbamoyl)-1H-imidazol-4-yl)-2-(methylamino)pyrimidin-4-yl)-N-cyclohexyl-6-methylpiperidine-3-carboxamide (115);
(3R,6S)-1-(6-(2-(2-(4-(aminomethyl)piperidin-1-yl)-3-fluorophenylcarbamoyl)-1H-imidazol-4-yl)-2-(methylamino)pyrimidin-4-yl)-N-cyclohexyl-6-methylpiperidine-3-carboxamide (116);
(3S,6R)-1-(6-(2-(2-((S)-2-(aminomethyl)morpholino)-3-fluorophenylcarbamoyl)-1H-imidazol-4-yl)-2-(methylamino)pyrimidin-4-yl)-N-cyclohexyl-6-methylpiperidine-3-carboxamide (117);
N-cyclohexyl-1-(6-(2-(3-fluoro-2-(2,7-diazaspiro[3.5]nonan-7-yl)phenylcarbamoyl)-1H-imidazol-4-yl)-2-(methylamino)pyrimidin-4-yl)-6-methylpiperidine-3-carboxamide (118);
N-cyclohexyl-1-(6-(2-(3-fluoro-2-(2,8-diazaspiro[4.5]decan-8-yl)phenylcarbamoyl)-1H-imidazol-4-yl)-2-(methylamino)pyrimidin-4-yl)-6-methylpiperidine-3-carboxamide (119);
(R)—N-(2-(4-(aminomethyl)piperidin-1-yl)-3-fluorophenyl)-4-(2-(methylamino)-6-(2-methylpiperazin-1-yl)pyrimidin-4-yl)-1H-imidazole-2-carboxamide (120);
(R)—N-(2-(4-(aminomethyl)piperidin-1-yl)-3-fluorophenyl)-4-(2-(methylamino)-6-(3-methylmorpholino)pyrimidin-4-yl)-1H-imidazole-2-carboxamide (121);
N-cyclohexyl-1-(6-(2-(3-fluoro-2-((R)-3-methylmorpholino)phenylcarbamoyl)-1H-imidazol-4-yl)-2-(methylamino)pyrimidin-4-yl)-6-methylpiperidine-3-carboxamide (122);
(R)-4-(6-(2-(aminomethyl)morpholino)-2-(methylamino)pyrimidin-4-yl)-N-(2-(4-(aminomethyl)piperidin-1-yl)-3-fluorophenyl)-1H-imidazole-2-carboxamide (123);

(S)—N-(2-(4-(aminomethyl)piperidin-1-yl)-3-fluorophenyl)-4-(2-(methylamino)-6-(3-methylpiperazin-1-yl)pyrimidin-4-yl)-1H-imidazole-2-carboxamide (124);

4-(6-(4-(aminomethyl)piperidin-1-yl)-2-(methylamino)pyrimidin-4-yl)-N-(2-(4-(aminomethyl)piperidin-1-yl)-3-fluorophenyl)-1H-imidazole-2-carboxamide (125);

(R)—N-(2-(4-(aminomethyl)piperidin-1-yl)-3-fluorophenyl)-4-(6-(3-aminopiperidin-1-yl)-2-(methylamino)pyrimidin-4-yl)-1H-imidazole-2-carboxamide (126);

1-(6-(2-(2-(4-(aminomethyl)piperidin-1-yl)-3-fluorophenylcarbamoyl)-1H-imidazol-4-yl)-2-(methylamino)pyrimidin-4-yl)-4-(methylamino)piperidine-4-carboxamide (127);

(S)—N-(2-(4-(aminomethyl)piperidin-1-yl)-3-fluorophenyl)-4-(6-(3-carbamoyl-3-methoxypyrrolidin-1-yl)-2-(methylamino)pyrimidin-4-yl)-1H-imidazole-2-carboxamide (128);

(S)—N-(2-(4-(aminomethyl)piperidin-1-yl)-3-fluorophenyl)-4-(6-(3-(cyclohexylcarbamoyl)-3-methoxypyrrolidin-1-yl)-2-(methylamino)pyrimidin-4-yl)-1H-imidazole-2-carboxamide (129);

(R)—N-(2-(4-(aminomethyl)piperidin-1-yl)-3-fluorophenyl)-4-(6-(3-(benzylcarbamoyl)-3-(methoxymethyl)pyrrolidin-1-yl)-2-(methylamino)pyrimidin-4-yl)-1H-imidazole-2-carboxamide (130);

(R)—N-(2-(4-(aminomethyl)piperidin-1-yl)-3-fluorophenyl)-4-(6-(3-(cyclopropylcarbamoyl)-3-(methoxymethyl)pyrrolidin-1-yl)-2-(methylamino)pyrimidin-4-yl)-1H-imidazole-2-carboxamide (131); and (R)—N-(2-(4-(aminomethyl)piperidin-1-yl)-3-fluorophenyl)-4-(6-(3-(cyclohexylcarbamoyl)-3-(methoxymethyl)pyrrolidin-1-yl)-2-(methylamino)pyrimidin-4-yl)-1H-imidazole-2-carboxamide (132).

The compounds according to the invention have pharmacological properties; in particular, the compounds of the present invention can be inhibitors, regulators or modulators of protein kinases, such as PDK1.

Methods for Making the Compounds of Formula (I)

The compounds of Formula (I) can be prepared from known or readily prepared starting materials, following methods known to one skilled in the art of organic synthesis. Methods useful for making the compounds of Formula (I) are set forth in the Examples below. Alternative synthetic pathways and analogous structures will be apparent to those skilled in the art of organic synthesis. All stereoisomers and tautomeric forms of the compounds are contemplated.

EXAMPLES

Solvents, reagents, and intermediates that are commercially available were used as received. Reagents and intermediates that are not commercially available were prepared in the manner as described below. $^1$H NMR spectra were obtained on a Varian spectrometer (400 MHz and 500 MHz) are reported as ppm down field from Me$_4$Si with number of protons, multiplicities, and coupling constants, in Hertz indicated parenthetically. Where LC/MS data are presented, analyses was performed using an Agilent 1100 Series LC w/MicroMass Quattro MS Varian Pursuit XR C18, 5 micron, 150 mm×4.6 mm ID gradient flow (0.1% TFA or 0.2% FA): 0 min—5% ACN, 7.5 min—100% ACN, 8.5 min—100% ACN, 8.51 min—5% ACN, 10 min—stop 3 ml/min. The retention time and observed parent ion are given. Where the description indicates the reaction mixture was purified by HPLC, the description refers to using a preparative Agilent 1100 Series LC/MSD SL system: Column Reverse Phase-Varian Pursuit XR 10 µC-18 250×21.2 mm; elution with gradient Acetonitrile/water with 0.1% TFA or 0.2% formic acid. The desired product was detected and collected by a mass-triggered automatic sample collector. Flash column chromatography was performed using pre-packed normal phase silica from Biotage, Inc.

The following solvents, reagents and reaction conditions may be referred to by their abbreviations:

Aq: aqueous
rac BINAP: racemic 2,2'-bis(diphenylphosphino)-1,1'-binaphthyl
g or gm: grams
psi: pounds per square inch
pH: concentration of hydronium ions in a solution
° C.: degrees Celsius
h: hours
THF: tetrahydrofuran
Et$_2$O: diethyl ether
SEM: 2-(trimethylsilyl)ethoxymethyl
LCMS: Liquid chromatography mass spectrometry
DCM: dichloromethane
N: Normal
mL: milliliter
NBS: N-Bromosuccinimide
NCS: N-Chlorosuccinimide
NIS: N-iodosuccinimide
r.t.: room temperature
MeOH: methanol
DIEA: diisopropylethylamine
DIPEA: diisopropylethylamine
DMAP: dimethylaminopyridine
EtOAc: ethyl acetate
EtOH: ethanol
DMF: dimethylformamide
wt %: weight percent
m/z: mass per charge
LiOH: lithium hydroxide
DMSO: dimethylsulfoxide
HATU: O-(7-azabenzotriazol-1-yl)-N,N,N',N'-tetramethyluronium hexafluorophosphate
HOBT: 1-hydroxybenzotriazole
IPA: isopropanol
NMM: 4-methylmorpholine
R$_t$: retention time
RP: reverse phase
SEM: β-(trimethylsilyl)ethoxy]methyl
SEMCl: β-(trimethylsilyl)ethoxy]methyl chloride
ACN: acetonitrile
CH$_3$CN: acetonitrile
MeCN: acetonitrile
MeI: iodomethane
r.t.: room temperature
pTSA: para-toluene sulfonic acid
CDI: N,N'-carbonyldiimidazole
mg: milligram
PMA: phosphomolybdic acid
LiHMDS: Lithium bis(trimethylsilyl)amide
HMDS: hexamethyldisilazane
Pd/C: palladium on carbon
H$_2$: hydrogen gas
PdCl$_2$ (dppf): [1,1'-bis(diphenylphosphino)ferrocene]dichloropalladium(II)
µmol: micromole
TFA: trifluoroacetic acid
NMP: N-methyl-2-pyrrolidone min: minute
DME: dimethylethane
AcOH: acetic acid
BOC: tertiary-butyloxycarbonyl
M: Molar
mmol: millimolar
Pd[P(t-Bu)$_3$]$_2$: bis(tributyl)Phosphine) palladium
Pd(PPh$_3$)$_4$: tetrakis(triphenylphosphine) palladium
EDCI: 1-ethyl-3-(3-dimethylaminopropyl)-carbodiimide
UV: ultraviolet
LDA: lithium diisopropylamide
Tf: trifluoromethanesulfonyl Representative Imidazole Carboxamide Compounds 1-96 were prepared as described in Examples 1-26 below. Other Imidazole Carboxamide Compounds can be readily prepared by those skilled in the art of organic synthesis using readily obtained starting materials and using synthetic routes similar to those described in the examples below.

Example 1

This example describes the preparation of Imidazole Carboxamide Compounds wherein the group

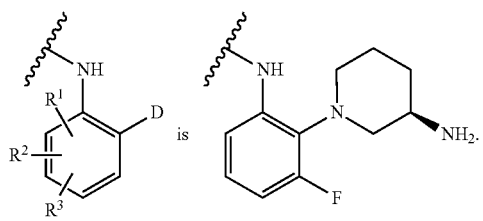

is

Preparation of N-[2-(3(R)-amino-1-piperidinyl)-3-fluorophenyl]-4-[1-(2-thienylmethyl)-1H-pyrazol-4-yl]-1H-imidazole-2-carboxamide (5)

Step A—Synthesis of Ethyl 1-((2-(trimethylsilyl)ethoxy)methyl)-1H-imidazole-2-carboxylate (Int-1a)

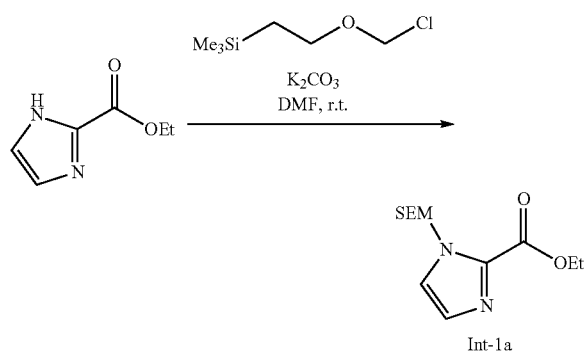

2-(Trimethylsilyl)ethoxymethyl chloride (12.8 g, 0.077 mol) was added to a stirred solution of ethyl imidazole-2-carboxylate (9.0 g, 0.064 mol) and potassium carbonate (17.7 g, 0.128 mol) in N,N-dimethylformamide (50 mL) at 0° C. The mixture was allowed to stir from 0° C. to r.t. overnight. Water and ethyl acetate were added and the layers were separated. The separated aqueous layer was extracted with ethyl acetate (×2). The combined organic layers were washed with water (×2). The separated organic layer was dried (MgSO$_4$) and filtered. The solvents were removed in vacuo and chromatographic purification (ethyl acetate-hexane) of the residue gave imidazole Int-1a (12 g, 70%) as a colorless oil. LCMS m/e (M+H$^+$)=271.1.

Step B—Synthesis of Ethyl 4-bromo-1-((2-(trimethylsilyl)ethoxy)methyl)-1H-imidazole-2-carboxylate (Int-1b)

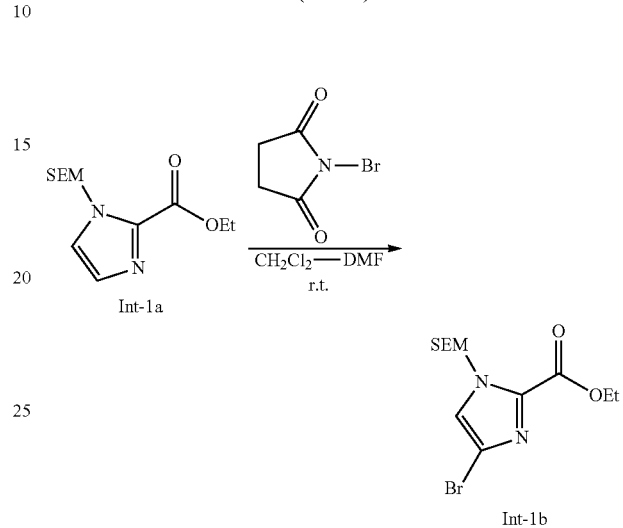

A mixture of imidazole Int-1a (6.3 g, 0.023 mol) and N-bromosuccinimide (6.2 g, 0.035 mol) was stirred in a mixture of dichloromethane (30 mL) and N,N-dimethylformamide (30 mL) at r.t. overnight. Dichloromethane and water were added, and the layers were separated. The separated aqueous layer was extracted with dichloromethane (×2), dried (MgSO$_4$) and filtered. The solvents were removed in vacuo and chromatographic purification (ethyl acetate—hexane) of the residue gave bromoimidazole Int-1b (5.2 g, 64%) as a white solid.

Step C—Synthesis of Lithium 4-bromo-1-((2-(trimethylsilyl)ethoxy)methyl)-1H-imidazole-2-carboxylate (Int-1c)

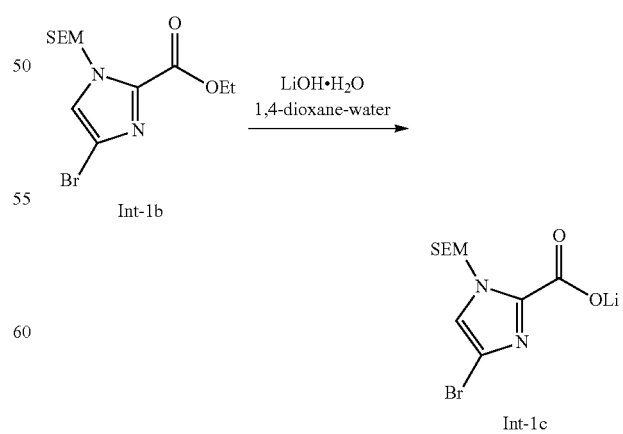

A solution of lithium hydroxide (94 mg, 2.23 mol) in water (5 mL) was added to a stirred solution of bromoimidazole Int-1b (0.65 g, 1.86 mmol) in 1,4-dioxane (10 mL) at r.t. The mixture was stirred at r.t. for 2 days and solvents were removed in vacuo to give bromoimidazolecarboxylate Int-1c as a white solid. The solid was used in the next step without further purification.

Step D—Synthesis of Preparation of (Int-1d)

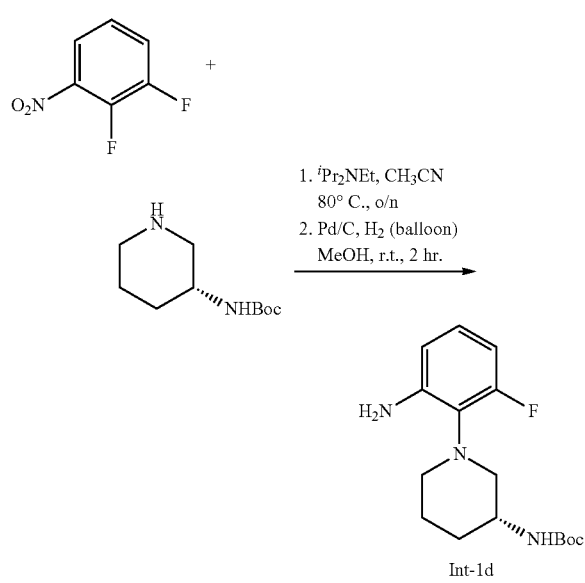

A mixture of 1,2-difluoro-3-nitrobenzene (2.38 g, 0.015 mmol), (R)-tert-butyl piperidin-3-ylcarbamate (3.0 g, 0.015 mmol) and N,N-diisopropylethylamine (5.2 ml, 0.030 mmol) was heated in acetonitrile (20 mL) at 80° C. overnight. The solvents were removed in vacuo, and chromatographic purification (ethyl acetate-hexanes) of the residue gave a nitropiperidine as orange oil (3.7 g, 72%).

A mixture of the nitropiperidine (3.51 g, 10.3 mmol), 10% palladium on carbon (2.2 g, 1.03 mmol, 50% wet) was stirred in methanol (100 mL) at r.t. under hydrogen (balloon) for 2 h. The solids were filtered through Celite®, and the solvents were removed in vacuo to give Int-Id as a grey foam (3.0 g, 94%).

Step E—(R)-tert-butyl 1-(2-(4-bromo-1-((2-(trimethylsilyl)ethoxy)methyl)-1H-imidazole-2-carboxamido)phenyl)piperidin-3-ylcarbamate (Int-1e)

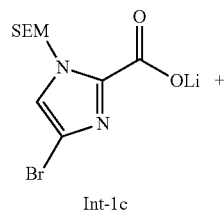

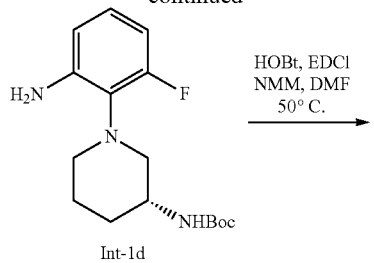

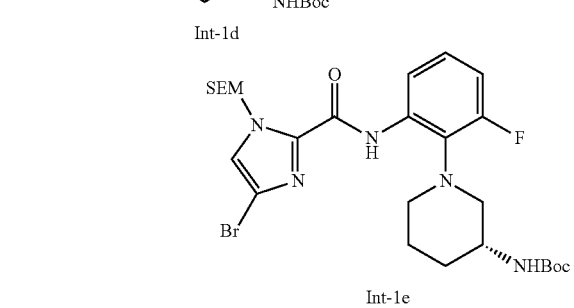

A mixture of carboxylate Int-1c (421 mg, 1.31 mmol), aniline Int-1d (406 mg, 1.31 mmol), 1-hydroxybenzotriazole hydrate (HOBt) (354 mg, 2.62 mmol), N-(3-dimethylaminopropyl)-N'-ethyl carbodiimide hydrochloride (EDCI) (500 mg, 2.62 mmol) and 4-methylmorpholine (NMM) (66 mg, 0.66 mmol) was stirred in N,N-dimethylformamide (10 mL) at 50° C. overnight. Water and ethyl acetate were added and the layers were separated. The separated organic layer was washed with water. The separated organic layer was dried (MgSO$_4$) and filtered. The solvents were removed in vacuo and chromatographic purification (ethyl acetate-hexane) of the residue gave amide Int-1e (609 mg, 76%) as a white solid.

Step F—Synthesis of (R)-tert-butyl 1-(2-fluoro-6-(4-(1-(thiophen-2-ylmethyl)-1H-pyrazol-4-yl)-1-((2-(trimethylsilyl)ethoxy)methyl)-1H-imidazole-2-carboxamido)phenyl)piperidin-3-ylcarbamate (Int-1c)

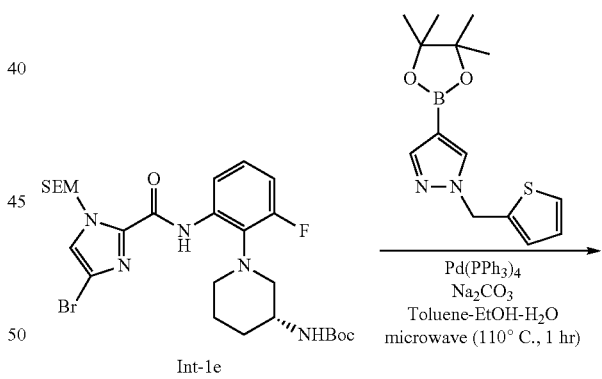

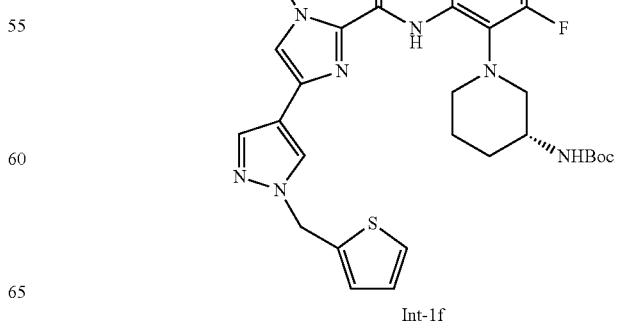

A mixture of bromide Int-1e (60 mg, 0.098 mmol), 4-(4,4,5,5-tetramethyl-1,3,2-dioxaborolan-2-yl)-1-(thiophen-2-yl-methyl)-1H-pyrazole (28 mg, 0.098 mmol) and sodium carbonate (31 mg, 0.30 mmol) in ethanol (1 mL), toluene (1 mL) and water (0.5 mL) at r.t. was purged with nitrogen gas for 5 min in a microwave vial. Tetrakistriphenylphosphorous palladium (12 mg, 0.0098 mmol) was added. The mixture was heated in a microwave reactor at 110° C. for 1 h. Water and ethyl acetate were added and the layers were separated. The separated aqueous layer was extracted with ethyl acetate. The separated organic layer was dried (MgSO$_4$) and filtered. The solvents were removed in vacuo and chromatographic purification (ethyl acetate-hexane) of the residue gave thiophene Int-1f as a colorless oil.

Step G—N-[2-(3(R)-amino-1-piperidinyl)-3-fluorophenyl]-4-[1-(2-thienylmethyl)-1H-pyrazol-4-yl]-1H-imidazole-2-carboxamide (5)

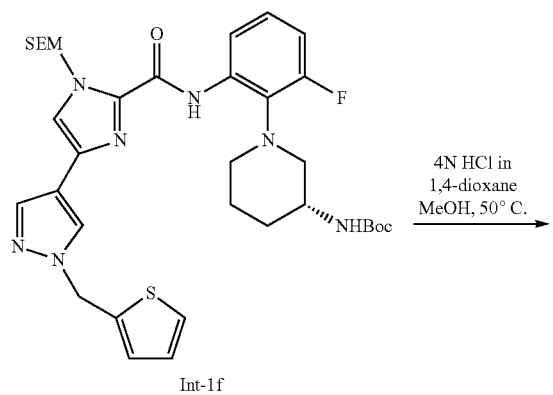

Int-1f

4N HCl in
1,4-dioxane
MeOH, 50° C.

-continued

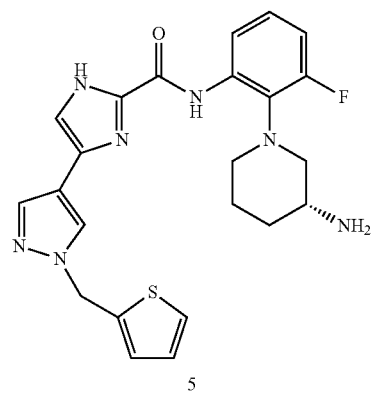

5

Thiophene Int-1f from above was stirred in 4 N hydrochloric acid in 1,4-dioxane and methanol at 60° C. for 3 h. The solvents were removed in vacuo. Chromatographic purification [dichloromethane-methanol (3% ammonia)] of the residue gave imidazole 5. Imidazole 5 was dissolved in MeOH and excess hydrochloride acid (1 M, in ether) was added. The solvents were removed to give hydrochloride salt of 5 (30 mg) as a yellow solid. LCMS m/e (M+H$^+$)=466.3.

Aniline Int-1e was coupled with the coupling partners listed in Table 1 below using the coupling procedures similar to that described in Step F. The intermediate coupling product was deprotected using procedures similar to that described in Step G. Thus, compounds 5, 7, 8, 10-14, 16, 19-23, 25-27, 38, and 39 were prepared from aniline Int-1b using procedures similar to those described above for Steps F and G.

TABLE 1

| Coupling Partner | Compound No. | MS m/e (M + H$^+$) | Name |
|---|---|---|---|
|  |  | 466.3 | N-[2-(3(R)-amino-1-piperidinyl)-3-fluorophenyl]-4-[1-(2-thienylmethyl)-1H-pyrazol-4-yl]-1H-imidazole-2-carboxamide |

TABLE 1-continued

| Coupling Partner | Compound No. | MS m/e (M + H⁺) | Name |
|---|---|---|---|
| 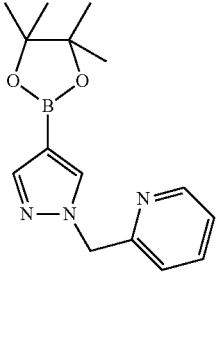 [SMILES: CC1(C)OB(c2cnn(Cc3ccccn3)c2)OC1(C)C] | 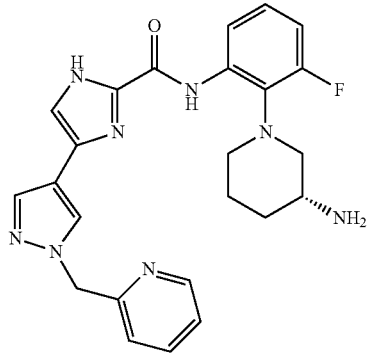 [SMILES: N[C@@H]1CCCN(c2c(F)cccc2NC(=O)c2nc(-c3cnn(Cc4ccccn4)c3)c[nH]2)C1] 7 | 461.3 | N-[2-(3(R)-amino-1-piperidinyl)-3-fluorophenyl]-4-[1-(2-pyridinylmethyl)-1H-pyrazol-4-yl]-1H-imidazole-2-carboxamide |
| 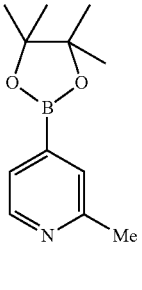 [SMILES: Cc1cc(B2OC(C)(C)C(C)(C)O2)ccn1] | 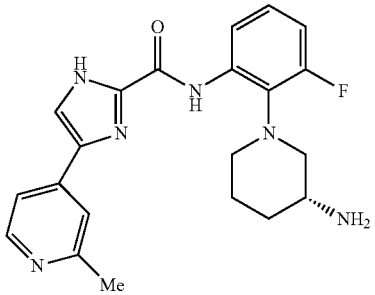 [SMILES: Cc1cc(-c2c[nH]c(C(=O)Nc3cccc(F)c3N3CCC[C@@H](N)C3)n2)ccn1] 8 | 395.2 | N-[2-(3(R)-amino-1-piperidinyl)-3-fluorophenyl]-4-(2-methyl-4-pyridinyl)-1H-imidazole-2-carboxamide |
| 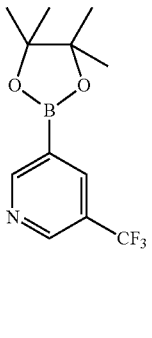 | 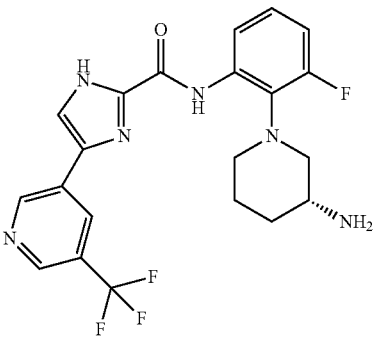 [SMILES: N[C@@H]1CCCN(c2c(F)cccc2NC(=O)c2nc(-c3cncc(C(F)(F)F)c3)c[nH]2)C1] 9 | | N-[2-(3(R)-amino-1-piperidinyl)-3-fluorophenyl]-4-[5-(trifluoromethyl)-3-pyridinyl]-1H-imidazole-2-carboxamide |
| 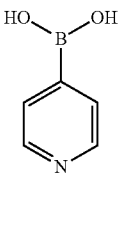 | 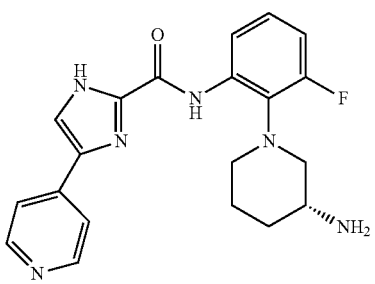 [SMILES: N[C@@H]1CCCN(c2c(F)cccc2NC(=O)c2nc(-c3ccncc3)c[nH]2)C1] 10 | 381.2 | N-[2-(3(R)-amino-1-piperidinyl)-3-fluorophenyl]-4-(4-pyridinyl)-1H-imidazole-2-carboxamide |

TABLE 1-continued

| Coupling Partner | Compound No. | MS m/e (M + H⁺) | Name |
|---|---|---|---|
| (pinacol boronate of 1H-pyrazol-4-yl) | 11 | 370.2 | N-[2-(3(R)-amino-1-piperidinyl)-3-fluorophenyl]-4-(1H-pyrazol-4-yl)-1H-imidazole-2-carboxamide |
| (pinacol boronate of 1-methyl-1H-pyrazol-4-yl) | 14 | 384.2 | N-[2-(3(R)-amino-1-piperidinyl)-3-fluorophenyl]-4-(1-methyl-1H-pyrazol-4-yl)-1H-imidazole-2-carboxamide |
| (pinacol boronate of 2-(trifluoromethyl)pyridin-4-yl) | 19 | 449.1 | N-[2-(3(R)-amino-1-piperidinyl)-3-fluorophenyl]-4-[2-(trifluoromethyl)-4-pyridinyl]-1H-imidazole-2-carboxamide |
| (pinacol boronate of 2-(NHBoc)pyridin-4-yl) | 20 | 396.1 | N-[2-(-3(R)-amino-1-piperidinyl)-3-fluorophenyl]-4-(2-amino-4-pyridinyl)-1H-imidazole-2-carboxamide |

TABLE 1-continued
| Coupling Partner | Compound No. | MS m/e (M + H$^+$) | Name |
|---|---|---|---|
| 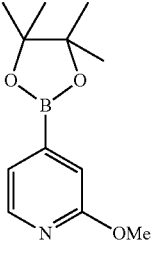 [SMILES: COc1cc(B2OC(C)(C)C(C)(C)O2)ccn1] | 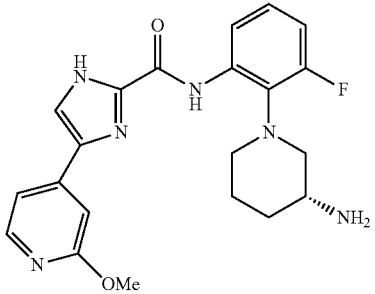 [SMILES: COc1cc(-c2c[nH]c(C(=O)Nc3cccc(F)c3N3CCC[C@@H](N)C3)n2)ccn1] 21 | 411.1 | N-[2-(3(R)-amino-1-piperidinyl)-3-fluorophenyl]-4-(2-methoxy-4-pyridinyl)-1H-imidazole-2-carboxamide |
| 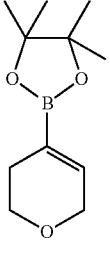 | 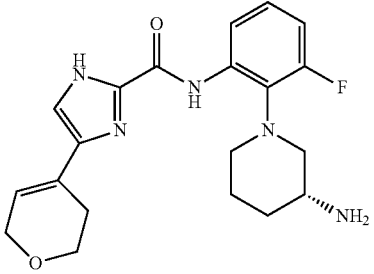 [SMILES: N[C@@H]1CCCN(c2c(F)cccc2NC(=O)c2nc(C3=CCOCC3)c[nH]2)C1] 22 | 386.1 | N-[2-(3(R)-amino-1-piperidinyl)-3-fluorophenyl]-4-(3,6-dihydro-2H-pyran-4-yl)-1H-imidazole-2-carboxamide |
| 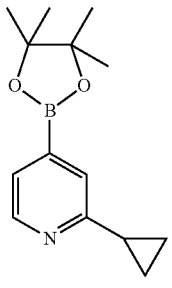 [SMILES: CC1(C)OB(c2ccnc(C3CC3)c2)OC1(C)C] | 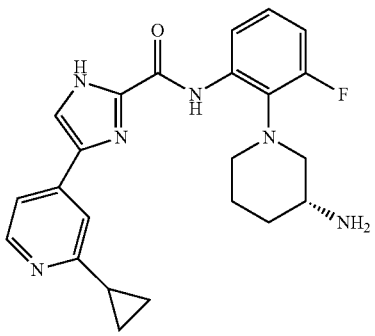 [SMILES: N[C@@H]1CCCN(c2c(F)cccc2NC(=O)c2nc(-c3ccnc(C4CC4)c3)c[nH]2)C1] 23 | 421.2 | N-[2-(3(R)-amino-1-piperidinyl)-3-fluorophenyl]-4-(2-cyclopropyl-4-pyridinyl)-1H-imidazole-2-carboxamide |

TABLE 1-continued

| Coupling Partner | Compound No. | MS m/e (M + H⁺) | Name |
|---|---|---|---|
| (pyridine-pinacol boronate, 2-OH) | 25 | 397.1 | N-[2-(3(R)-amino-1-piperidinyl)-3-fluorophenyl]-4-(2-hydroxy-4-pyridinyl)-1H-imidazole-2-carboxamide |
| 2,4-difluorophenylboronic acid | 38 | 416.1 | N-[2-(3(R)-amino-1-piperidinyl)-3-fluorophenyl]-4-(2,4-difluorophenyl)-1H-imidazole-2-carboxamide |
| (2-pyrazolyl-pyridine pinacol boronate) | 39 | 447.2 | N-[2-(3(R)-amino-1-piperidinyl)-3-fluorophenyl]-4-[2-(1H-pyrazol-1-yl)-4-pyridinyl]-1H-imidazole-2-carboxamide |

Example 2

This example describes the preparation of Imidazole Carboxamide Compounds wherein the group is The preparation is specifically described for N-[2-[4-(aminomethyl)-1-piperidinyl]-3-fluorophenyl]-4-(2-methyl-4-pyridinyl)-1H-imidazole-2-carboxamide (18).

Step A—Synthesis of tert-butyl (1-(2-fluoro-6-nitrophenyl)piperidin-4-yl)methylcarbamate (Int-2a)

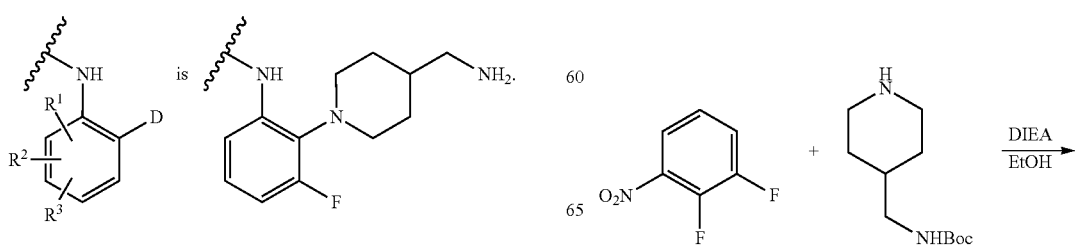

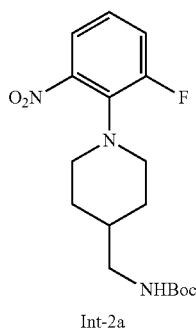

Int-2a

To a solution of 2,3-difluoronitrobenzene (5.0 g, 31 mmol) in EtOH (25 mL) were added tert-butyl piperidin-4-ylmethylcarbamate (8.1 g, 38 mmol), and N,N-diisopropylethylamine (6.6 mL, 38 mmol). The reaction was irradiated to 110° C. for 20 min by microwave. The crude reaction mixture was diluted with EtOAc, washed with 1 N HCl and brine, dried over MgSO₄ and concentrated to yield nitrobenzene Int-2a (11.2 g, 99%) as yellow crystals. The crude product was used without further purification.

Step B—Synthesis of: tert-butyl (1-(2-amino-6-fluorophenyl)piperidin-4-yl)methylcarbamate (Int-2b)

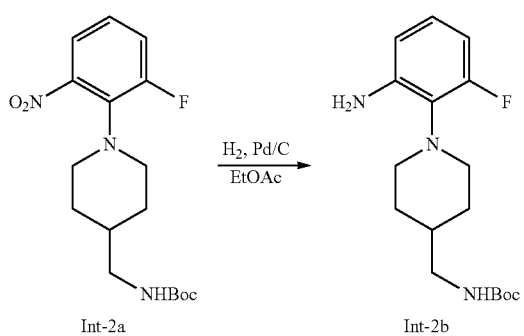 [SMILES: "EtOAc" ; CC(C)(C)OC(=O)NCC1CCN(c2c(F)cccc2[N+](=O)[O-])CC1 ; CC(C)(C)OC(=O)NCC1CCN(c2c(N)cccc2F)CC1]

To a solution of nitrobenzene Int-2a (5.2 g, 14.7 mmol) in EtOAc (40 mL) was added 10% Pd/C (150 mg). The flask was evacuated and filled with H₂ three times. Then the reaction mixture was stirred at r.t. under 1 atm of H₂ overnight. The reaction was filtered through a fiberglass filter paper and then concentrated to yield aniline Int-2b (4.9 g, quant.) as a beige solid. The crude aniline Int-2b was used without further purification.

Step C—Synthesis of tert-butyl (1-(2-(4-bromo-1-((2-(trimethylsilyl)ethoxy)methyl)-1H-imidazole-2-carboxamido)phenyl)piperidin-4-yl)methylcarbamate (Int-2c)

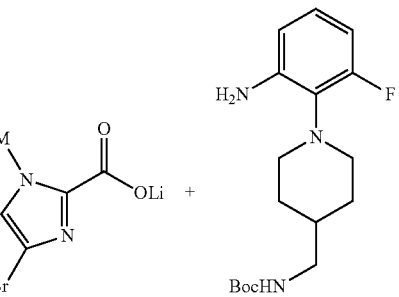

Int-1c   Int-2b

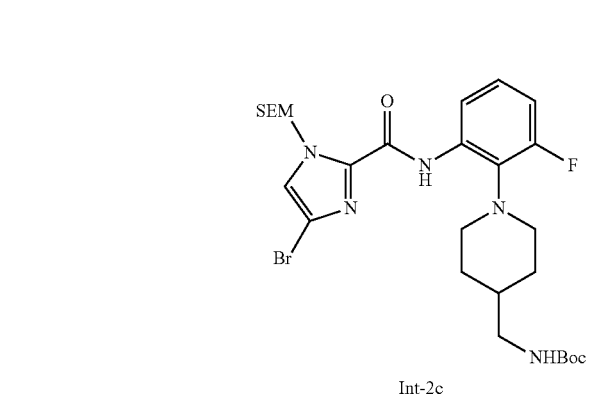

Int-2c

A mixture of carboxylate Int-1c (55 mg, 0.17 mmol), aniline Int-2b (55 mg, 0.17 mmol), HOBt (46 mg, 0.34 mmol), EDCI (65 mg, 0.34 mmol) and NMM (7 mg, 0.086 mmol) was stirred in N,N-dimethylformamide (3 mL) at 50° C. overnight. Water and ethyl acetate were added and the layers were separated. The separated organic layer was washed with water. The separated organic layer was dried (MgSO₄) and filtered. The solvents were removed in vacuo and chromatographic purification (ethyl acetate-hexane) of the residue gave amide Int-2c (85 mg, 79%) as an orange oil. LCMS m/e (M+H⁺)=626.2.

Step D—Synthesis of tert-butyl (1-(2-(4-(2-methylpyridin-4-yl)-1-((2-(trimethylsilyl)ethoxy)methyl)-1H-imidazole-2-carboxamido)phenyl)piperidin-4-yl)methylcarbamate (Int-2d)

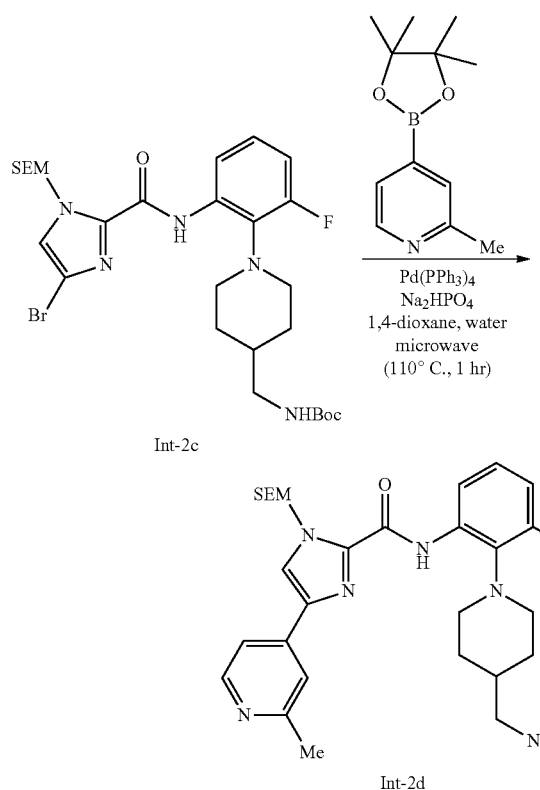

Int-2c

Int-2d

A mixture of amide Int-2c (74 mg, 0.12 mmol), 2-methylpyridine-4-boronic acid pinacol ester (31 mg, 0.14 mmol) and sodium hydrogen phosphate (50 mg, 0.35 mmol) in 1,4-dioxane (2 mL) and water (1 mL) at r.t. was purged with nitrogen gas for 5 min in a microwave vial. Tetrakistriphenylphosphorous palladium (14 mg, 0.012 mmol) was added. The mixture was heated in a microwave reactor at 110° C. for 1 h. Water and ethyl acetate were added and layers were separated. The separated aqueous layer was extracted with ethyl acetate. The separated organic layer was dried (MgSO$_4$) and filtered. The solvents were removed in vacuo and chromatographic purification (ethyl acetate-hexane) of the residue gave pyridine Int-2d (62 mg, 82%) as a colorless oil. LCMS m/e (M+H$^+$)=639.3.

Step E—N-[2-[4-(aminomethyl)-1-piperidinyl]-3-fluorophenyl]-4-(2-methyl-4-pyridinyl)-1H-imidazole-2-carboxamide (18)

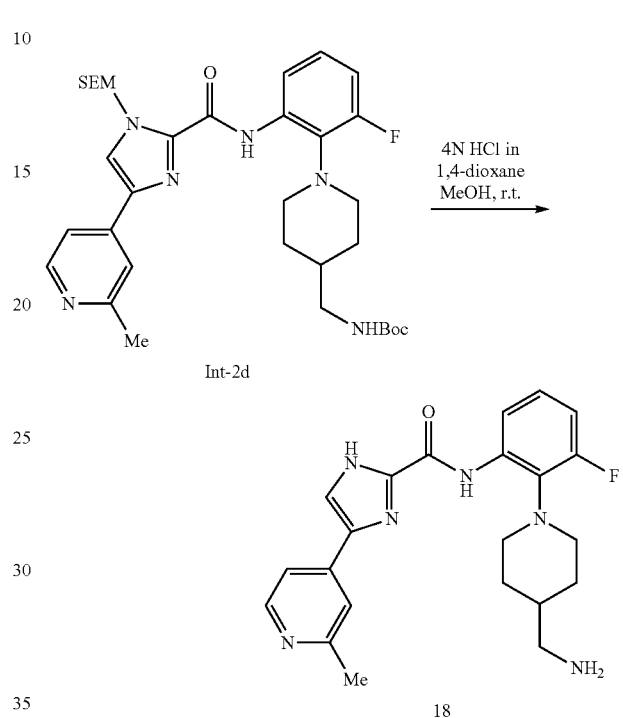

Int-2d

18

Pyridine Int-2d (62 mg, 0.097 mmol) was stirred in 4 N hydrochloric acid in 1,4-dioxane (1 mL) and methanol (4 mL) at 50° C. for 2 h. The solvents were removed in vacuo. Chromatographic purification [dichloromethane-methanol (7 N ammonia)] of the residue imidazole 18 (35 mg, 88%) as a white solid. LCMS m/e (M+H$^+$)=409.2.

Aniline Int-2d was coupled with the coupling partners listed in Table 2 below using coupling procedures similar to that described in Step D. The intermediate coupling product was then deprotected using procedures similar to that described in Step E. Thus, compounds 18, 27, 30-37, 41, 42, 44, 45, 48, 53, 56, and 63 were prepared from aniline Int-2d using the procedures described above.

TABLE 2

| Coupling Partner | Compound | MS m/e (M + H$^+$) | |
|---|---|---|---|
| [structure] | [structure] | 409.2 | N-[2-[4-(aminomethyl)-1-piperidinyl]-3-fluorophenyl]-4-(2-methyl-4-pyridinyl)-1H-imidazole-2-carboxamide |

TABLE 2-continued

| Coupling Partner | Compound | MS m/e (M + H⁺) | |
|---|---|---|---|
| 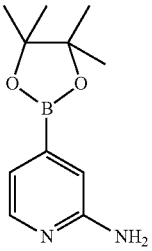 [SMILES: CC1(C)OB(c2ccnc(N)c2)OC1(C)C] | 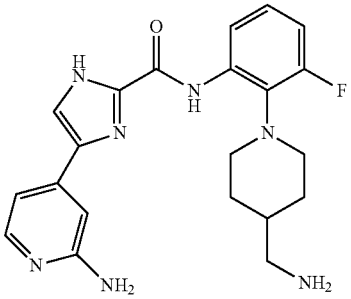 [SMILES: NCC1CCN(c2c(F)cccc2NC(=O)c2nc(-c3ccnc(N)c3)c[nH]2)CC1] | 410.2 | N-[2-[4-(aminomethyl)-1-piperidinyl]-3-fluorophenyl]-4-(2-amino-4-pyridinyl)-1H-imidazole-2-carboxamide |
| 18 | 27 | | |
| 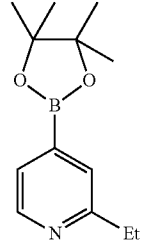 [SMILES: CCc1cc(B2OC(C)(C)C(C)(C)O2)ccn1] | 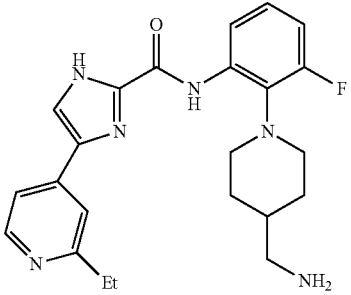 [SMILES: CCc1cc(-c2c[nH]c(C(=O)Nc3cccc(F)c3N3CCC(CN)CC3)n2)ccn1] | 423.2 | N-[2-[4-(aminomethyl)-1-piperidinyl]-3-fluorophenyl]-4-(2-ethyl-4-pyridinyl)-1H-imidazole-2-carboxamide |
| | 30 | | |
| 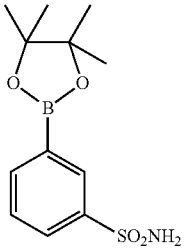 [SMILES: CC1(C)OB(c2cccc(S(N)(=O)=O)c2)OC1(C)C] | 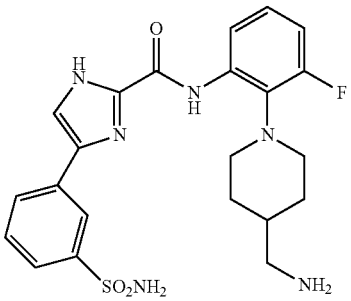 [SMILES: NCC1CCN(c2c(F)cccc2NC(=O)c2nc(-c3cccc(S(N)(=O)=O)c3)c[nH]2)CC1] | 473.1 | N-[2-[4-(aminomethyl)-1-piperidinyl]-3-fluorophenyl]-4-[3-(aminosulfonyl)phenyl]-1H-imidazole-2-carboxamide |
| | 31 | | |
| 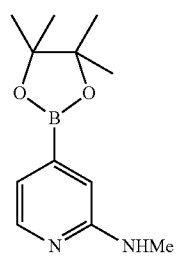 [SMILES: CNc1cc(B2OC(C)(C)C(C)(C)O2)ccn1] | 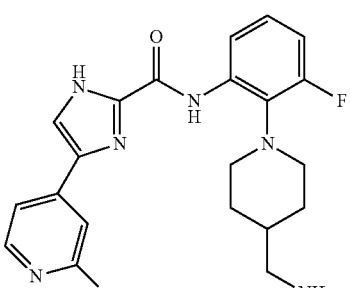 | 424.2 | N-[2-[4-(aminomethyl)-1-piperidinyl]-3-fluorophenyl]-4-[2-(methylamino)-4-pyridinyl]-1H-imidazole-2-carboxamide |
| | 32 | | |

TABLE 2-continued

| Coupling Partner | Compound | MS m/e (M + H⁺) | |
|---|---|---|---|
| (pinacol boronate of 2-NHAc-pyridin-4-yl) | 33 | 452.1 | 4-[2-(acetylamino)-4-pyridinyl]-N-[2-[4-(aminomethyl)-1-piperidinyl]-3-fluorophenyl]-1H-imidazole-2-carboxamide |
| (pinacol boronate of 3-chlorophenyl) | 34 | 428.1 | N-[2-[4-(aminomethyl)-1-piperidinyl]-3-fluorophenyl]-4-(3-chlorophenyl)-1H-imidazole-2-carboxamide |
| (pinacol boronate of 2-NHBn-pyridin-4-yl) | 35 | 500.2 | N-[2-[4-(aminomethyl)-1-piperidinyl]-3-fluorophenyl]-4-[2-[(phenylmethyl)amino]-4-pyridinyl]-1H-imidazole-2-carboxamide |
| (pinacol boronate of 2-NMe₂-pyridin-4-yl) | 36 | 438.4 | N-[2-[4-(aminomethyl)-1-piperidinyl]-3-fluorophenyl]-4-[2-(dimethylamino)-4-pyridinyl]-1H-imidazole-2-carboxamide |

TABLE 2-continued

| Coupling Partner | Compound | MS m/e (M + H+) | |
|---|---|---|---|
| 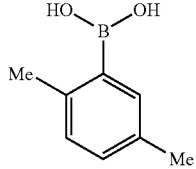 [SMILES: Cc1ccc(C)c(B(O)O)c1] | 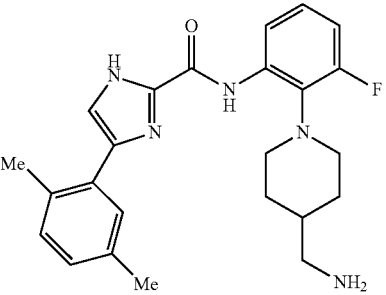 [SMILES: Cc1ccc(C)c(-c2c[nH]c(C(=O)Nc3cccc(F)c3N3CCC(CN)CC3)n2)c1] 37 | 422.2 | N-[2-[4-(aminomethyl)-1-pipendinyl]-3-fluorophenyl]-4-(2,5-dimethylphenyl)-1H-imidazole-2-carboxamide |
| 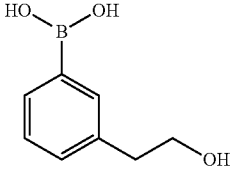 [SMILES: OCCc1cccc(B(O)O)c1] | 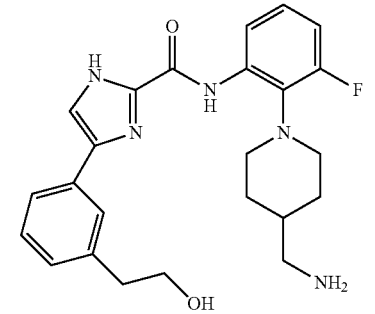 [SMILES: NCC1CCN(c2c(F)cccc2NC(=O)c2nc(-c3cccc(CCO)c3)c[nH]2)CC1] 41 | 438.2 | N-[2-[4-(aminomethyl)-1-piperidinyl]-3-fluorophenyl]-4-[3-(2-hydroxyethyl)phenyl]-1H-imidazole-2-carboxamide |
| 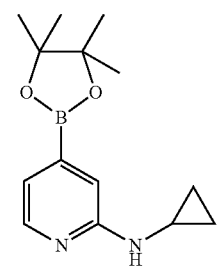 [SMILES: CC1(C)OB(c2ccnc(NC3CC3)c2)OC1(C)C] | 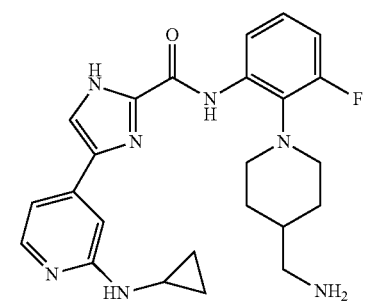 [SMILES: NCC1CCN(c2c(F)cccc2NC(=O)c2nc(-c3ccnc(NC4CC4)c3)c[nH]2)CC1] 42 | 450.2 | N-[2-[4-(aminomethyl)-1-piperidinyl]-3-fluorophenyl]-4-[2-(cyclopropylamino)-4-pyridinyl]-1H-imidazole-2-carboxamide |
| 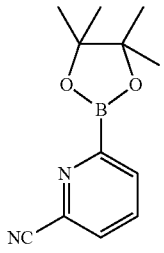 [SMILES: CC1(C)OB(c2cccc(C#N)n2)OC1(C)C] | 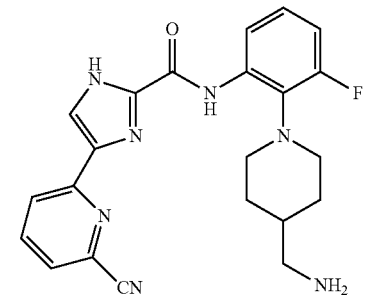 [SMILES: N#Cc1cccc(-c2c[nH]c(C(=O)Nc3cccc(F)c3N3CCC(CN)CC3)n2)n1] 44 | 420.1 | N-[2-[4-(aminomethyl)-1-piperidinyl]-3-fluorophenyl]-4-(6-cyano-2-pyridinyl)-1H-imidazole-2-carboxamide |

TABLE 2-continued

| Coupling Partner | Compound | MS m/e (M + H⁺) | |
|---|---|---|---|
| | | 442.1 | 4-(5-acetyl-2-thienyl)-N-[2-[4-(aminomethyl)-1-piperidinyl]-3-fluorophenyl]-1H-imidazole-2-carboxamide |
| | 45 | | |
| | | 452.1 | N-[2-[4-(aminomethyl)-1-piperidinyl]-3-fluorophenyl]-4-[3-(trifluoromethyl)-1H-pyrazol-5-yl]-1H-imidazole-2-carboxamide |
| | 48 | | |
| | | 384.2 | N-[2-[4-(aminomethyl)-1-piperidinyl]-3-fluorophenyl]-4-(1H-pyrazol-4-yl)-1H-imidazole-2-carboxamide |
| | 53 | | |
| | | 452.2 | methyl 3-[2-[[[2-[4-(aminomethyl)-1-piperidinyl]-3-fluorophenyl]amino]carbonyl]-1H-imidazol-4-yl]benzoate |
| | 56 | | |

| Coupling Partner | Compound | MS m/e (M + H⁺) | |
|---|---|---|---|
| (structure: pyrimidine boronic acid) | (structure: compound 63) | 396.2 | N-[2-[4-(aminomethyl)-1-piperidinyl]-3-fluorophenyl]-4-(5-pyrimidinyl)-1H-imidazole-2-carboxamide |

Example 3

Preparation of N-[2-(3(R)-amino-1-piperidinyl)-3-fluorophenyl]-4-bromo-1H-imidazole-2-carboxamide (12)

Example 4

Preparation of N-[2-[3(R)-[(aminocarbonyl)amino]-1-piperidinyl]-3-fluorophenyl]-4-bromo-1H-imidazole-2-carboxamide (15)

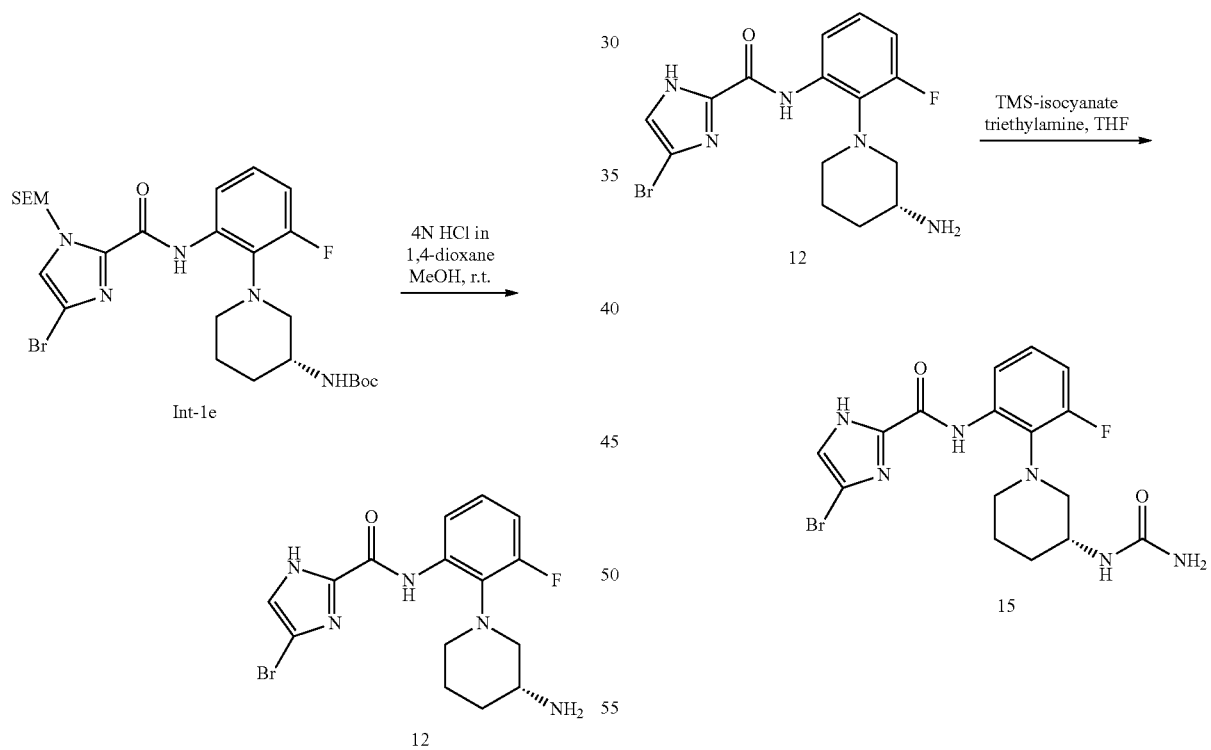

Amide Int-1e (51 mg, 0.083 mmol) was stirred in 4 N hydrochloric acid in 1,4-dioxane (5 mL) at 50° C. for 2 h. The solvents were removed in vacuo. Chromatographic purification [dichloromethane-methanol (7 N ammonia)] of the residue gave imidazole 12 (28 mg, 88%) as a colorless oil. LCMS m/e (M+H⁺)=382.2.

A mixture of imidazole 12 (29 mg, 0.076 mmol), trimethylsilyl isocyanate (18 mg, 0.15 mmol) and triethylamine (31 mg, 0.30 mmol) in tetrahydrofuran (1 mL) was stirred at r.t. for 4 h. Methanol (1 mL) was added and the mixture was stirred at r.t for 1 h. The solvents were removed in vacuo and chromatographic purification (ethyl acetate-hexane) of the residue gave urea 15 (21 mg, 64%) as a colorless oil. LCMS m/e (M+H⁺)=425.2.

Example 5

Preparation of N-[2-(3(R)-amino-1-piperidinyl)-3-fluorophenyl]-4-[1-(phenylmethyl)-1H-pyrazol-4-yl]-1H-imidazole-2-carboxamide (4)

Step A—Synthesis of Ethyl 4-(1-benzyl-1H-pyrazol-4-yl)-1-((2-(trimethylsilyl)ethoxy)methyl)-1H-imidazole-2-carboxylate (Int-5a)

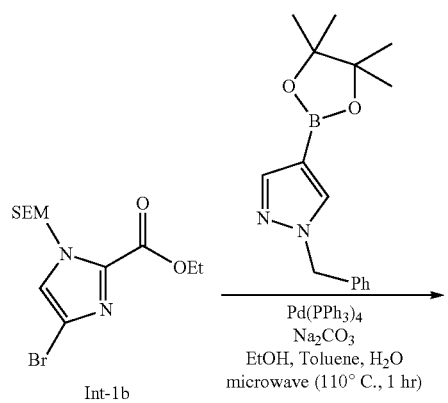

A mixture of bromoimidazole Int-1b (0.46 g, 1.32 mmol), 1-benzylpyrazole-4-boronic acid pinacol ester (0.45 g, 1.58 mmol) and sodium carbonate (420 mg, 3.96 mmol) in toluene (1 mL), ethanol (1 mL) and water (0.5 mL) at r.t. was purged with nitrogen gas for 5 min in a microwave vial. Tetrakistriphenylphosphorous palladium (152 mg, 0.132 mmol) was added. The mixture was heated in a microwave reactor at 110° C. for 1 h. Water and ethyl acetate were added and layers were separated. The separated aqueous layer was extracted with ethyl acetate. The separated organic layer was dried (MgSO₄) and filtered. The solvents were removed in vacuo and chromatographic purification (ethyl acetate-hexane) of the residue gave pyrazole Int-5a (0.38 g, 69%) as a yellow oil.

Step B—Synthesis of Lithium 4-(1-benzyl-1H-pyrazol-4-yl)-1-((2-(trimethylsilyl)ethoxy)methyl)-1H-imidazole-2-carboxylate (Int-5b)

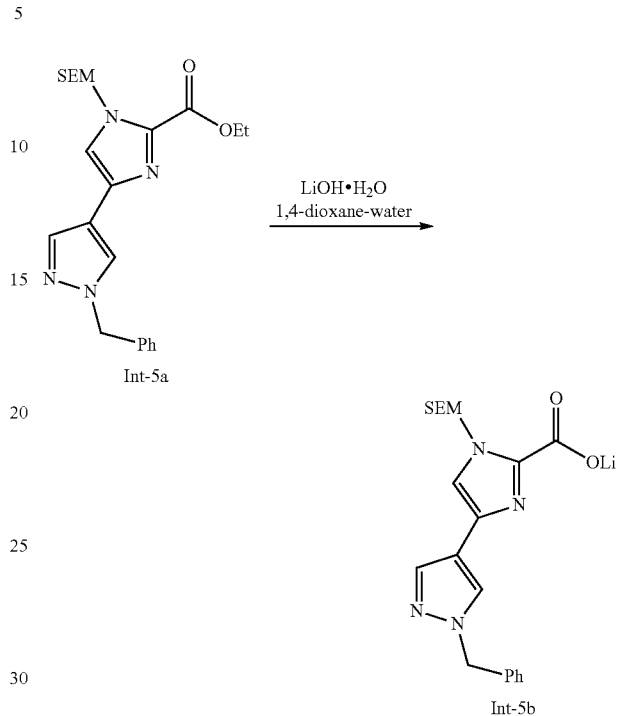

A solution of lithium hydroxide (38 mg, 0.90 mol) in water (3 mL) was added to a stirred solution of pyrazole Int-5a (320 mg, 0.75 mmol) in 1,4-dioxane (6 mL) at r.t. The mixture was stirred at r.t. overnight and solvents were removed in vacuo to give carboxylate Int-5b as a white solid. The solid was used in the next step without further purification.

Step C—Synthesis of (R)-tert-butyl 1-(2-(4-(1-benzyl-1H-pyrazol-4-yl)-1-((2-(trimethylsilyl)ethoxy)methyl)-1H-imidazole-2-carboxamido)-6-fluorophenyl)piperidin-3-ylcarbamate (Int-5c)

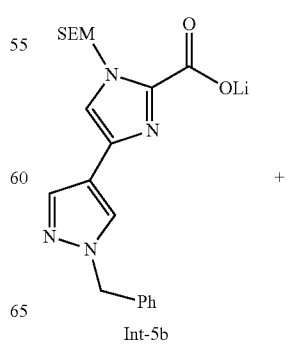

+

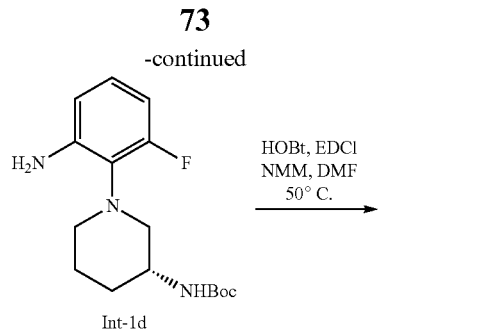

Int-1d

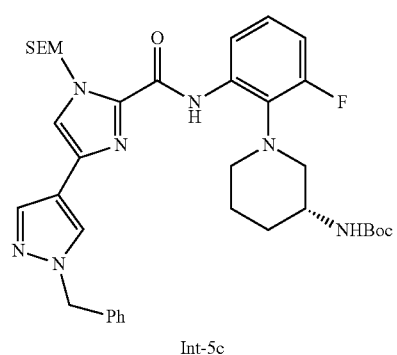

Int-5c

A mixture of carboxylate Int-5b (55 mg, 0.14 mmol), aniline Int-id (44 mg, 0.14 mmol), HOBt (37 mg, 0.28 mmol), EDCI (53 mg, 0.28 mmol) and NMM (7 mg, 0.069 mmol) was stirred in N,N-dimethylformamide (2 mL) at 50° C. overnight. Water and ethyl acetate were added, and the layers were separated. The separated organic layer was washed with water. The separated organic layer was dried (MgSO$_4$) and filtered. The solvents were removed in vacuo and chromatographic purification (ethyl acetate-hexane) of the residue gave amide Int-5c (76 mg, 80%) as a white solid.

Step D—Synthesis of N-[2-(3(R)-amino-1-piperidinyl)-3-fluorophenyl]-4-[1-(phenylmethyl)-1H-pyrazol-4-yl]-1H-imidazole-2-carboxamide (4)

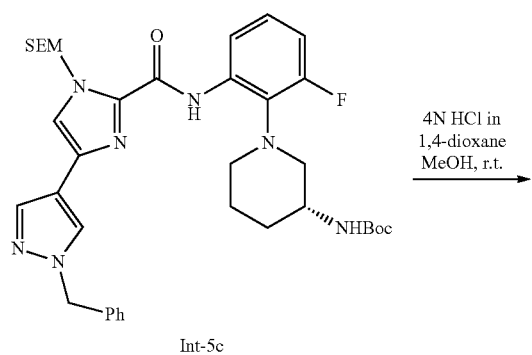

Int-5c

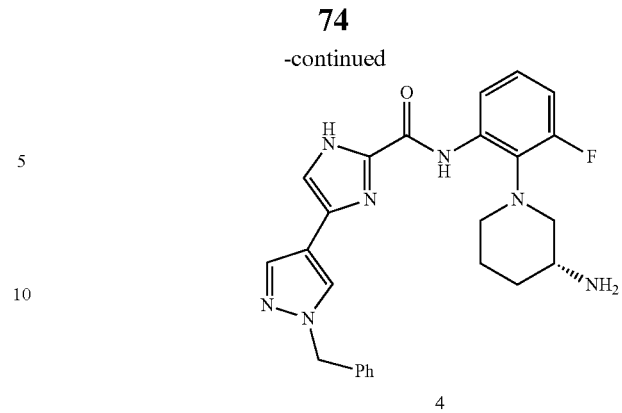

Amide Int-5c (11 mmol) was stirred in a mixture of methanol (1 mL) and 4 N hydrochloric acid in 1,4-dioxane (3 mL) at r.t. overnight. The solvents were removed in vacuo. Chromatographic purification [dichloromethane-methanol (7 N ammonia)] of the residue gave imidazole 4 (45 mg, 88%) as a colorless oil. LCMS m/e (M+H$^+$)=460.3.

Example 6

Preparation of N-[2-(3(R)-amino-1-piperidinyl)-3-fluorophenyl]-4-[1-(3-pyridinylmethyl)-1H-pyrazol-4-yl]-1H-imidazole-2-carboxamide (13)

Step A—Synthesis of (R)-tert-butyl 1-(2-(4-(1H-pyrazol-4-yl)-1-((2-(trimethylsilyl)ethoxy)methyl)-1H-imidazole-2-carboxamido)-6-fluorophenyl)piperidin-3-ylcarbamate (Int-6a)

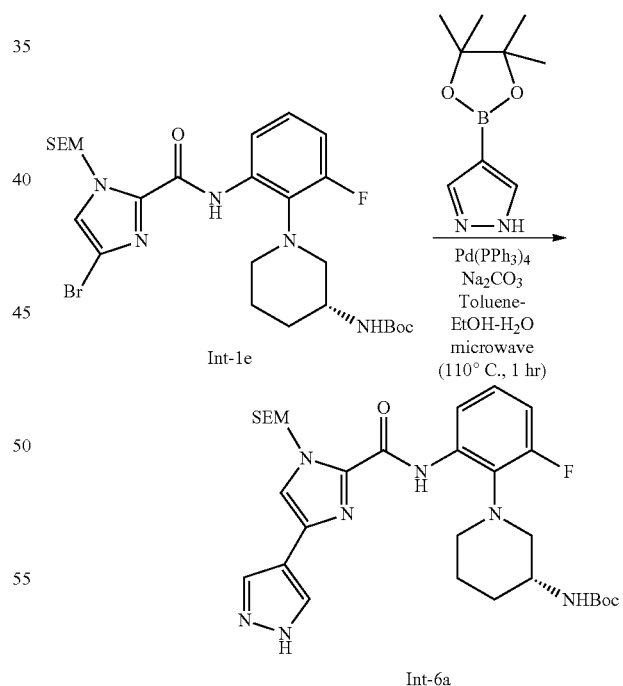

A mixture of bromide Int-1e (200 mg, 0.33 mmol), 4-(4,4,5,5-tetramethyl-1,3,2-dioxaborolan-2-yl)-1H-pyrazole (64 mg, 0.33 mmol) and sodium carbonate (104 mg, 0.98 mmol) in ethanol (1 mL), toluene (1 mL) and water (0.5 mL) at r.t. was purged with nitrogen gas for 5 min in a microwave vial. Tetrakistriphenyl-phosphorous palladium (38 mg, 0.033 mmol) was added. The mixture was heated in a microwave reactor at 110° C. for 1 h. Water and ethyl acetate were added and layers were separated. The separated aqueous layer was extracted with ethyl acetate. The separated organic layer was dried (MgSO₄) and filtered. The solvents were removed in vacuo and chromatographic purification (ethyl acetate-hexane) of the residue gave pyrazole Int-6a (73 mg, 37%) as a white solid.

Step B—Synthesis of (R)-tert-butyl 1-(2-fluoro-6-(4-(1-(pyridin-3-ylmethyl)-1H-pyrazol-4-yl)-1-((2-(trimethylsilyl)ethoxy)methyl)-1H-imidazole-2-carboxamido)phenyl)piperidin-3-ylcarbamate (Int-6b)

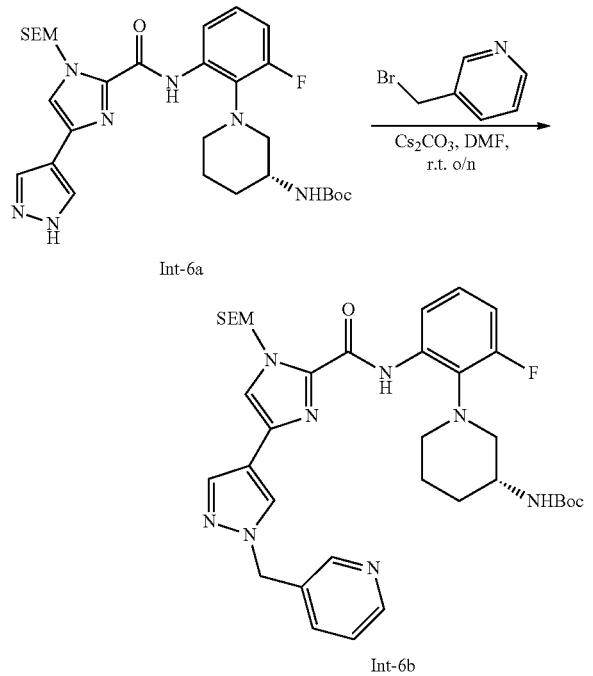

A mixture of pyrazole Int-6a (30 mg, 0.050 mmol), 3-(bromomethyl)pyridine (14 mg, 0.055 mmol) and cesium carbonate (39 mg, 0.10 mmol) in N,N-dimethylformamide (2 mL) was stirred at r.t. overnight. Water and ethyl acetate were added, and the layers were separated. The separated aqueous layer was extracted with ethyl acetate. The separated organic layer was dried (MgSO₄) and filtered. The solvents were removed in vacuo and chromatographic purification (ethyl acetate-hexane) of the residue gave pyridine Int-6b.

Step C—N-[2-(3(R)-amino-1-piperidinyl)-3-fluorophenyl]-4-[1-(3-pyridinylmethyl)-1H-pyrazol-4-yl]-1H-imidazole-2-carboxamide (13)

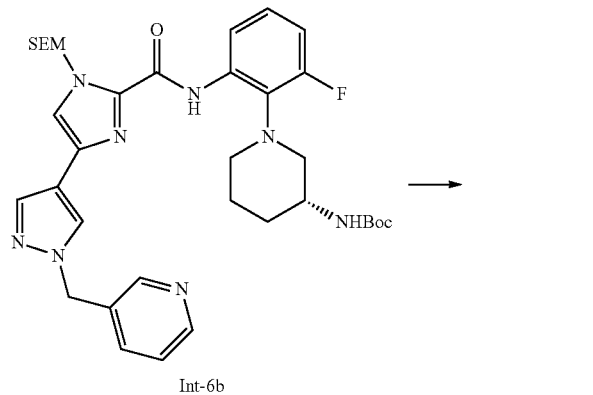

Pyridine Int-6b from above was stirred in 4 N hydrochloric acid in 1,4-dioxane and methanol at r.t. overnight. The solvents were removed in vacuo. Chromatographic purification [dichloromethane-methanol (10% ammonia)] of the residue gave imidazole 13. Imidazole 13 was dissolved in MeOH and excess hydrochloric acid (1 M, in ether) was added. The solvents were removed to give hydrochloric salt of 13 (8 mg) as brown solid. LCMS m/e (M+H⁺)=461.3.

Example 7

Preparation of 4-(2-amino-6-methyl-4-pyridinyl)-N-[2-(3(R)-amino-1-piperidinyl)-3-fluorophenyl]-1H-imidazole-2-carboxamide (24)

Step A—Synthesis of (R)-tert-butyl 1-(2-(4-(2-chloro-6-methylpyridin-4-yl)-1-((2-(trimethylsilyl)ethoxy)methyl)-1H-imidazole-2-carboxamido)-6-fluorophenyl)piperidin-3-ylcarbamate (Int-7a)

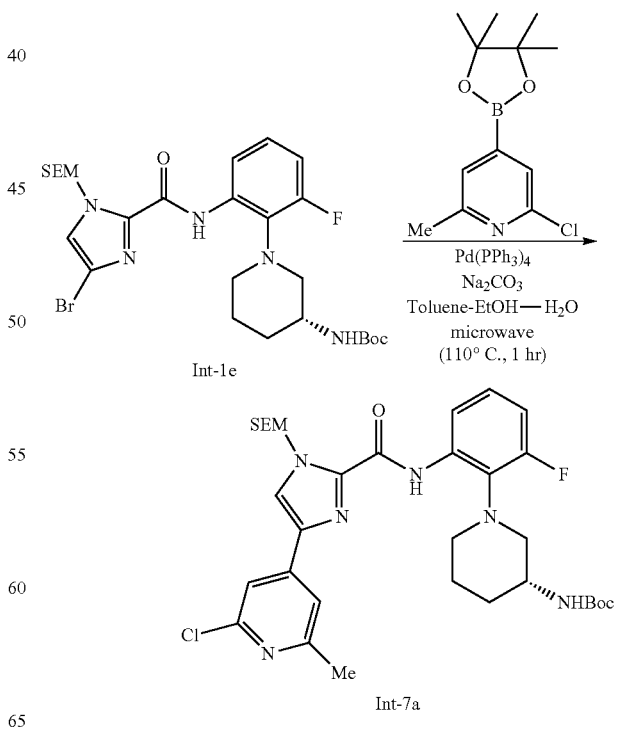

A mixture of bromide Int-1e (372 mg, 0.061 mmol), 2-chloro-6-methyl-4-(4,4,5,5-tetramethyl-1,3,2-dioxaborolan-2-yl)pyridine (154 mg, 0.061 mmol) and sodium carbonate (194 mg, 1.83 mmol) in ethanol (2 mL), toluene (2 mL) and water (1 mL) at r.t. was purged with nitrogen gas for 5 min in a microwave vial. Tetrakistriphenylphosphorous palladium (70 mg, 0.061 mmol) was added. The mixture was heated in a microwave reactor at 100° C. for 1 h. Water and ethyl acetate were added and layers were separated. The separated aqueous layer was extracted with ethyl acetate. The separated organic layer was dried (MgSO$_4$) and filtered. The solvents were removed in vacuo and chromatographic purification (ethyl acetate-hexane) of the residue gave chloropyridine Int-7a (60 mg, 15%) as white foam. LCMS m/e (M+H$^+$)=659.2.

Step B—Synthesis of 4-(2-amino-6-methyl-4-pyridinyl)-N-[2-(3(R)-amino-1-piperidinyl)-3-fluorophenyl]-1H-imidazole-2-carboxamide (24)

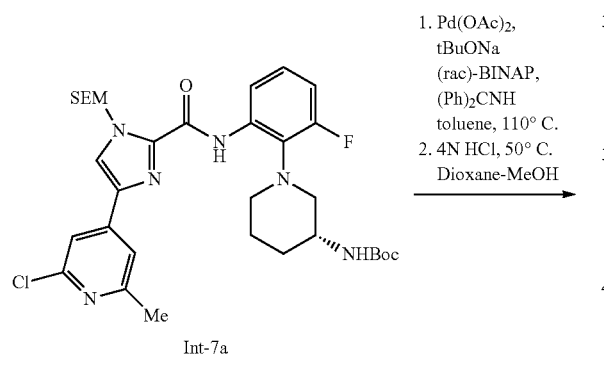

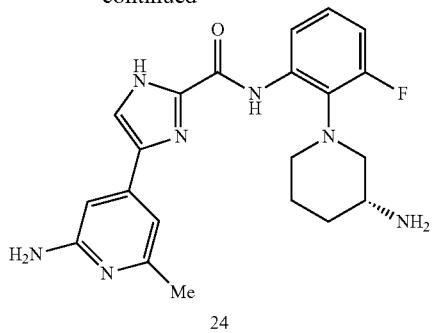

A mixture of chloropyridine Int-7a (30 mg, 0.046 mmol), palladium (II) acetate (0.5 mg, 0.0023 mmol), rac-BINAP (6 mg, 0.0091 mmol), sodium tert-butoxide (7 mg, 0.068 mmol), diphenylmethanimine (16 mg, 0.091 mmol) was stirred in toluene (2 mL) at r.t. The mixture was purged with nitrogen for 5 min. and was heated at 110° C. for 4 h. After being cooled to r.t., methanol (2 mL) and 4 N hydrochloric acid in 1,4-dioxane (2 mL) were added. The mixture was heated at 50° C. for 1 h. After being cooled to r.t. and solvents were removed in vacuo. Chromatographic purification [dichloromethane-methanol (7 N ammonia)] of the residue gave aminopyridine 24 (12 mg, 62%) as a white foam. LCMS m/e (M+H$^+$)=410.1.

Example 8

Preparation of N-[2-(3(R)-amino-1-piperidinyl)-3-fluorophenyl]-4-[2-(hydroxymethyl)-4-pyridinyl]-1H-imidazole-2-carboxamide (26)

Step A—(R)-methyl 4-(2-(2-(3-(tert-butoxycarbonylamino)piperidin-1-yl)-3-fluorophenylcarbamoyl)-1-((2-(trimethylsilyl)ethoxy)methyl)-1H-imidazol-4-yl)picolinate (Int-8a)

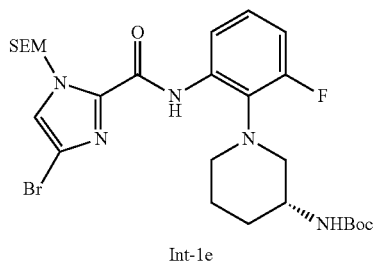

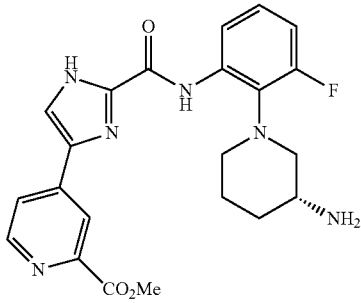
Int-8a

A mixture of bromide Int-13 (90 mg, 0.15 mmol), 4-(4,4,5,5-tetramethyl-1,3,2-dioxaborolan-2-yl)picolinonitrile (37 mg, 0.16 mmol) and sodium hydrogen phosphate (63 mg, 0.44 mmol) in 1,4-dioxane (2 mL) and water (1 mL) at r.t. was purged with nitrogen gas for 5 min in a microwave vial. Tetrakistriphenylphosphorous palladium (17 mg, 0.015 mmol) was added. The mixture was heated in a microwave reactor at 110° C. for 1 h. Water and ethyl acetate were added and layers were separated. The separated aqueous layer was extracted with ethyl acetate. The separated organic layer was dried (MgSO$_4$) and filtered. The solvents were removed in vacuo and chromatographic purification (ethyl acetate-hexane) of the residue gave a colorless oil. The colorless oil was stirred in methanol (2 mL) and 4 N hydrochloric acid in 1,4-dioxane (2 mL) at 50° C. overnight. After being cooled to r.t. and solvents were removed in vacuo. Chromatographic purification [dichloromethane-methanol (7 N ammonia)] of the residue gave methyl ester Int-8a (20 mg, 31%) as a white foam. LCMS m/e (M+H$^+$)=439.1.

Step B—N-[2-(3(R)-amino-1-piperidinyl)-3-fluorophenyl]-4-[2-(hydroxymethyl)-4-pyridinyl]-1H-imidazole-2-carboxamide (26)

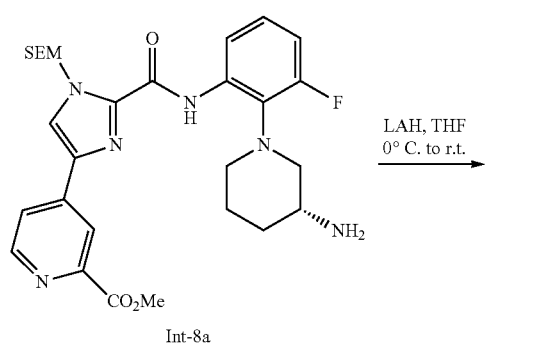

Methyl ester Int-8a (20 mg, 0.046 mmol) was stirred in tetrahydrofuran (2 mL) at 0° C. Lithium aluminum hydride (0.1 mL, 1 M in tetrahydrofuran) was added. The mixture was allowed to warm to r.t. and was quenched with a saturated solution of potassium sodium tartrate. Methanol and silica were added and the solvents were removed in vacuo. Chromatographic purification [dichloromethane-methanol (7 N ammonia)] of the residue gave hydroxymethylpyridine 26 (10 mg, 55%) as a colorless oil. LCMS m/e (M+H$^+$)=411.1.

Example 9

Preparation of N-[5-amino-2-(3(R)-amino-1-piperidinyl)phenyl]-1H-imidazole-2-carboxamide (1)

Step A—Synthesis of Int-9a

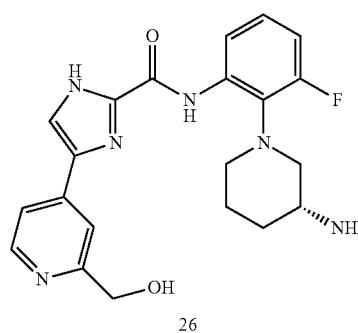

A mixture of 4-fluoro-3-nitroaniline (30 g, 0.192 mol), di-t-butylcarbonate (84 g, 0.384 mol) was stirred in ethanol (300 mL) at r.t. for 1 week. The solvents were removed in vacuo and chromatographic purification (ethyl acetate-hexane) of the residue gave tert-butyl 4-fluoro-3-nitrophenylcarbamate (43 g, 88%) as a white solid.

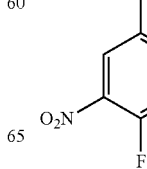 + 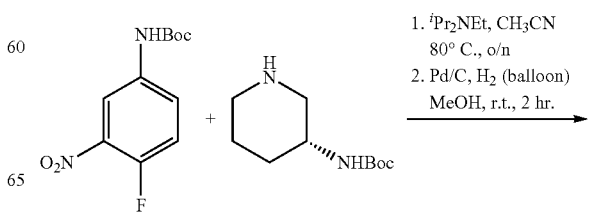

-continued

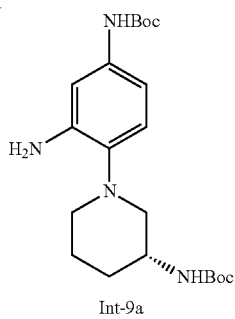

Int-9a

Using the starting materials, tert-butyl 4-fluoro-3-nitrophenylcarbamate and (R)-tert-butyl piperidin-3-ylcarbamate, Int-9a was prepared using procedures similar to those described in Step D of Example 1.

Step B—Synthesis of Int-9b

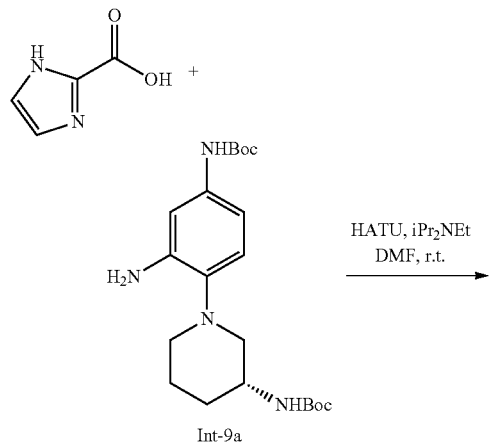

Int-9a

A mixture of 1H-imidazole-2-carboxylic acid (15 mg, 0.13 mmol), aniline Int-9a (54 mg, 0.13 mmol), diisopropylethylamine (46 µL, 0.27 mmol) and HATU (56 mg, 0.15 mmol) was stirred in N,N-dimethylformamide (3 mL) at r.t. overnight. Water and ethyl acetate were added, and the layers were separated. The separated organic layer was washed with water. The separated organic layer was dried (MgSO₄) and filtered. The solvents were removed in vacuo and chromatographic purification (ethyl acetate-hexane) of the residue gave amide Int-9b (21 mg, 32%) as a white solid.

Step C—Synthesis of N-[5-amino-2-(3(R)-amino-1-piperidinyl)phenyl]-1H-imidazole-2-carboxamide (1)

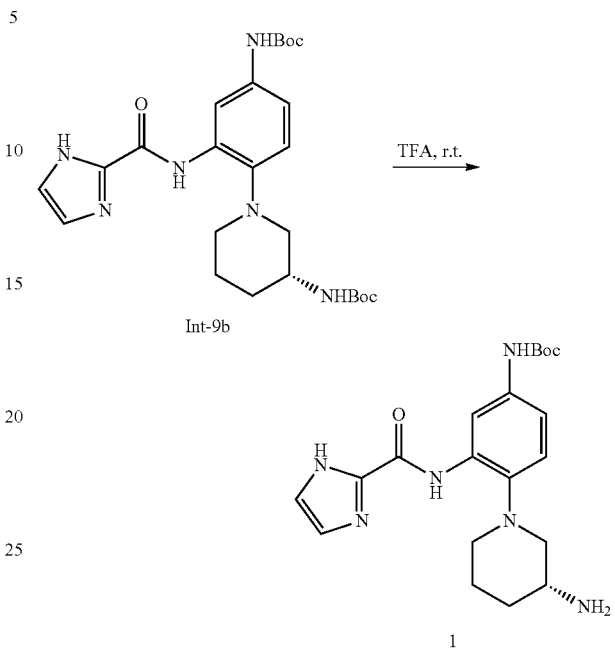

Amide Int-9b (21 mg, 0.042 mmol) was stirred in trifluoroacetic acid (3 mL) for 2 h. The solvents were removed in vacuo. Chromatographic purification [dichloromethane-methanol (7 N ammonia)] of the residue gave imidazole 1 (9 mg, 73%) as a white solid. LCMS m/e (M+H⁺)=301.2.

Example 10

Preparation of N-[5-amino-2-(3(R)-amino-1-piperidinyl)phenyl]-4-bromo-1H-imidazole-2-carboxamide (16)

Step A—Synthesis of Int 10a

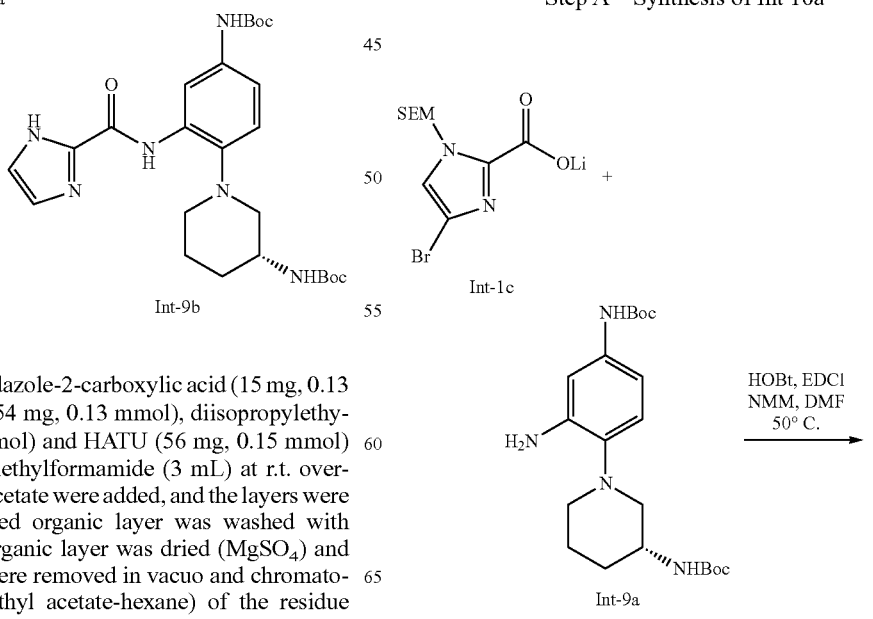

Int-1c

Int-9a

-continued

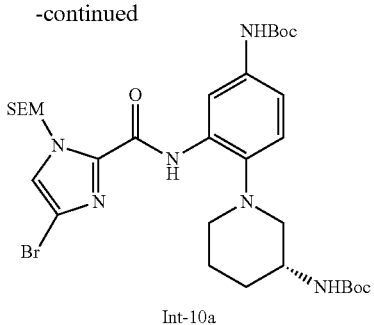
Int-10a

A mixture of carboxylate Int-1c (56 mg, 0.17 mmol), aniline Int-9a (71 mg, 0.17 mmol), HOBt (47 mg, 0.35 mmol), EDCI (66 mg, 0.35 mmol) and NMM (9 mg, 0.087 mmol) was stirred in N,N-dimethylformamide (3 mL) at 50° C. overnight. Water and ethyl acetate were added, and the layers were separated. The separated organic layer was washed with water. The separated organic layer was dried (MgSO$_4$) and filtered. The solvents were removed in vacuo and chromatographic purification (ethyl acetate-hexane) of the residue gave amide Int-10a (96 mg, 78%) as a white solid.

Step B—Synthesis of N-[5-amino-2-(3(R)-amino-1-piperidinyl)phenyl]-4-bromo-1H-imidazole-2-carboxamide (16)

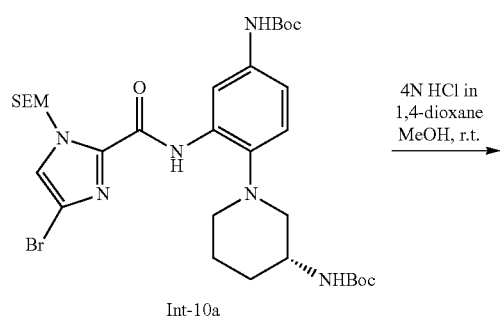

Amide Int-10a (25 mg, 0.035 mmol) was stirred in 4 N hydrochloric acid in 1,4-dioxane (2 mL) at r.t. overnight. The solvents were removed in vacuo. Chromatographic purification [dichloromethane-methanol (7 N ammonia)] of the residue gave imidazole 16 (11 mg, 83%) as a white solid. LCMS m/e (M+H$^+$)=489.

Example 11

Preparation of N-[5-amino-2-[4-(aminomethyl)-1-piperidinyl]phenyl]-1H-imidazole-2-carboxamide (3)

Step A—Synthesis of Int-11a

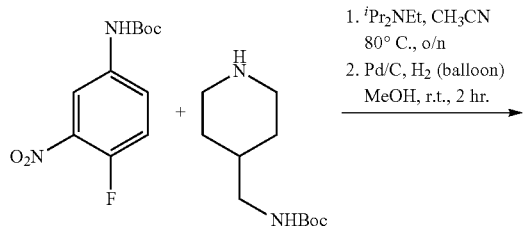

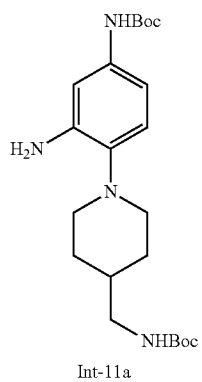
Int-11a

Using the starting materials, tert-butyl 4-fluoro-3-nitrophenylcarbamate and tert-butyl piperidin-4-ylmethylcarbamate, Int-11a was prepared using procedures similar to those described in Step D of Example 1.

Step B—Synthesis of Int-11b

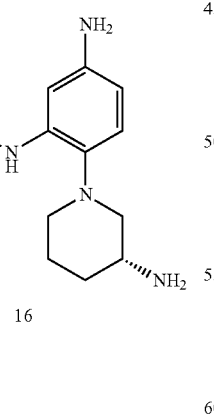
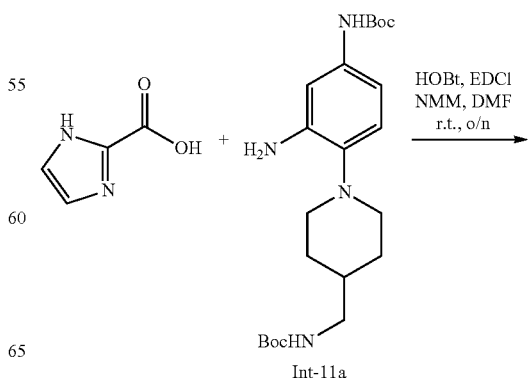
Int-11a

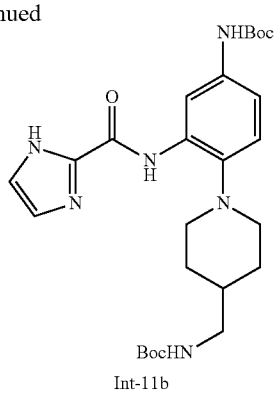

Int-11b

A mixture of 1H-imidazole-2-carboxylic acid (15 mg, 0.13 mmol), aniline Int-11a (56 mg, 0.13 mmol), HOBt (36 mg, 0.27 mmol), EDCI (51 mg, 0.27 mmol) and NMM (7 mg, 0.067 mmol) was stirred in N,N-dimethylformamide (2 mL) at r.t. overnight. Water and ethyl acetate were added, and the layers were separated. The separated organic layer was washed with water. The separated organic layer was dried (MgSO$_4$) and filtered. The solvents were removed in vacuo and chromatographic purification (ethyl acetate-hexane) of the residue gave amide Int-11b (57 mg, 83%) as a white solid.

Step C—Synthesis of N-[5-amino-2-[4-(aminomethyl)-1-piperidinyl]phenyl]-1H-imidazole-2-carboxamide (3)

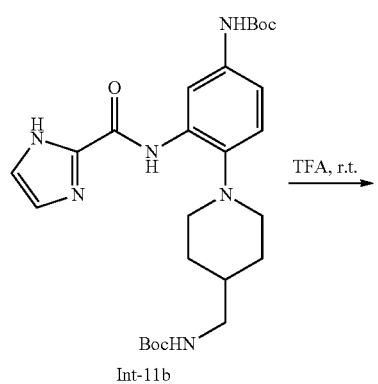

Int-11b

TFA, r.t.

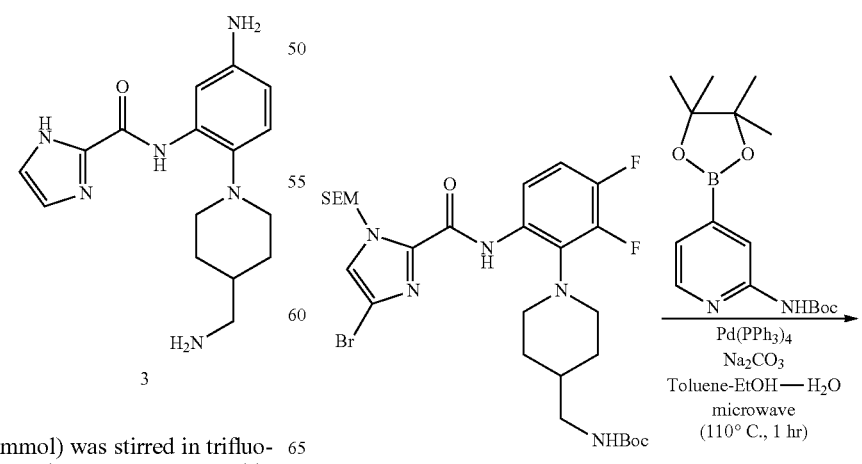

3

Amide Int-11b (57 mg, 0.11 mmol) was stirred in trifluoroacetic acid (3 mL) for 1 h. The solvents were removed in vacuo. Chromatographic purification [dichloromethane-methanol (7 N ammonia)] of the residue gave imidazole 3 (24 mg, 70%) as a white solid. LCMS m/e (M+H$^+$)=315.2.

Example 12

Preparation of N-[2-[4-(aminomethyl)-1-piperidinyl]-3,4-difluorophenyl]-4-(2-amino-4-pyridinyl)-1H-imidazole-2-carboxamide (28)

Step A—Synthesis of Int-12a

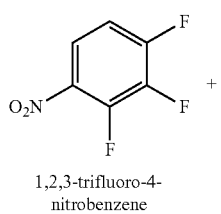

1,2,3-trifluoro-4-nitrobenzene

+

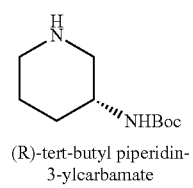

(R)-tert-butyl piperidin-3-ylcarbamate

1. $^i$Pr$_2$NEt, CH$_3$CN
80° C., o/n
2. Pd/C, H$_2$ (balloon)
MeOH, r.t., 2 hr.

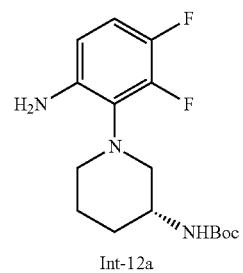

Int-12a

Using the starting materials, 1,2,3-trifluoro-4-nitrobenzene and (R)-tert-butyl piperidin-3-ylcarbamate, Int-12a was prepared using procedures similar to those described in Step D of Example 1.

Step B—Synthesis of Int-12b

-continued

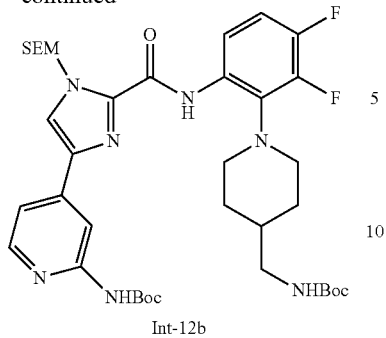
Int-12b

A mixture of bromide Int-12a (65 mg, 0.10 mmol), tert-butyl 4-(4,4,5,5-tetramethyl-1,3,2-dioxaborolan-2-yl)pyridin-2-ylcarbamate (27 mg, 0.12 mmol) and sodium carbonate (32 mg, 0.30 mmol) in ethanol (1 mL), toluene (1 mL) and water (0.5 mL) at r.t. was purged with nitrogen gas for 5 min in a microwave vial. Tetrakistriphenylphosphorous palladium (12 mg, 0.010 mmol) was added. The mixture was heated in a microwave reactor at 110° C. for 1 h. Water and ethyl acetate were added, and the layers were separated. The separated aqueous layer was extracted with ethyl acetate. The separated organic layer was dried (MgSO$_4$) and filtered. The solvents were removed in vacuo and chromatographic purification (ethyl acetate-hexane) of the residue gave aminopyridine Int-12b (46 mg, 69%) as a colorless oil. LCMS m/e (M+H$^+$)=658.3.

Step C—Synthesis of N-[2-[4-(aminomethyl)-1-piperidinyl]-3,4-difluorophenyl]-4-(2-amino-4-pyridinyl)-1H-imidazole-2-carboxamide (28)

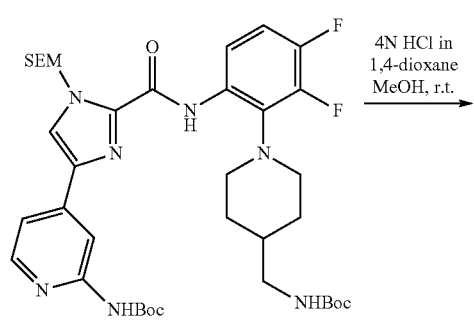
Int-12b

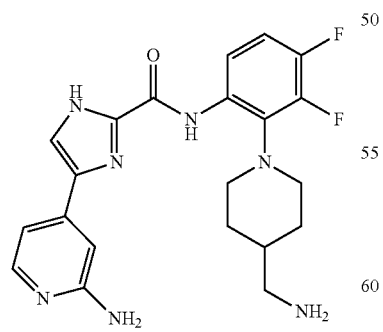
28

Aminopyridine Int-12b (46 mg, 0.097 mmol) was stirred in 4 N hydrochloric acid in 1,4-dioxane (2 mL) and methanol (2 mL) at 50° C. for 2 h. The solvents were removed in vacuo.

Chromatographic purification [dichloromethane-methanol (7 N ammonia)] of the residue gave imidazole 28 (24 mg, 81%) as a white solid. LCMS m/e (M+H$^+$)=428.1.

Example 13

Preparation of 4-(2-amino-4-pyridinyl)-N-[2-[4-[(dimethylamino)methy]-1-piperidinyl]phenyl]-1H-imidazole-2-carboxamide (40)

Step A and B—Synthesis of Int-13b

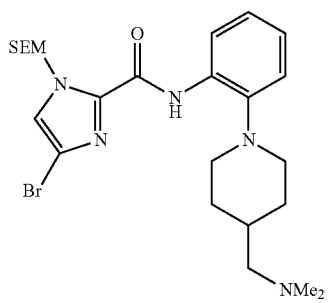
Int-13b

Starting from 1-fluoro-2-nitrobenzene and N,N-dimethyl-1-(piperidin-4-yl)methanamine (Int-13a), Int-13b was prepared using procedures similar to those described in Steps D and E of Example 1.

Step B—Synthesis of tert-butyl 4-(2-(2-(4-((dimethylamino)methyl)piperidin-1-yl)phenylcarbamoyl)-1-((2-(trimethylsilyl)ethoxy)methyl)-1H-imidazol-4-yl)pyridin-2-ylcarbamate (Int-13c)

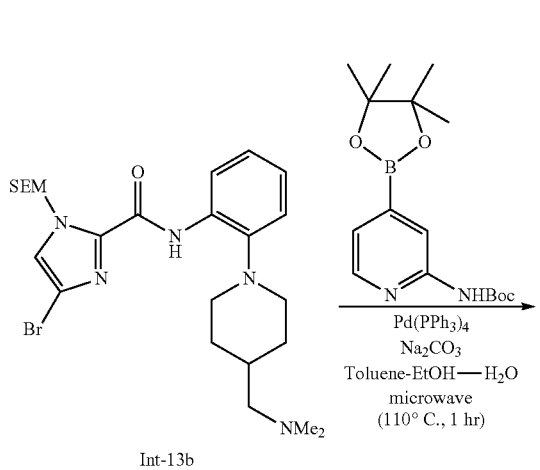
Int-13b

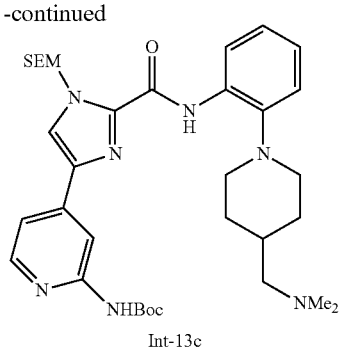

Int-13c

A mixture of bromide Int-13b (55 mg, 0.10 mmol), tert-butyl 4-(4,4,5,5-tetramethyl-1,3,2-dioxaborolan-2-yl)pyridin-2-ylcarbamate (39 mg, 0.12 mmol) and sodium carbonate (33 mg, 0.31 mmol) in ethanol (1 mL), toluene (1 mL) and water (0.5 mL) at r.t. was purged with nitrogen gas for 5 min in a microwave vial. Tetrakistriphenylphosphorous palladium (12 mg, 0.010 mmol) was added. The mixture was heated in a microwave reactor at 110° C. for 1 h. Water and ethyl acetate were added and the layers were separated. The separated aqueous layer was extracted with ethyl acetate. The separated organic layer was dried (MgSO$_4$) and filtered. The solvents were removed in vacuo and chromatographic purification (ethyl acetate-hexane) of the residue gave aminopyridine Int-13c (27 mg, 41%) as a colorless oil.

Step C—4-(2-amino-4-pyridinyl)-N-[2-[4-[(dimethylamino)methyl]-1-piperidinyl]phenyl]-1H-imidazole-2-carboxamide (40)

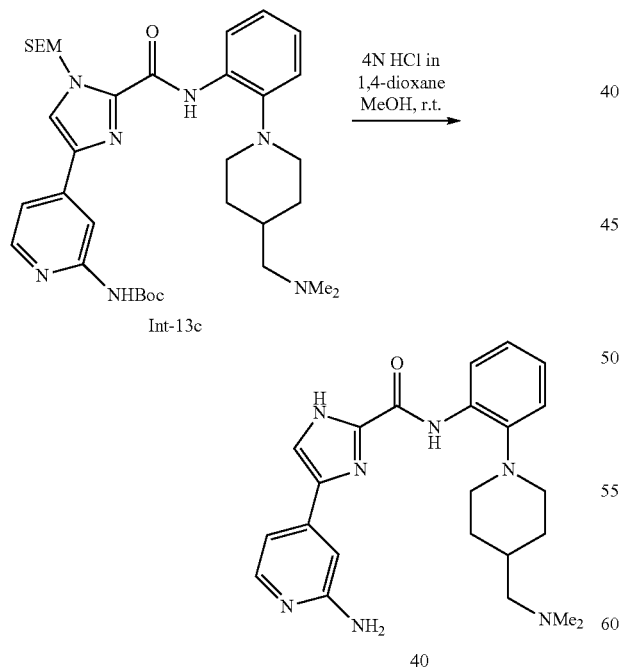

40

Aminopyridine Int-13c (62 mg, 0.097 mmol) was stirred in 4 N hydrochloric acid in 1,4-dioxane (1 mL) and methanol (4 mL) at 50° C. for 2 h. The solvents were removed in vacuo. Chromatographic purification [dichloromethane-methanol (7 N ammonia)] of the residue gave imidazole 40 (13 mg, 77%) as a white solid. LCMS m/e (M+H$^+$)=420.2.

Example 14

Preparation of 1-[4-amino-2-[(1H-imidazol-2-ylcarbonyl)amino]phenyl]-4-(methylamino)-4-piperidinecarboxamide (2)

Step A—Synthesis of Int-14b

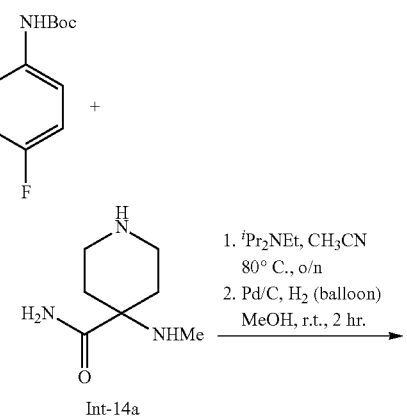

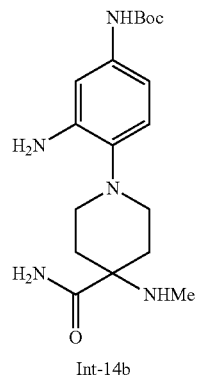

Int-14b

Using the starting materials, 1 tert-butyl 4-fluoro-3-nitrophenylcarbamate and 4-(methylamino)piperidine-4-carboxamide, Int-14b was prepared using procedures similar to those described in Step D of Example 1. The synthesis of 4-(methylamino)piperidine-4-carboxamide (Int-14a) is described in U.S. Pat. No. 3,155,669 and Metwally et al., *J. Medicinal Chem.* 41, 5084-5093 (1998).

Step B—Synthesis of tert-butyl 4-(4-carbamoyl-4-(methylamino)piperidin-1-yl)-3-(1H-imidazole-2-carboxamido)phenylcarbamate (Int-14b)

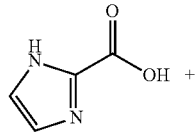

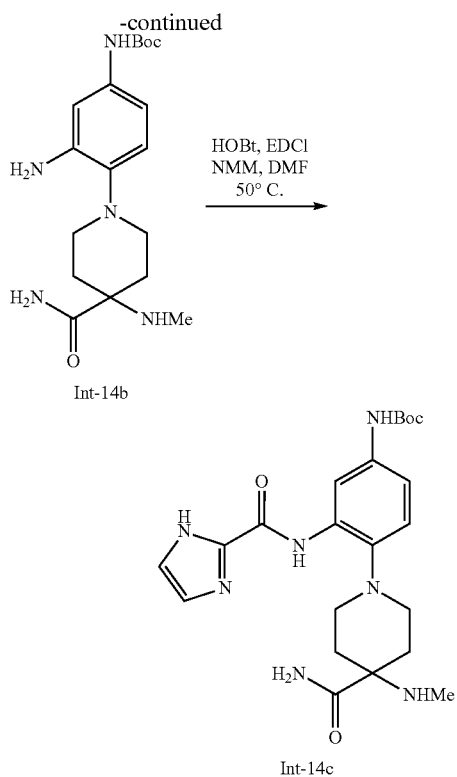

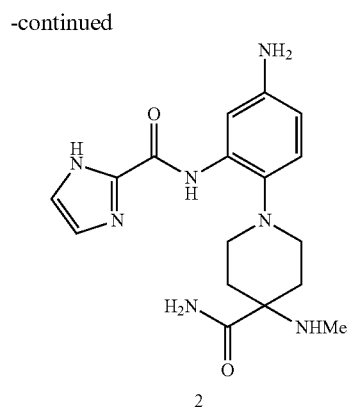

Amide Int-14c (26 mg, 0.057 mmol) was stirred in trifluoroacetic acid (3 mL) for 1 h. The solvents were removed in vacuo. Chromatographic purification [dichloromethane-methanol (7 N ammonia)] of the residue gave imidazole 2 (16 mg, 78%) as a white solid. LCMS m/e (M+H$^+$)=358.2.

A mixture of 1H-imidazole-2-carboxylic acid (19 mg, 0.17 mmol), aniline Int-14b (60 mg, 0.17 mmol), HATU (69 mg, 0.18 mmol), diisopropylethylamine (57 µL, 0.33 mmol) was stirred in N,N-dimethylformamide (2 mL). Water and ethyl acetate were added, and the layers were separated. The separated organic layer was washed with water. The separated organic layer was dried (MgSO$_4$) and filtered. The solvents were removed in vacuo and chromatographic purification (ethyl acetate-hexane) of the residue gave amide Int-14c (26 mg, 35%) as a white solid.

Step C—Synthesis of 1-[4-amino-2-[(1H-imidazol-2-ylcarbonyl)amino]phenyl]-4-(methylamino)-4-piperidinecarboxamide (2)

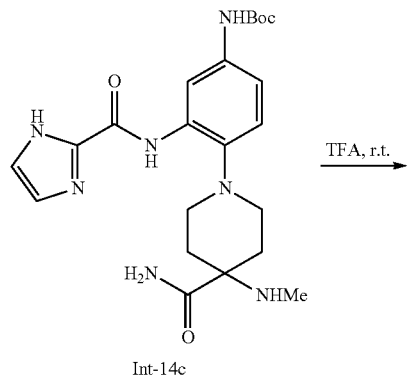

Example 15

Preparation of N-[2-[4-(aminomethyl)-1-piperidinyl]-5-(1H-pyrazol-4-yl)phenyl]-4-(1H-pyrazol-4-yl)-1H-imidazole-2-carboxamide (51)

Step A—Synthesis of 4-(4,4,5,5-tetramethyl-1,3,2-dioxaborolan-2-yl)-1-((2-(trimethylsilyl)ethoxy)methyl)-1H-pyrazole (Int-15a)

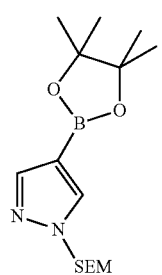 [SMILES: CC1(C)OB(c2cnn(COCC[Si](C)(C)C)c2)OC1(C)C]

To a solution of 4-(4,4,5,5-tetramethyl-1,3,2-dioxaborolan-2-yl)-1H-pyrazole (8.2 g, 41 mmol) in NMP (60 mL) was added K$_2$CO$_3$ (12 g, 82 mmol) and 2-(trimethylsilyl)ethoxymethyl chloride (7.8 mL, 43 mmol) in sequence. The reaction mixture was stirred at r.t. under N$_2$ for 16 h. Then, the reaction mixture was diluted and filtered, and then the filtrate was diluted with EtOAc (300 mL). The resulting solution was washed with sat. NaHCO$_3$ (aq) (3×200 mL), H$_2$O (4×200 mL), brine (1×200 mL), dried over Na$_2$SO$_4$, filtered, concentrated and dried in vacuo to yield intermediate Int-15a (11.4 g, 86%) as a clear yellowish oil.

Step B—Synthesis of tert-butyl (1-(4-bromo-2-nitrophenyl)piperidin-4-yl)methylcarbamate (Int-15b)

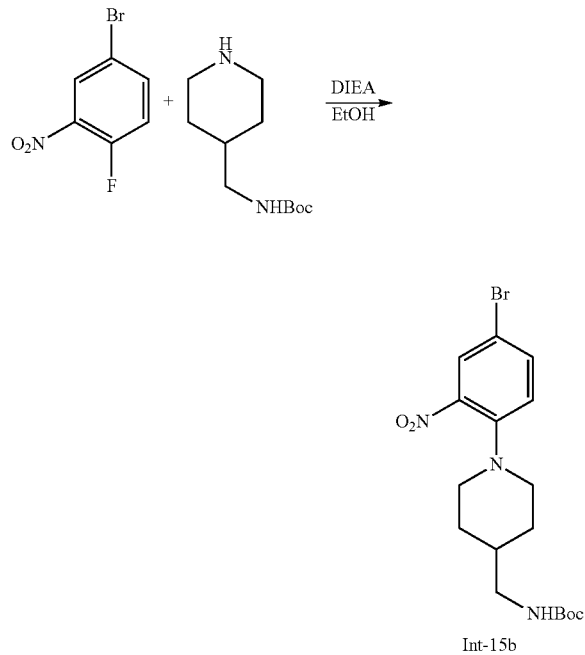

Nitrobenzene Int-15b was prepared by following similar procedures to those described in Step A of Example 2 using 4-bromo-1-fluoro-2-nitrobenzene and tert-butyl piperidin-4-ylmethylcarbamate as starting materials.

Step C—Synthesis of tert-butyl (1-(2-nitro-4-(1-((2-(trimethylsilyl)ethoxy)methyl)-1H-pyrazol-4-yl)phenyl)piperidin-4-yl)methylcarbamate (Int-15c)

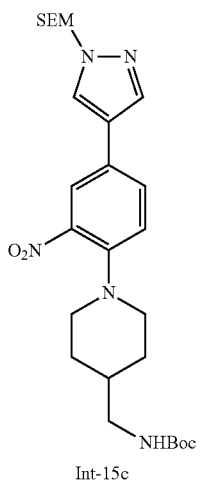

A mixture of nitrobenzene Int-15b (200 mg, 0.483 mmol), boronic ester Int-15a (235 mg, 0.724 mmol), tetrakis(triphenylphosphine)palladium (56 mg, 0.048 mmol), and potassium phosphate tribasic (310 mg, 1.45 mmol) in DMF (3 mL) and water (1 mL) was purged with nitrogen gas for 40 min in a microwave vial. The mixture was irradiated at 120° C. for 20 min by microwave. The reaction mixture was diluted with EtOAc, washed with sat NaHCO₃ (aq), brine, dried over MgSO₄, filtered, and concentrated. The crude product was purified by column chromatography using EtOAc and hexanes as eluents to yield the pyrazole Int-15c (227 mg, 88%) as an orange oil.

Step D—Synthesis of tert-butyl (1-(2-amino-4-(1-((2-(trimethylsilyl)ethoxy)methyl)-1H-pyrazol-4-yl)phenyl)piperidin-4-yl)methylcarbamate (Int-15d)

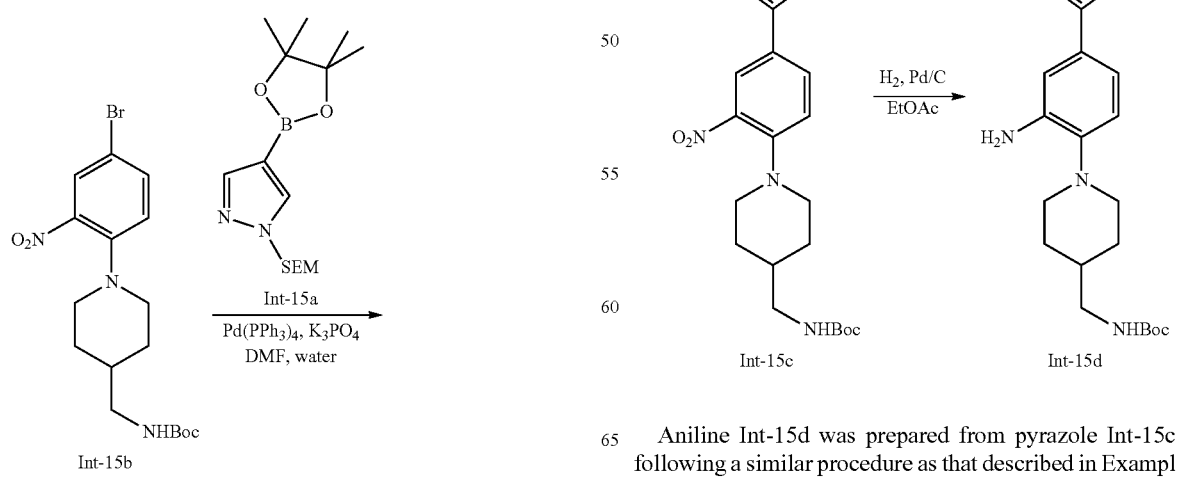

Aniline Int-15d was prepared from pyrazole Int-15c by following a similar procedure as that described in Example 2, Step B.

Step E—Synthesis of tert-butyl (1-(2-(4-bromo-1-((2-(trimethylsilyl)ethoxy)methyl)-1H-imidazole-2-carboxamido)-4-(1-((2-(trimethylsilyl)ethoxy)methyl)-1H-pyrazol-4-yl)phenyl)piperidin-4-yl)methylcarbamate (Int-15e)

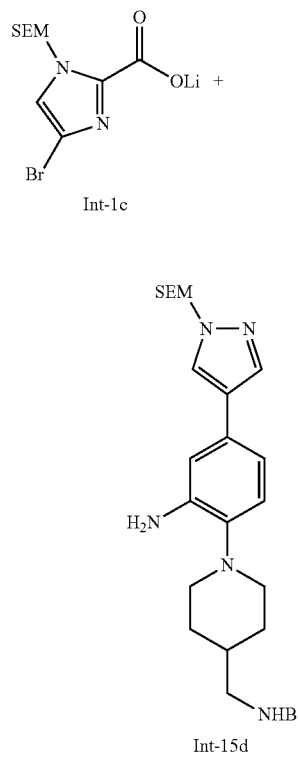

Step F—Synthesis of tert-butyl (1-(4-(1-((2-(trimethylsilyl)ethoxy)methyl)-1H-pyrazol-4-yl)-2-(1-((2-(trimethylsilyl)ethoxy)methyl)-4-(1-((2-(trimethylsilyl)ethoxy)methyl)-1H-pyrazol-4-yl)-1H-imidazole-2-carboxamido)phenyl)piperidin-4-yl)methylcarbamate (Int-15f)

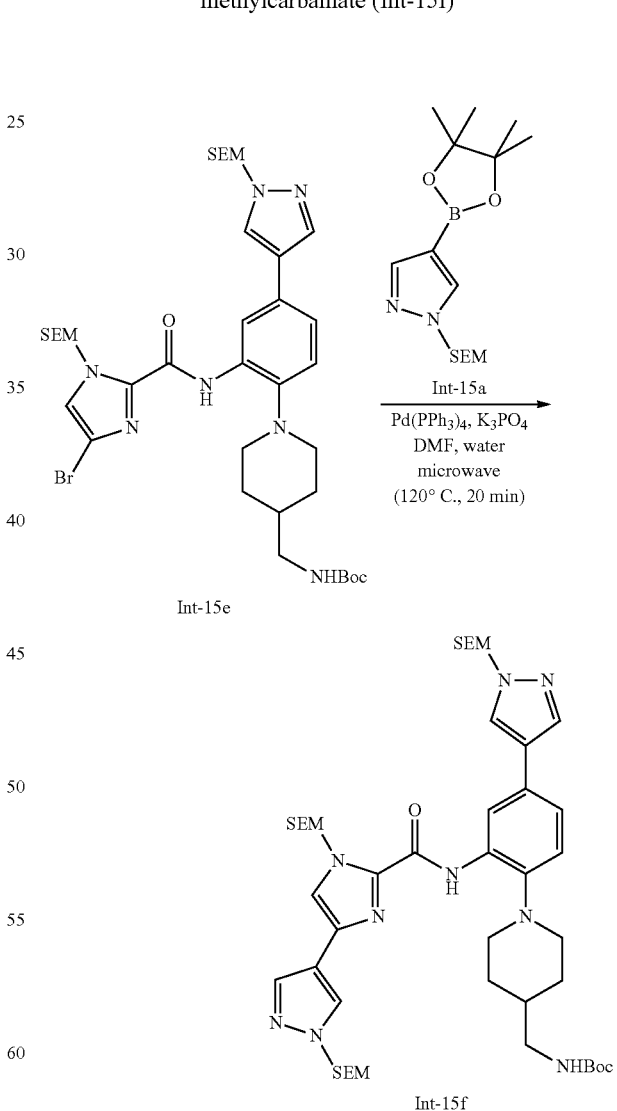

To a solution of lithium 4-bromo-1-((2-(trimethylsilyl)ethoxy)methyl)-1H-imidazole-2-carboxylate Int-1c (29 mg, 0.088 mmol) and Int-15d (40 mg, 0.080 mmol) in DMF (3 mL) were added O-(7-azabenzotriazol-1-yl)-N,N,N',N'-tetramethyluronium hexafluorophosphate (39 mg, 0.096 mmol, HATU), and 4-dimethylaminopyridine (5 mg, DMAP). The reaction mixture was stirred at r.t. for 19 h. Then, the reaction mixture was diluted with EtOAc (50 mL), washed with sat. NaHCO$_{3(aq)}$ (2×50 mL), H$_2$O (4×50 mL), brine (1×50 mL), dried over Na$_2$SO$_4$, filtered, and concentrated. The crude product was purified by column chromatography using EtOAc and hexanes as eluents to yield amide Int-15e (52 mg, 81%) as a white solid. LCMS m/e (M+H$^+$)=804.2

Amide Int-15f was prepared from Int-15e and Int-15a by following a similar procedure to that described in Example 1, Step F. LCMS m/e (M+H$^+$)=923.4.

Step G—Synthesis of N-[2-[4-(aminomethyl)-1-piperidinyl]-5-(1H-pyrazol-4-yl)phenyl]-4-(1H-pyrazol-4-yl)-1H-imidazole-2-carboxamide (51)

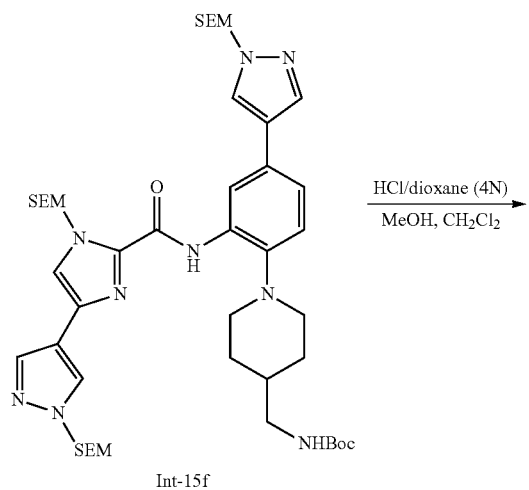

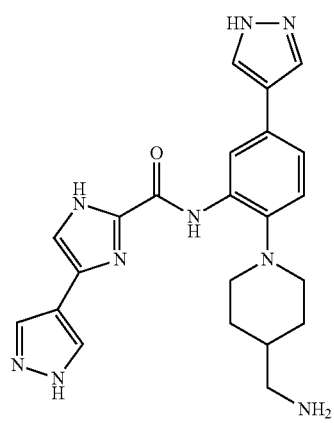

To a solution of Int-15f (43 mg, 0.047 mmol) in CH$_2$Cl$_2$ (2 mL) and MeOH (1 mL) was added a solution of HCl in dioxane (4 N, 500 µL). The reaction mixture was treated with additional HCl in dioxane (4N, 250 µL) after 5 h of stirring at r.t. The reaction mixture was stirred at r.t. for 20 h. Then, the reaction mixture was diluted with Et$_2$O (10 mL) and filtered to yield the hydrochloric acid salts of the amide 51 (19 mg, 77%) as a white solid. LCMS m/e (M+H$^+$)=432.2.

Example 16

Preparation of N-[2-[4-(1-amino-1-methylethyl)-1-piperidinyl]-3-fluorophenyl]-4-(2-methyl-4-pyridinyl)-1H-imidazole-2-carboxamide (67)

Step A—Synthesis of Ethyl-4-(2-methylpyridin-4-yl)-1-((2-(trimethylsilyl)ethoxy)methyl)-1H-imidazole-2-carboxylate (Int-16a)

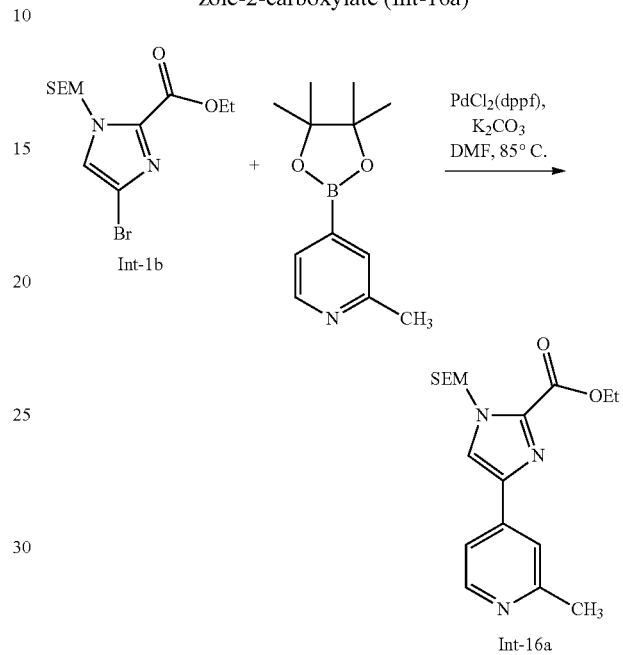

A mixture of bromoimidazole Int-1b (1.00 g, 2.85 mmol), 2-methylpyridine 4-boronic acid pinacol ester (0.75 g, 3.42 mmol) and potassium carbonate (1.18 g, 8.55 mmol) in DMF (15 mL) at r.t. was purged with nitrogen gas for 5 min. PdCl$_2$(dppf) was added. The mixture was heated at 85° C. for 16 h. Water and ethyl acetate were added and the layers were separated. The separated aqueous layer was extracted with ethyl acetate. The separated organic layer was filtered through Celite®, washed with brine and dried over sodium sulfate. The solvents were removed in vacuo and chromatographic purification (ethyl acetate-hexane) of the residue gave Int-16a (0.61 g, 59%) as a yellow oil.

Step B—4-(2-methylpyridin-4-yl)-1-((2-(trimethylsilyl)ethoxy)methy)-1H-imidazole-2-carboxylic acid (Int-16b)

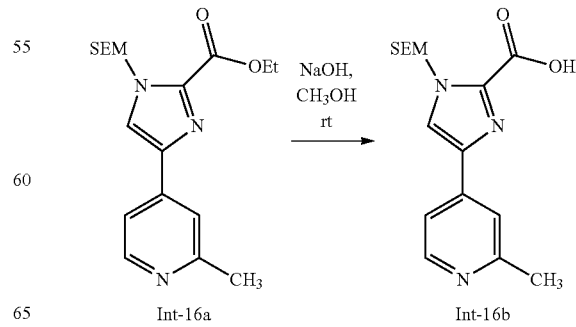

A mixture of Int-16a (0.69 g, 1.91 mmol) and NaOH (9 mL, 18 mmol) in methanol (9 mL) was stirred at room temperature overnight. The solvent was removed in vacuo. The reaction was then neutralized with HCl (9 mL, 18 mmol), extracted with ethyl acetate. The separated organic layer washed with brine and dried over sodium sulfate. The solvents were removed in vacuo to give carboxylic acid Int-16b (285 mg, 45%) as a light brown solid

Step C—Synthesis of tert-butyl 4-(2-(benzyloxycarbonylamino)propan-2-yl)piperidine-1-carboxylate (Int-16d)

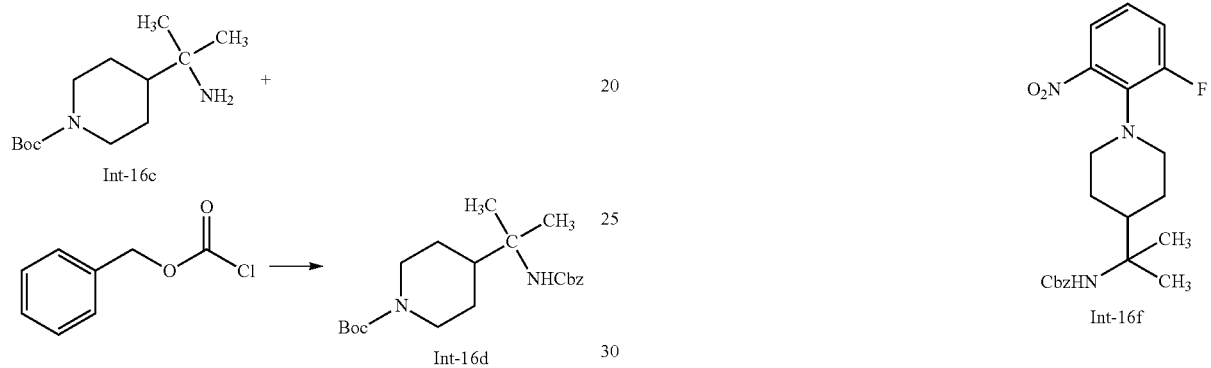

A mixture of amine Int-16c (0.55 g, 2.27 mmol) (prepared according to *Synthesis* 2006, 24, 4143), potassium carbonate (0.99 g, 7.14 mmol) in diethyl ether (12 mL) and water (4 mL) was cooled to 0° C. Benzylchloroformate (1.22 g, 7.14 mmol) was added and the reaction was warmed up to 25° C. stirred for 90 minutes. The mixture was diluted with ethyl acetate (30 mL), washed with water (10 mL) and brine (10 mL), dried over sodium sulfate, filtered, and purified on silica gel (ethyl acetate-hexane) to give amine Int-16d (0.62 g, 73%) as a white solid.

Step D—Synthesis of Benzyl-2-(piperidin-4-yl)propan-2-ylcarbamate (Int-16e)

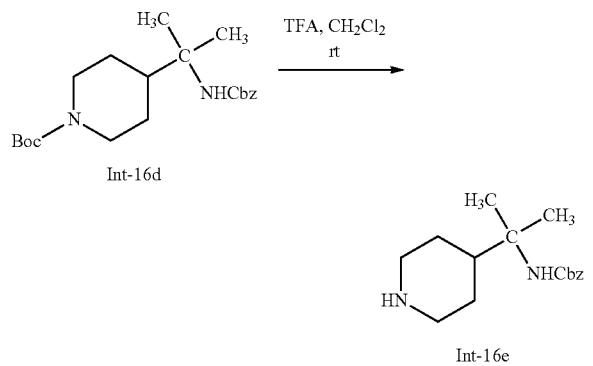

A mixture of piperidine Int-16d (0.62 g, 1.66 mmol) and TFA (4 mL) in dichloromethane (4 mL) was stirred at 25° C. for 4 h. The solvent and excess TFA were removed in vacuo to give amine Int-16e (0.47 g, >99%) as a clear oil.

Step E—Synthesis of Benzyl-2-(1-(2-fluoro-6-nitrophenyl)piperidin-4-yl)propan-2-ylcarbamate (Int-16f)

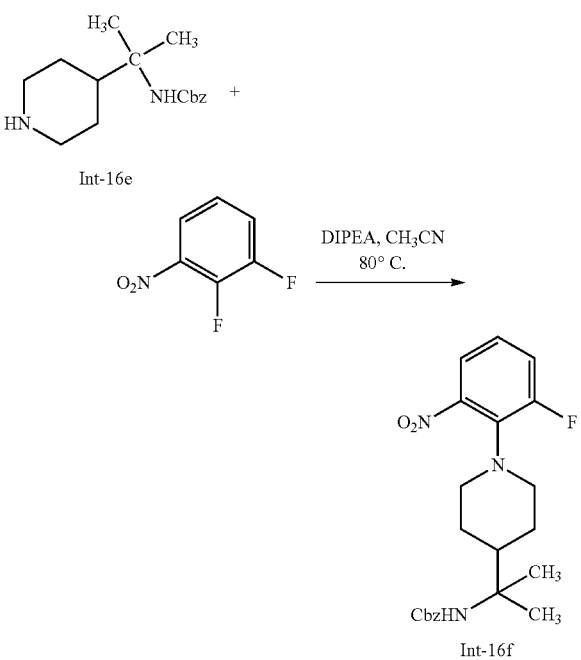

A mixture of amine Int-16e (200 mg, 0.72 mmol), difluoro nitrobenzene (115 mg, 0.72 mmol), and DIPEA (374 mg, 2.90 mmol) in acetonitrile (5 mL) was stirred at 80° C. overnight. After cooling to room temperature, the mixture was diluted with ethyl acetate (30 mL), washed with water (10 mL) and brine (10 mL), dried over sodium sulfate, filtered, and the solvent removed in vacuo to give Int-16f (300 mg, >99%) as an orange foam.

Step F—Synthesis of Benzyl 2-(1-(2-amino-6-fluorophenyl)piperidin-4-yl)propan-2-ylcarbamate (Int-16g)

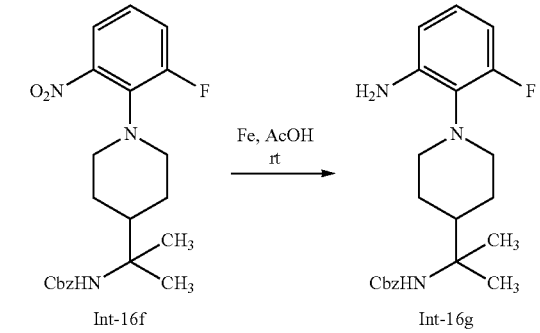 [SMILES: CC(C)(NC(=O)OCc1ccccc1)C1CCN(c2c(F)cccc2[N+](=O)[O-])CC1 ; CC(C)(NC(=O)OCc1ccccc1)C1CCN(c2c(N)cccc2F)CC1]

A mixture of Int-16f (300 mg, 0.72 mmol) and iron powder (400 mg, 7.4 mmol) in acetic acid (10 mL) was stirred at room temperature overnight. The solvent was removed in vacuo.

The reaction was quenched with a mixture of ethyl acetate (20 mL) and saturated aqueous sodium bicarbonate (20 mL). The reaction mixture was stirred for 10 minutes. The separated organic layer was washed with brine and dried over sodium sulfate, filtered, and purified on silica gel (ethyl acetate-hexane) to give amine Int-16g (250 mg, 90%) as a white solid.

Step G—Sythesis of Benzyl2-(1-(2-fluoro-6-(4-(2-methylpyridin-4-yl)-1-((2-(trimethylsilyl)ethoxy)methyl)-1H-imidazole-2-carboxamido)phenyl)piperidin-4-yl)propan-2-ylcarbamate (Int-16h)

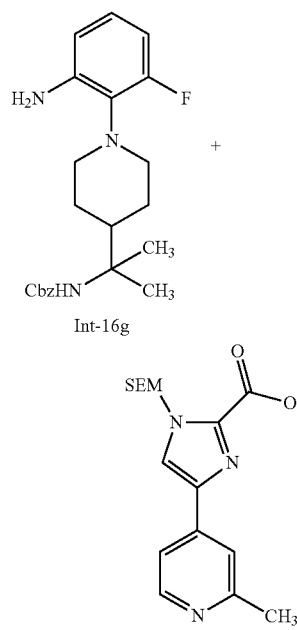

A mixture of aniline Int-16g (80 mg, 0.24 mmol), acid Int-16b (77 mg, 0.20 mmol), HATU (115 mg, 0.30 mmol) and DIPEA (77 mg, 0.6 mmol) in DMF (3 mL) was stirred at room temperature overnight. The mixture was diluted with ethyl acetate (25 mL), washed with saturated aqueous sodium bicarbonate (10 mL) and brine (10 mL), dried over sodium sulfate and filtered. The solvent was removed in vacuo, and the residue was purified on silica gel (ethyl acetate-hexane) to give compound Int-16h (38 mg, 27%) as a yellow oil.

Step H—Synthesis of N-(2-(4-(2-aminopropan-2-yl)piperidin-1-yl)-3-fluouophenyl)-4-(2-methylpyridin-4-yl)1-((2-(trimethylsilyl)ethoxy)methyl)-1H-imidazole-2-carboxamide (Int-16i)

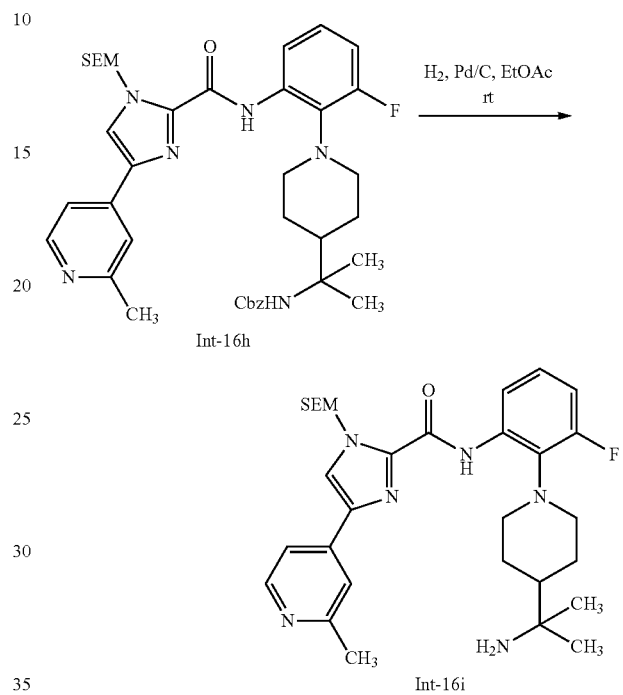

A mixture of Int-16h (38 mg, 0.054 mmol) and Pd/C (20 mg, 0.094 mmol) in ethyl acetate (4 mL) was stirred under a balloon of hydrogen gas at room temperature overnight. The reaction was filtered through a pad of diatomaceous earth and the solvent was removed in vacuo to give Int-16i (30 mg, >99%) as a yellow foam.

Step I—Synthesis of N-[2-[4-(1-amino-1-methylethyl)-1-piperidinyl]-3-fluorophenyl]-4-(2-methyl-4-pyridinyl)-1H-imidazole-2-carboxamide (67)

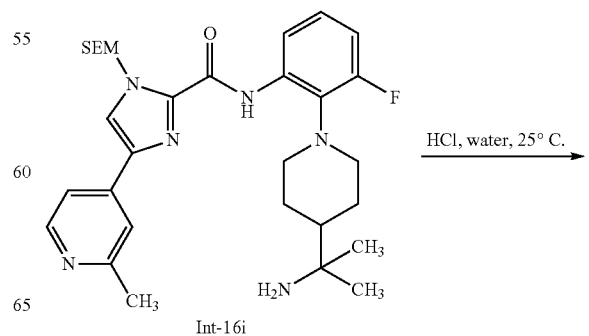

-continued

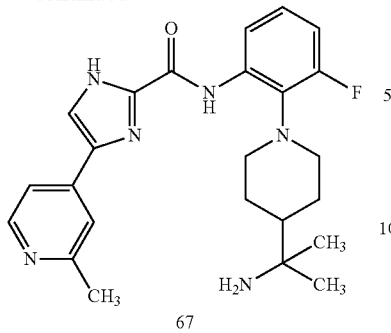

67

A mixture of amide Int-16i (30 mg, 0.054 mmol) and HCl (4 N in dioxane, 2 mL) in water (0.5 mL) was stirred at 25° C. for 3 h. The solvent was removed in vacuo and the residue purified on prep-HPLC to afford 67 (24 mg, 27%) as a yellow solid. ESI MS m/e (M+H$^+$)=437.4.

Example 17

This example describes the preparation of Imidazole Carboxamide Compounds wherein R$^6$ is H, and T is

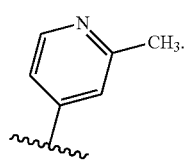 [SMILES: *c1ccnc(C)c1]

Preparation of N-[3-fluoro-2-[4-[(methylamino)methyl]-1-piperidinyl]phenyl]-4-(2-methyl-4-pyridinyl)-1H-imidazole-2-carboxamide (57)

Step A—Synthesis of tert-Butyl (1-(2-fluoro-6-nitrophenyl)piperidin-4-yl)methyl(methyl)carbamate (Int-17a)

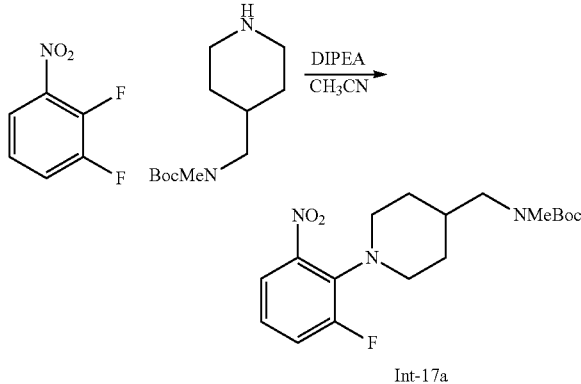

To a flask containing 2,3-difluoronitrobenzene (167 mg, 1.05 mmol) in CH$_3$CN (11 mL) was added diisopropylethylamine (0.37 mL, 2.1 mmol) followed by the piperidine reagent (240 mg, 1.05 mmol). The reaction was heated at 80° C. for 18 h. The solvents were removed in vacuo and the residue was purified by chromatography (ethyl acetate-hexane) to give Int-17a (0.385 g, 99% yield) as a bright yellow oil. LCMS m/e (M+H$^+$)=368.3.

Step B—Synthesis of tert-Butyl (1-(2-fluoro-6-nitrophenyl)piperidin-4-yl)methyl(methyl)carbamate (Int-17b)

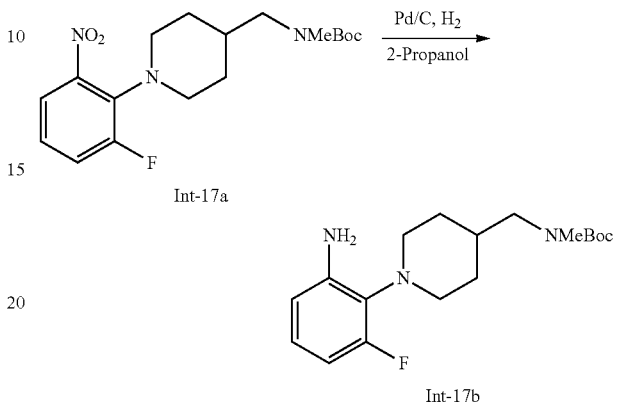

To a flask containing Int-17a (173 mg, 0.47 mmol) in 2-propanol (5 mL) was added Pd/C (~100 mg). The reaction was stirred under H$_2$ (1 atm) overnight. The reaction was filtered through a pad of Celite®, and the solvents were removed in vacuo to give Int-17b (122 mg, 76% yield) as a colorless oil/film. LCMS m/e (M+H$^+$)=338.3.

Step C—Synthesis of tert-Butyl (1-(2-fluoro-6-(4-(2-methylpyridin-4-yl)-1-((2-(trimethylsilyl)ethoxy)methyl)-1H-imidazole-2-carboxamido)phenyl)piperidin-4-yl)methyl(methyl)carbamate (Int-17c)

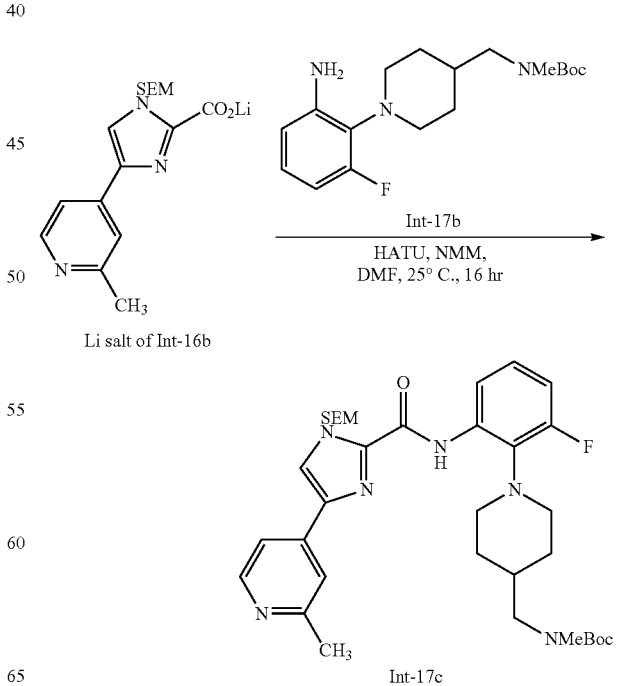

To a flask containing the lithium salt Int-16b (12 mg, 0.04 mmol) and Int-17b (12 mg, 0.04 mmol) in DMF (1 mL) was added NMM (0.02 mL, 0.18 mmol) and HATU (40 mg, 0.11 mmol). The reaction was stirred at r.t. overnight. Water (5 mL) was added to the reaction flask and the resulting solid was collected via filtration to give Int-17c (21 mg, 91% yield) as a yellow solid. LCMS m/e (M+H$^+$)=653.5.

Step D—Synthesis of N-[3-fluoro-2-[4-[(methylamino)methyl]-1-piperidinyl]phenyl]-4-(2-methyl-4-pyridinyl)-1H-imidazole-2-carboxamide (57)

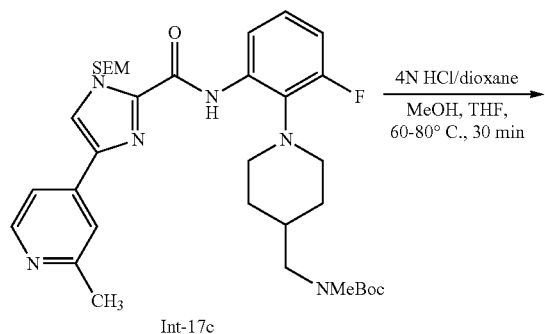

Int-17c

4N HCl/dioxane
MeOH, THF,
60-80° C., 30 min

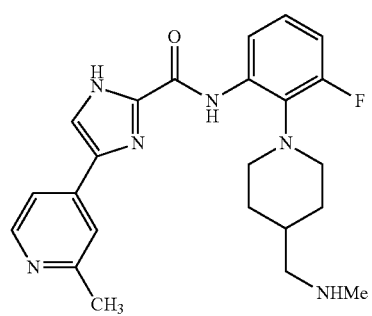

57

To a flask containing Int-17c (21 mg, 0.03 mmol) in THF (0.3 mL) and MeOH (0.3 mL) was added a solution of 4 N HCl in 1,4-dioxane (1 mL). The reaction was heated at 60-80° C. for 30 min. Ether was carefully added and the solid was collected by filtration to give 57 (9.6 mg, 60% yield) as an off-white solid. LCMS m/e (M+H$^+$)=423.2.

Compounds 50, 52, 54, 55, and 58 were prepared by essentially the same procedures as described in Steps A-D. Thus the amines listed in Table 3 below were reacted with difluoro nitrobenzene followed by reduction of the nitro moiety to provide the intermediate anilines.

TABLE 3

| Amine | Compound | LCMS m/e (M + H$^+$) | |
|---|---|---|---|
| ![amine 50] | ![compound 50] | 437.2 | N-[2-[4-[(dimethylamino)methyl]-1-piperidinyl]-3-fluorophenyl]-4-(2-methyl-4-pyridinyl)-1H-imidazole-2-carboxamide |
| | 50 | | |
| ![amine 52] | ![compound 52] | 437.2 | N-[2-[4-(aminomethyl)-4-ethyl-1-piperidinyl-3-fluorophenyl]-4-(2-methyl-4-pyridinyl)-1H-imidazole-2-carboxamide |
| | 52 | | |

TABLE 3-continued

| Amine | Compound | LCMS m/e (M + H⁺) | |
|---|---|---|---|
| (structure with NH, N-Boc diazabicyclo) | 54 (imidazole carboxamide compound) | 407.2 | N-[2-(3,8-diazabicyclo[3.2.1]oct-3-yl)-3-fluorophenyl]-4-(2-methyl-4-pyridinyl)-1H-imidazole-2-carboxamide |
| (structure with 4-methyl-4-(NHBoc-methyl)piperidine) | 55 | 423.2 | N-[2-[4-(aminomethyl)-4-methyl-1-piperidinyl]-3-fluorophenyl]-4-(2-methyl-4-pyridinyl)-1H-imidazole-2-carboxamide |
| (structure with octahydropyrrolo[3,4-c]pyrrole, N-Boc) | 58 | 407.2 | N-[3-fluoro-2-(hexahydropyrrolo[3,4-c]pyrrol-2(1H)-yl)phenyl]-4-(2-methyl-4-pyridinyl)-1H-imidazole-2-carboxamide |

Example 18

Preparation of N-[3-fluoro-2-(octahydro-6H-pyrrolo[2,3-c]pyridin-6-yl)phenyl]-4-(2-methyl-4-pyridinyl)-1H-imidazole-2-carboxamide (43)

Step A—Synthesis of tert-butyl 6-(2-fluoro-6-nitrophenyl)octahydro-1H-pyrrolo[2,3-c]pyridine-1-carboxylate (Int-18b)

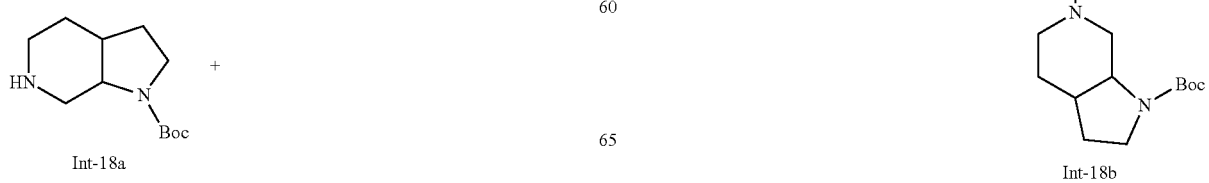

A mixture of amine Int-18a (920 mg, 4.1 mmol) (prepared according to Le Huerou, Y. et. al. WO 2009/140320), difluoro-nitr (678 mg, 4.1 mmol), and DIPEA (1.05 g, 8.2 mmol) in acetonitrile (12 mL) was stirred at 80° C. overnight. After cooling to room temperature, the mixture was diluted with ethyl acetate (60 mL), washed with water (20 mL) and brine (20 mL), dried over sodium sulfate, filtered, and the solvent removed in vacuo to give Int-18b (1.5 g, >99%) as an orange foam.

Step B—Synthesis of tert-butyl 6-(2-amino-6-fluorophenyl)octahydro-1H-pyrrolo[2,3-c]pyridine-1-carboxylate (Int-18c)

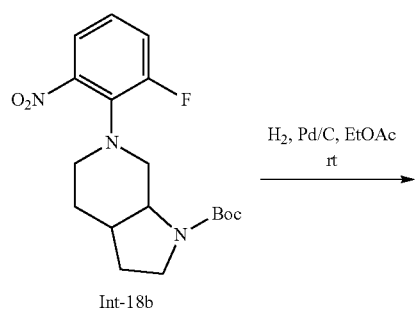

Int-18b

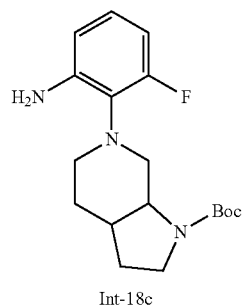

Int-18c

A mixture of Int-18b (1.5 g, 4.1 mmol) and Pd/C (500 mg, 0.236 mmol) in ethyl acetate (10 mL) was stirred under a balloon of hydrogen gas at room temperature overnight. The reaction was filtered through a pad of diatomaceous earth and the solvent was removed in vacuo to give aniline Int-18c (1.27 mg, 93%) as a white solid.

Step C—Synthesis of tert-butyl 6-(2-fluoro-6-(4-(2-methylpyridin-4-yl)-1-((2-(trimethylsilyl)ethoxy)methyl)-1H-imidazole-2-carboxamido)phenyl)octahydro-1H-pyrrolo[2,3-c]pyridine-1-carboxylate (Int-18d)

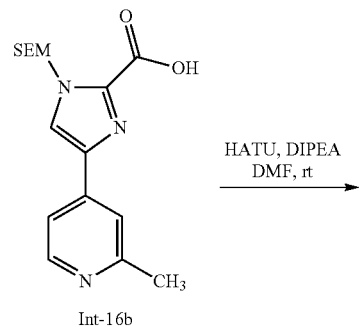

Int-16b

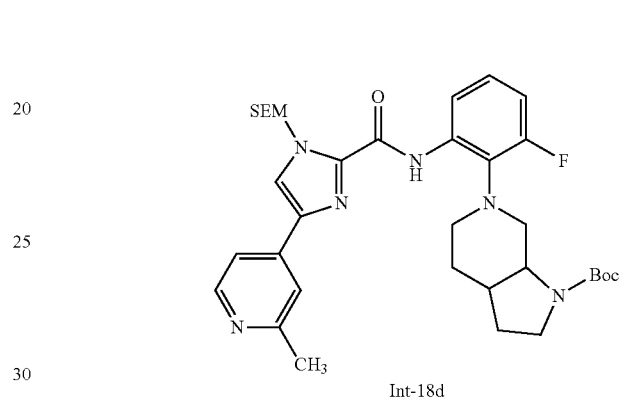

Int-18d

A mixture of aniline Int-18c (100 mg, 0.3 mmol), acid Int-16b (120 mg, 0.36 mmol), HATU (170 mg, 0.45 mmol) and DIPEA (116 mg, 0.9 mmol) in DMF (2 mL) was stirred at room temperature overnight. The mixture was diluted with ethyl acetate (75 mL), washed with saturated aqueous sodium bicarbonate (20 mL) and brine (20 mL), dried over sodium sulfate, filtered, the solvent removed in vacuo, and purified on silica gel (ethyl acetate-hexane) to give compound Int-18d (130 mg, 51%).

Step D—Synthesis of N-[3-fluoro-2-(octahydro-6H-pyrrolo[2,3-c]pyridin-6-yl)phenyl]-4-(2-methyl-4-pyridinyl)-1H-imidazole-2-carboxamide (43)

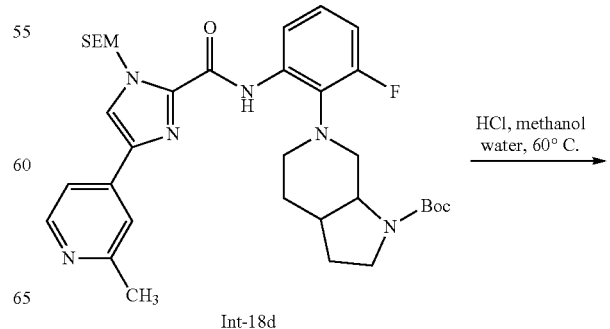

Int-18d

-continued

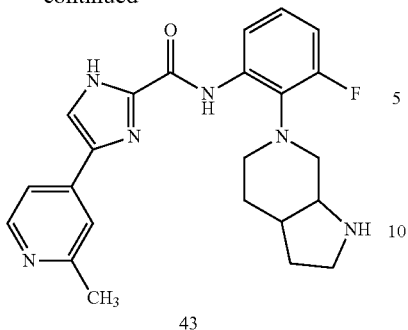

43

A mixture of amide Int-18d (130 mg, 0.2 mmol) and HCl (4 N in dioxane, 4 mL) in methanol (2 mL) and water (1 mL) was stirred at 60° C. overnight. After cooling to room temperature, the solvent was removed in vacuo and the residue purified on prep-HPLC to afford 43 (35 mg, 48%) as a white solid. ESI MS m/e (M+H$^+$)=421.

Example 19

Preparation of N-[2-(2,9-diazaspiro[5.5]undec-9-yl)-3-fluorophenyl]-4-(2-methyl-4-pyridinyl)-1H-imidazole-2-carboxamide (46)

Step A—Synthesis of tert-butyl 9-(2-fluoro-6-nitrophenyl)-2,9-diazaspiro[5.5]undecane-2-carboxylate (Int-19b)

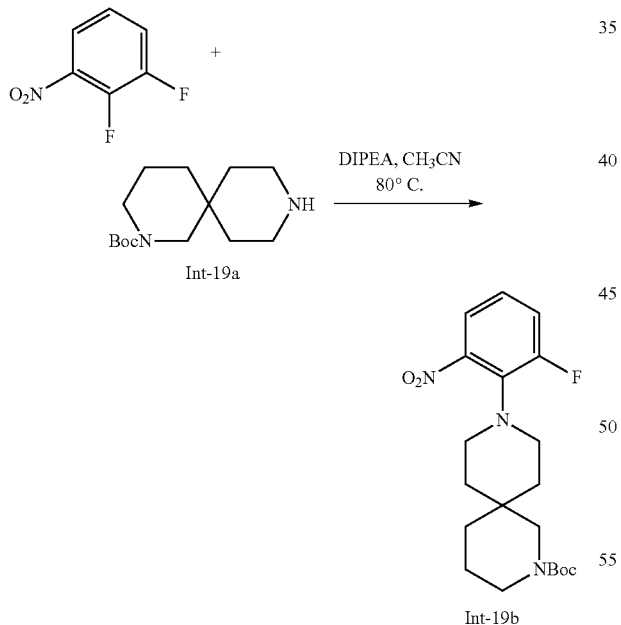

A mixture of difluoro nitrobenzene (188 mg, 1.18 mmol), amine Int-19a, (300 mg, 1.18 mmol), and DIPEA (305 mg, 2.36 mmol) in acetonitrile (4 mL) was stirred at 80° C. overnight. After cooling to room temperature, the mixture was diluted with ethyl acetate (30 mL), washed with water (10 mL) and brine (10 mL), dried over sodium sulfate, filtered, and the solvent removed in vacuo to give Int-19b (470 mg, >99%) as an orange foam.

Step B—Synthesis of tert-butyl 9-(2-amino-6-fluorophenyl)-2,9-diazaspiro[5.5]undecane-2-carboxylate (Int-19c)

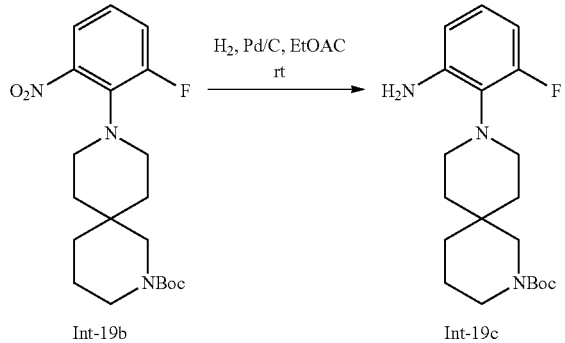 [SMILES: CC(C)(C)OC(=O)N1CCCC2(CCN(c3c(F)cccc3[N+](=O)[O-])CC2)C1 ; CC(C)(C)OC(=O)N1CCCC2(CCN(c3c(N)cccc3F)CC2)C1]

A mixture of Int-19b (464 mg, 1.18 mmol) and Pd/C (500 mg, 0.236 mmol) in ethyl acetate (11 mL) was stirred under a balloon of hydrogen gas at room temperature overnight. The reaction was filtered through a pad of diatomaceous earth and the solvent was removed in vacuo to give aniline Int-19c (389 mg, 91%) as a tan foam.

Step C—Synthesis of tert-butyl 9-(2-fluoro-6-(4-(2-methylpyridin-4-yl)-1-((2-(trimethylsilyl)ethoxy) methyl)-1H-imidazole-2-carboxamido)phenyl)-2,9-diazaspiro[5.5]undecane-2-carboxylate (Int-19d)

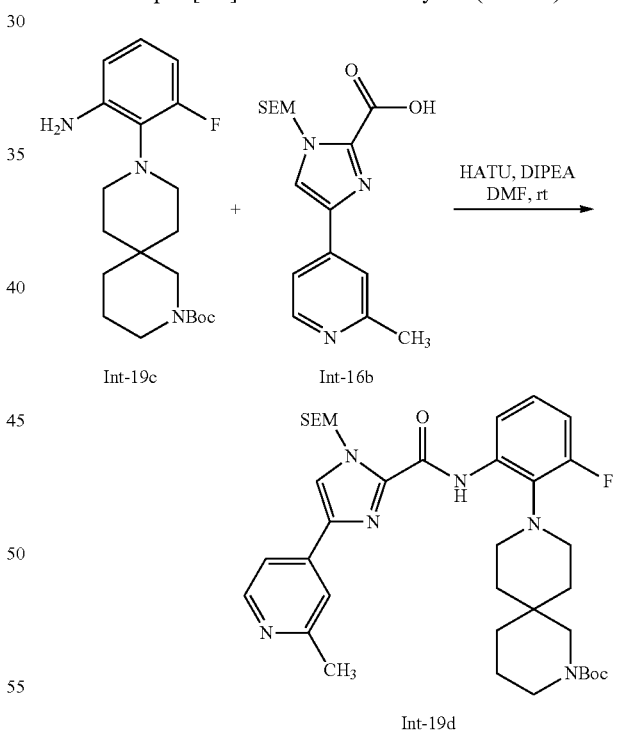

A mixture of aniline Int-19c (279 mg, 0.768 mmol), acid Int-16b (130 mg, 0.64 mmol), HATU (365 mg, 0.96 mmol) and DIPEA (248 mg, 1.92 mmol) in DMF (9 mL) was stirred at room temperature overnight. The mixture was diluted with ethyl acetate (75 mL), washed with saturated aqueous sodium bicarbonate (20 mL) and brine (20 mL), dried over sodium sulfate, filtered, the solvent removed in vacuo, and purified on silica gel (methanol-dichloromethane) to give compound Int-19d (130 mg, 49%) as a brown oil.

Step D—Synthesis of N-[2-(2,9-diazaspiro[5.5]undec-9-yl)-3-fluorophenyl]-4-(2-methyl-4-pyridinyl)-1H-imidazole-2-carboxamide (46)

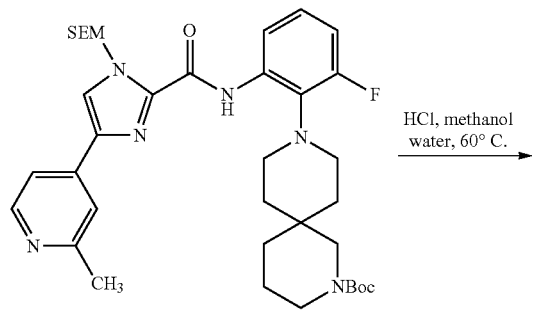

Int-19d

HCl, methanol
water, 60° C.

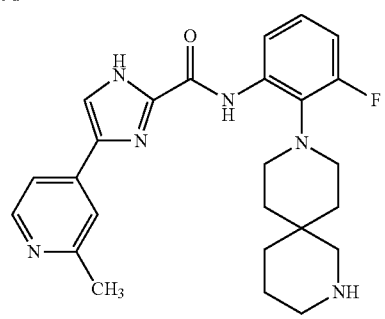

46

A mixture of amide Int-19d (130 mg, 0.192 mmol) and HCl (4 N in dioxane, 5 mL) in methanol (3 mL) and water (1 mL) was stirred at 60° C. overnight. After cooling to room temperature, the solvent was removed in vacuo and the residue purified by preparative HPLC to afford 46 (25 mg, 27%) as a yellow solid. ESI MS m/e (M+H$^+$)=449.1.

Example 20

This example describes the preparation of Imidazole Carboxamide Compounds wherein R$^6$ is H, T is

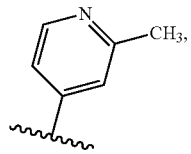 [SMILES: *c1ccnc(C)c1]

and D is

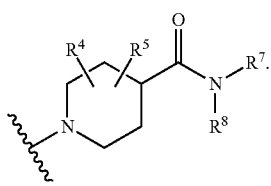

The preparation is illustrated by the preparation of N-ethyl-1-[2-fluoro-6-[[[4-(2-methyl-4-pyridinyl)-1H-imidazol-2-yl]carbonyl]amino]phenyl]-4-piperidinecarboxamide (60).

Step A—Synthesis of Methyl 1-(2-fluoro-6-nitrophenyl)piperidine-4-carboxylate (Int-20a)

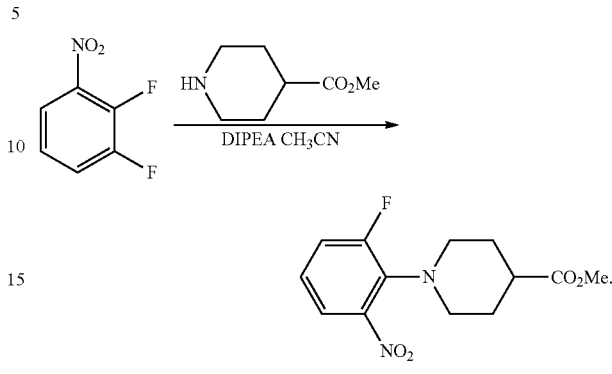

Int-20a

A mixture of difluoronitrobenzene (0.34 mL, 3.10 mmol), methyl isonipecotate (0.51 mL, 3.78 mmol), and diisopropylethylamine (1.08 mL, 6.20 mmol) in acetonitrile (15 mL) was heated at 80° C. overnight. The solvents were removed in vacuo. Chromatographic purification (20% ethyl acetate:hexane) of the residue gave Int-20a (0.85 g, 97%) as a yellow oil.

Step B—Synthesis of Methyl 1-(2-amino-6-fluorophenyl)piperidine-4-carboxylate (Int-20b)

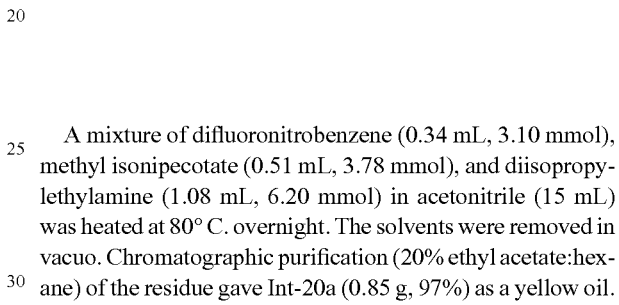

Int-20a

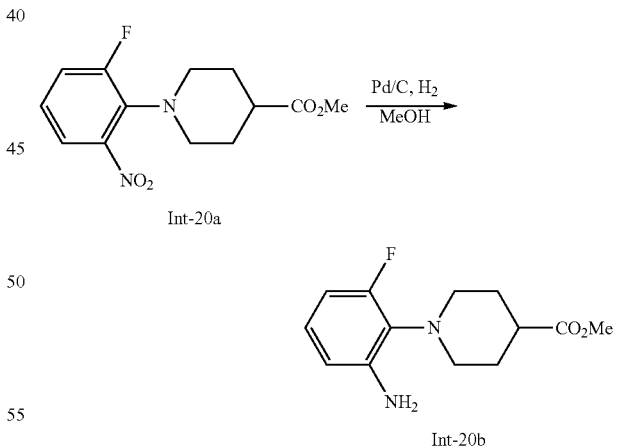

Int-20b

A mixture of Int-20a (471 mg, 1.67 mmol) and palladium on carbon (0.1 eq in Pd) was stirred in methanol (18 mL) under hydrogen (1 atm) at r.t. overnight. The solid was filtered through a pad of Celite® and solvents were removed in vacuo to give Int-20b (412 mg, 98%) as a solid/oil. This product was used without further purification.

Step C—Synthesis of Methyl 1-(2-fluoro-6-(4-(2-methylpyridin-4-yl)-1-((2-(trimethylsilyl)ethoxy)methyl)-1H-imidazole-2-carboxamido)phenyl)piperidine-4-carboxylate (Int-20c)

Step D—Synthesis of 1-(2-fluoro-6-(4-(2-methylpyridin-4-yl)-1-((2-(trimethylsilyl)ethoxy)methyl)-1H-imidazole-2-carboxamido)phenyl)piperidine-4-carboxylic acid (Int-20d)

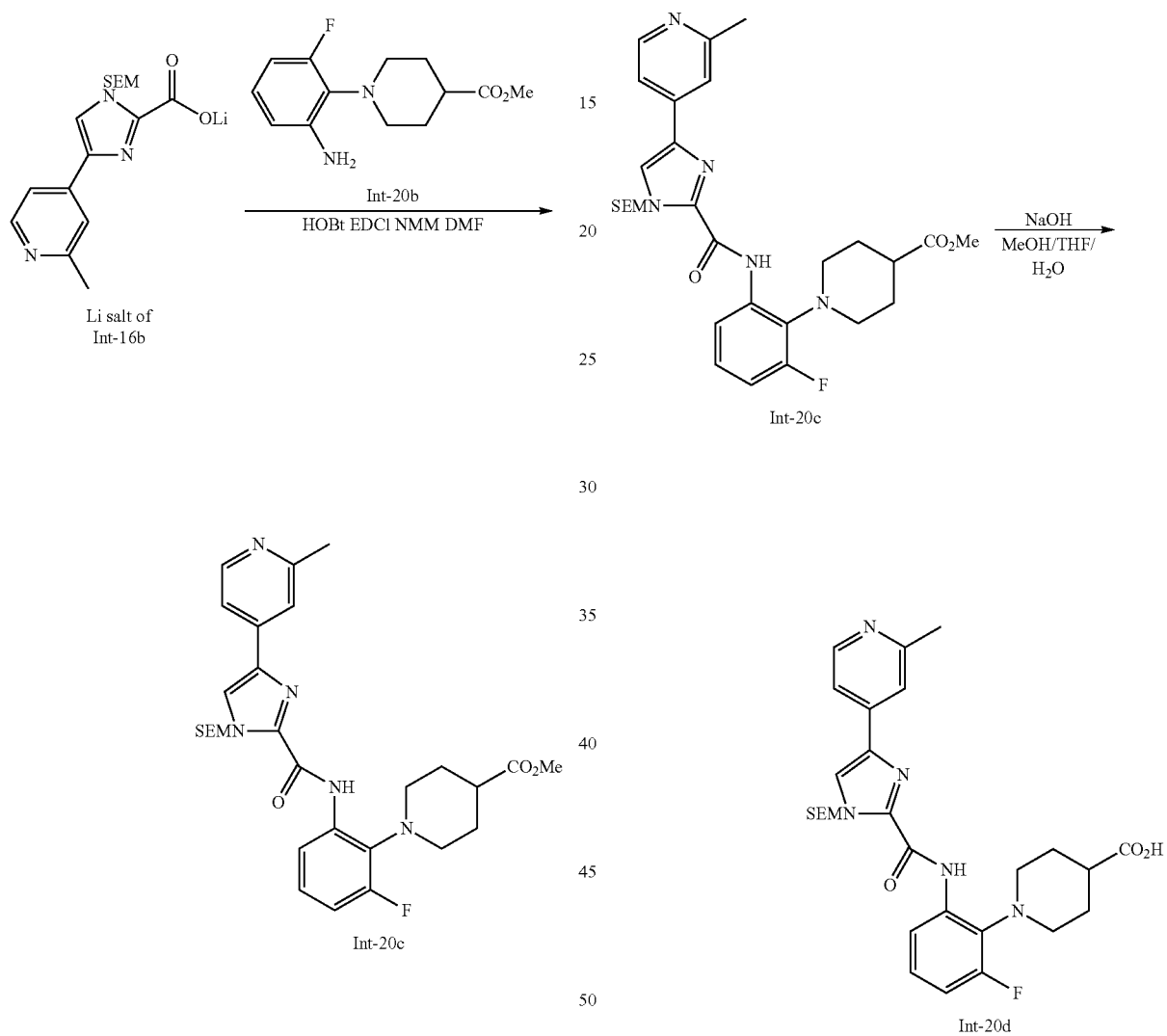

A mixture of the lithium salt of Int-16b (72 mg, 0.21 mmol), Int-20b (57 mg, 0.24 mmol), 1-hydroxybenzotriazole hydrate (HOBt) (59 mg, 0.44 mmol), N-(3-dimethylaminopropyl)-N'-ethyl carbodiimide hydrochloride (EDCI) (99 mg, 0.52 mmol), and 4-methylmorpholine (NMM) (0.01 mL, 0.09 mmol) was stirred in N,N-dimethylformamide (3 mL) at 55° C. overnight. Water and ethyl acetate were added, and the layers were separated. The organic layer was washed with water, dried over $Na_2SO_4$, filtered, and concentrated in vacuo. Chromatographic purification (70% ethyl acetate:hexane) of the residue gave Int-20c (71 mg, 61%).

Methyl ester Int-20c (71 mg, 0.13 mmol) was dissolved in MeOH/THF (2 mL each), and water (0.5 mL) was added to the round-bottomed flask. Sodium hydroxide (4 pellets) was added to the round-bottomed flask, and the mixture was stirred vigorously at r.t. overnight. The solvents were concentrated in vacuo and 4 N HCl was slowly added to the solid until a neutral pH was reached. The solid product that crashed out was filtered and dried under vacuum to give Int-20d (50 mg, 72%) as a white solid.

Step E—Synthesis of N-ethyl-1-(2-fluoro-6-(4-(2-methylpyridin-4-yl)-1-((2-(trimethylsilyl)ethoxy)methyl)-1H-imidazole-2-carboxamido)phenyl)piperidine-4-carboxamide (Int-20e)

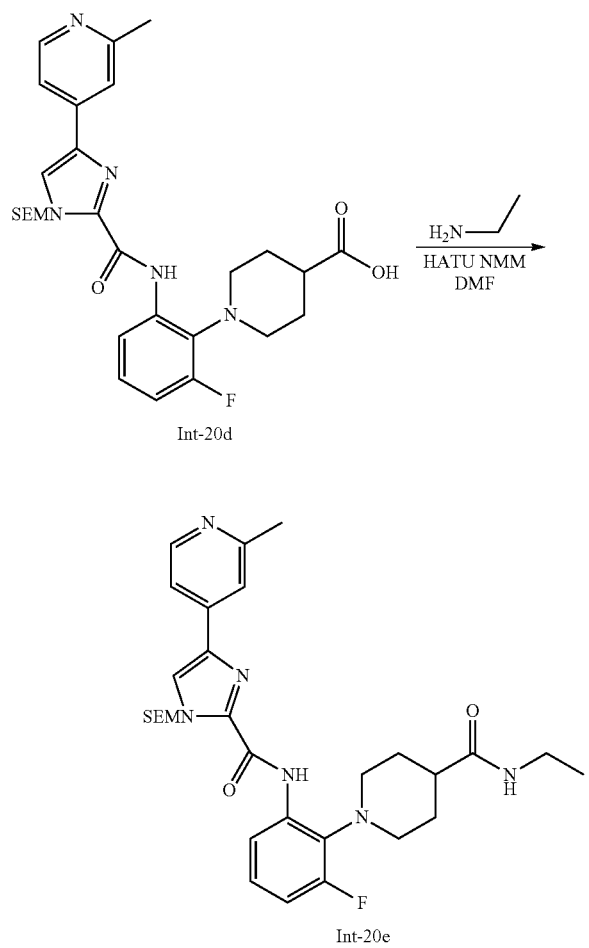

Ethyl amine (0.2 mL, 0.41 mmol) was dissolved in N,N-dimethylformamide (3 mL), Int-20d (28 mg, 0.05 mmol), O-(7-Azabenzotriazol-1-yl)-N,N,N',N'-tetramethyluronium PF$_6$ (HATU) (65 mg, 0.17 mmol), and 4-methylmorpholine (NMM) (0.03 mL, 0.27 mmol) were added to the round-bottomed flask, and the reaction mixture was stirred at 55° C. overnight. The reaction was cooled to r.t. and water was added to the round-bottomed flask. The solid that crashed out was filtered, washed with water, and dried under vacuum to give Int-20e (17.9 mg, 60%) as a brown solid.

Step F—Synthesis of N-ethyl-1-[2-fluoro-6-[[[4-(2-methyl-4-pyridinyl)-1H-imidazol-2-yl]carbonyl]amino]phenyl]-4-piperidinecarboxamide (60)

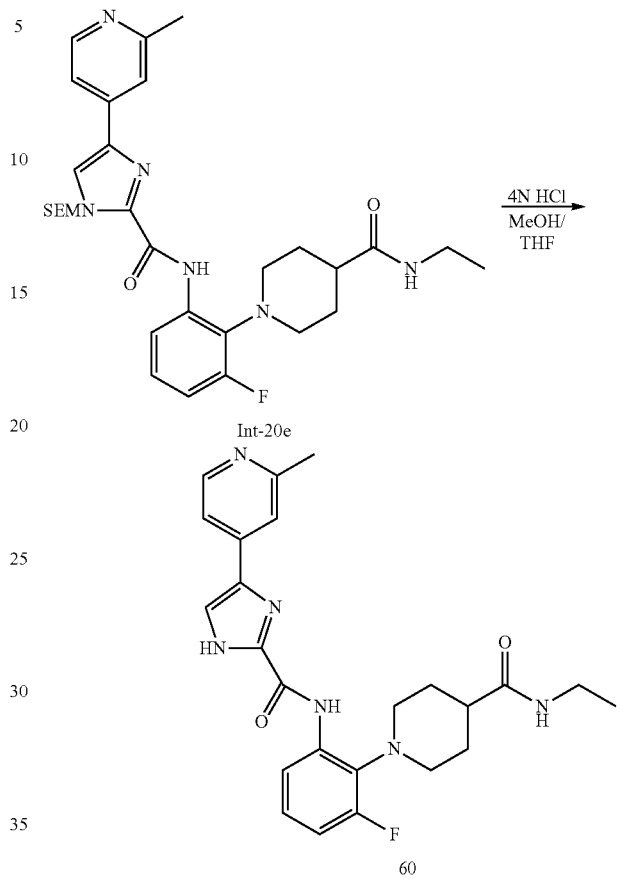

To a solution of Int-20e (17.9 mg, 0.03 mmol) in THF (0.5 mL) and MeOH (0.5 mL) was added 4 N HCl (1.0 mL, excess). The reaction was stirred at 75° C. for 30 min. The solvents were concentrated in vacuo and ether was added to the round-bottomed flask. The solid was collected by filtration to give compound 60 (13.1 mg, 94%) as a tan solid.

Using similar procedures to those described in Steps E and F, compounds 59, 60, 61, 62, 64-66, and 78-96 were prepared from Int-20d and the appropriate amines. The LCMS values are set forth for each of these compounds in Table 4 below.

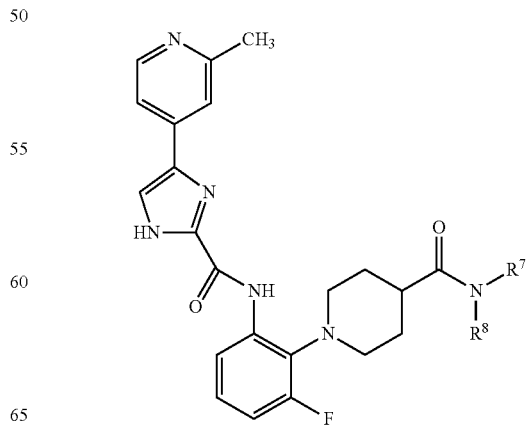

TABLE 4

| # | Structure | MW | LCMS MH+ m/z | HPLC MS $t_R$ | Name |
|---|---|---|---|---|---|
| 60 | | 450.5 | 451.2 | 1.58 | N-ethyl-1-[2-fluoro-6-[[[4-(2-methyl-4-pyridinyl)-1H-imidazol-2-yl]carbonyl]amino]phenyl]-4-piperidinecarboxamide |
| 62 | | 534.5 | 535.2 | 1.93 | 1-[2-fluoro-6-[[[4-(2-methyl-4-pyridinyl)-1H-imidazol-2-yl]carbonyl]amino]phenyl]-N-(3,3,3-trifluoro-2-hydroxypropyl)-4-piperidinecarboxamide |
| 65 | | 526.6 | 527.2 | 2.09 | 1-[2-fluoro-6-[[[4-(2-methyl-4-pyridinyl)-1H-imidazol-2-yl]carbonyl]amino]phenyl]-N-(1(R)-phenylethyl)-4-piperidinecarboxamide |
| 59 | | 436.5 | 437.1 | 1.53 | 1-[2-fluoro-6-[[[4-(2-methyl-4-pyridinyl)-1H-imidazol-2-yl]carbonyl]amino]phenyl]-N-methyl-4-piperidinecarboxamide |
| 61 | | 450.5 | 451.2 | 1.63 | 1-[2-fluoro-6-[[[4-(2-methyl-4-pyridinyl)-1H-imidazol-2-yl]carbonyl]amino]phenyl]-N,N-dimethyl-4-piperidinecarboxamide |
| 64 | | 494.5 | 495.2 | 2.01 | N-[3-fluoro-2-[4-[(3(S)-fluoro-1-pyrrolidinyl)carbonyl]-1-piperidinyl]phenyl]-4-(2-methyl-4-pyridinyl)-1H-imidazole-2-carboxamide |
| 66 | | 462.5 | 463.2 | 2.01 | N-[2-[4-(1-azetidinylcarbonyl)-1-piperidinyl]-3-fluorophenyl]-4-(2-methyl-4-pyridinyl)-1H-imidazole-2-carboxamide |
| 78 | | 518.6 | 519.2 | 2.00 | N-[3-fluoro-2-[4-(8-oxa-3-azabicyclo[3.2.1]oct-3-ylcarbonyl)-1-piperidinyl]phenyl]-4-(2-methyl-4-pyridinyl)-1H-imidazole-2-carboxamide |
| 79 | | 504.6 | 505.2 | 1.95 | N-[3-fluoro-2-[4-(2-oxa-5-azabicyclo[2.2.1]hept-5-ylcarbonyl)-1-piperidinyl]phenyl]-4-(2-methyl-4-pyridinyl)-1H-imidazole-2-carboxamide |
| 80 | | 522.6 | 523.2 | 1.81 | N-[3-fluoro-2-[4-[[3-(hydroxymethyl)-4-morpholinyl]carbonyl]-1-piperidinyl]phenyl]-4-(2-methyl-4-pyridinyl)-1H-imidazole-2-carboxamide |

TABLE 4-continued

| # | R6/R7 structure | MW | LCMS MH+ m/z | HPLC MS t_R | Name |
|---|---|---|---|---|---|
| 81 | 3-(aminomethyl)morpholine-4-carbonyl | 521.6 | 522.2 | 1.80 | N-[2-[4-[[3-(aminomethyl)-4-morpholinyl]carbonyl]-1-piperidinyl]-3-fluorophenyl]-4-(2-methyl-4-pyridinyl)-1H-imidazole-2-carboxamide |
| 82 | C(=O)NH2 | 422.5 | 423.2 | 1.87 | 1-[2-fluoro-6-[[[4-(2-methyl-4-pyridinyl)-1H-imidazol-2-yl]carbonyl]amino]phenyl]-4-piperidinecarboxamide |
| 83 | C(=O)NH-CH2CH2-NH2 | 465.5 | 466.2 | 1.75 | N-(2-aminoethyl)-1-[2-fluoro-6-[[[4-(2-methyl-4-pyridinyl)-1H-imidazol-2-yl]carbonyl]amino]phenyl]-4-piperidinecarboxamide |
| 84 | C(=O)NH-(2-aminocyclohexyl) | 519.6 | 520.2 | 1.84 | N-(2-aminocyclohexyl)-1-[2-fluoro-6-[[[4-(2-methyl-4-pyridinyl)-1H-imidazol-2-yl]carbonyl]amino]phenyl]-4-piperidinecarboxamide |
| 85 | C(=O)NH-(CH2)4-NHMe | 507.6 | 508.2 | 1.79 | 1-[2-fluoro-6-[[[4-(2-methyl-4-pyridinyl)-1H-imidazol-2-yl]carbonyl]amino]phenyl]-N-[4-(methylamino)butyl]-4-piperidinecarboxamide |
| 86 | C(=O)NH-CH2CH2-NHEt | 493.6 | 494.2 | 1.79 | N-[2-(ethylamino)ethyl]-1-[2-fluoro-6-[[[4-(2-methyl-4-pyridinyl)-1H-imidazol-2-yl]carbonyl]amino]phenyl]-4-piperidinecarboxamide |
| 87 | 3,8-diazabicyclo[3.2.1]octane-8-carbonyl | 517.6 | 518.2 | 1.79 | N-[2-[4-(3,8-diazabicyclo[3.2.1]oct-8-yl)carbonyl)-1-piperidinyl]-3-fluorophenyl]-4-(2-methyl-4-pyridinyl)-1H-imidazole-2-carboxamide |
| 88 | C(=O)NH-CH2-(1-aminocyclopentyl) | 519.6 | 520.2 | 1.81 | N-[(1-aminocyclopentyl)methyl]-1-[2-fluoro-6-[[[4-(2-methyl-4-pyridinyl)-1H-imidazol-2-yl]carbonyl]amino]phenyl]-4-piperidinecarboxamide |
| 89 | 2-(aminomethyl)morpholine-4-carbonyl | 521.6 | 522.2 | 1.79 | N-[2-[4-[[2-(aminomethyl)-4-morpholinyl]carbonyl]-1-piperidinyl]-3-fluorophenyl]-4-(2-methyl-4-pyridinyl)-1H-imidazole-2-carboxamide |

TABLE 4-continued

| # | R6/R7 structure | MW | LCMS MH+ m/z | HPLC MS $t_R$ | Name |
|---|---|---|---|---|---|
| 90 | (morpholinyl with 2-hydroxyethyl) | 536.6 | 537.2 | 1.95 | N-[3-fluoro-2-[4-[[2-(2-hydroxyethyl)-4-morpholinyl]carbonyl]-1-piperidinyl]phenyl]-4-(2-methyl-4-pyridinyl)-1H-imidazole-2-carboxamide |
| 91 | (3,6-diazabicyclo[3.2.1]octane) | 517.6 | 518.2 | 1.78 | N-[2-[4-(3,6-diazabicyclo[3.2.1]oct-3-ylcarbonyl)-1-piperidinyl]-3-fluorophenyl]-4-(2-methyl-4-pyridinyl)-1H-imidazole-2-carboxamide |
| 92 | (3(R)-fluoropyrrolidinyl) | 494.5 | 495.2 | 2.04 | N-[3-fluoro-2-[4-[(3(R)-fluoro-1-pyrrolidinyl)carbonyl]-1-piperidinyl]phenyl]-4-(2-methyl-4-pyridinyl)-1H-imidazole-2-carboxamide |
| 93 | (3-oxo-2,8-diazaspiro[4.5]decane) | 559.6 | 560.2 | 1.92 | N-[3-fluoro-2-[4-[(3-oxo-2,8-diazaspiro[4.5]dec-8-yl)carbonyl]-1-piperidinyl]phenyl]-4-(2-methyl-4-pyridinyl)-1H-imidazole-2-carboxamide |
| 94 | (2,7-diazaspiro[3.5]nonane) | 531.6 | 532.2 | 1.80 | N-[2-[4-(2,7-diazaspiro[3.5]noN-7-ylcarbonyl)-1-piperidinyl]-3-fluorophenyl]-4-(2-methyl-4-pyridinyl)-1H-imidazole-2-carboxamide |
| 95 | (2-(1-aminoethyl)-morpholinyl) | 535.6 | 536.2 | 1.85 | N-[2-[4-[[2-(1-aminoethyl)-4-morpholinyl]carbonyl]-1-piperidinyl]-3-fluorophenyl]-4-(2-methyl-4-pyridinyl)-1H-imidazole-2-carboxamide |
| 96 | (4-hydroxy-4-(2-pyridinyl)piperidinyl) | 583.7 | 584.2 | 1.80 | N-[3-fluoro-2-[4-[[4-hydroxy-4-(2-pyridinyl)-1-piperidinyl]carbonyl]-1-piperidinyl]phenyl]-4-(2-methyl-4-pyridinyl)-1H-imidazole-2-carboxamide |

Example 21

Preparation of N-[2-[2-(dimethylamino)ethoxy]phenyl]-4-[1-(phenylmethyl)-1H-pyrazol-4-yl]-1H-imidazole-2-carboxamide (6)

Step A—Synthesis of 4-(1-benzyl-1H-pyrazol-4-yl)-N-(2-(2-(dimethylamino)ethylamino)phenyl)-1-((2-(trimethylsilyl)ethoxy)methyl)-1H-imidazole-2-carboxamide (Int-21b)

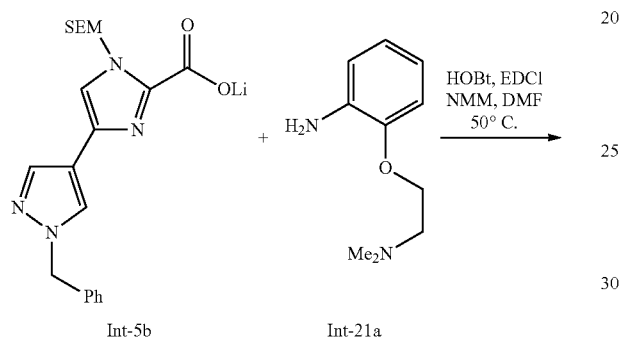

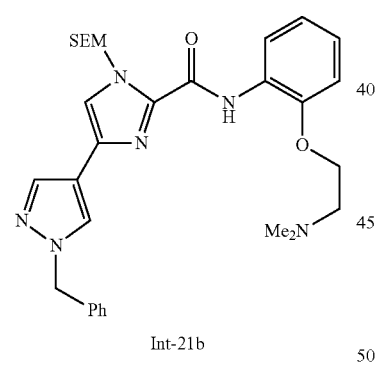

A mixture of carboxylate Int-5b (106 mg, 0.27 mmol), aniline Int-21a (48 mg, 0.27 mmol), HOBt (72 mg, 0.53 mmol), EDCI (102 mg, 0.53 mmol) and NMM (14 mg, 0.13 mmol) was stirred in N,N-dimethylformamide (3 mL) at 50° C. overnight. Water and ethyl acetate were added and layers were separated.

The separated organic layer was washed with water. The separated organic layer was dried (MgSO$_4$) and filtered. The solvents were removed in vacuo and chromatographic purification (ethyl acetate-hexane) of the residue gave amide Int-21b (107 mg, 72%) as a white solid.

Step B—Synthesis of N-[2-[2-(dimethylamino)ethoxy]phenyl]-4-[1-(phenylmethyl)-1H-pyrazol-4-yl]-1H-imidazole-2-carboxamide (6)

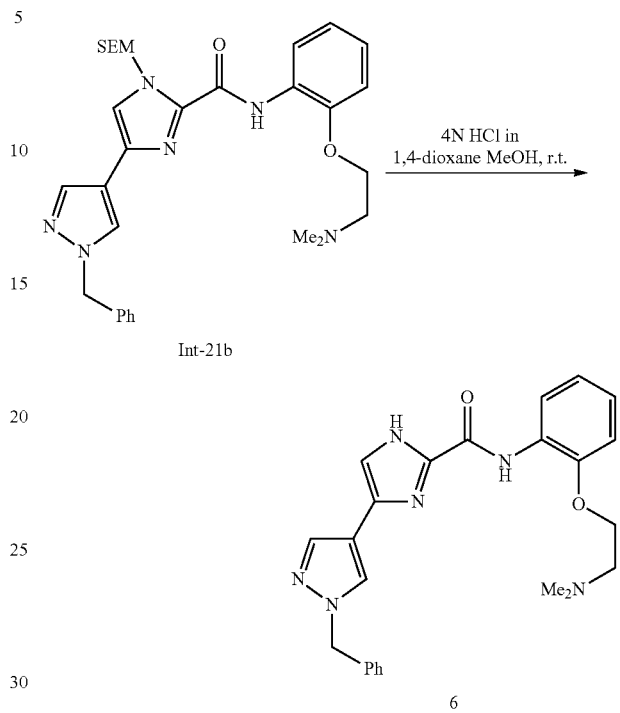

Amide Int-21b (107 mg, 0.19 mmol) was stirred in 4 N hydrochloric acid in 1,4-dioxane (5 mL) at 50° C. for 4 h. The solvents were removed in vacuo. Chromatographic purification [dichloromethane-methanol (7 N ammonia)] of the residue gave imidazole 6 (70 mg, 85%) as a colorless oil. LCMS m/e (M+H$^+$)=431.2.

Example 22

Preparation of N-[2-[2-(dimethylamino)ethoxy]phenyl]-4-(1H-indol-3-yl)-1H-imidazole-2-carboxamide (17)

Step A—Synthesis of 4-bromo-N-(2-(2-(dimethylamino)ethylamino)phenyl)-1-((2-(trimethylsilyl)ethoxy)methyl)-1H-imidazole-2-carboxamide (Int-22a)

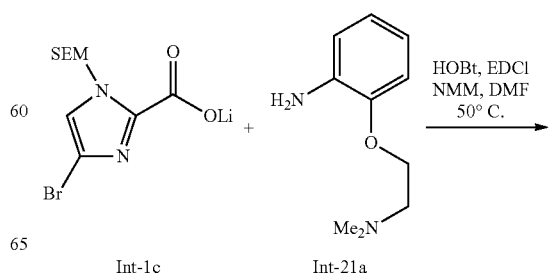

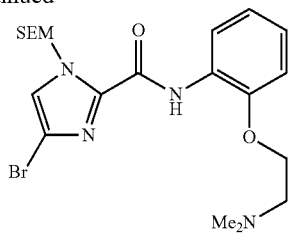

Int-22a

A mixture of carboxylate Int-1c (148 mg, 0.46 mmol), aniline Int-21a (83 mg, 10.46 mmol), HOBt (125 mg, 0.92 mmol), EDCI (176 mg, 0.92 mmol) and NMM (23 mg, 0.23 mmol) was stirred in N,N-dimethylformamide (5 mL) at 50° C. overnight. Water and ethyl acetate were added, and the layers were separated. The separated organic layer was washed with water. The separated organic layer was dried (MgSO$_4$) and filtered. The solvents were removed in vacuo and chromatographic purification (ethyl acetate-hexane) of the residue gave amide Int-22a (156 mg, 70%) as a white solid.

Step B—Synthesis of N-(2-(2-(dimethylamino)ethoxy)phenyl)-4-(1-(phenylsulfonyl)-1H-indol-3-yl)-1-((2-(trimethylsilyl)ethoxy)methyl)-1H-imidazole-2-carboxamide (Int-22b)

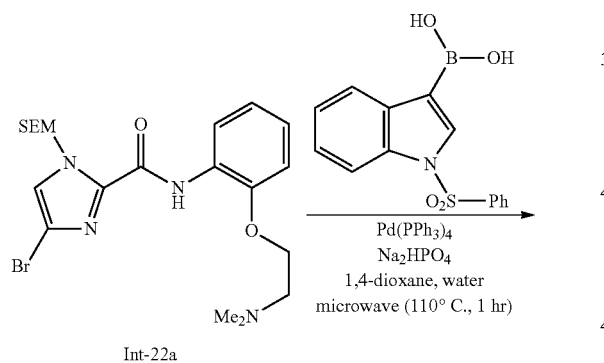

Int-22b

A mixture of bromoimidazole Int-22a (98 mg, 0.20 mmol), 1-(phenylsulfonyl)-3-indazole boronic acid (73 mg, 0.24 mmol) and sodium hydrogen phosphate (86 mg, 0.61 mmol) in 1,4-dioxane (4 mL) and water (2 mL) at r.t. was purged with nitrogen gas for 5 min in a microwave vial. Tetrakistriphenylphosphorous palladium was added. The mixture was heated in a microwave reactor at 110° C. for 1 h. Water and ethyl acetate were added, and the layers were separated. The separated aqueous layer was extracted with ethyl acetate. The separated organic layer was dried (MgSO$_4$) and filtered. The solvents were removed in vacuo and chromatographic purification (ethyl acetate-hexane) of the residue gave indole Int-22b (112 mg, 84%) as a colorless oil.

Step C—Synthesis of N-(2-(2-(dimethylamino)ethoxy)phenyl)-4-(1-(phenylsulfonyl)-1H-indol-3-yl)-1H-imidazole-2-carboxamide (Int-22c)

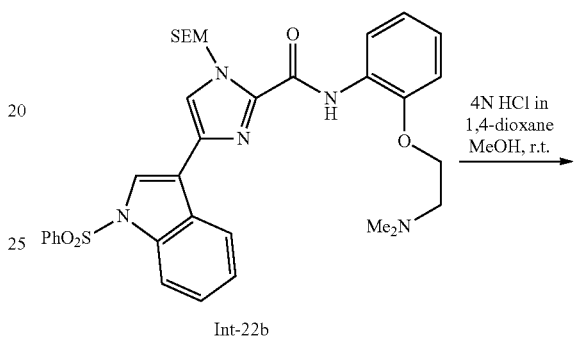

Int-22b

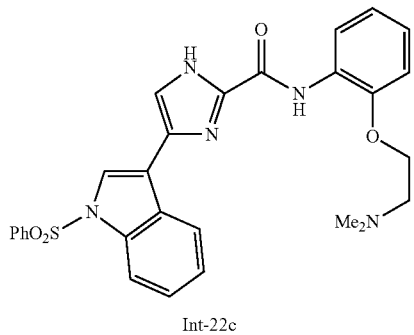

Int-22c

Amide Int-22b (112 mg, 0.068 mmol) was stirred in 4 N hydrochloric acid in 1,4-dioxane (5 mL) at 50° C. for 4 h. The solvents were removed in vacuo to give indole Int-22c as a yellow solid. The product was used in the next step without further purification. LCMS m/e (M+H$^+$)=530.1.

Step D—Synthesis of N-[2-[2-(dimethylamino)ethoxy]phenyl]-4-(H-indol-3-yl)-1H-imidazole-2-carboxamide (17)

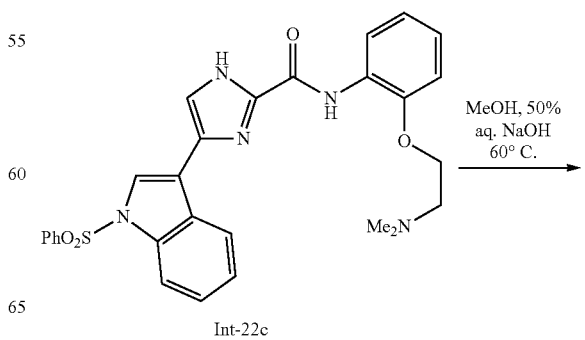

Int-22c

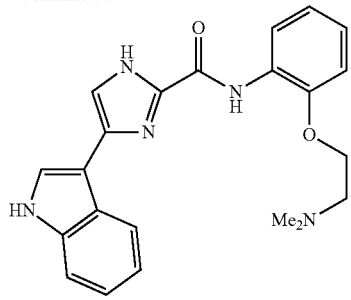

17

Indole Int-22c (87 mg) was stirred in a mixture of methanol (5 mL) and 50% aqueous sodium hydroxide solution at 60° C. for 3 h. The solvents were removed in vacuo. Water and ethyl acetate were added, and the layers were separated. The separated aqueous layer was extracted with ethyl acetate (×4). The combined organic layers were dried (MgSO$_4$) and filtered. The solvents were removed in vacuo, and chromatographic purification (ethyl acetate-methanol) of the residue gave imidazole 17 (43 mg) as a yellow oil. LCMS m/e (M+H$^+$)=390.1.

Example 23

Preparation of 4-(2-amino-6-methyl-4-pyrimidinyl)-N-[2-(3(R)-amino-1-piperidinyl)-3-fluorophenyl]-1H-imidazole-2-carboxamide (29)

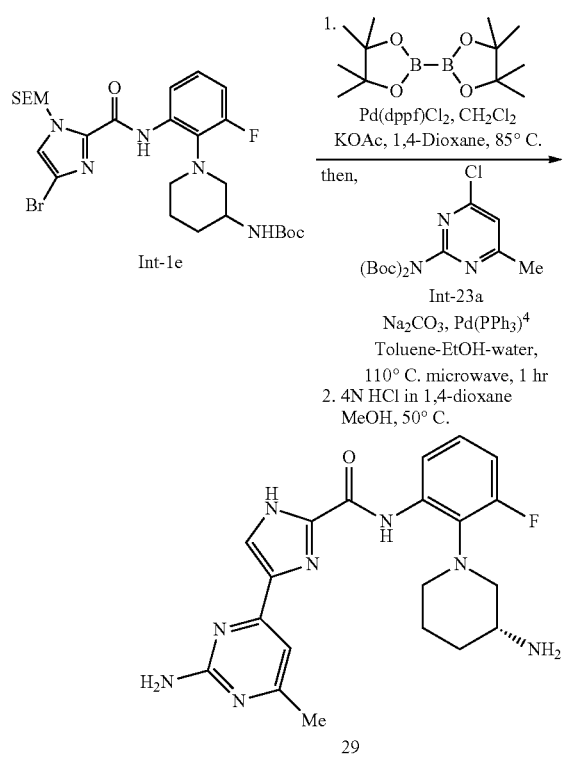

A mixture of bromide Int-1e (78 mg, 0.13 mmol), bis(pinacolato)diboron (48 mg, 0.19 mmol), potassium acetate (37 mg, 0.38 mmol) and Pd(dppf)Cl$_2$.CH$_2$Cl$_2$ (10 mg, 0.013 mmol) in 1,4-dioxane (5 mL) at r.t. was purged with nitrogen gas for 5 min in a sealed-tube. The mixture was heated at 85° C. overnight. The mixture was cooled to r.t. and transferred to a microwave vial. Chloropyrimidine Int-23a (87 mg, 0.25 mmol), sodium carbonate (67 mg, 0.64 mmol) in ethanol (2 mL), toluene (2 mL) and water (1 mL) and Pd(PPh$_3$)$_4$ (15 mg, 0.013 mmol) were added. The mixture was purged with nitrogen gas for 5 min and then heated in a microwave reactor at 110° C. for 1 h. Water and ethyl acetate were added, and the layers were separated. The separated organic layer was dried (MgSO$_4$) and filtered. The solvents were removed in vacuo and chromatographic purification (ethyl acetate-hexane) of the residue gave impure pyrimidine as a colorless oil.

The colorless oil was stirred in 4 N hydrochloric acid in 1,4-dioxane (2 mL) and methanol (2 mL) at 50° C. for 2 h. The solvents were removed in vacuo. Chromatographic purification [dichloromethane-methanol (7 N ammonia)] of the residue gave pyrimidine 29 (15 mg, 28%, 2 steps) as a white solid. LCMS m/e (M+H$^+$)=411.2.

Example 24

Preparation of N-[2-[4-(aminomethyl)-1-piperidinyl]-3-fluorophenyl]-4-(2

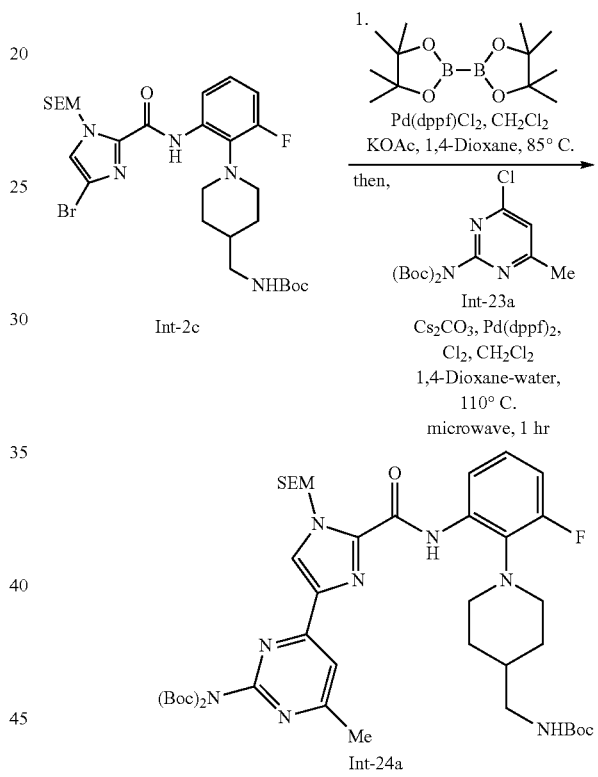

Step A—Synthesis of Int-24a

A mixture of bromide Int-2c (74 mg, 0.12 mmol), bis(pinacolato)diboron (66 mg, 0.26 mmol), potassium acetate (39 mg, 0.39 mmol) and Pd(dppf)Cl$_2$.CH$_2$Cl$_2$ (11 mg, 0.013 mmol) in 1,4-dioxane (5 mL) at r.t. was purged with nitrogen gas for 5 min in a sealed-tube. The mixture was heated at 85° C. overnight. The mixture was cooled to r.t. and was transferred to a microwave vial. Chloropyrimidine Int-23a (90 mg, 0.26 mmol) in 1,4-Dioxane (1 mL) and cesium carbonate (213 mg, 0.66 mmol) in water (2 mL) and Pd(dppf)Cl$_2$.CH$_2$Cl$_2$ (11 mg, 0.013 mmol) were added. The mixture was purged with nitrogen gas for 5 min and was heated in a microwave reactor at 110° C. for 1 h. Water and ethyl acetate were added, and the layers were separated. The separated organic layer was dried (MgSO$_4$) and filtered. The solvents were removed in vacuo and chromatographic purification (ethyl acetate-hexane) of the residue gave pyrimidine Int-24a (54 mg, 48%) as a colorless oil. LCMS m/e (M+H$^+$)=855.4.

Step B—Synthesis of N-[2-[4-(aminomethyl)-1-piperidinyl]-3-fluorophenyl]-4-(2-amino-6-methyl-4-pyrimidinyl)-1H-imidazole-2-carboxamide (47)

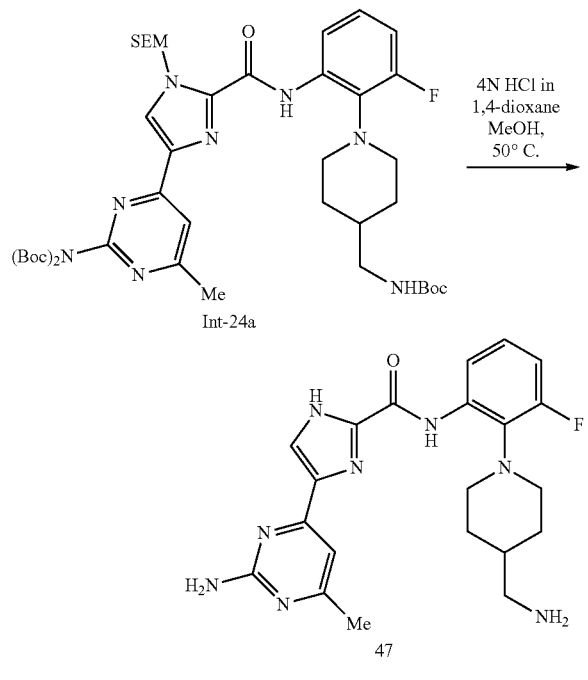

Pyrimidine Int-24a (54 mg, 0.063 mmol) was stirred in 4 N hydrochloric acid in 1,4-dioxane (2 mL) and methanol (2 mL) at 50° C. for 2 h. The solvents were removed in vacuo. Chromatographic purification [dichloromethane-methanol (7 N ammonia)] of the residue gave imidazole 47 (20 mg, 77%) as a white solid. LCMS m/e (M+H⁺)=425.2.

Using similar procedures to those described in Steps A and B, N-[2-[4-(aminomethyl)-1-piperidinyl]-3-fluorophenyl]-4-(6-amino-2-methyl-4-pyrimidinyl)-1H-imidazole-2-carboxamide (49)

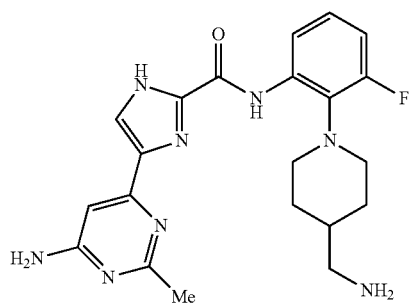

was prepared from Int-2c and

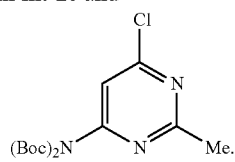

LCMS m/e (M+H⁺)=425.2.

Example 25

This example describes the preparation of Imidazole Carboxamide Compounds wherein R⁶ is H, T is a substituted pyrimidine moiety, and D is

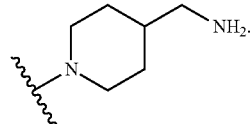 [SMILES: *N1CCC(CN)CC1]

The preparation is illustrated by the preparation of compound 69.

Step A—Synthesis of Int-25a

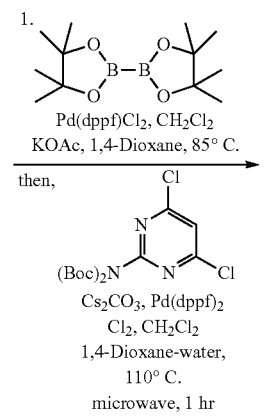

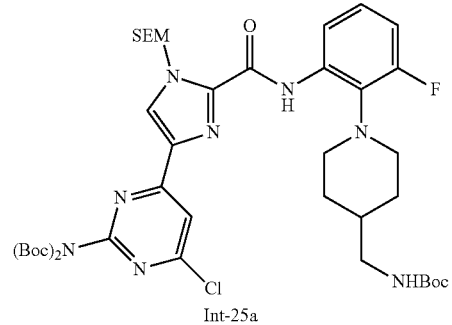

Starting from Int-2c and the protected dichloropyrimidine, Int-25a was prepared using similar procedures as described in Step A of Example 24.

Step B—Synthesis of Int-25b

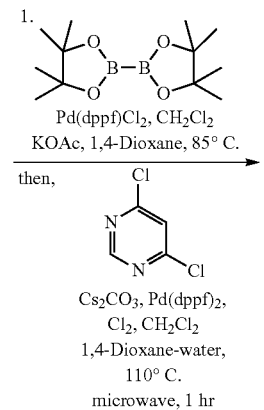

133

-continued

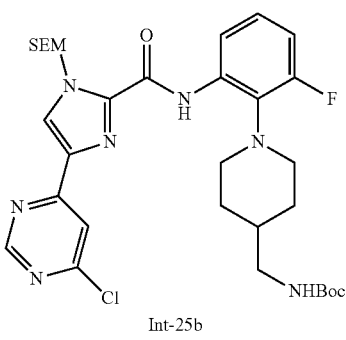
Int-25b

Starting from Int-2c and 4,6-dichloropyrimidine, Int-25b was prepared using similar procedures as described in Step A of Example 24.

Step C—Synthesis of N-[2-[4-(aminomethyl)-1-piperidinyl]-3-fluorophenyl]-4-[2-amino-6-[(phenylmethyl)amino]-4-pyrimidinyl]-1H-imidazole-2-Carboxamide (69)

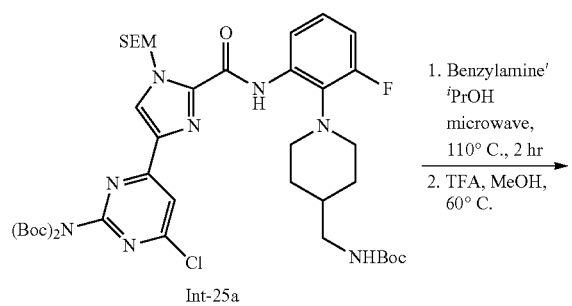
Int-25a

1. Benzylamine/
   $^i$PrOH
   microwave,
   110° C., 2 hr
2. TFA, MeOH,
   60° C.

134

-continued

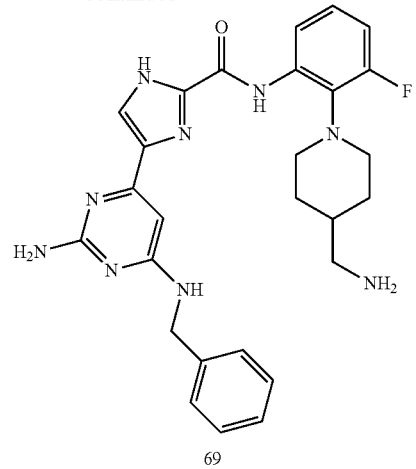
69

A solution of Int-25a (40 mg, 0.046 mmol) and benzylamine (25 mg, 0.23 mmol) in isopropyl alcohol (3 ml) was heated at 110° C. in a microwave reactor for 2 h. The solvents were removed in vacuo. The residue was diluted with ethyl acetate and water. The layers were separated and the separated organic layer was dried (MgSO$_4$) and filtered. The solvents were removed in vacuo. Chromatographic purification (ethyl acetate-hexanes) gave a benzylaminopyrimidine intermediate as a colorless oil. The benzylaminopyrimidine intermediate was stirred in trifluoroacetic acid (3 mL) for 2 h at 60° C. The solvents were removed in vacuo and chromatographic purification [dichloromethane-methanol (7 N ammonia)] of the residue gave compound 69 (11 mg, 45%, 2 steps) as a colorless oil. LCMS m/e (M+H$^+$)=516.3.

Compounds 70-77 were prepared by essentially the same procedures as described in Steps A and B for the preparation of compound 69. Thus the amines listed in the Table 5 below were reacted with Int-25a or Int-25b followed by acid deprotection to provide compounds 70-77.

TABLE 5

| Amine | Compound | LCMS m/e (M + H$^+$) | |
|---|---|---|---|
| ![H2N-CH2-C6H4-CF3] | ![compound 70] | 584.2 | N-[2-[4-(aminomethyl)-1-piperidinyl]-3-fluorophenyl]-4-[2-amino-6-[[[4-(trifluoromethyl)phenyl]methyl]amino]-4-pyrimidinyl]-1H-imidazole-2-carboxamide |

70

US 8,623,857 B2

TABLE 5-continued

| Amine | Compound | LCMS m/e (M + H+) | |
|---|---|---|---|
| 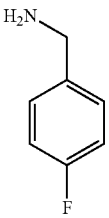 | 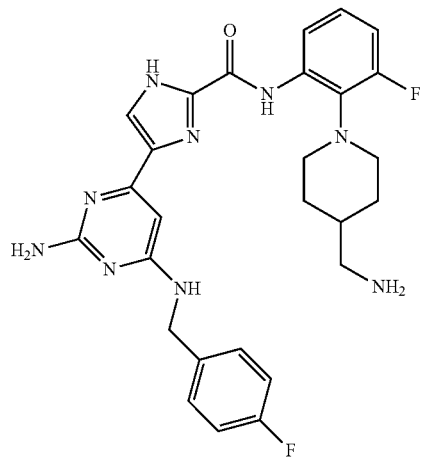 [SMILES: NCC1CCN(c2c(F)cccc2NC(=O)c2nc(-c3cc(NCc4ccc(F)cc4)nc(N)n3)c[nH]2)CC1]  71 | 534.2 | 4-[2-amino-6-[[(4-fluorophenyl)methyl]amino]-4-pyrimidinyl]-N-[2-[4-(aminomethyl)-1-piperidinyl]-3-fluorophenyl]-1H-imidazole-2-carboxamide |
| 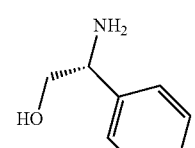 | 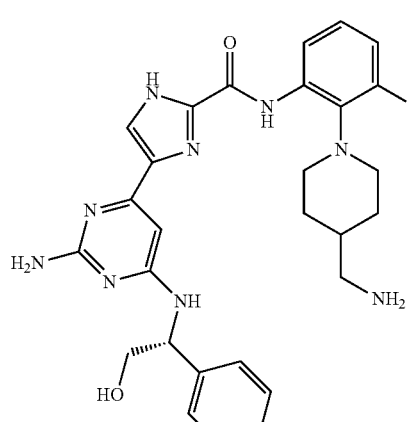  72 | 546.3 | 4-[2-amino-6-[[2-hydroxy-1(R)-phenylethyl]amino]-4-pyrimidinyl]-N-[2-[4-(aminomethyl)-1-piperidinyl]-3-fluorophenyl]-1H-imidazole-2-carboxamide |
| 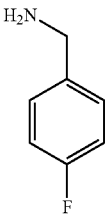 | 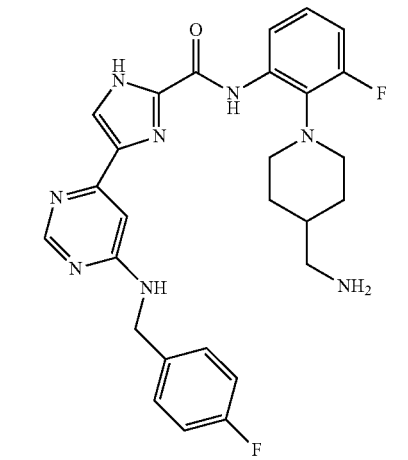 [SMILES: NCC1CCN(c2c(F)cccc2NC(=O)c2nc(-c3cc(NCc4ccc(F)cc4)ncn3)c[nH]2)CC1]  73 | 519.2 | N-[2-[4-(aminomethyl)-1-piperidinyl]-3-fluorophenyl]-4-[6-[[(4-fluorophenyl)methyl]amino]-4-pyrimidinyl]-1H-imidazole-2-carboxamide |

TABLE 5-continued

| Amine | Compound | LCMS m/e (M + H+) | |
|---|---|---|---|
| 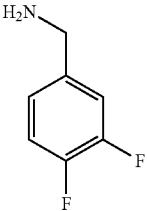 | 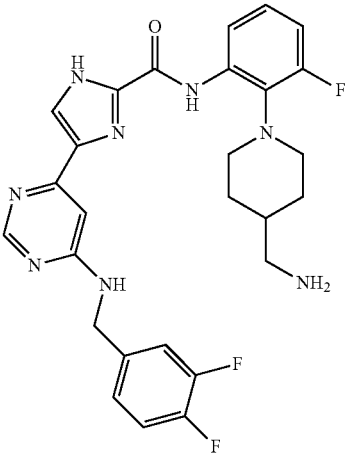 [SMILES: NCC1CCN(c2c(F)cccc2NC(=O)c2nc(-c3cc(NCc4ccc(F)c(F)c4)ncn3)c[nH]2)CC1]
74 | 537.3 | N-[2-[4-(aminomethyl)-1-piperidinyl]-3-fluorophenyl]-4-[6-[[(3,4-difluorophenyl)methyl]amino]-4-pyrimidinyl]-1H-imidazole-2-carboxamide |
| 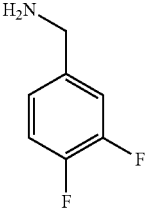 | 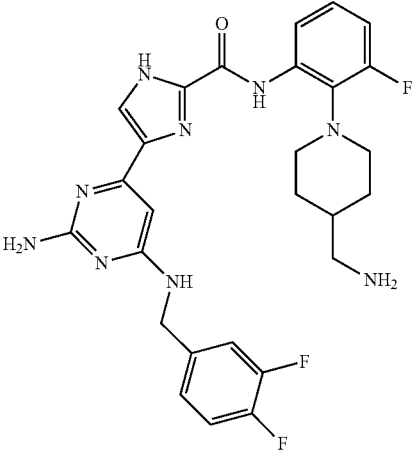
75 | 552.2 | 4-[2-amino-6-[[(3,4-difluorophenyl)methyl]amino]-4-pyrimidinyl]-N-[2-[4-(aminomethyl)-1-piperidinyl]-3-fluorphenyl]-1H-imidazole-2-carboxamide |
| 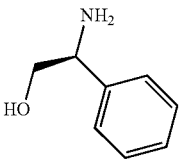 | 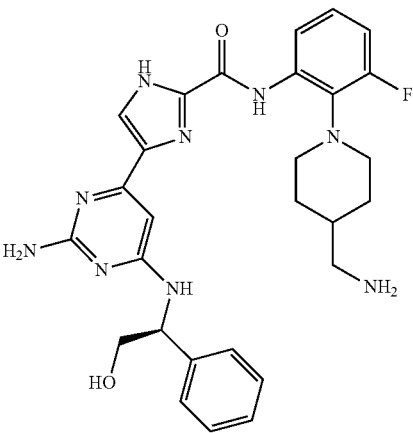 [SMILES: NCC1CCN(c2c(F)cccc2NC(=O)c2nc(-c3cc(N[C@H](CO)c4ccccc4)nc(N)n3)c[nH]2)CC1]
77 | 546.2 | 4-[2-amino-6-[(2-hydroxy-1(S)-phenylethyl)amino]-4-pyrimidinyl]-N-[2-[4-(aminomethyl)-1-piperidinyl]-3-fluorophenyl]-1H-imidazole-2-carboxamide |

TABLE 5-continued

| Amine | Compound | LCMS m/e (M + H+) | |
|---|---|---|---|
| 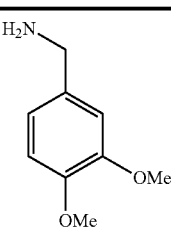 | 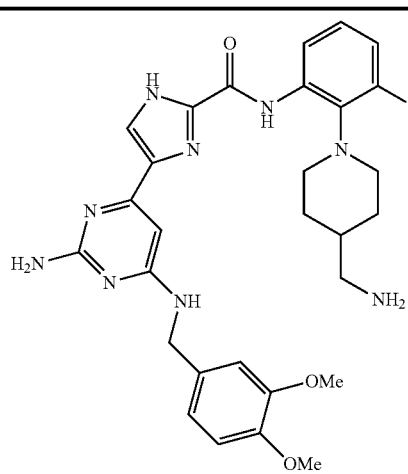 | 576.3 | 4-[2-amino-6-[[(3,4-dimethoxyphenyl)methyl]amino]-4-pyrimidinyl]-N-[2-[4-(aminomethyl)-1-piperidinyl]-3-fluorophenyl]-1H-imidazole-2-carboxamide |
| | 76 | | |

Example 26

Preparation of 2-amino-6-(2-(2-(4-(aminomethyl)piperidin-1-yl)-3-fluorophenylcarbamoyl)-1H-imidazol-4-yl)pyrimidine-4-carboxamide (68)

Step A—Synthesis of Int-26a

Starting from Int-2c and methyl 2,6-dichloropyrimidine-4-carboxylate, Int-26a was prepared using similar procedures as described in Step A of Example 24.

Step B—Synthesis of Compound 68

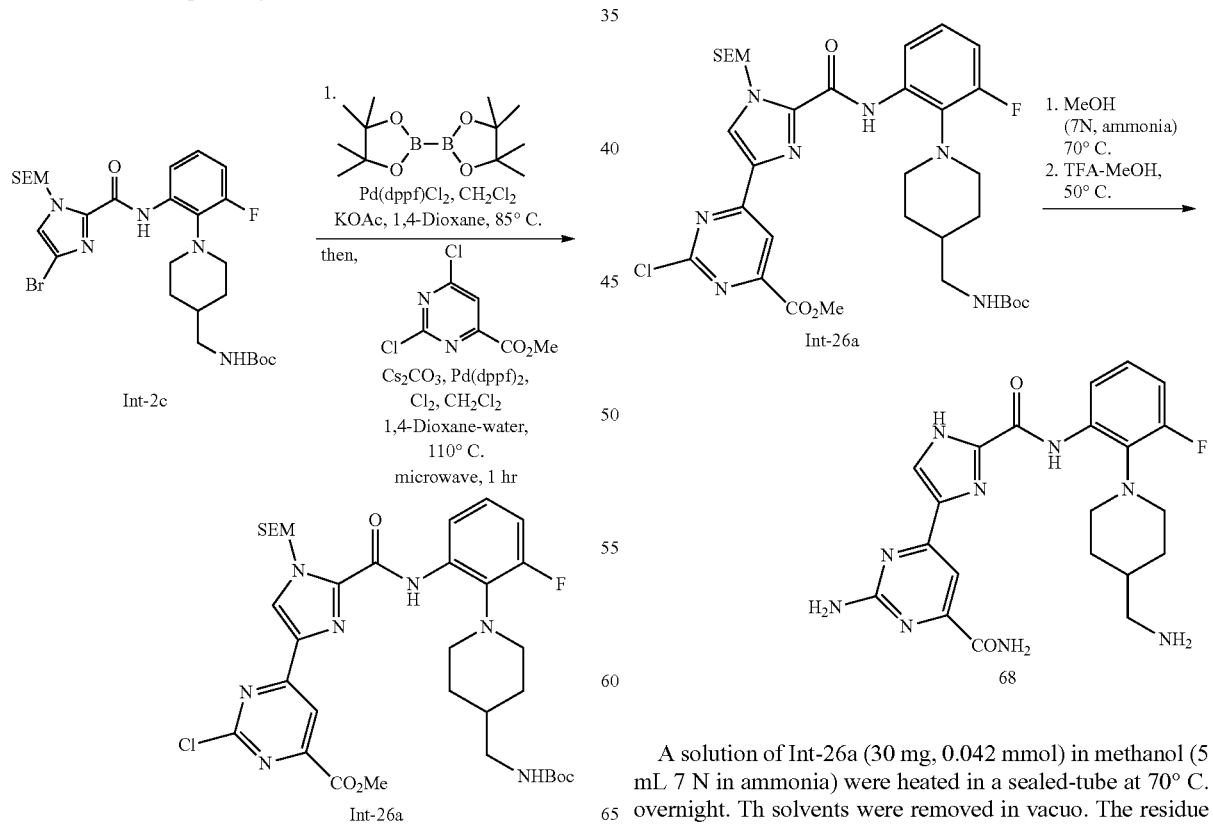

A solution of Int-26a (30 mg, 0.042 mmol) in methanol (5 mL 7 N in ammonia) were heated in a sealed-tube at 70° C. overnight. Th solvents were removed in vacuo. The residue was stirred in trifluoroacetic acid (2 mL) and methanol (2 mL) at 50° C. for 2 h. The solvents were removed in vacuo and chromatographic purification [dichloromethane-methanol (7N in ammonia)] of the residue gave 68 (13 mg, 68%). LCMS m/e (M+H⁺)=454.1.

Example 27

Imidazole Carboxamide Compounds can be prepared which bear $^2$H substituents. This example describes a method useful for preparing Imidazole Carboxamide Compounds wherein $R^6$ is $^2$H.

The methyl ester Int-27a is heated with palladium on carbon in the presence of $^2$H$_2$O to provide the deuterium-containing intermediate Int-27b. Alternatively, Int-27b is prepared by treating Int-27a with N-bromosuccinimide followed by hydrogenation with deuterium gas. Int-27b is converted to Int-27c using procedures similar to those described in Steps A and B of Example 1.

Int-27c is saponified as described in Step C of Example 1 to provide Int-27d.

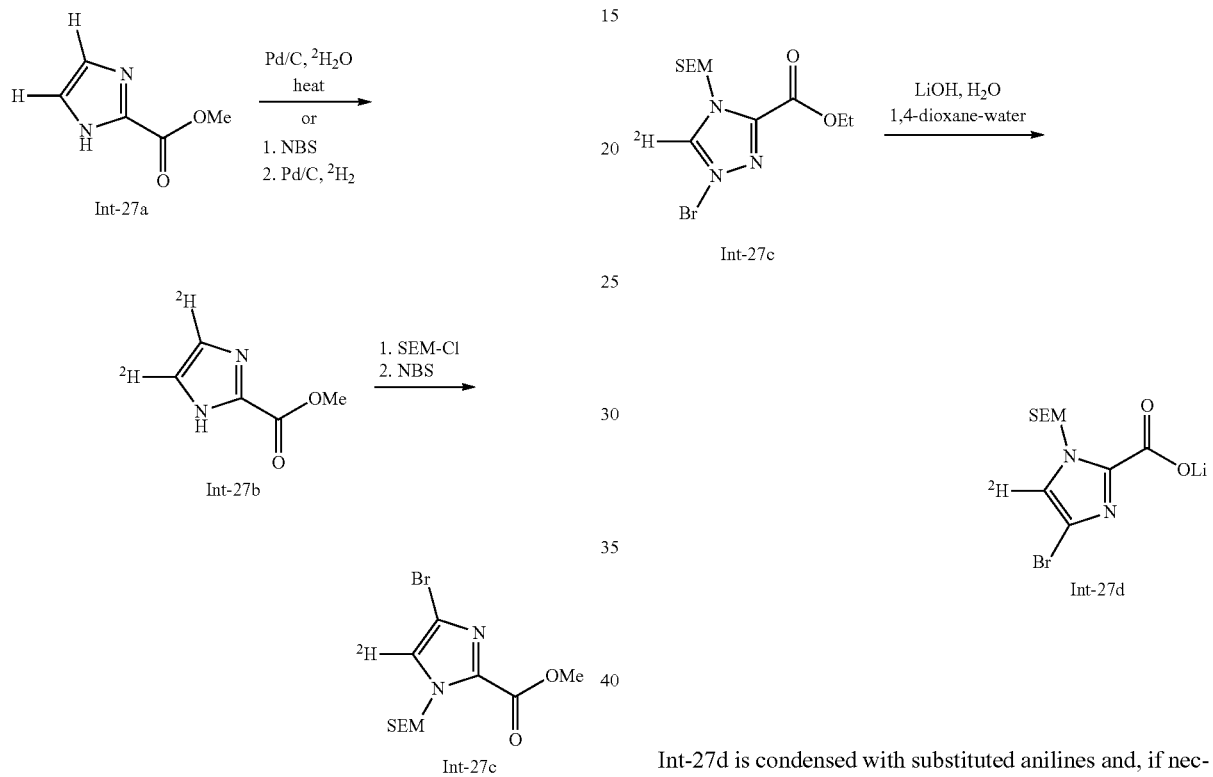

Int-27d is condensed with substituted anilines and, if necessary, is deprotected to provide Imidazole Carboxamide Compounds such as Int-27e and Int-27f wherein $R^6={}^2$H.

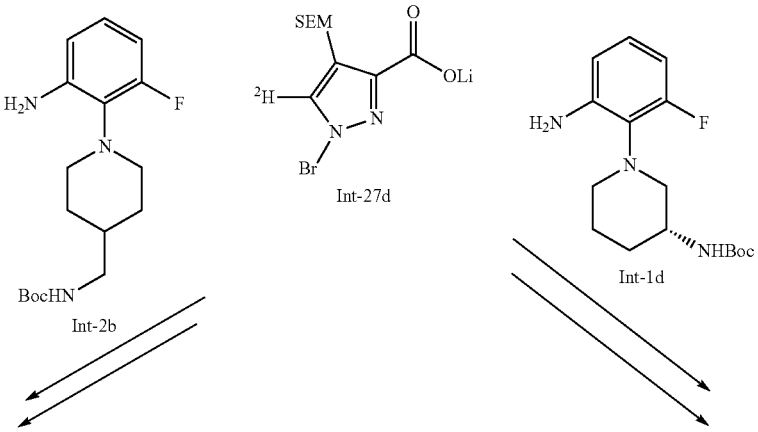

143

-continued

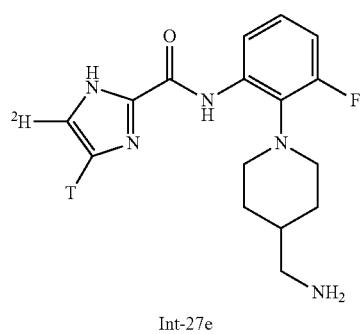

Int-27e

144

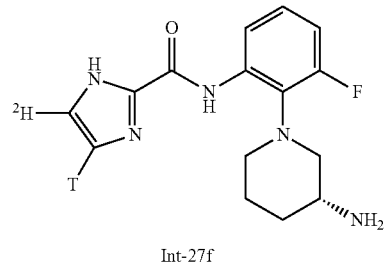

Int-27f

Example 28

This example describes a method useful for preparing Imidazole Carboxamide Compounds wherein $R^1$ is $^2H$.

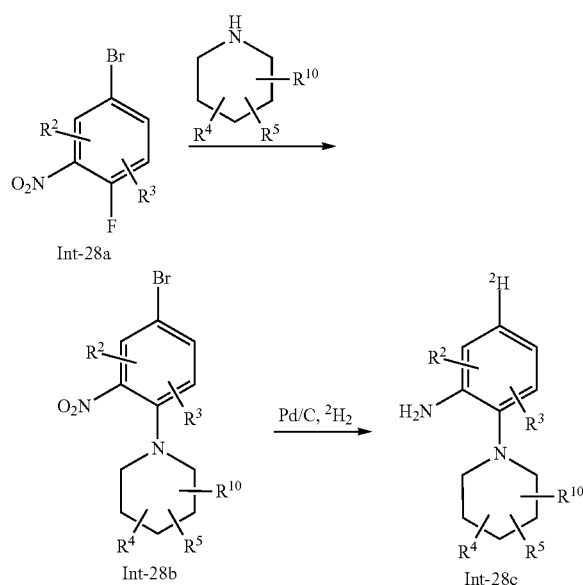

The nitrobenzene Int-28a is displaced with the substituted piperidine using conditions such as those described above in Step A of Example 2 to provide Int-28b. Hydrogenation of Int-28b with Pd/C in deuterium gas provides aniline Int-28c. Int-28c can be condensed with various imidazole carboxylic acid intermediates and deprotected as described above to provide Imidazole Carboxamide Compounds wherein $R^1$ is $^2H$.

Example 29

The assay used to test the compounds' abilities to inhibit phosphorylation of a substrate by PDK1 uses the IMAP® technology system available from Molecular Devices (Silicon Valley, Calif., United States). The technology enables the detection of the phosphorylation of protein substrates by PDK1 and does not require the addition of antibodies to detect substrate phosphorylation. The technology is based on the high-affinity interaction of trivalent metal containing nanoparticles (beads) with phospho-groups on the substrate of interest. The readout for the assay was fluorescence polarization (FP) which increased once the fluorescently labeled substrate was phosphorylated and was bound to the beads as opposed to the unphosphorylated substrate which did not bind the beads and had relatively lower polarization.

In a microwell assay format, the fluorescently-labeled peptide substrate from glycogen synthase-1, 5FAM-PLSRTLS-VSSLPGL-NH$_2$ (SEQ ID NO:1), Molecular Devices part no RP7045), was phosphorylated in a kinase reaction. Addition of the IMAP® Binding System (available from Molecular Devices) stopped the kinase reaction and specifically bound the phosphorylated substrates. Phosphorylation and subsequent binding of the substrate to the beads was detected by FP.

The PDK1 IMAP assay utilized recombinant human PDK1 produced in Sf9 insect cells and containing amino acids 51-556 of the human PDK1 enzyme. The assay measured the change in fluorescence polarization caused by phosphorylation of a peptide substrate by PDK1. Addition of small molecule PDK1 inhibitors results in the reduction of peptide phosphorylation changing the fluorescence polarization which is measured using a fluorescence plate reader. The assay was performed in a 384-well plate with 10 nM PDK1 enzyme, 100 nM peptide substrate 1 (SEQ ID NO:1), 100 nM activated peptide PIFtide and 2.5 uM ATP for 1.5 hours. PIFtide is added separately to the IMAP reaction at 100 nM. The peptide sequence of PIFtide is RREPRILSEEEQEM-FRDFDYIADWC (SEQ ID NO:2). PIFtide is a peptide sequence that interacts with PDK-1 and is derived from PRK2 kinase, a PDK-1 substrate. This sequence is present in the hydrophobic motif present in PDK-1 substrates and binds to the kinase domain of PDK-1. It is thought to act as a docking site for PDK-1 on the substrate and in vitro has been shown enhance PDK-1 phosphorylation of substrates by approximately 4-fold. See Biondi et al., *EMBO* 19, 979-988 (2000).

The detection beads were then added and allowed to incubate for 1 hour at room temperature and the fluorescence was then read. Staurosporine, a broad spectrum kinase inhibitor, was used as a positive control for the assay resulting in typical IC$_{50}$s of 3 nM. Test compounds in 100% DMSO at a range of concentrations were added at 0.5 µl 15 minutes prior to ATP addition. The fluorescence polarization units (mP) generated with 1 uM stauroporine is considered to be background mP and the mP units generated with DMSO is considered to be total mP for each assay. The IC$_{50}$ value is calculated based on fitting the mP units to the total and background mP and the concentration required to inhibit the mP units by 50% is reported to be the IC$_{50}$.

Table 6 below lists representative compounds of the invention with activity data whereby the IC$_{50}$ values are rated "A", "B," "C," or "D." The IC$_{50}$ values are rated "A" for IC$_{50}$ values in the range of 1 nM to 50 nM, "B" for IC$_{50}$ values in the range from 51 nM to 250 nM, "C" for $IC_{50}$ values in the range from 251 nM to 1 μM, and "D" for $IC_{50}$ values in the range from 1-5 μM.

TABLE 6

| Compound | $IC_{50}$ |
|---|---|
| 1 | B |
| 2 | D |
| 3 | C |
| 4 | B |
| 5 | B |
| 6 | D |
| 7 | D |
| 8 | A |
| 9 | D |
| 10 | C |
| 11 | B |
| 12 | B |
| 13 | B |
| 14 | C |
| 15 | D |
| 16 | B |
| 17 | C |
| 18 | A |
| 19 | B |
| 20 | A |
| 21 | B |
| 22 | C |
| 23 | B |
| 24 | A |
| 25 | D |
| 26 | A |
| 27 | A |
| 28 | B |
| 29 | A |
| 30 | A |
| 31 | B |
| 32 | A |
| 33 | B |
| 34 | B |
| 35 | A |
| 36 | C |
| 37 | D |
| 38 | C |
| 39 | C |
| 40 | C |
| 41 | B |
| 42 | B |
| 43 | B |
| 44 | C |
| 45 | D |
| 46 | B |
| 47 | A |
| 48 | C |
| 49 | B |
| 50 | C |
| 51 | C |
| 52 | B |
| 53 | A |
| 54 | D |
| 55 | B |
| 56 | B |
| 57 | C |
| 58 | D |
| 59 | D |
| 60 | D |
| 61 | D |
| 62 | D |
| 63 | D |
| 64 | D |
| 65 | D |
| 66 | D |
| 67 | B |
| 68 | A |
| 69 | A |
| 70 | B |
| 71 | A |
| 72 | A |
| 73 | B |

TABLE 6-continued

| Compound | $IC_{50}$ |
|---|---|
| 74 | B |
| 75 | A |
| 76 | C |
| 77 | A |
| 78 | C |
| 79 | D |
| 80 | C |
| 81 | B |
| 82 | D |
| 83 | B |
| 84 | B |
| 85 | C |
| 86 | C |
| 87 | 8 |
| 88 | B |
| 89 | B |
| 90 | C |
| 91 | B |
| 92 | D |
| 93 | C |
| 94 | B |
| 95 | C |
| 96 | D |

Preparation of Intermediates 60a-q (Table 7)

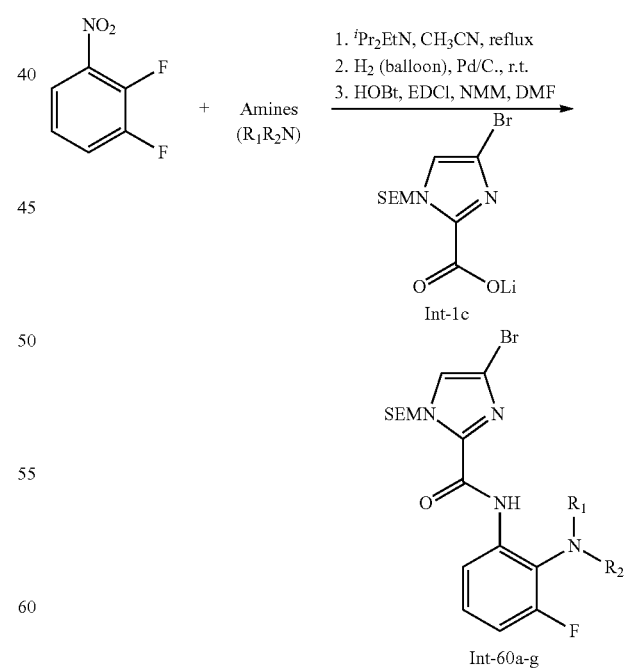

Starting from amines (see Table 7) and 1,2-difluoro-3-nitrobenzene, intermediates 60a-g were prepared using procedures as described for the preparation of Int-2.

TABLE 7

| Amines (R₁R₂N) | Intermediates (60) |
|---|---|
| a | |
| b | |
| c | |
| d | |
| e | |

TABLE 7-continued

| Amines (R₁R₂N) | Intermediates (60) |
|---|---|
| f | 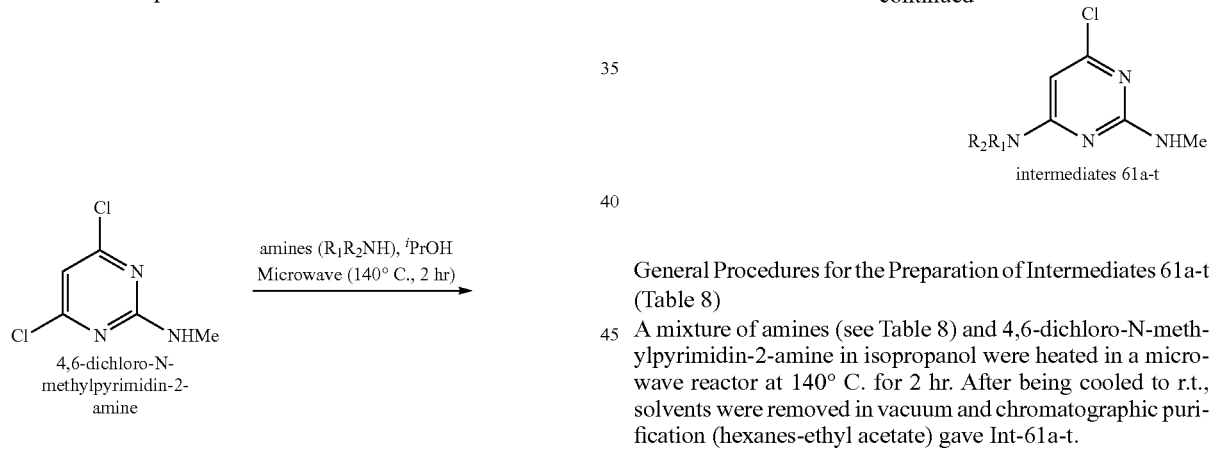 |
| g | |

Preparation of Intermediates 61a-61t

General Procedures for the Preparation of Intermediates 61a-t (Table 8)

A mixture of amines (see Table 8) and 4,6-dichloro-N-methylpyrimidin-2-amine in isopropanol were heated in a microwave reactor at 140° C. for 2 hr. After being cooled to r.t., solvents were removed in vacuum and chromatographic purification (hexanes-ethyl acetate) gave Int-61a-t.

TABLE 8

| | Amines | Intermediate (61) |
|---|---|---|
| a | | |

TABLE 8-continued
| Amines | Intermediate (61) |
|---|---|
| b 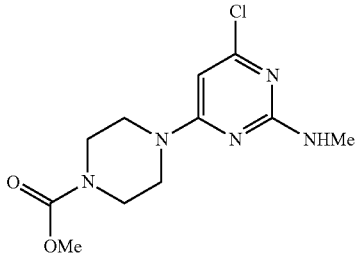 [SMILES: CNc1nc(Cl)cc(N2CCN(C(=O)OC)CC2)n1] | 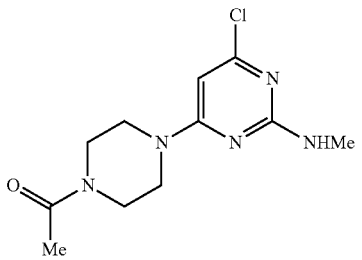 [SMILES: CNc1nc(Cl)cc(N2CCN(C(C)=O)CC2)n1] |
| c | |
| b | |
| e | |
| f | |

TABLE 8-continued

| | Amines | Intermediate (61) |
|---|---|---|
| g | morpholine-2-carboxylic acid ethyl ester | 4-chloro-6-(2-ethoxycarbonylmorpholin-4-yl)-2-(methylamino)pyrimidine |
| h | (S)-1-Boc-3-methylpiperazine | 4-chloro-6-((S)-4-Boc-2-methylpiperazin-1-yl)-2-(methylamino)pyrimidine |
| i | (S)-3-methylmorpholine | 4-chloro-6-((S)-3-methylmorpholin-4-yl)-2-(methylamino)pyrimidine |
| j | (S)-2-(Boc-aminomethyl)morpholine | 4-chloro-6-((S)-2-(Boc-aminomethyl)morpholin-4-yl)-2-(methylamino)pyrimidine |
| k | (S)-1-Boc-2-methylpiperazine | 4-chloro-6-((S)-4-Boc-3-methylpiperazin-1-yl)-2-(methylamino)pyrimidine |
| l | 4-(Boc-aminomethyl)piperidine | 4-chloro-6-(4-(Boc-aminomethyl)piperidin-1-yl)-2-(methylamino)pyrimidine |

TABLE 8-continued
| | Amines | Intermediate (61) |
|---|---|---|
| m | 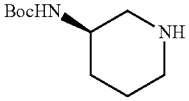 | 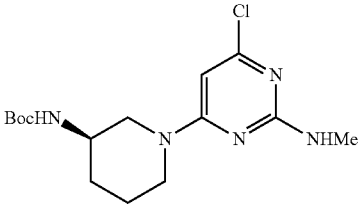 [SMILES: CNc1nc(Cl)cc(N2CCC[C@@H](NC(=O)OC(C)(C)C)C2)n1] |
| n | 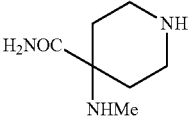 | 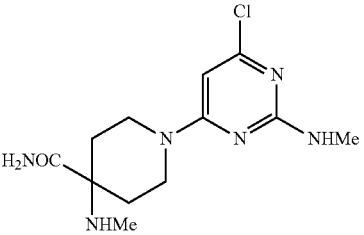 [SMILES: CNc1nc(Cl)cc(N2CCC(NC)(C(N)=O)CC2)n1] |
| o | 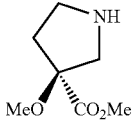 | 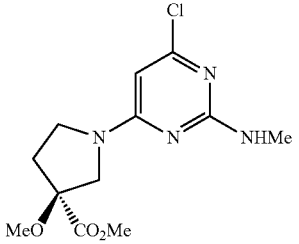 [SMILES: CNc1nc(Cl)cc(N2CC[C@@](OC)(C(=O)OC)C2)n1] |
| p | 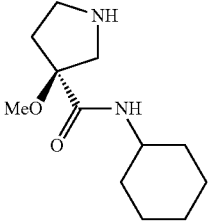 [SMILES: CO[C@@]1(C(=O)NC2CCCCC2)CCNC1] | 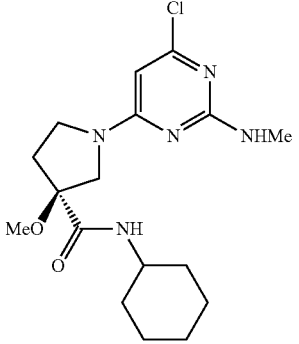 [SMILES: CNc1nc(Cl)cc(N2CC[C@@](OC)(C(=O)NC3CCCCC3)C2)n1] |
| q | 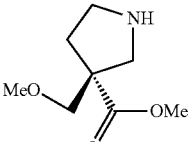 | 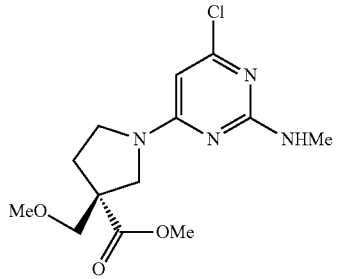 [SMILES: CNc1nc(Cl)cc(N2CC[C@@](COC)(C(=O)OC)C2)n1] |

TABLE 8-continued
| Amines | Intermediate (61) |
|---|---|
| r 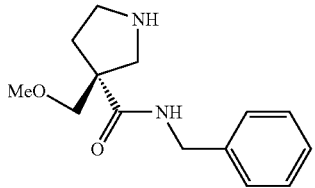 [SMILES: COC[C@@]1(C(=O)NCc2ccccc2)CCNC1] | 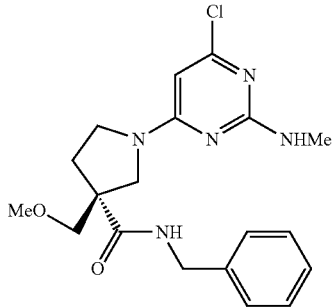 [SMILES: CNc1nc(Cl)cc(N2CC[C@@](COC)(C(=O)NCc3ccccc3)C2)n1] |
| s 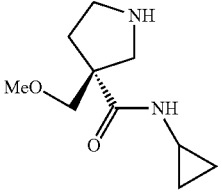 [SMILES: COC[C@@]1(C(=O)NC2CC2)CCNC1] | 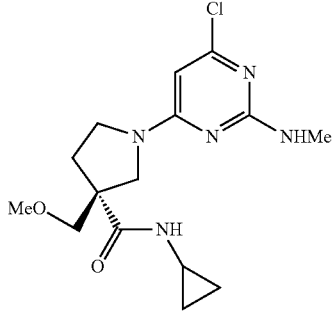 [SMILES: CNc1nc(Cl)cc(N2CC[C@@](COC)(C(=O)NC3CC3)C2)n1] |
| t 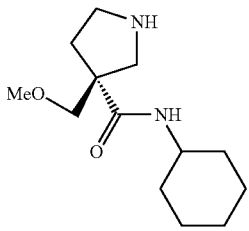 [SMILES: COC[C@@]1(C(=O)NC2CCCCC2)CCNC1] | 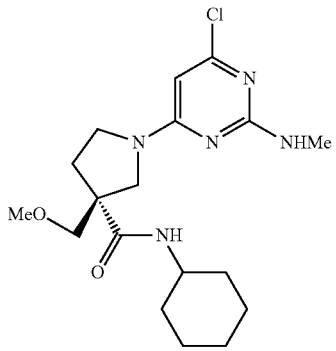 [SMILES: CNc1nc(Cl)cc(N2CC[C@@](COC)(C(=O)NC3CCCCC3)C2)n1] |

Preparation of Compound 97 to Compound 132
(Table 10)

Starting from intermediate 1e, 2c, or 60a-g and intermediates 61a-t, compounds 97-132 were prepared using procedures as described in Steps A and B in Example 24.

TABLE 10

| Comp # | Structure | LCMS m/e (M + H⁺) | IC50 | Name |
|---|---|---|---|---|
| 97 | 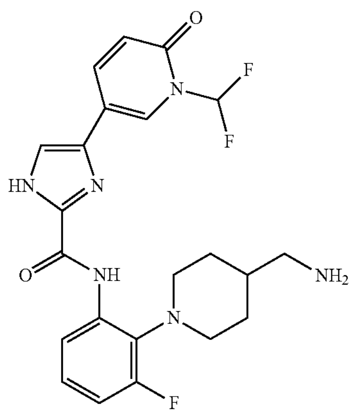 [SMILES: NCC1CCN(c2c(F)cccc2NC(=O)c2nc(-c3ccc(=O)n(C(F)F)c3)c[nH]2)CC1] | 460.7 | B | N-(2-(4-(aminomethyl)piperidin-1-yl)-3-fluorophenyl)-4-(1-(difluoromethyl)-6-oxo-1,6-dihydropyridin-3-yl)-1H-imidazole-2-carboxamide |
| 98 | 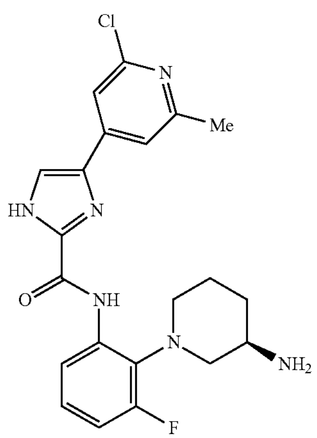 [SMILES: Cc1cc(-c2c[nH]c(C(=O)Nc3cccc(F)c3N3CCC[C@@H](N)C3)n2)cc(Cl)n1] | 428.7 | C | (R)-N-(2-(3-aminopiperidin-1-yl)-3-fluorophenyl)-4-(2-chloro-6-methylpyridin-4-yl)-1H-imidazole-2-carboxamide |
| 99 | 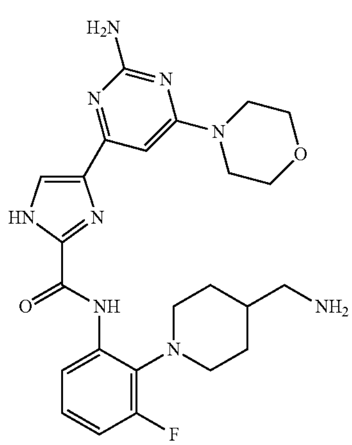 [SMILES: NCC1CCN(c2c(F)cccc2NC(=O)c2nc(-c3cc(N4CCOCC4)nc(N)n3)c[nH]2)CC1] | 495.7 | A | 4-(2-amino-6-morpholinopyrimidin-4-yl)-N-(2-(4-(aminomethyl)piperidin-1-yl)-3-fluorophenyl)-1H-imidazole-2-carboxamide |

TABLE 10-continued

| Comp # | Structure | LCMS m/e (M + H+) | IC50 | Name |
|---|---|---|---|---|
| 100 | 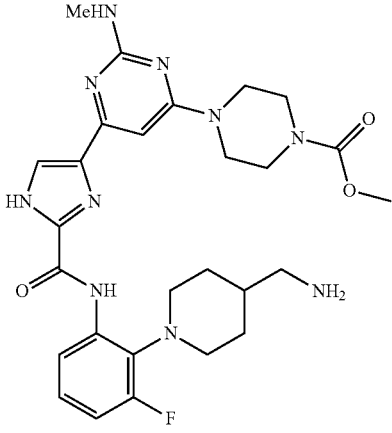 [SMILES: CNc1nc(-c2c[nH]c(C(=O)Nc3cccc(F)c3N3CCC(CN)CC3)n2)cc(N2CCN(C(=O)OC)CC2)n1] | 566.7 | A | methyl 4-(6-(2-(2-(4-(aminomethyl)piperidin-1-yl)-3-fluorophenyl-carbamoyl)-1H-imidazol-4-yl)-2-(methylamino)pyrimidin-4-yl)piperazine-1-carboxylate |
| 101 | 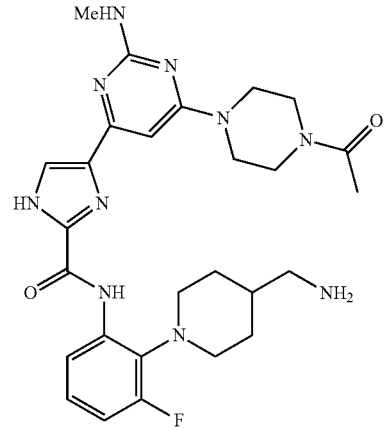 [SMILES: CNc1nc(-c2c[nH]c(C(=O)Nc3cccc(F)c3N3CCC(CN)CC3)n2)cc(N2CCN(C(C)=O)CC2)n1] | 781.5 | A | 4-(6-(4-acetylpiperazin-1-yl)-2-(methylamino)pyrimidin-4-yl)-N-(2-(4-(aminomethyl)piperidin-1-yl)-3-fluorophenyl)-1H-imidazole-2-carboxamide |
| 102 | 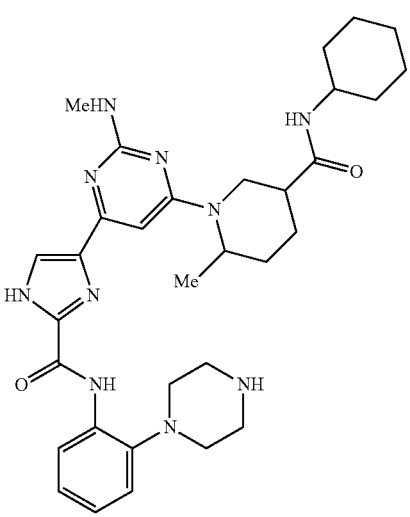 [SMILES: CNc1nc(-c2c[nH]c(C(=O)Nc3ccccc3N3CCNCC3)n2)cc(N2CC(C(=O)NC3CCCCC3)CCC2C)n1]<br>cis-racemic | 600.7 | A | N-cyclohexyl-6-methyl-1-(2-(methylamino)-6-(2-(2-(piperazin-1-yl)phenylcarbamoyl)-1H-imidazol-4-yl)pyrimidm-4-yl)piperidine-3-carboxamide |

TABLE 10-continued

| Comp # | Structure | LCMS m/e (M + H⁺) | IC50 | Name |
|---|---|---|---|---|
| 103 | 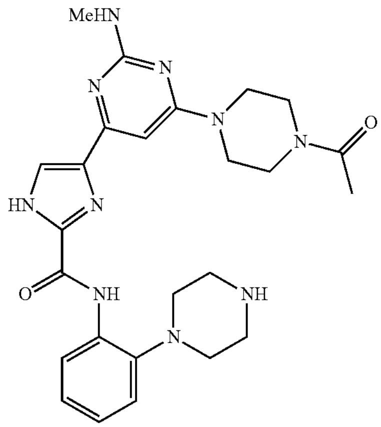 [SMILES: CNc1nc(-c2c[nH]c(C(=O)Nc3ccccc3N3CCNCC3)n2)cc(N2CCN(C(C)=O)CC2)n1] | 504.7 | B | 4-(6-(4-acetylpiperazin-1-yl)-2-(methylamino)pyrimidin-4-yl)-N-(2-(piperazin-1-yl)phenyl)-1H-imidazole-2-carboxamide |
| 104 | trans-racemic | 600.7 | B | N-cyclohexyl-6-methyl-1-(2-(methylamino)-6-(2-(2-(piperazin-1-yl)phenylcarbamoyl)-1H-imidazol-4-yl)pyrimidin-4-yl)piperidine-3-carboxamide |
| 105 | 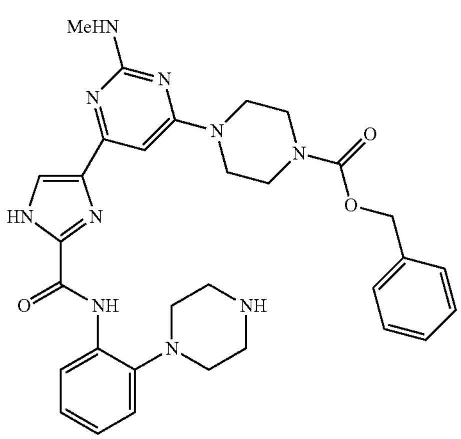 [SMILES: CNc1nc(-c2c[nH]c(C(=O)Nc3ccccc3N3CCNCC3)n2)cc(N2CCN(C(=O)OCc3ccccc3)CC2)n1] | 596.7 | D | benzyl 4-(2-(methylamino)-6-(2-(2-(piperazin-1-yl)phenylcarbamoyl)-1H-imidazol-4-yl)pyrimidin-4-yl)piperazine-1-carboxylate |

TABLE 10-continued

| Comp # | Structure | LCMS m/e (M + H⁺) | IC50 | Name |
|---|---|---|---|---|
| 106 | 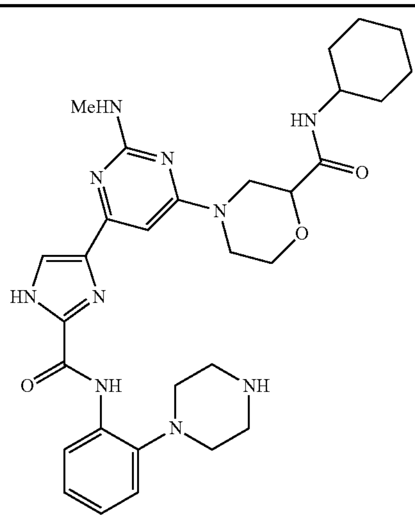 | 588.7 | B | N-cyclohexyl-4-(2-(methylamino)-6-(2-(2-(piperazin-1-yl)phenylcarbamoyl)-1H-imidazol-4-yl)pyrimidin-4-yl)morpholine-2-carboxamide |
| 107 | cis-racemic | 646.7 | A | 1-(6-(2-(2-(4-(aminomethyl)piperidin-1-yl)-3-fluorophenyl-carbamoyl)-1H-imidazol-4-yl)-2-(methylamino)pyrimidin-4-yl)-N-cyclohexyl-6-methylpiperidine-3-carboxamide |
| 108 | cis-racemic | 615.7 | A | N-cyclohexyl-6-methyl-1-(2-(methylamino)-6-(2-(2-(piperidin-4-yloxy)phenyl-carbamoyl)-1H-imidazol-4-yl)pyrimidin-4-yl)piperidine-3-carboxamide |

| Comp # | Structure | LCMS m/e (M + H⁺) | IC50 | Name |
|---|---|---|---|---|
| 109 | 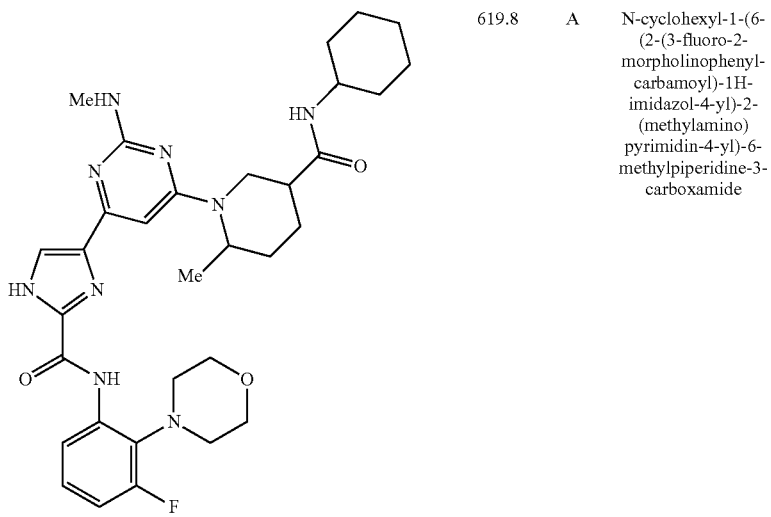 cis-racemic | 619.8 | A | N-cyclohexyl-1-(6-(2-(3-fluoro-2-morpholinophenyl-carbamoyl)-1H-imidazol-4-yl)-2-(methylamino)pyrimidin-4-yl)-6-methylpiperidine-3-carboxamide |
| 110 | 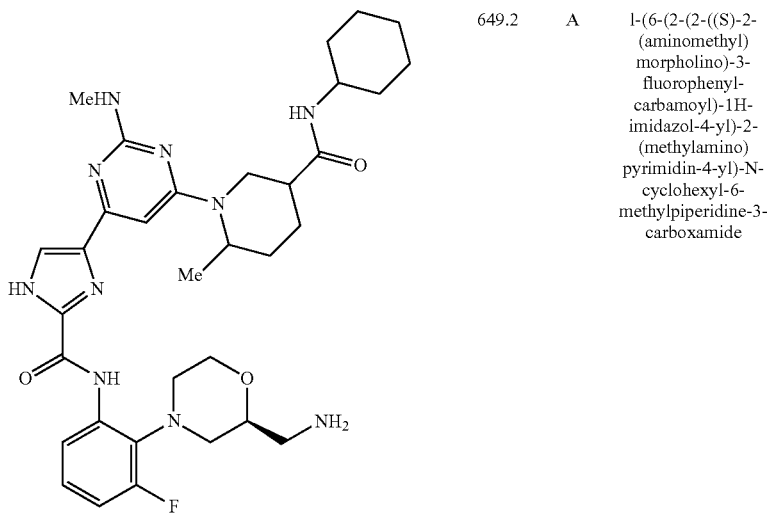 cis-racemic | 649.2 | A | 1-(6-(2-(2-((S)-2-(aminomethyl)morpholino)-3-fluorophenyl-carbamoyl)-1H-imidazol-4-yl)-2-(methylamino)pyrimidin-4-yl)-N-cyclohexyl-6-methylpiperidine-3-carboxamide |

TABLE 10-continued
| Comp # | Structure | LCMS m/e (M + H+) | IC50 | Name |
|---|---|---|---|---|
| 111 | 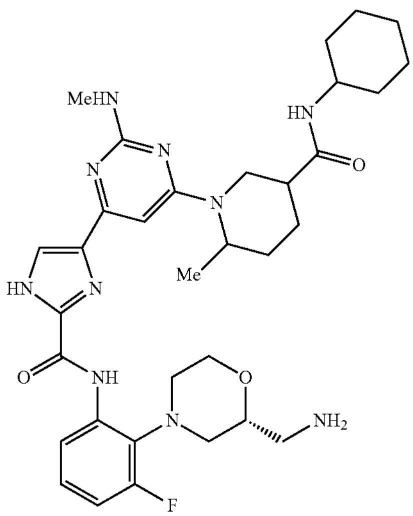 [SMILES: CNc1nc(-c2c[nH]c(C(=O)Nc3cccc(F)c3N3CCO[C@H](CN)C3)n2)cc(N2CC(C(=O)NC3CCCCC3)CCC2C)n1] | 649.2 | A | 1-(6-(2-(2-((R)-2-(aminomethyl)morpholino)-3-fluorophenyl-carbamoyl)-1H-imidazol-4-yl)-2-(methylamino)pyrimidin-4-yl)-N-cyclohexyl-6-methylpiperidine-3-carboxamide |
| 112 | 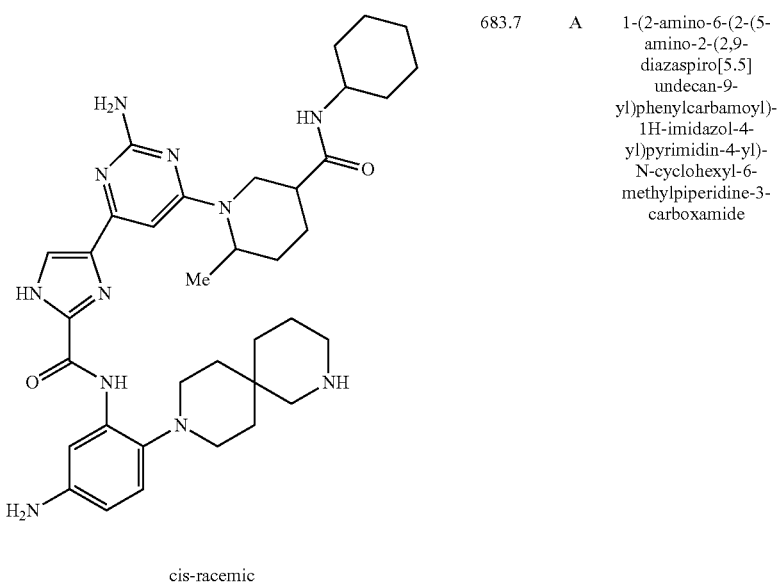 cis-racemic | 683.7 | A | 1-(2-amino-6-(2-(5-amino-2-(2,9-diazaspiro[5.5]undecan-9-yl)phenylcarbamoyl)-1H-imidazol-4-yl)pyrimidin-4-yl)-N-cyclohexyl-6-methylpiperidine-3-carboxamide |

TABLE 10-continued
| Comp # | Structure | LCMS m/e (M + H+) | IC50 | Name |
|---|---|---|---|---|
| 113 | 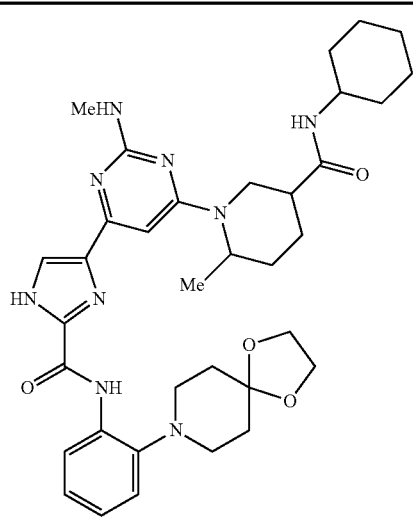<br>cis-racemic | 658.2 | A | 1-(6-(2-(2-(1,4-dioxa-8-azaspiro[4.5]decan-8-yl)phenylcarbamoyl)-1H-imidazol-4-yl)-2-(methylamino)pyrimidin-4-yl)-N-cyclohexyl-6-methylpiperidine-3-carboxamide |
| 114 | 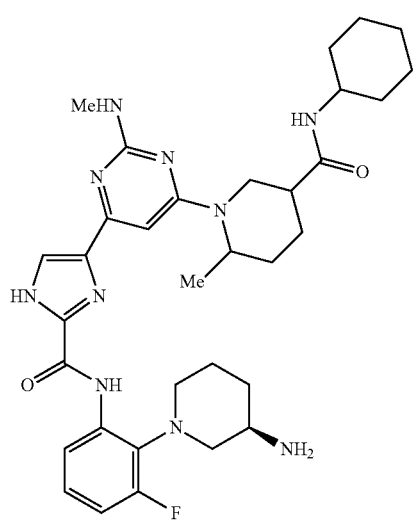 [SMILES: CNc1nc(-c2c[nH]c(C(=O)Nc3cccc(F)c3N3CCC[C@@H](N)C3)n2)cc(N2CC(C(=O)NC3CCCCC3)CCC2C)n1]<br>cis-racemic | 633.2 | A | 1-(6-(2-(2-((R)-3-aminopiperidin-1-yl)-3-fluorophenyl-carbamoyl)-1H-imidazol-4-yl)-2-(methylamino)pyrimidin-4-yl)-N-cyclohexyl-6-methylpiperidine-3-carboxamide |

TABLE 10-continued

| Comp # | Structure | LCMS m/e (M + H⁺) | IC50 | Name |
|---|---|---|---|---|
| 115 | 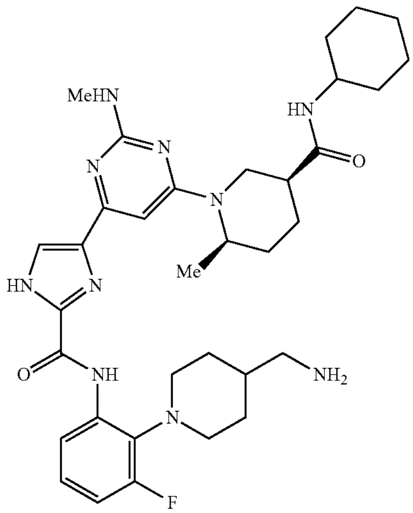 [SMILES: CNc1nc(-c2c[nH]c(C(=O)Nc3cccc(F)c3N3CCC(CN)CC3)n2)cc(N2C[C@@H](C(=O)NC3CCCCC3)CC[C@H]2C)n1] | 647.2 | A | (3S,6R)-1-(6-(2-(2-(4-(aminomethyl)piperidin-1-yl)-3-fluorophenyl-carbamoyl)-1H-imidazol-4-yl)-2-(methylamino)pyrimidin-4-yl)-N-cyclohexyl-6-methylpiperidine-3-carboxamide |
| 116 | 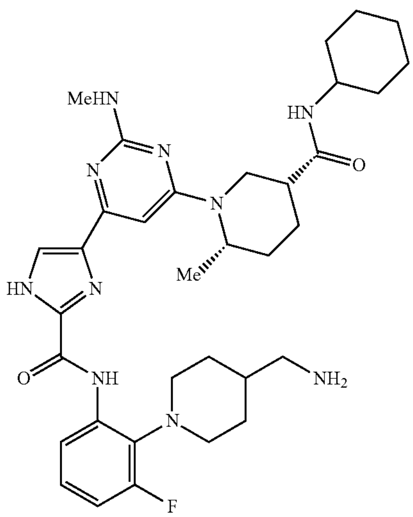 | 647.2 | A | (3R,6S)-1-(6-(2-(2-(4-(aminomethyl)piperidin-1-yl)-3-fluorophenyl-carbamoyl)-1H-imidazol-4-yl)-2-(methylamino)pyrimidin-4-yl)-N-cyclohexyl-6-methylpiperidine-3-carboxamide |
| 117 | 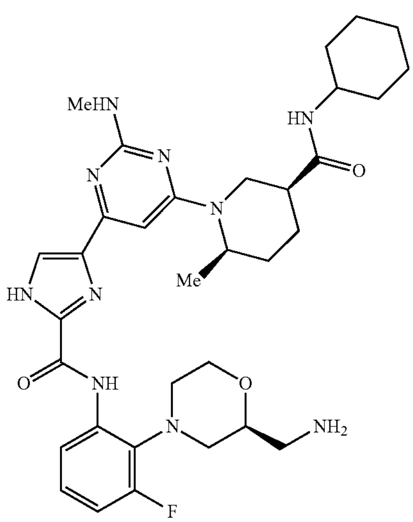 [SMILES: CNc1nc(-c2c[nH]c(C(=O)Nc3cccc(F)c3N3CCO[C@@H](CN)C3)n2)cc(N2C[C@@H](C(=O)NC3CCCCC3)CC[C@H]2C)n1] | 649.2 | A | (3S,6R)-1-(6-(2-(2-((S)-2-(aminomethyl)morpholino)-3-fluorophenyl-carbamoyl)-1H-imidazol-4-yl)-2-(methylamino)pyrimidin-4-yl)-N-cyclohexyl-6-methylpiperidine-3-carboxamide |

TABLE 10-continued

| Comp # | Structure | LCMS m/e (M + H⁺) | IC50 | Name |
|---|---|---|---|---|
| 118 | 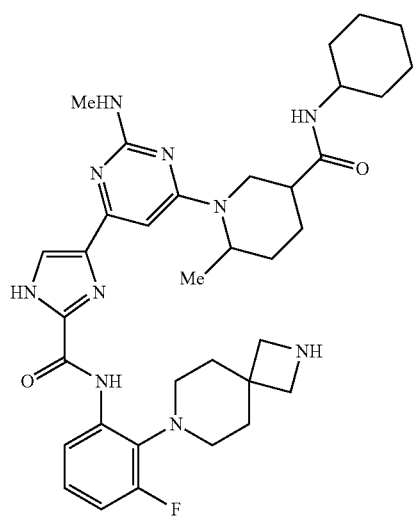 [SMILES: CNc1nc(-c2c[nH]c(C(=O)Nc3cccc(F)c3N3CCC4(CC3)CNC4)n2)cc(N2CC(C(=O)NC3CCCCC3)CCC2C)n1] cis-racemic | 659.2 | A | N-cyclohexyl-1-(6-(2-(3-fluoro-2-(2,7-diazaspiro[3.5]nonan-7-yl)phenylcarbamoyl)-1H-imldazol-4-yl)-2-(methylamino)pyrimidin-4-yl)-6-methylpiperidine-3-carboxamide |
| 119 | 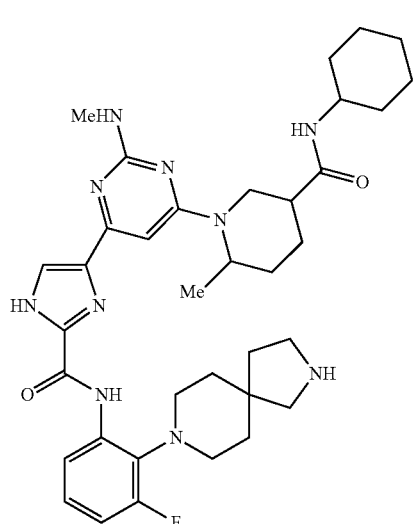 cis-racemic | 673.2 | A | N-cyclohexyl-1-(6-(2-(3-fluoro-2-(2,8-diazaspiro[4.5]decan-8-yl)phenylcarbamoyl)-1H-imidazol-4-yl)-2-(methylamino)pyrimidin-4-yl)-6-methylpiperidine-3-carboxamide |
| 120 | 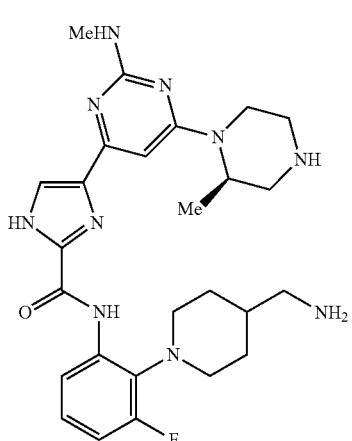 | 522.7 | A | (R)-N-(2-(4-(aminomethyl)piperidin-1-yl)-3-fluorophenyl)-4-(2-(methylamino)-6-(2-methylpiperazin-1-yl)pyrimidin-4-yl)-1H-imidazole-2-carboxamide |

TABLE 10-continued

| Comp # | Structure | LCMS m/e (M + H+) | IC50 | Name |
|---|---|---|---|---|
| 121 | 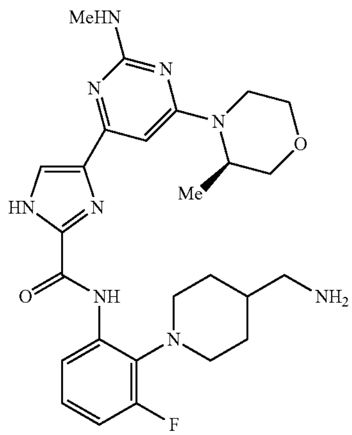 [SMILES: CNc1nc(-c2c[nH]c(C(=O)Nc3cccc(F)c3N3CCC(CN)CC3)n2)cc(N2CCOC[C@H]2C)n1] | 523.8 | A | (R)-N-(2-(4-(aminomethyl)piperidin-1-yl)-3-fluorophenyl)-4-(2-(methylamino)-6-(3-methylmorpholino)pyrimidin-4-yl)-1H-imidazole-2-carboxamide |
| 122 | cis-racemic | 633.7 | A | N-cyclohexyl-1-(6-(2-(3-fluoro-2-((R)-3-methylmorpholino)phenylcarbamoyl)-1H-imidazol-4-yl)-2-(methylamino)pyrimidin-4-yl)-6-methylpiperidine-3-carboxamide |
| 123 | 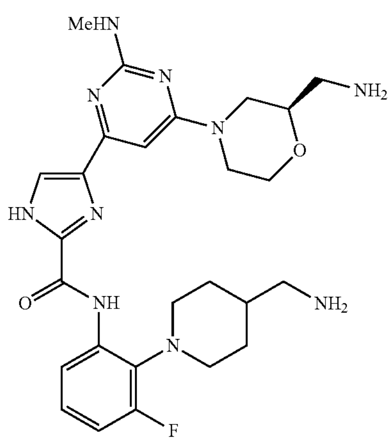 [SMILES: CNc1nc(-c2c[nH]c(C(=O)Nc3cccc(F)c3N3CCC(CN)CC3)n2)cc(N2CCO[C@H](CN)C2)n1] | 538.8 | A | (R)-4-(6-(2-(aminomethyl)morpholino)-2-(methylamino)pyrimidin-4-yl)-N-(2-(4-(aminomethyl)piperidin-1-yl)-3-fluorophenyl)-1H-imidazole-2-carboxamide |

TABLE 10-continued

| Comp # | Structure | LCMS m/e (M + H⁺) | IC50 | Name |
|---|---|---|---|---|
| 124 | 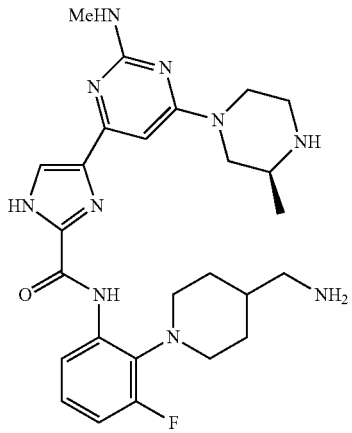 [SMILES: CNc1nc(-c2c[nH]c(C(=O)Nc3cccc(F)c3N3CCC(CN)CC3)n2)cc(N2CCN[C@@H](C)C2)n1] | 522.8 | A | (S)-N-(2-(4-(aminomethyl)piperidin-1-yl)-3-fluorophenyl)-4-(2-(methylamino)-6-(3-methylpiperazin-1-yl)pyrimidin-4-yl)-1H-imidazole-2-carboxamide |
| 125 | 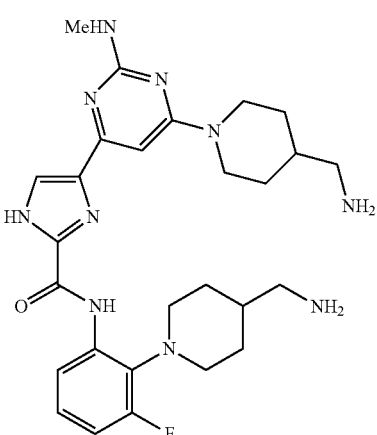 | 536.9 | A | 4-(6-(4-(aminomethyl)piperidin-1-yl)-2-(methylamino)pyrimidin-4-yl)-N-(2-(4-(aminomethyl)piperidin-1-yl)-3-fluorophenyl)-1H-imidazole-2-carboxamide |
| 126 | 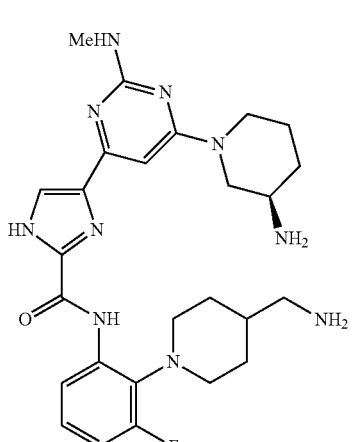 | 522.9 | A | (R)-N-(2-(4-(aminomethyl)piperidin-1-yl)-3-fluorophenyl)-4-(6-(3-aminopiperidin-1-yl)-2-(methylamino)pyrimidin-4-yl)-1H-imidazole-2-carboxamide |

TABLE 10-continued

| Comp # | Structure | LCMS m/e (M + H⁺) | IC50 | Name |
|---|---|---|---|---|
| 127 | 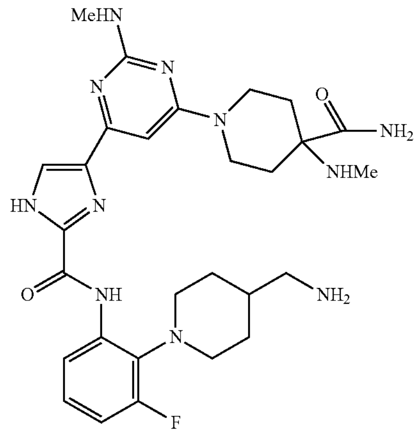 [SMILES: CNc1nc(-c2c[nH]c(C(=O)Nc3cccc(F)c3N3CCC(CN)CC3)n2)cc(N2CCC(NC)(C(N)=O)CC2)n1] | 580.2 | A | 1-(6-(2-(2-(4-(aminomethyl)piperidin-1-yl)-3-fluorophenyl-carbamoyl)-1H-imidazol-4-yl)-2-(methylamino)pyrimidin-4-yl)-4-(methylamino)piperidine-4-carboxamide |
| 128 | 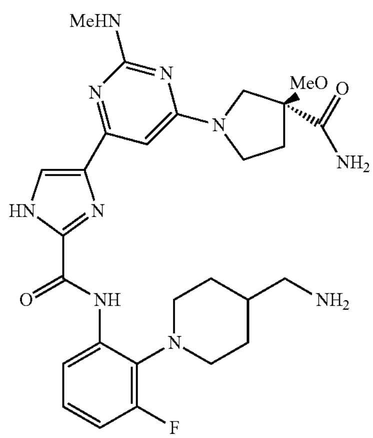 [SMILES: CNc1nc(-c2c[nH]c(C(=O)Nc3cccc(F)c3N3CCC(CN)CC3)n2)cc(N2CC[C@@](OC)(C(N)=O)C2)n1] | 566.8 | A | (S)-N-(2-(4-(aminomethyl)piperidin-1-yl)-3-fluorophenyl)-4-(6-(3-carbamoyl-3-methoxypyrrolidin-1-yl)-2-(methylamino)pyrimidin-4-yl)-1H-imidazole-2-carboxamide |
| 129 | 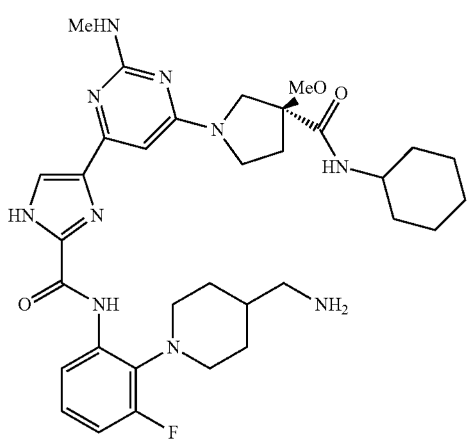 [SMILES: CNc1nc(-c2c[nH]c(C(=O)Nc3cccc(F)c3N3CCC(CN)CC3)n2)cc(N2CC[C@@](OC)(C(=O)NC3CCCCC3)C2)n1] | 648.9 | A | (S)-N-(2-(4-(aminomethyl)piperidin-1-yl)-3-fluorophenyl)-4-(6-(3-(cyclohexyl-carbamoyl)-3-methoxypyrrolidin-1-yl)-2-(methylamino)pyrimidin-4-yl)-1H-imidazole-2-carboxamide |

TABLE 10-continued

| Comp # | Structure | LCMS m/e (M + H+) | IC50 | Name |
|---|---|---|---|---|
| 130 | 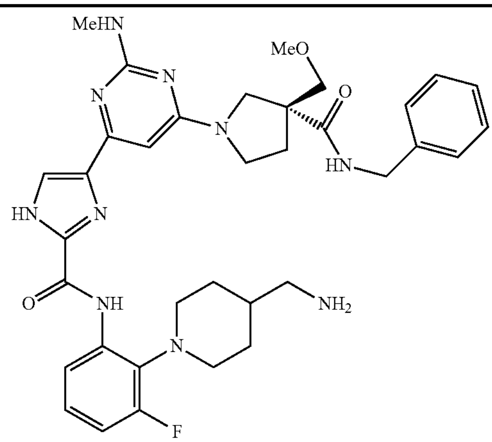 | 595.8 | A | (R)-N-(2-(4-(aminomethyl) piperidin-1-yl)-3-fluorophenyl)-4-(6-(3-(benzylcarbamoyl)-3-(methoxymethyl) pyrrolidin-1-yl)-2-(methylamino) pyrimidin-4-yl)-1H-imidazole-2-carboxamide |
| 131 | 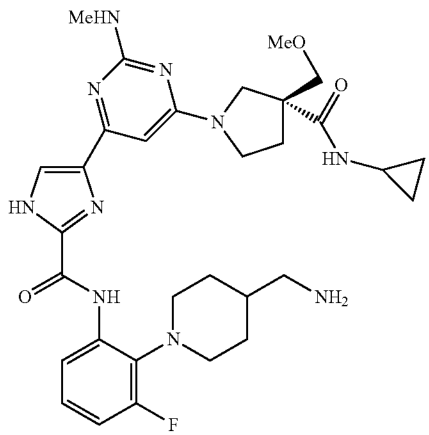 [SMILES: CNc1nc(-c2c[nH]c(C(=O)Nc3cccc(F)c3N3CCC(CN)CC3)n2)cc(N2CC[C@@](COC)(C(=O)NC3CC3)C2)n1] | 670.8 | A | (R)-N-(2-(4-(aminomethyl) piperidin-1-yl)-3-fluorophenyl)-4-(6-(3-(cyclopropyl-carbamoyl)-3-(methoxymethyl) pyrrolidin-1-yl)-2-(methylamino) pyrimidin-4-yl)-1H-imidazole-2-carboxamide |
| 132 | 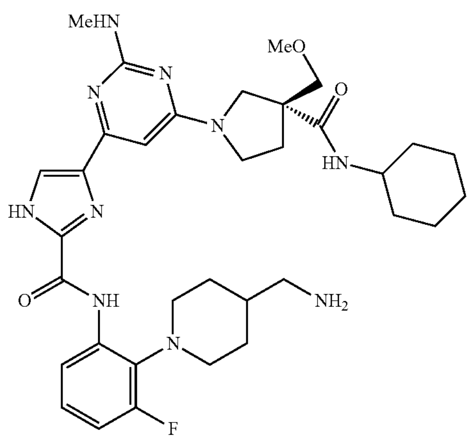 [SMILES: CNc1nc(-c2c[nH]c(C(=O)Nc3cccc(F)c3N3CCC(CN)CC3)n2)cc(N2CC[C@@](COC)(C(=O)NC3CCCCC3)C2)n1] | 620.9 | A | (R)-N-(2-(4-(aminomethyl) piperidin-1-yl)-3-fluorophenyl)-4-(6-(3-(cyclohexyl-carbamoyl)-3-(methoxymethyl) pyrrolidin-1-yl)-2-(methylamino) pyrimidin-4-yl)-1H-imidazole-2-carboxamide |

Uses of the Imidazole Carboxamide Compounds

The Imidazole Carboxamide Compounds are useful in human and veterinary medicine in the therapy of proliferative diseases such as cancer other non-cancer proliferative disorders. The Imidazole Carboxamide Compounds are useful where inhibiting PDK1 or inhibiting PDK1 variants is indicated, such as in treating various diseases associated with abnormal PDK1 signaling and/or abnormal signaling upstream or downstream of PDK1 (or variants thereof), which is often associated with up-regulated activity of one or more receptor tyrosine kinases, Ras, PDK1, PKB/Akt, RSK, PKC, 70S6K, or SGK. In some embodiments, the compounds of the invention are useful in inhibiting PDK1 variants wherein the wild type PDK1 contains one or more point mutations, insertions, or deletions. Examples of PDK1 variants include PDK1T354M and PDK1D527E.

While not being bound by any specific theory, it believed that the Imidazole Carboxamide Compounds are useful in treating proliferative diseases such as cancer and other proliferative diseases because of their PDK1 inhibitory activity.

The general value of the compounds of the invention in inhibiting PDK1 can be determined, for example, using the fluorescence polarization-based assay described above in Example 29. In addition, the general value of the compounds of the invention in inhibiting PDK1 function can be evaluated using other known assays such as those described in Xu et al. in *J. Biomol. Screen.* 14, 1257-1262 (2009).

The Imidazole Carboxamide Compounds can be used to treat diseases and disorders characterized by excessive or pathologically elevated cell growth such as is characteristic of various cancers and non-cancer proliferative disorders. Examples of cancers for which the Imidazole Carboxamide Compounds are useful, include lung cancer, bronchial cancer, prostate cancer, breast cancer, pancreatic cancer, colon cancer, rectal cancer, colorectal cancer, thyroid cancer, liver cancer, intrahepatic bile duct cancer, hepatocellular cancer, gastric cancer, glioma/glioblastoma, endometrial cancer, melanoma, kidney cancer, renal pelvic cancer, urinary bladder cancer, uterine corpus cancer, uterine cervical cancer, ovarian cancer, multiple myeloma, esophageal cancer, acute myelogenous leukemia, chronic myelogenous leukemia, lymphocytic leukemia, myeloid leukemia, bram cancer, oral cavity cancer, and pharyngeal cancer, laryngeal cancer, small intestinal cancer, non-Hodgkin's lymphoma, and villous colon adenoma.

In some embodiments, the compounds of the invention are used to treat cancers of the prostate, lung, colon, or breast.

Examples of non-cancer proliferative disorders for which the Imidazole Carboxamide Compounds are useful include neuro-fibromatosis, atherosclerosis, pulmonary fibrosis, arthritis, psoriasis, glomerulonephritis, restenosis, proliferative diabetic retinopathy (PDR), hypertrophic scar formation, inflammatory bowel disease, transplantation rejection, angiogenesis, and endotoxic shock.

Thus, in one embodiment the invention provides a method of treating a patient (e.g., human) having a disease or disorder characterized by excessive or pathologically elevated cell growth by administering a therapeutically effective amount of an Imidazole Carboxamide Compound, or a pharmaceutically acceptable salt of said compound to the patient. In some embodiments, the disease or disorder being treated is a cancer. In other embodiments, the disease or disorder being treated are non-cancer proliferative disorders.

In the therapies described above, a preferred dosage for administration to a patient is about 0.001 to 1000 mg/kg of body weight/day of the Imidazole Carboxamide Compound. An especially preferred dosage is about 0.01 to 25 mg/kg of body weight/day of the Imidazole Carboxamide Compound, or a pharmaceutically acceptable salt of said compound.

Combination Therapies

The Imidazole Carboxamide Compounds may also be useful in combination (administered together or sequentially) with one or more of other therapies such as radiation therapy and/or chemotherapeutic regimens with therapeutic agents other than the Imidazole Carboxamide Compounds for treating a disease or disorder characterized by excessive or pathologically elevated cell growth, such as cancer.

In one embodiment, the invention provides a method of treating a disease or disorder characterized by excessive or pathologically elevated cell growth, the method comprising administering an Imidazole Carboxamide Compound or a pharmaceutically acceptable salt thereof, and one or more of a MAP Kinase pathway inhibitor such as bRaf, MEK, or ERK inhibitors to a patient in need thereof. In one embodiment, the disease or disorder is cancer.

In one specific embodiment of the method, the Imidazole Carboxamide Compound or a pharmaceutically acceptable salt thereof is administered with a bRaf inhibitor.

In another embodiment, the Imidazole Carboxamide Compound or a pharmaceutically acceptable salt thereof is administered with a MEK inhibitor.

In yet another embodiment, the Imidazole Carboxamide Compound or a pharmaceutically acceptable salt thereof is administered with an ERK inhibitor such as those described in U.S. Patent Application Publication Nos. 2007/0191604, 2009/0118284, and 2007/0232610; U.S. application Ser. No. 12/601,476, filed Jun. 17, 2008; and in U.S. Provisional Application No. 61/247,238, filed Sep. 30, 2009. The disclosures of the aforementioned patent publications and applications are incorporated herein by reference in their entireties.

In another embodiment, the invention provides a method of treating a disease or disorder characterized by excessive or pathologically elevated cell growth, the method comprising administering an Imidazole Carboxamide Compound or a pharmaceutically acceptable salt thereof, and one or more of a PI3 Kinase pathway inhibitor, such as an mTOR or AKT inhibitor, to a patient in need of such treatment. In one embodiment, the disease or disorder is cancer.

In a specific embodiment of the method, the Imidazole Carboxamide Compound or a pharmaceutically acceptable salt thereof is administered with an mTOR inhibitor such as those described in U.S. Provisional Application No. 61/168,093, filed Apr. 9, 2009; U.S. Provisional Application No. 61/222,529, filed Jul. 2, 2009; and 61/296,252, filed Jan. 19, 2010. The disclosures of the aforementioned provisional applications are hereby incorporated by reference in their entireties.

In another specific embodiment of the method, the Imidazole Carboxamide Compound or a pharmaceutically acceptable salt thereof is administered with an mTOR inhibitor such as Ridaforolimus, also known as AP 23573, MK-8669 and deforolimus. Ridaforolimus is a unique, non-prodrug analog of rapamycin that has antiproliferative activity in a broad range of human tumor cell lines in vitro and in murine tumor xenograft models utilizing human tumor cell lines. Ridaforolimus has been administered to patients with advanced cancer and is currently in clinical development for various advanced malignancies, including studies in patients with advanced soft tissue or bone sarcomas. Thus far, these trials have demonstrated that ridaforolimus is generally well-tolerated with a predictable and manageable adverse event profile, and it possesses anti-tumor activity in a broad range of cancers. A description and preparation of ridaforolimus is described in U.S. Pat. No. 7,091,213 to Ariad Gene Therapeutics, Inc., which is hereby incorporated by reference in its entirety.

In another specific embodiment of the method, the Imidazole Carboxamide Compound or a pharmaceutically acceptable salt thereof is administered with an AKT inhibitor such as MK-2206, which is described in U.S. Pat. No. 7,576,209 to Kelly et al. MK-2206 is a highly selective non-ATP competitive allosteric AKT inhibitor that is currently in clinical development in patients with advanced solid tumor.

The Imidazole Carboxamide Compounds may also be useful in combination (administered together or sequentially) with one or more of anticancer treatments such as radiation therapy, and/or one or more anti-cancer agents different from the Imidazole Carboxamide Compounds. Combinations of an Imidazole Carboxamide Compound with one or more anti-cancer agents different from the Imidazole Carboxamide Compounds are referred to herein as the "the combination anticancer agents of the invention."

In one embodiment, the invention provides a method of treating cancer, comprising administering an amount (such as 0.1 mg to 5000 mg) of an Imidazole Carboxamide Compound or a pharmaceutically acceptable salt thereof, and an amount (such as 0.1 mg to 5000 mg) of one or more additional anticancer drugs to a patient in need thereof.

In one embodiment, the Imidazole Carboxamide Compound and the additional anti-cancer agent(s) are administered in doses commonly employed when such agents are used as monotherapy for treating cancer.

The Imidazole Carboxamide Compound and the additional therapeutic agent(s) can act additively or synergistically. For instance, in one embodiment, the Imidazole Carboxamide Compound and the additional anticancer agent(s) are administered in doses lower than the doses commonly employed when such agents are used as monotherapy for treating cancer.

In another embodiment, the Imidazole Carboxamide Compound and the additional anticancer agent(s) act synergistically and are administered in doses lower than the doses commonly employed when such agents are used as monotherapy for treating cancer.

In one embodiment, the Imidazole Carboxamide Compound and the additional anti-cancer agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

In other embodiments, the Imidazole Carboxamide Compounds may also be administered sequentially with known anticancer or cytotoxic agents when a combination formulation is inappropriate. The invention is not limited by the sequence of administration; the Imidazole Carboxamide Compounds may be administered either prior to or after administration of the known anticancer or cytotoxic agent. The order of administration for the sequence depends on the particular combinations chosen. For example, the cytotoxic activity of the cyclin-dependent kinase inhibitor flavopiridol is affected by the sequence of administration with anticancer agents. *Cancer Research,* (1997) 57, 3375. Selecting the appropriate administration sequence is well within the skill of medical practitioners, such as attending physicians.

Another aspect of the invention is a method of treating one or more a disease or disorder characterized by excessive or pathologically elevated cell growth e.g., cancer, comprising administering to a patient, e.g., a human patient, in need of such treatment: an amount of a first compound, which is an Imidazole Carboxamide Compound, or a pharmaceutically acceptable salt thereof; and an amount of at least one second compound, the second compound being an anticancer agent different from the Imidazole Carboxamide Compound, wherein the amounts of the first compound and the second compound result in a therapeutic effect.

Non-limiting examples of suitable additional anti-cancer agents are selected from the group consisting of MAP Kinase pathway inhibitors (e.g., bRaf, MEK, or ERK inhibitors) hormones, PI3 Kinase pathway inhibitors (e.g., mTOR inhibitors, AKT inhibitors), hormone analogues and antihormones (e.g., tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g., anastrozole, letrozole, liarozole, vorozole, exemestane, atamestane), LHRH agonists and antagonists (e.g., goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g., antifolates such as methotrexate, raltitrexed, pyrimidine analogues such as 5-fluorouracil, capecitabine and gemcitabine, purine and adenosine analogues such as mercaptopurine, thioguanine, cladribine and pentostatin, cytarabine, fludarabine); antitumour antibiotics (e.g., anthracyclins such as doxorubicin, daunorubicin, epirubicin and idarubicin, mitomycin-C, bleomycin, dactinomycin, plicamycin, streptozocin); platinum derivatives (e.g., cisplatin, oxaliplatin, carboplatin); alkylation agents (e.g., estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g., Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

The combination anticancer agents of the invention can be administered separately, simultaneously, or sequentially to a patient. The combination anticancer agents of the invention can also be cyclically administered. Cycling therapy involves the administration of one anticancer agent of the invention for a period of time, followed by the administration of a second anticancer agent of the invention for a period of time and repeating this sequential administration, i.e., the cycle, in order to reduce the development of resistance to one or both of the combination anticancer agents of the invention, to avoid or reduce the side effects of one or both of the combination anticancer agents of the invention, and/or to improve the efficacy of the treatment.

In one embodiment, the combination anticancer agents of the invention are administered simultaneously to a patient in separate compositions. The combination anticancer agents of the invention may be administered to a patient by the same or different routes of administration.

When the combination anticancer agents of the invention are administered to a patient concurrently, the term "simultaneously" is not limited to the administration of the combination anticancer agents of the invention at exactly the same time, but rather it is meant that they are administered to a patient in a sequence and within a time interval such that they can act synergistically to provide an increased benefit than if they were administered otherwise. For example, the combination anticancer agents of the invention may be administered at the same time or sequentially in any order at different points in time; however, if not administered at the same time, they should be administered sufficiently close in time so as to provide the desired therapeutic effect, preferably in a synergistic fashion.

Compositions and Administration

This invention is also directed to pharmaceutical compositions which comprise at least one Imidazole Carboxamide Compound, or a pharmaceutically acceptable salt of said compound and at least one pharmaceutically acceptable carrier.

When administered to a patient, the Imidazole Carboxamide Compounds can be administered as a component of a composition that comprises a pharmaceutically acceptable carrier or vehicle. The present invention provides pharmaceutical compositions comprising an effective amount of at least one Imidazole Carboxamide Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Imidazole Carboxamide Compounds of the present invention may also be delivered transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., anticancer activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Imidazole Carboxamide Compound is administered orally.

In another embodiment, the Imidazole Carboxamide Compound is administered intravenously.

In another embodiment, the Imidazole Carboxamide Compound is administered topically.

In still another embodiment, the Imidazole Carboxamide Compounds is administered sublingually.

In one embodiment, a pharmaceutical preparation comprising at least one Imidazole Carboxamide Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Imidazole Carboxamide Compound(s) by weight or volume. In various embodiments, the present compositions can contain, in one embodiment, from about 1% to about 70% or from about 5% to about 60% of the Imidazole Carboxamide Compound(s) by weight or volume.

The quantity of Imidazole Carboxamide Compound in a unit dose of preparation may be varied or adjusted from about 0.1 mg to about 5000 mg. In various embodiments, the quantity is from about 10 mg to about 5000 mg, about 10 mg to about 1000 mg, 1 mg to about 500 mg, 1 mg to about 100 mg, and 1 mg to about 50 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

For administration to human patients, the amount and frequency of administration of the Imidazole Carboxamide Compounds will be regulated according to the judgment of the attending clinician considering such factors as age, condition and size of the patient as well as severity of the symptoms being treated. Generally, a total daily dosage of the Imidazole Carboxamide Compounds range from about 0.1 to about 5000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 5000 mg/day, administered in a single dose or in 2-4 divided doses. In another embodiment, the dosage is from about 100 to about 5000 mg/day, administered in a single dose or in 2-4 divided doses. In still another embodiment, the dosage is from about 500 to about 5000 mg/day, administered in a single dose or in 2-4 divided doses.

The compositions of the invention can further comprise one or more additional therapeutic agents, selected from those specified above. Accordingly, in one embodiment, the present invention provides compositions comprising: (i) at least one Imidazole Carboxamide Compound or a pharmaceutically acceptable salt thereof; (ii) one or more additional therapeutic agents, e.g., anticancer agents, that are not an Imidazole Carboxamide Compound; and (iii) a pharmaceutically acceptable carrier, wherein the amounts in the composition are together effective to treat disease or disorder characterized by excessive or pathologically elevated cell growth, such as cancer.

Kits

Another aspect of this invention is a kit comprising a therapeutically effective amount of at least one Imidazole Carboxamide Compound, or a pharmaceutically acceptable salt of said compound, and a pharmaceutically acceptable carrier, vehicle or diluent.

Yet another aspect of this invention is a kit comprising an amount of at least one Imidazole Carboxamide Compound, or a pharmaceutically acceptable salt of said compound and an amount of at least one additional anti-cancer agent listed above, wherein the amounts of the two or more active ingredients result in a desired therapeutic effect. In one embodiment, the at least one Imidazole Carboxamide Compound and the at least one additional anti-cancer agent are provided in the same container. In one embodiment, the at least one Imidazole Carboxamide Compound and the at least one additional anti-cancer agent are provided in separate containers.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the Formula (I)

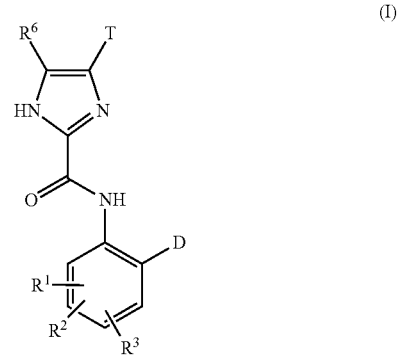

(I)

wherein:

T is $R^A$, H, $C_1$-$C_6$ alkyl, ($C_2$-$C_3$ alkynylene)-($C_1$-$C_6$ alkyl), or ($C_2$-$C_3$ alkynylene)-cyclopropyl;

wherein $R^A$ is selected from the group consisting of:
(i) 5- to 10-membered mono- or bicyclic heteroaryl wherein said heteroaryl of $R^A$ contains one to three heteroatoms selected from the group consisting of nitrogen, oxygen, and sulfur;
(ii) 4- to 7-membered monocyclic heterocyclyl wherein said heterocyclyl of $R^A$ contains at least one ring nitrogen atom ring member, and optionally one additional heteroatom selected from the group consisting of nitrogen, oxygen, and sulfur;
(iii) 4- to 7-membered monocyclic heterocyclenyl wherein said heterocyclenyl of $R^A$ contains one heteroatom selected from the group consisting of nitrogen, oxygen, and sulfur;
(iv) phenyl;
(v) $C_3$-$C_7$ cycloalkyl; and
(vi) $C_3$-$C_7$ cycloalkenyl;

wherein said $R^A$ is unsubstituted or substituted by one to three moieties selected from the group consisting of $C_1$-$C_3$ alkyl, $C_1$-$C_3$ alkoxy, halo, $C_1$-$C_3$ fluoroalkyl, hydroxy, amino, $C_1$-$C_6$ alkylamino, $C_1$-$C_6$ dialkylamino, $C_1$-$C_6$ hydroxyalkyl, $C_1$-$C_6$ alkylamino, cyano, —C(O)—($C_1$-$C_6$ alkyl), —C(O)—O—($C_1$-$C_6$ alkyl), sulfonamido, —N(H)—C(O)—($C_1$-$C_6$ alkyl), benzylamino, —Y—$R^9$, and —C(O)—N($R^{11}$)$_2$;

Y is a bond, $C_1$-$C_3$ alkylene, —O—, —N(H)—, or —N(H)—($C_1$-$C_3$ alkylene), wherein said $C_1$-$C_3$ alkylene or —N(H)—($C_1$-$C_3$ alkylene) of Y is unsubstituted or substituted by $C_1$-$C_3$ hydroxyalkyl;

$R^9$ is
(i) phenyl;
(ii) 5- to 6-membered heteroaryl, wherein said heteroaryl of $R^9$ contains one to two heteroatoms selected from the group consisting of nitrogen, oxygen, and sulfur; or
(iii) $C_3$-$C_7$ cycloalkyl;
wherein said $R^9$ is unsubstituted or substituted by one to two $C_1$-$C_3$ alkyl, $C_1$-$C_3$ alkoxy, halo, or $C_1$-$C_3$ fluoroalkyl;

each $R^{11}$ is independently H, $C_1$-$C_6$ alkyl, -($C_1$-$C_3$ alkylene)-N($C_1$-$C_3$ alkyl)$_2$, —($C_1$-$C_3$ alkylene)-$R^B$, or optionally, the $R^{11}$ groups together with the nitrogen atom to which they are attached, form a 5- to 6-membered heterocyclyl containing one to two nitrogen atoms, which is heterocyclyl is optionally substituted by $C_1$-$C_3$ alkyl;

wherein $R^B$ is phenyl, pyridinyl, pyrimidinyl, pyrazinyl, or pyridazinyl, wherein said $R^B$ is unsubstituted or substituted by one to two $C_1$-$C_3$ alkyl, $C_1$-$C_3$ alkoxy, halo, or $C_1$-$C_3$ fluoroalkyl;

$R^6$ is H, $^2$H, $C_1$-$C_3$ alkyl, or $C_1$-$C_3$ alkoxy;

D is
(i) —($C_1$-$C_3$ dialkylamino)-($C_1$-$C_3$ alkoxy);
(ii) —C(O)—N(H)-heterocyclyl wherein said heterocyclyl moiety is a 5- to 6-membered ring containing one to two nitrogen atoms, and is unsubstituted or substituted by one to two $C_1$-$C_3$ alkyl, $C_1$-$C_3$ alkoxy, halo, or phenyl;

(iii) a group of the formula

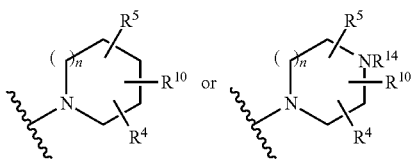

wherein
n is 0, 1, or 2;
$R^4$, $R^5$ and $R^{10}$ are independently H, $C_1$-$C_3$ alkyl, fluoro, hydroxy, amino, $C_1$-$C_3$ alkylamino, $C_1$-$C_3$ dialkylamino, ureido, azetidinyl, pyrrolidinyl, piperidino, pyrazolyl, —($C_1$-$C_3$)alkylene-OH, -M-N($R^7$)($R^8$), or —N($R^7$)—C(O)($R^8$);
M is
(i) a direct bond;
(ii) —C(O)—;
(iii) —($C_1$-$C_3$ alkylene)-C(O)—;
(iv) $C_1$-$C_3$ alkylene; or
(v) a ring of the formula E

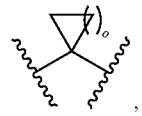

E wherein o is 1, 2, 3, or 4;
wherein ring E or said alkylene of M is unsubstituted or substituted by one to two $C_1$-$C_3$ alkyl;
$R^7$ and $R^8$ are independently selected from the group consisting of H, $C_1$-$C_3$ alkyl, ($C_1$-$C_6$ alkylene)-NH$_2$, ($C_1$-$C_6$ alkylene)-N(H)($C_1$-$C_3$ alkyl), ($C_1$-$C_6$ alkylene)-N($C_1$-$C_3$ alkyl)$_2$, ($C_3$-$C_6$ cycloalkyl)-NH$_2$, ($C_1$-$C_3$ alkylene)-($C_3$-$C_6$ cycloalkyl)-NH$_2$, (3,3,3-trifluoro-2-hydroxy) propyl, and $C_1$-$C_3$ alkanoyl;
or optionally, wherein $R^4$, $R^5$, or $R^{10}$ is -M-N($R^7$)($R^8$), $R^7$ and $R^8$ together with the nitrogen atom to which it is attached form
(i) $R^C$, wherein $R^C$ is a 4- to 10-membered mono- or bicyclic heterocyclyl containing one nitrogen atom and one additional heteroatom selected from the group consisting of nitrogen, oxygen and sulfur, and wherein $R^C$ is unsubstituted or substituted by 1 to 4 $R^{15}$ moieties; or
(ii) $R^D$, wherein $R^D$ is a 4- to 10-membered mono- or bicyclic heterocyclyl containing one nitrogen atom and wherein $R^D$ is substituted by $R^{16}$, and wherein $R^D$ is optionally and additionally substituted by 1 to 3 $R^{15}$;
wherein each $R^{15}$ is independently selected from the group consisting of $C_1$-$C_3$ alkyl, fluoro, $C_1$-$C_3$ trifluoroalkyl, ($C_1$-$C_3$ alkylene)-OH, ($C_1$-$C_3$ alkylene)-NH$_2$, and ($C_1$-$C_3$ alkylene)-C(O)NH$_2$, or optionally two $R^{15}$ moieties together with the carbon atom to which they are attached form a carbonyl;
wherein $R^{16}$ is selected from the group consisting of ($C_1$-$C_3$ alkylene)-OH, ($C_1$-$C_3$ alkylene)-NH$_2$, and ($C_1$-$C_3$ alkylene)- C(O)NH$_2$;
or two of $R^4$, $R^5$ and $R^{10}$ together with the carbon atom(s) to which they are attached form a 5- or 6-membered cycloalkyl or heterocyclyl ring containing one to two heteroatoms selected from the group consisting of nitrogen, oxygen, and sulfur;

$R^{14}$ is H or $C_1$-$C_3$ alkyl;

$R^1$, $R^2$ and $R^3$ are independently selected from the group consisting of H, $^2$H, halo, $C_1$-$C_3$ alkyl, amino, $C_1$-$C_3$ alkylamino, $C_1$-$C_3$ dialkylamino, carbamyl, hydroxy, cyano, trifluoromethyl, $C_3$-$C_7$ cycloalkyl, and 5- to 6-membered heteroaryl containing one or two heteroatoms selected from the group consisting of nitrogen, oxygen, and sulfur;

or a pharmaceutically acceptable salt thereof.

2. The compound of claim 1 or a pharmaceutically acceptable salt thereof, wherein $R^6$ is H.

3. The compound of claim 1 or a pharmaceutically acceptable salt thereof, wherein D is

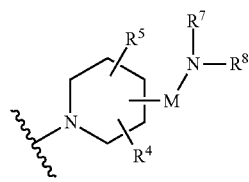

wherein

M is a direct bond, —C(O)—, or methylene;

$R^4$ and $R^5$ are independently selected from the group consisting of H, $C_1$-$C_3$ alkyl, and fluoro, and $R^7$ and $R^8$ are independently selected from the group consisting of H, $C_1$-$C_3$ alkyl, —CH$_2$CH$_2$NH$_2$, —CH$_2$CH$_2$NHCH$_2$CH$_3$, —CH$_2$CH$_2$CH$_2$CH$_2$NHCH$_3$, cyclohexylamino, or optionally $R^7$ and $R^8$ together with the nitrogen atom to which it is attached form:

(i) $R^C$, wherein $R^C$ is a 4- to 10-membered mono- or bicyclic heterocyclyl containing one nitrogen atom and one additional heteroatom selected from the group consisting of nitrogen, oxygen and sulfur, and wherein $R^C$ is unsubstituted or substituted by 1 to 4 $R^{15}$ moieties; or (ii) $R^D$, wherein $R^D$ is a 4- to 10-membered mono- or bicyclic heterocyclyl containing one nitrogen atom and wherein $R^D$ is substituted by $R^{16}$, and wherein $R^D$ is optionally and additionally substituted by 1 to 3 $R^5$;

wherein each $R^{15}$ is independently selected from the group consisting of $C_1$-$C_3$ alkyl, fluoro, $C_1$-$C_3$ trifluoroalkyl, ($C_1$-$C_3$ alkylene)-OH, ($C_1$-$C_3$ alkylene)-NH$_2$, and ($C_1$-$C_3$ alkylene)-C(O)NH$_2$, or optionally two $R^{15}$ moieties together with the carbon atom to which they are attached form a carbonyl;

wherein $R^{16}$ is selected from the group consisting of ($C_1$-$C_3$ alkylene)-OH, ($C_1$-$C_3$ alkylene)-NH$_2$, and ($C_1$-$C_3$ alkylene)-C(O)NH$_2$.

4. The compound of claim 1 or a pharmaceutically acceptable salt thereof, wherein D is selected from the group consisting of:

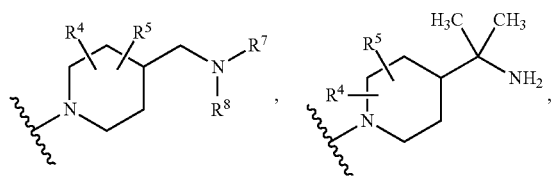

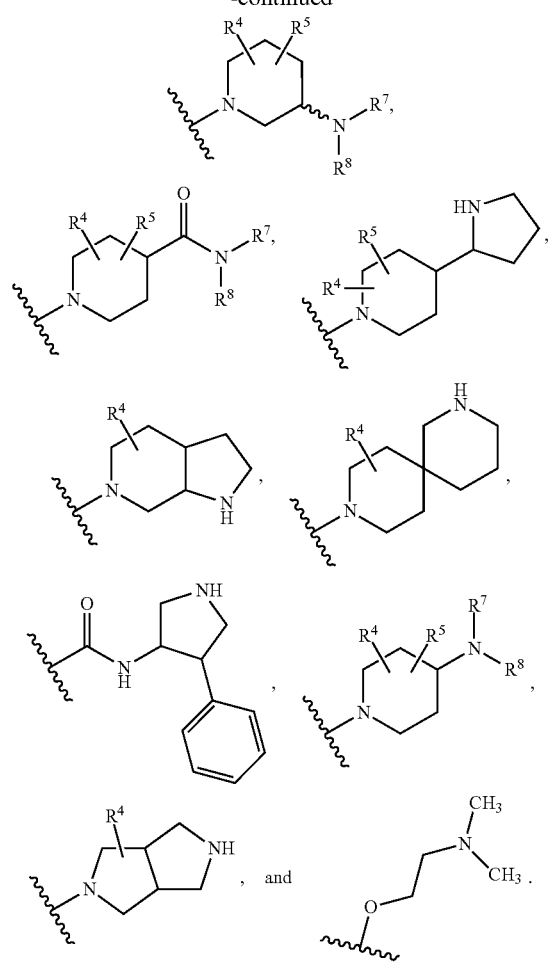

5. The compound of claim 1 or a pharmaceutically acceptable salt thereof, wherein T is selected from the group consisting of H and $R^A$; wherein $R^A$ is selected from the group consisting of cyclopropyl, phenyl, pyrazolyl, thienyl, pyridinyl, pyrimidinyl, pyridazinyl, indolyl, piperidinyl, piperazinyl, and dihydropyranyl, wherein $R^A$ is unsubstituted or substituted by one to three moieties selected from the group consisting of $C_1$-$C_3$ alkyl, $C_1$-$C_3$ alkoxy, halo, trifluoromethyl, hydroxy, amino, $C_1$-$C_6$ alkylamino, $C_1$-$C_6$ dialkylamino, $C_1$-$C_6$ hydroxyalkyl, cyano, —C(O)—($C_1$-$C_6$ alkyl), —C(O)—O—($C_1$-$C_6$ alkyl), sulfonamido, —N(H)—C(O)—($C_1$-$C_6$ alkyl), benzylamino, —Y—$R^9$, and —C(O)N($R^{11}$)$_2$.

6. The compound of claim 5 or a pharmaceutically acceptable salt thereof, wherein T is selected from the group consisting of:

H, 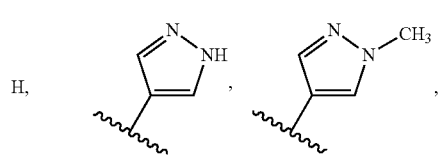

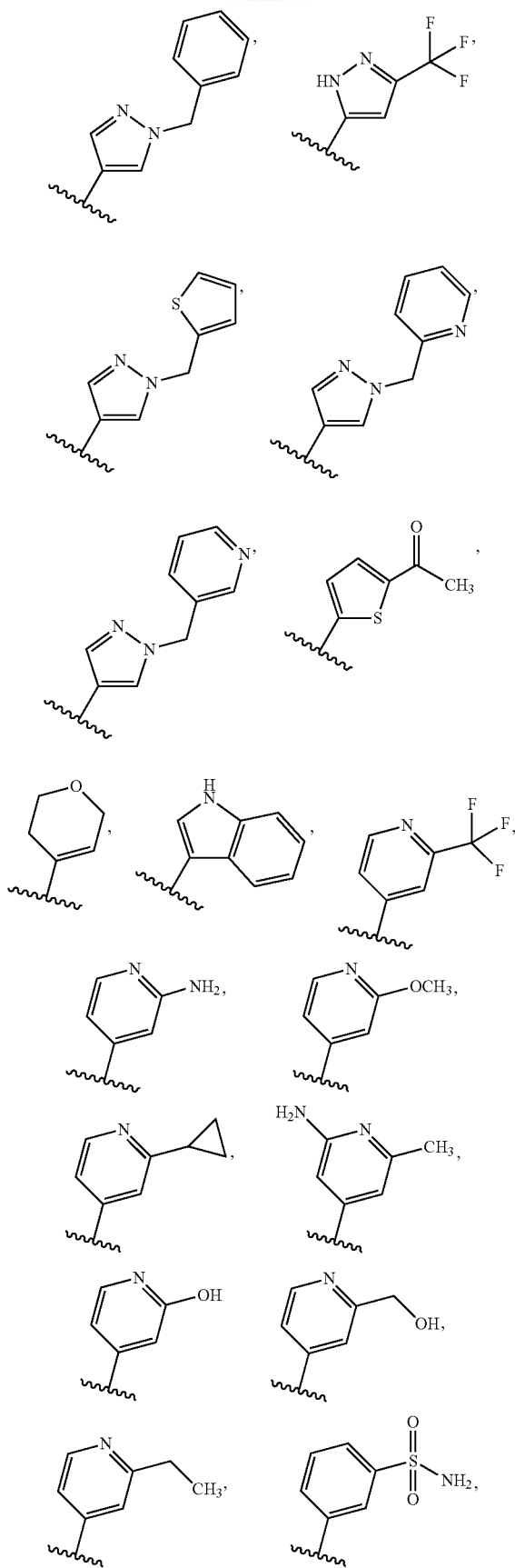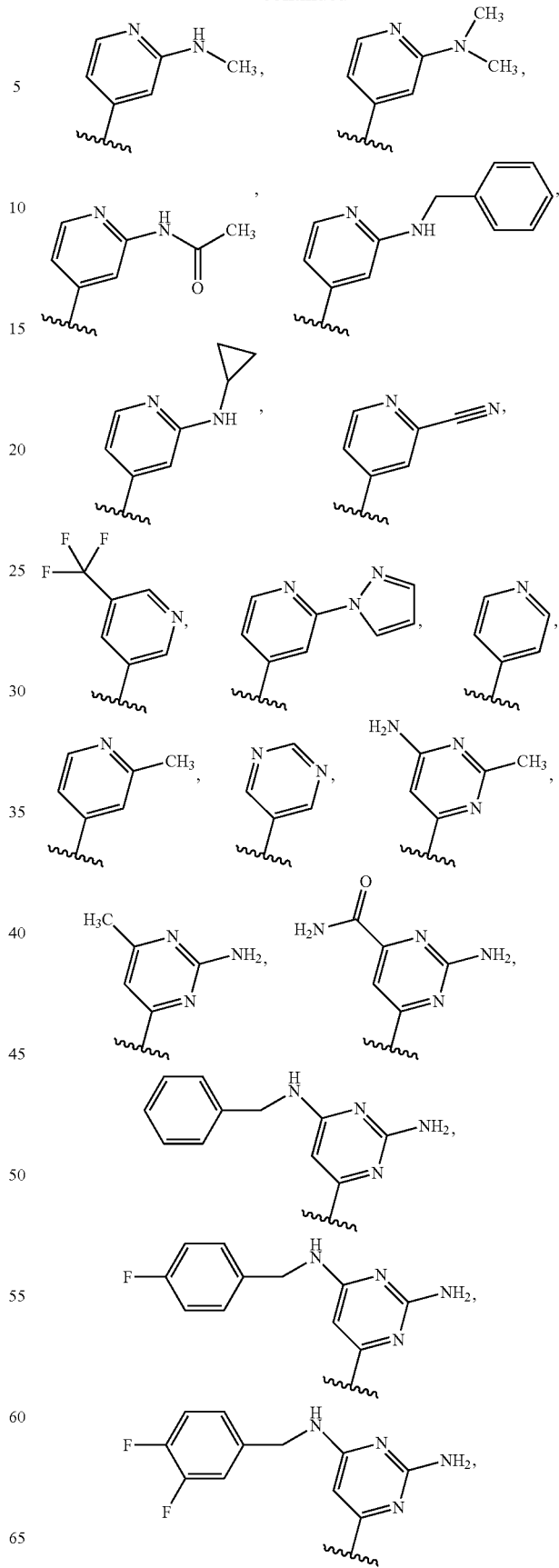

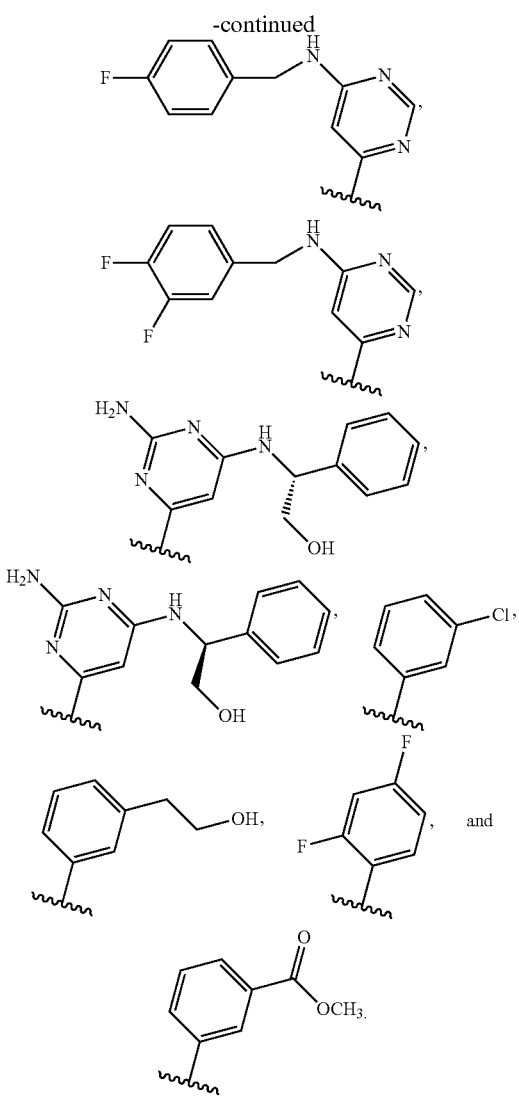

7. The compound of claim 1 or a pharmaceutically acceptable salt thereof, wherein:

T is $R^A$, wherein $R^A$ is selected from the group consisting of substituted or unsubstituted cyclopropyl, phenyl, pyrazolyl, pyridinyl, pyrimidinyl, indolyl, piperidinyl, piperazinyl, and dihydropyranyl, wherein $R^A$ is unsubstituted or substituted by one to three moieties selected from the group consisting of $C_1$-$C_3$ alkyl, $C_1$-$C_3$ alkoxy, halo, trifluoromethyl, hydroxy, amino, $C_1$-$C_6$ alkylamino, $C_1$-$C_6$ dialkylamino, $C_1$-$C_6$ hydroxyalkyl, sulfonamido, —N(H)—C(O)—($C_1$-$C_3$ alkyl), benzylamino, —Y—$R^9$, and —C(O)N($R^{11}$)$_2$;

D is

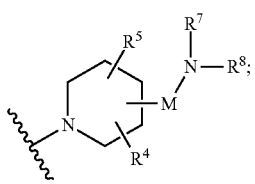

M is a direct bond, —C(O)—, or methylene;

$R^4$ and $R^5$ are independently selected from the group consisting of H, $C_1$-$C_3$ alkyl, and fluoro;

$R^7$ and $R^8$ are independently selected from the group consisting of H, $C_1$-$C_3$ alkyl, —CH$_2$CH$_2$NH$_2$, —CH$_2$CH$_2$NHCH$_2$CH$_3$, —CH$_2$CH$_2$CH$_2$CH$_2$NHCH$_3$, cyclohexylamino, or optionally $R^7$ and $R^8$ together with the nitrogen atom to which it is attached form:
  (i) $R^C$, wherein $R^C$ is a 4- to 10-membered mono- or bicyclic heterocyclyl containing one nitrogen atom and one additional heteroatom selected from the group consisting of nitrogen, oxygen and sulfur, and wherein $R^C$ is unsubstituted or substituted by 1 to 4 $R^{15}$ moieties; or
  (ii) $R^D$, wherein $R^D$ is a 4- to 10-membered mono- or bicyclic heterocyclyl containing one nitrogen atom and wherein $R^D$ is substituted by $R^{16}$, and wherein $R^D$ is optionally and additionally substituted by 1 to 3 $R^{15}$;

wherein each $R^{15}$ is independently selected from the group consisting of $C_1$-$C_3$ alkyl, fluoro, $C_1$-$C_3$ trifluoroalkyl, ($C_1$-$C_3$ alkylene)-OH, ($C_1$-$C_3$ alkylene)-NH$_2$, and ($C_1$-$C_3$ alkylene)-C(O)NH$_2$, or optionally two $R^{15}$ moieties together with the carbon atom to which they are attached form a carbonyl;

wherein $R^{16}$ is selected from the group consisting of ($C_1$-$C_3$ alkylene)-OH, ($C_1$-$C_3$ alkylene)-NH$_2$, and ($C_1$-$C_3$ alkylene)-C(O)NH$_2$;

$R^6$ is H; and $R^1$, $R^2$, and $R^3$ are independently selected from the group consisting of H, fluoro, and pyrazolyl.

8. The compound of claim 1 or a pharmaceutically acceptable salt thereof, wherein $R^1$, $R^2$, and $R^3$ are independently selected from the group consisting of H, halo, and pyrazolyl.

9. The compound of claim 1 or a pharmaceutically acceptable salt thereof, wherein the compound has the Formula (Ia):

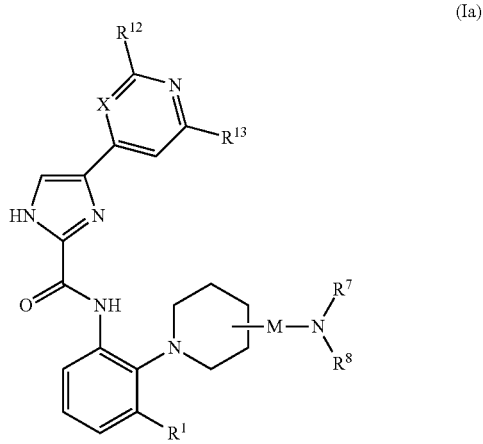

(Ia)

X is CH or N;

$R^{12}$ and $R^{13}$ are independently selected from the group consisting of H, $C_1$-$C_3$ alkyl, amino, $C_1$-$C_3$ alkylamino, carbamyl, hydroxymethyl, benzylamino, 4-fluorobenzylamino, 3,4-difluorobenzylamino, 4-trifluorobenzylamino, 3,4-dimethoxybenzylamino, and 2-hydroxy-1-phenylethylamino;

$R^1$ is H or halo;

M is a direct bond or methylene; and
R⁷ and R⁸ are independently H or $C_1$-$C_3$ alkyl.
10. The compound of claim 9 or a pharmaceutically acceptable salt thereof, wherein the moiety
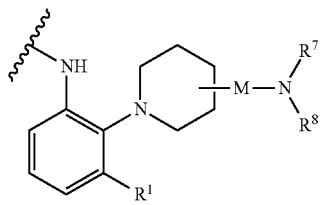
is selected from the group consisting of
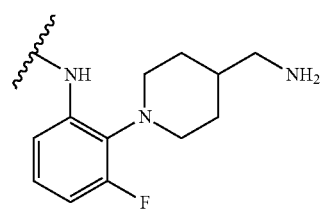
and
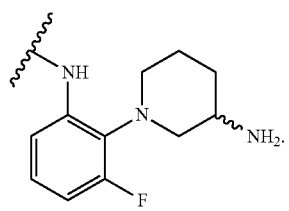
11. The compound of claim 9 or a pharmaceutically acceptable salt thereof wherein the moiety
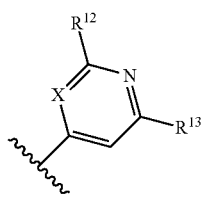
is selected from the group consisting of
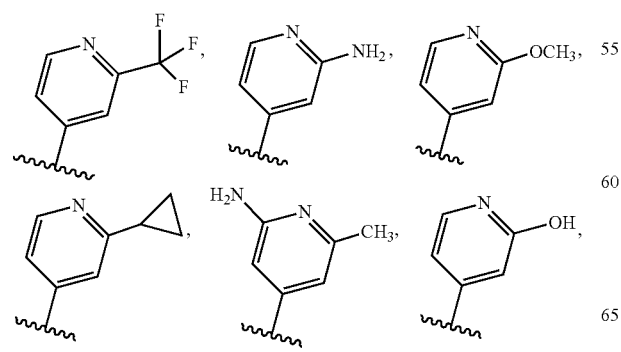
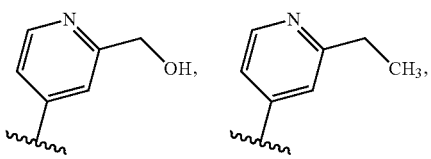
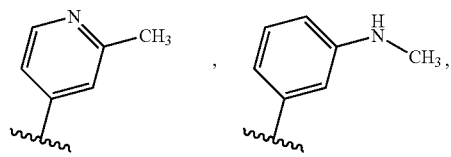
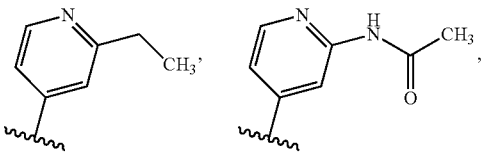
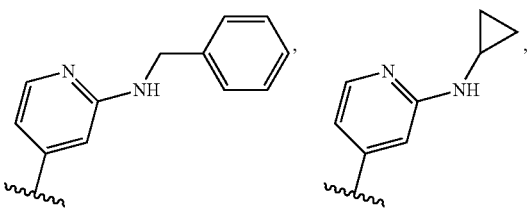
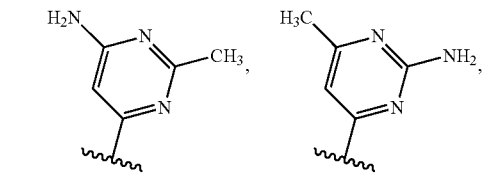
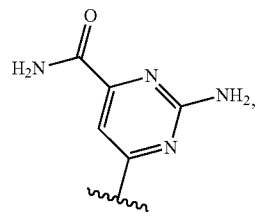
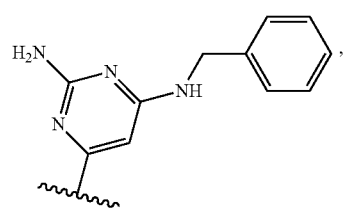
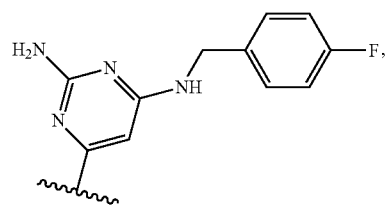
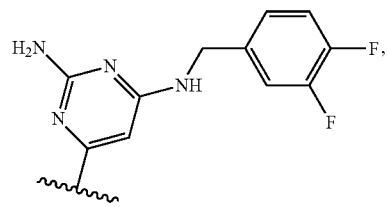

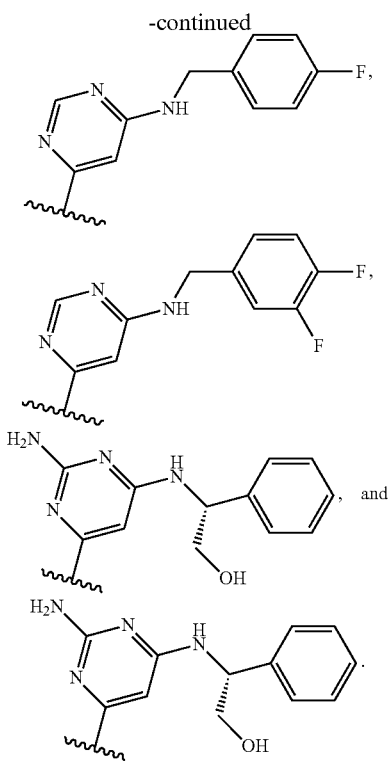

12. A compound selected from one of the following compounds:

N-[5-amino-2-(3(R)-amino-1-piperidinyl)phenyl]-1H-imidazole-2-carboxamide;
1-[4-amino-2-[(1H-imidazol-2-ylcarbonyl)amino]phenyl]-4-(methylamino)-4-piperidinecarboxamide;
N-[5-amino-2-[4-(aminomethyl)-1-piperidinyl]phenyl]-1H-imidazole-2-carboxamide;
N-[2-(3(R)-amino-1-piperidinyl)-3-fluorophenyl]-4-[1-(phenylmethyl)-1H-pyrazol-4-yl]-1H-imidazole-2-carboxamide;
N-[2-(3(R)-amino-1-piperidinyl)-3-fluorophenyl]-4-[1-(2-thienylmethyl)-1H-pyrazol-4-yl]-1H-imidazole-2-carboxamide;
N-[2-[2-(dimethylamino)ethoxy]phenyl]-4-[1-(phenylmethyl)-1H-pyrazol-4-yl]-1H-imidazole-2-carboxamide;
N-[2-(3(R)-amino-1-piperidinyl)-3-fluorophenyl]-4-[1-(2-pyridinylmethyl)-1H-pyrazol-4-yl]-1H-imidazole-2-carboxamide;
N-[2-(3(R)-amino-1-piperidinyl)-3-fluorophenyl]-4-(2-methyl-4-pyridinyl)-1H-imidazole-2- carboxamide;
N-[2-(3(R)-amino-1-piperidinyl)-3-fluorophenyl]-4-[5-(trifluoromethyl)-3-pyridinyl]-1H-imidazole-2-carboxamide;
N-[2-(3(R)-amino-1-piperidinyl)-3-fluorophenyl]-4-(4-pyridinyl)-1H-imidazole-2-carboxamide;
N-[2-(3(R)-amino-1-piperidinyl)-3-fluorophenyl]-4-(1H-pyrazol-4-yl)-1H-imidazole-2-carboxamide;
N-[2-(3(R)-amino-1-piperidinyl)-3-fluorophenyl]-4-bromo-1H-imidazole-2-carboxamide;
N-[2-(3(R)-amino-1-piperidinyl)-3-fluorophenyl]-4-[1-(3-pyridinylmethyl)-1H-pyrazol-4-yl]-1H-imidazole-2-carboxamide;
N-[2-(3(R)-amino-1-piperidinyl)-3-fluorophenyl]-4-(1-methyl-1H-pyrazol-4-yl)-1H-imidazole-2-carboxamide;
N-[2-[3(R)-[(aminocarbonyl)amino]-1-piperidinyl]-3-fluorophenyl]-4-bromo-1H-imidazole-2-carboxamide;
N-[5-amino-2-(3(R)-amino-1-piperidinyl)phenyl]-4-bromo-1H-imidazole-2-carboxamide;
N-[2-[2-(dimethylamino)ethoxy]phenyl]-4-(1H-indol-3-yl)-1H-imidazole-2-carboxamide;
N-[2-[4-(aminomethyl)-1-piperidinyl]-3-fluorophenyl]-4-(2-methyl-4-pyridinyl)-1H-imidazole-2-carboxamide;
N-[2-(3(R)-amino-1-piperidinyl)-3-fluorophenyl]-4-[2-(trifluoromethyl)-4-pyridinyl]-1H-imidazole-2-carboxamide;
N-[2-(-3(R)-amino-1-piperidinyl)-3-fluorophenyl]-4-(2-amino-4-pyridinyl)-1H-imidazole-2-carboxamide;
N-[2-(3(R)-amino-1-piperidinyl)-3-fluorophenyl]-4-(2-methoxy-4-pyridinyl)-1H-imidazole-2-carboxamide;
N-[2-(3(R)-amino-1-piperidinyl)-3-fluorophenyl]-4-(3,6-dihydro-2h-pyran-4-yl)-1H-imidazole-2-carboxamide;
N-[2-(3(R)-amino-1-piperidinyl)-3-fluorophenyl]-4-(2-cyclopropyl-4-pyridinyl)-1H-imidazole-2-carboxamide;
4-(2-amino-6-methyl-4-pyridinyl)-N-[2-(3(R)-amino-1-piperidinyl)-3-fluorophenyl]-1H-imidazole-2-carboxamide;
N-[2-(3(R)-amino-1-piperidinyl)-3-fluorophenyl]-4-(2-hydroxy-4-pyridinyl)-1H-imidazole-2-carboxamide;
N-[2-(3(R)-amino-1-piperidinyl)-3-fluorophenyl]-4-[2-(hydroxymethyl)-4-pyridinyl]-1H-imidazole-2-carboxamide;
N-[2-[4-(aminomethyl)-1-piperidinyl]-3-fluorophenyl]-4-(2-amino-4-pyridinyl)-1H-imidazole-2-carboxamide;
N-[2-[4-(aminomethyl)-1-piperidinyl]-3,4-difluorophenyl]-4-(2-amino-4-pyridinyl)-1H-imidazole-2-carboxamide;
4-(2-amino-6-methyl-4-pyrimidinyl)-N-[2-(3(R)-amino-1-piperidinyl)-3-fluorophenyl]-1H-imidazole-2-carboxamide;
N-[2-[4-(aminomethyl)-1-piperidinyl]-3-fluorophenyl]-4-(2-ethyl-4-pyridinyl)-1H-imidazole-2-carboxamide;
N-[2-[4-(aminomethyl)-1-piperidinyl]-3-fluorophenyl]-4-[3-(aminosulfonyl)phenyl]-1H-imidazole-2-carboxamide;
N-[2-[4-(aminomethyl)-1-piperidinyl]-3-fluorophenyl]-4-[2-(methylamino)-4-pyridinyl]-1H-imidazole-2-carboxamide;
4-[2-(acetylamino)-4-pyridinyl]-N-[2-[4-(aminomethyl)-1-piperidinyl]-3-fluorophenyl]-1H-imidazole-2-carboxamide;
N-[2-[4-(aminomethyl)-1-piperidinyl]-3-fluorophenyl]-4-(3-chlorophenyl)-1H-imidazole-2-carboxamide;
N-[2-[4-(aminomethyl)-1-piperidinyl]-3-fluorophenyl]-4-[2-[(phenylmethyl)amino]-4-pyridinyl]-1H-imidazole-2-carboxamide;
N-[2-[4-(aminomethyl)-1-piperidinyl]-3-fluorophenyl]-4-[2-(dimethylamino)-4-pyridinyl]-1H-imidazole-2-carboxamide;
N-[2-[4-(aminomethyl)-1-piperidinyl]-3-fluorophenyl]-4-(2,5-dimethylphenyl)-1H-imidazole-2-carboxamide;
N-[2-(3(R)-amino-1-piperidinyl)-3-fluorophenyl]-4-(2,4-difluorophenyl)-1H-imidazole-2-carboxamide;
N-[2-(3(R)-amino-1-piperidinyl)-3-fluorophenyl]-4-[2-(1H-pyrazol-1-yl)-4-pyridinyl]-1H-imidazole-2-carboxamide;
4-(2-amino-4-pyridinyl)-N-[2-[4-[(dimethylamino)methyl]-1-piperidinyl]phenyl]-1H-imidazole-2-carboxamide;

N-[2-[4-(aminomethyl)-1-piperidinyl]-3-fluorophenyl]-4--[3-(2-hydroxyethyl)phenyl]-1H-imidazole-2-carboxamide;

N-[2-[4-(aminomethyl)-1-piperidinyl]-3-fluorophenyl]-4-[2-(cyclopropylamino)-4-pyridinyl]-1H-imidazole-2-carboxamide;

N-[3-fluoro-2-(octahydro-6h-pyrrolo[2,3-c]pyridin-6-yl)phenyl]-4-(2-methyl-4-pyridinyl)-1H-imidazole-2-carboxamide;

N-[2-[4-(aminomethyl)-1-piperidinyl]-3-fluorophenyl]-4-(6-cyano-2-pyridinyl)-1H-imidazole-2-carboxamide;

4-(5-acetyl-2-thienyl)-N-[2-[4-(aminomethyl)-1-piperidinyl]-3-fluorophenyl]-1H-imidazole-2-carboxamide;

N-[2-(2,9-diazaspiro[5.5]undec-9-yl)-3-fluorophenyl]-4-(2-methyl-4-pyridinyl)-1H-imidazole-2-carboxamide;

N-[2-[4-(aminomethyl)-1-piperidinyl]-3-fluorophenyl]-4-(2-amino-6-methyl-4-pyrimidinyl)-1H-imidazole-2-carboxamide;

N-[2-[4-(aminomethyl)-1-piperidinyl]-3-fluorophenyl]-4-[3-(trifluoromethyl)-1H-pyrazol-5-yl]-1H-imidazole-2-carboxamide;

N-[2-[4-(aminomethyl)-1-piperidinyl]-3-fluorophenyl]-4-(6-amino-2-methyl-4-pyrimidinyl)-1H-imidazole-2-carboxamide;

N-[2-[4-[(dimethylamino)methyl]-1-piperidinyl]-3-fluorophenyl]-4-(2-methyl-4-pyridinyl)-1H-imidazole-2-carboxamide;

N-[2-[4-(aminomethyl)-1-piperidinyl]-5-(1H-pyrazol-4-yl)phenyl]-4-(1H-pyrazol-4-yl)-1H-imidazole-2-carboxamide;

N-[2-[4-(aminomethyl)-4-ethyl-1-piperidinyl]-3-fluorophenyl]-4-(2-methyl-4-pyridinyl)-1H-imidazole-2-carboxamide;

N-[2-[4-(aminomethyl)-1-piperidinyl]-3-fluorophenyl]-4-(1H-pyrazol-4-yl)-1H-imidazole-2-carboxamide;

N-[2-(3,8-diazabicyclo [3.2.1]oct-3-yl)-3-fluorophenyl]-4-(2-methyl-4-pyridinyl)-1H-imidazole-2-carboxamide;

N-[2-[4-(aminomethyl)-4-methyl-1-piperidinyl]-3-fluorophenyl]-4-(2-methyl-4-pyridinyl)-1H-imidazole-2-carboxamide;

methyl 3-[2-[[[2-[4-(aminomethyl)-1-piperidinyl]-3-fluorophenyl]amino]carbonyl]-1H-imidazol-4-yl]benzoate;

N-[3-fluoro-2-[4-[(methylamino)methyl]-1-piperidinyl]phenyl]-4-(2-methyl-4-pyridinyl)-1H-imidazole-2-carboxamide;

N-[3-fluoro-2-(hexahydropyrrolo [3,4-c]pyrrol-2(1H)-yl)phenyl]-4-(2-methyl-4-pyridinyl)-1H-imidazole-2-carboxamide;

1-[2-fluoro-6-[[[4-(2-methyl-4-pyridinyl)-1H-imidazol-2-yl]carbonyl]amino]phenyl]-N-methyl-4-piperidinecarboxamide;

N-ethyl-1-[2-fluoro-6-[[[4-(2-methyl-4-pyridinyl)-1H-imidazol-2-yl]carbonyl]amino]phenyl]-4-piperidinecarboxamide;

1-[2-fluoro-6-[[[4-(2-methyl-4-pyridinyl)-1H-imidazol-2-yl]carbonyl]amino]phenyl]-N,N-dimethyl-4-piperidinecarboxamide;

1-[2-fluoro-6-[[[4-(2-methyl-4-pyridinyl)-1H-imidazol-2-yl]carbonyl]amino]phenyl]-N-(3,3,3-trifluoro-2-hydroxypropyl)-4-piperidinecarboxamide;

N-[2-[4-(aminomethyl)-1-piperidinyl]-3-fluorophenyl]-4-5-pyrimidinyl)-1H-imidazole-2-carboxamide;

N-[3-fluoro-2-[4-[(3(S)-fluoro-1-pyrrolidinyl)carbonyl]-1-piperidinyl]phenyl]-4-(2-methyl-4-pyridinyl)-1H-imidazole-2-carboxamide;

1-[2-fluoro-6-[[[4-(2-methyl-4-pyridinyl)-1H-imidazol-2-yl]carbonyl]amino]phenyl]-N-(1(R)-phenylethyl)-4-piperidinecarboxamide;

N-[2-[4-(1-azetidinylcarbonyl)-1-piperidinyl]-3-fluorophenyl]-4-(2-methyl-4-pyridinyl)-1H-imidazole-2-carboxamide;

N-[2-[4-(1-amino-1-methylethyl)-1-piperidinyl]-3-fluorophenyl]-4-(2-methyl-4-pyridinyl)-1H-imidazole-2-carboxamide;

6-[2-[[[2-[4-(aminomethyl)-1-piperidinyl]-3-fluorophenyl]amino]carbonyl]-1H-imidazol-4-yl]-2-hydroxy-4-pyrimidinecarboxamide;

N-[2-[4-(aminomethyl)-1-piperidinyl]-3-fluorophenyl]-4-[2-amino-6-[(phenylmethyl)amino]-4-pyrimidinyl]-1H-imidazole-2-carboxamide;

N-[2-[4-(aminomethyl)-1-piperidinyl]-3-fluorophenyl]-4-[2-amino-6-[[[4-(trifluoromethyl)phenyl]methyl]amino]-4-pyrimidinyl]-1H-imidazole-2-carboxamide;

4-[2-amino-6-[[(4-fluorophenyl)methyl]amino]-4-pyrimidinyl]-N-[2-[4-(aminomethyl)-1-piperidinyl]-3-fluorophenyl]-1H-imidazole-2-carboxamide;

4-[2-amino-6-[[2-hydroxy-1(R)-phenylethyl]amino]-4-pyrimidinyl]-N-[2-[4-(aminomethyl)-1-piperidinyl]-3-fluorophenyl]-1H-imidazole-2-carboxamide;

N-[2-[4-(aminomethyl)-1-piperidinyl]-3-fluorophenyl]-4-[6-[[(4-fluorophenyl)methyl]amino]-4-pyrimidinyl]-1H-imidazole-2-carboxamide;

N-[2-[4-(aminomethyl)-1-piperidinyl]-3-fluorophenyl]-4-[6-[[(3,4-difluorophenyl)methyl]amino]-4-pyrimidinyl]-1H-imidazole-2-carboxamide;

4-[2-amino-6-[[(3,4-difluorophenyl)methyl]amino]-4-pyrimidinyl]-N-[2-[4-(aminomethyl)-1-piperidinyl]-3-fluorophenyl]-1H-imidazole-2-carboxamide;

4-[2-amino-6-[[(3,4-dimethoxyphenyl)methyl]amino]-4-pyrimidinyl]-N-[2-[4-(aminomethyl)-1-piperidinyl]-3-fluorophenyl]-1H-imidazole-2-carboxamide;

4-[2-amino-6-[(2-hydroxy-1(S)-phenylethyl)amino]-4-pyrimidinyl]-N-[2-[4-(aminomethyl)-1-piperidinyl]-3-fluorophenyl]-1H-imidazole-2-carboxamide;

N-[3-fluoro-2-[4-(8-oxa-3-azabicyclo [3.2.1]oct-3-ylcarbonyl)-1-piperidinyl]phenyl]-4-(2-methyl-4-pyridinyl)-1H-imidazole-2-carboxamide;

N-[3-fluoro-2-[4-(2-oxa-5-azabicyclo [2.2.1]hept-5-ylcarbonyl)-1-piperidinyl]phenyl]-4-(2-methyl-4-pyridinyl)-1H-imidazole-2-carboxamide;

N-[3-fluoro-2-[4-[[3-(hydroxymethyl)-4-morpholinyl]carbonyl]-1-piperidinyl]phenyl]-4-(2-methyl-4-pyridinyl)-1H-imidazole-2-carboxamide;

N-[2-[4-[[3-(aminomethyl)-4-morpholinyl]carbonyl]-1-piperidinyl]-3-fluorophenyl]-4-(2-methyl-4-pyridinyl)-1H-imidazole-2-carboxamide;

1-[2-fluoro-6-[[[4-(2-methyl-4-pyridinyl)-1H-imidazol-2-yl]carbonyl]amino]phenyl]-4-piperidinecarboxamide;

N-(2-aminoethyl)-1-[2-fluoro-6-[[[4-(2-methyl-4-pyridinyl)-1H-imidazol-2-yl]carbonyl]amino]phenyl]-4-piperidinecarboxamide;

N-(2-aminocyclohexyl)-1-[2-fluoro-6-[[[4-(2-methyl-4-pyridinyl)-1H-imidazol-2-yl]carbonyl]amino]phenyl]-4-piperidinecarboxamide;

1-[2-fluoro-6-[[[4-(2-methyl-4-pyridinyl)-1H-imidazol-2-yl]carbonyl]amino]phenyl]-N-[4-(methylamino)butyl]-4-piperidinecarboxamide;

N-[2-(ethylamino)ethyl]-1-[2-fluoro-6-[[[4-(2-methyl-4-pyridinyl)-1H-imidazol-2-yl]carbonyl]amino]phenyl]-4-piperidinecarboxamide;

N-[2-[4-(3,8-diazabicyclo[3.2.1]oct-8-ylcarbonyl)-1-piperidinyl]-3-fluorophenyl]-4-(2-methyl-4-pyridinyl)-1H-imidazole-2-carboxamide;

N-[(1-aminocyclopentyl)methyl]-1-[2-fluoro-6-[[[4-(2-methyl-4-pyridinyl)-1H-imidazol-2-yl]carbonyl]amino]phenyl]-4-piperidinecarboxamide;

N-[2-[4-[[2-(aminomethyl)-4-morpholinyl]carbonyl]-1-piperidinyl]-3-fluorophenyl]-4-(2-methyl-4-pyridinyl)-1H-imidazole-2-carboxamide;

N-[3-fluoro-2-[4-[[2-(2-hydroxyethyl)-4-morpholinyl]carbonyl]-1-piperidinyl]phenyl]-4-(2-methyl-4-pyridinyl)-1H-imidazole-2-carboxamide;

N-[2-[4-(3,6-diazabicyclo[3.2.1]oct-3-ylcarbonyl)-1-piperidinyl]-3-fluorophenyl]-4-(2-methyl-4-pyridinyl)-1H-imidazole-2-carboxamide;

N-[3-fluoro-2-[4-[(3(R)-fluoro-1-pyrrolidinyl)carbonyl]-1-piperidinyl]phenyl]-4-(2-methyl-4-pyridinyl)-1H-imidazole-2-carboxamide;

N-[3-fluoro-2-[4-[(3-oxo-2,8-diazaspiro[4.5]dec-8-yl)carbonyl]-1-piperidinyl]phenyl]-4-(2-methyl-4-pyridinyl)-1H-imidazole-2-carboxamide;

N-[2-[4-(2,7-diazaspiro[3.5]noN-7-ylcarbonyl)-1-piperidinyl]-3-fluorophenyl]-4-(2-methyl-4-pyridinyl)-1H-imidazole-2-carboxamide;

N-[2-[4-[[2-(1-aminoethyl)-4-morpholinyl]carbonyl]-1-piperidinyl]-3-fluorophenyl]-4-(2-methyl-4-pyridinyl)-1H-imidazole-2-carboxamide;

N-[3-fluoro-2-[4-[[4-hydroxy-4-(2-pyridinyl)-1-piperidinyl]carbonyl]-1-piperidinyl]phenyl]-4-(2-methyl-4-pyridinyl)-1H-imidazole-2-carboxamide;

N-(2-(4-(aminomethyl)piperidin-1-yl)-3-fluorophenyl)-4-1-(difluoromethyl)-6-oxo-1,6-dihydropyridin-3-yl)-1H-imidazole-2-carboxamide;

(R)-N-(2-(3-aminopiperidin-1-yl)-3-fluorophenyl)-4-(2-chloro-6-methylpyridin-4-yl)-1H-imidazole-2-carboxamide;

4-(2-amino-6-morpholinopyrimidin-4-yl)-N-(2-(4-(aminomethyl)piperidin-1-yl)-3-fluorophenyl)-1H-imidazole-2-carboxamide;

methyl 4-(6-(2-(2-(4-(aminomethyl)piperidin-1-yl)-3-fluorophenylcarbamoyl)-1H-imidazol-4-yl)-2-(methylamino)pyrimidin-4-yl)piperazine-1-carboxylate;

4-(6-(4-acetylpiperazin-1-yl)-2-(methylamino)pyrimidin-4-yl)-N-(2-(4-(aminomethyl)piperidin-1-yl)-3-fluorophenyl)-1H-imidazole-2-carboxamide;

N-cyclohexyl-6-methyl-1-(2-(methylamino)-6-(2-(2-(piperazin-1-yl)phenylcarbamoyl)-1H-imidazol-4-yl)pyrimidin-4-yl)piperidine-3-carboxamide;

4-(6-(4-acetylpiperazine-1-yl)-2-(methylamino)pyrimidin-4-yl)-N-(2-(piperazin-1-yl)phenyl)-1H-imidazole-2-carboxamide;

N-cyclohexyl-6-methyl-1-(2-(methylamino)-6-(2-(2-(piperazin-1-yl)phenylcarbamoyl)-1H-imidazol-4-yl)pyrimidin-4-yl)piperidine-3-carboxamide;

benzyl 4-(2-(methylamino)-6-(2-(2-(piperazin-1-yl)phenylcarbamoyl)-1H-imidazol-4-yl)pyrimidin-4-yl)piperazine-1-carboxylate;

N-cyclohexyl-4-(2-(methylamino)-6-(2-(2-(piperazin-1-yl)phenylcarbamoyl)-1H-imidazol-4-yl)pyrimidin-4-yl)morpholine-2-carboxamide;

1-(6-(2-(2-(4-(aminomethyl)piperidin-1-yl)-3-fluorophenylcarbamoyl)-1H-imidazol-4-yl)-2-(methylamino)pyrimidin-4-yl)-N-cyclohexyl-6-methylpiperidine-3-carboxamide;

N-cyclohexyl-1-(6-(2-(3-fluoro-2-morpholinophenylcarbamoyl)-1H-imidazol-4-yl)-2-(methylamino)pyrimidin-4-yl)-6-methylpiperidine-3-carboxamide;

1-(6-(2-(2-((S)-2-(aminomethyl)morpholino)-3-fluorophenylcarbamoyl)-1H-imidazol-4-yl)-2-(methylamino)pyrimidin-4-yl)-N-cyclohexyl-6-methylpiperidine-3-carboxamide;

1-(6-(2-(2-((R)-2-(aminomethyl)morpholino)-3-fluorophenylcarbamoyl)-1H-imidazol-4-yl)-2-(methylamino)pyrimidin-4-yl)-N-cyclohexyl-6-methylpiperidine-3-carboxamide;

1-(2-amino-6-(2-(5-amino-2-(2,9-diazaspiro [5.5]undecan-9-yl)phenylcarbamoyl)-1H-imidazol-4-yl)pyrimidin-4-yl)-N-cyclohexyl-6-methylpiperidine-3-carboxamide;

1-(6-(2-(2-(1,4-dioxa-8-azaspiro [4.5]decan-8-yl)phenylcarbamoyl)-1H-imidazol-4-yl)-2-(methylamino)pyrimidin-4-yl)-N-cyclohexyl-6-methylpiperidine-3-carboxamide;

1-(6-(2-(2-((R)-3-aminopiperidin-1-yl)-3fluorophenylcarbamoyl)-1H-imidazol-4-yl)-2-(methylamino)pyrimidin-4-yl)-N-cyclohexyl-6-methylpiperidine-3-carboxamide;

(3S,6R)-1-(6-(2-(2-(4-(aminomethyl)piperidin-1-yl)-3-fluorophenylcarbamoyl)-1H-imidazol-4-yl)-2-(methylamino)pyrimidin-4-yl)-N-cyclohexyl-6-methylpiperidine-3-carboxamide;

(3R,6S)-1-(6-(2-(2-(4-(aminomethyl)piperidin-1-yl)-3-fluorophenylcarbamoyl)-1H-imidazol- 4-yl)-2-(methylamino)pyrimidin-4-yl)-N-cyclohexyl-6-methylpiperidine-3-carboxamide;

(3S,6R)-1-(6-(2-(2-((S)-2-(aminomethyl)morpholino)-3-fluorophenylcarbamoyl)-1H-imidazol-4-yl)-2-(methylamino)pyrimidin-4-yl)-N-cyclohexyl-6-methylpiperidine-3-carboxamide;

N-cyclohexyl-1-(6-(2-(3-fluoro-2-(2,7-diazaspiro [3.5]nonan-7-yl)phenylcarbamoyl)-1H-imidazol-4-yl)-2-(methylamino)pyrimidin-4-yl)-6-methylpiperidine-3-carboxamide;

N-cyclohexyl-1-(6-(2-(3-fluoro-2-(2,8-diazaspiro [4.5]decan-8-yl)phenylcarbamoyl)-1H-imidazol-4-yl)-2-(methylamino)pyrimidin-4-yl)-6-methylpip eridine-3-carboxamide;

(R)-N-(2-(4-(aminomethyl)piperidin-1-yl)-3-fluorophenyl)-4-(2-(methylamino)-6-(2-methylpiperazin-1-yl)pyrimidin-4-yl)-1H-imidazole-2-carboxamide;

(R)-N-(2-(4-(aminomethyl)piperidin-1-yl)-3-fluorophenyl)-4-(2-(methylamino)-6-(3-methylmorpholino)pyrimidin-4-yl)-1H-imidazole-2-carboxamide;

N-cyclohexyl-1-(6-(2-(3-fluoro-2-(R)-3-methylmorpholino)phenylcarbamoyl)-1H-imidazol-4-yl)-2-(methylamino)pyrimidin-4-yl)-6-methylpiperidine-3-carboxamide;

(R)-4-(6-(2-(aminomethyl)morpholino)-2-(methylamino)pyrimidin-4-yl)-N-(2-(4-(aminomethyl)piperidin-1-yl)-3-fluorophenyl)-1H-imidazole-2-carboxamide;

(S)-N-(2-(4-(aminomethyl)piperidin-1-yl)-3-fluorophenyl)-4-(2-(methylamino)-6-(3-methylpiperazin-1-yl)pyrimidin-4-yl)-1H-imidazole-2-carboxamide;

4-(6-(4-(aminomethyl)piperidin-1-yl)-2-(methylamino)pyrimidin-4-yl)-N-(2-(4-(aminomethyl)piperidin-1-yl)-3-fluorophenyl)-1H-imidazole-2-carboxamide;

(R)-N-(2-(4-(aminomethyl)piperidin-1-yl)-3-fluorophenyl)-4-(6-(3-aminopiperidin-1-yl)-2-(methylamino)pyrimidin-4-yl)-1H-imidazole-2-carboxamide;

1-(6-(2-(2-(4-(aminomethyl)piperidin-1-yl)-3-fluorophenylcarbamoyl)-1H-imidazol-4-yl)-2-(methylamino)pyrimidin-4-yl)-4-(methylamino)piperidine-4-carboxamide;

(S)-N-(2-(4-(aminomethyl)piperidin-1-yl)-3-fluorophenyl)-4-(6-(3-carbamoyl-3-methoxypyrrolidin-1-yl)-2-(methylamino)pyrimidin-4-yl)-1H-imidazole-2-carboxamide;

(S)-N-(2-(4-(aminomethyl)piperidin-1-yl)-3-fluorophenyl)-4-(6-(3-(cyclohexylcarbamoyl)-3-methoxypyrrolidin-1-yl)-2-(methylamino)pyrimidin-4-yl)-1H-imidazole-2-carboxamide;

(R)-N-(2-(4-(aminomethyl)piperidin-1-yl)-3-fluorophenyl)-4-(6-(3-(benzylcarbamoyl)-3-(methoxymethyl)pyrrolidin-1-yl)-2-(methylamino)pyrimidin-4-yl)-1H-imidazole-2-carboxamide;

(R)-N-(2-(4-(aminomethyl)piperidin-1-yl)-3-fluorophenyl)-4-(6-(3-(cyclopropylcarbamoyl)-3-(methoxymethyl)pyrrolidin-1-yl)-2-(methylamino)pyrimidin-4-yl)-1H-imidazole-2-carboxamide; and (R)-N-(2-(4-(aminomethyl)piperidin-1-yl)-3-fluorophenyl)-4-(6-(3-(cyclohexylcarbamoyl)-3-(methoxymethyl)pyrrolidin-1-yl)-2-(methylamino)pyrimidin-4-yl)-1H-imidazole-2-carboxamide;

or a pharmaceutically acceptable salt thereof.

13. A pharmaceutical composition comprising a therapeutically effective amount of a compound of claim 1, or a pharmaceutically acceptable salt thereof, and a pharmaceutically acceptable carrier.

14. A compound of claim 1, or a pharmaceutically acceptable salt thereof for use in treating PDK-1 related cancers.

15. A combination comprising a compound of claim 1, or a pharmaceutically acceptable salt thereof and an additional anti-cancer agent for simultaneous, separate or sequential use in treating PDK-1 related cancer.

16. A method of treating a disease or disorder characterized by excessive or pathologically elevated cell growth comprising administering a therapeutically effective amount of a compound of claim 1 or a pharmaceutically acceptable salt thereof to a patient in need of such treatment.

17. The method of claim 16, wherein the disease or disorder is cancer.

18. A method of treating cancer comprising administering a compound of claim 1 or pharmaceutically acceptable salt thereof and an additional anti-cancer to a patient in need of such treatment.

* * * * *